(12) United States Patent
Gbadegesin et al.

(10) Patent No.: US 9,493,837 B2
(45) Date of Patent: Nov. 15, 2016

(54) GENES CAUSING HEREDITARY KIDNEY DISEASE OR MALFORMATION OF THE URINARY TRACT

(71) Applicant: Duke University, Durham, NC (US)

(72) Inventors: Rasheed A. Gbadegesin, Durham, NC (US); Michelle P. Winn, Durham, NC (US)

(73) Assignee: DUKE UNIVERSITY, Durham, NC (US)

( * ) Notice: Subject to any disclaimer, the term of this patent is extended or adjusted under 35 U.S.C. 154(b) by 211 days.

(21) Appl. No.: 14/044,602

(22) Filed: Oct. 2, 2013

(65) Prior Publication Data

US 2014/0106352 A1     Apr. 17, 2014

Related U.S. Application Data

(60) Provisional application No. 61/708,986, filed on Oct. 2, 2012.

(51) Int. Cl.
  *C07H 21/04*  (2006.01)
  *C12Q 1/68*   (2006.01)
  *C07K 14/00*  (2006.01)

(52) U.S. Cl.
  CPC ............. *C12Q 1/6883* (2013.01); *C07K 14/00* (2013.01); *C12Q 2600/156* (2013.01)

(58) Field of Classification Search
  None
  See application file for complete search history.

(56) References Cited

PUBLICATIONS

NEB catalog (1998/1999), pp. 121, 284.*
Andre et al. (GenBank AXF21872, Jul. 16, 2009).*
Sproat et al. (Genbank Accession DJ100618, Mar. 14, 2008).*
Andre et al. (Genbank Accession No. AXF21023, Sep. 2009).*
Gbadegesin, R.A. et al., "Genetic testing in nephrotic syndrome: Challenges and opportunities," (2013) Nat. Rev. Nephrol. 9(3):179-184 doi:10.1038/nrneph.2012.286.
Gbadegesin, R.A. et al., "TNXB Mutations can cause vesicoureteral reflux," (2013) J. Am. Soc. Nephrol. 24(8):1313-1322 doi: 10.1681/ASN.2012121148.

* cited by examiner

*Primary Examiner* — Jeanine A Goldberg
(74) *Attorney, Agent, or Firm* — Andrus Intellectual Property Law, LLP

(57) ABSTRACT

Isolated nucleotides encoding polypeptides with mutations leading to amino acid substitutions linked to hereditary kidney disease or malformation of the urinary tract are provided herein. Constructs, cells, probes and inhibitory molecules comprising these mutations are also provided and may be used in screening assays for candidate agents to treat or reverse these diseases or alternatively to provide diagnostic tests. Methods of diagnosing subjects likely to develop these diseases or to be carriers of these diseases are also provided.

5 Claims, 37 Drawing Sheets
(25 of 37 Drawing Sheet(s) Filed in Color)

Figure 1
Figure 1A
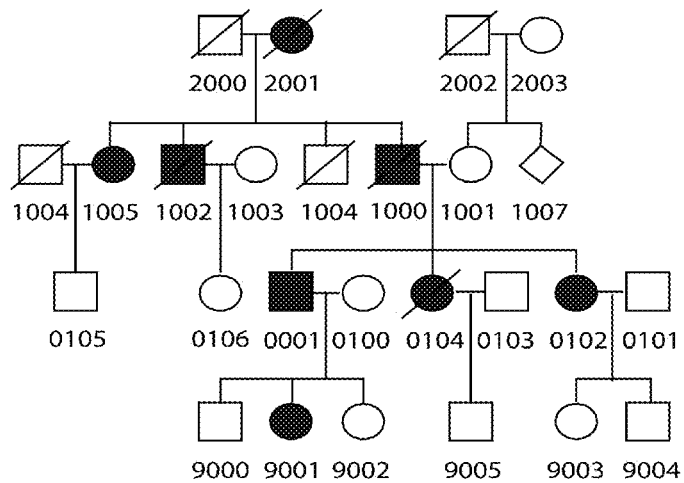
Figure 1B
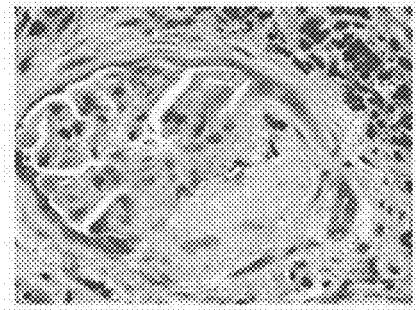
Figure 1C
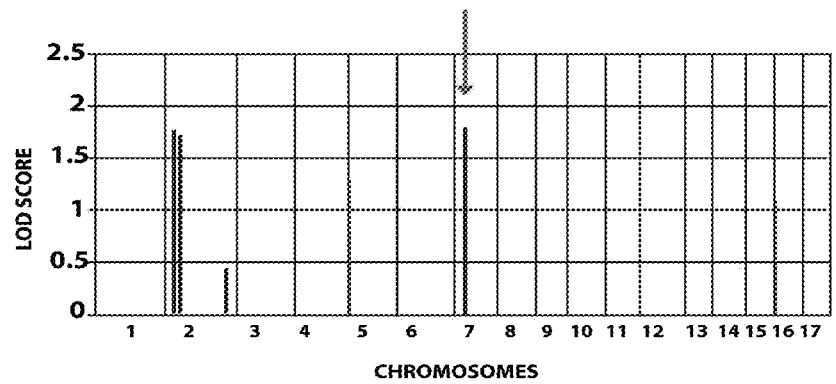

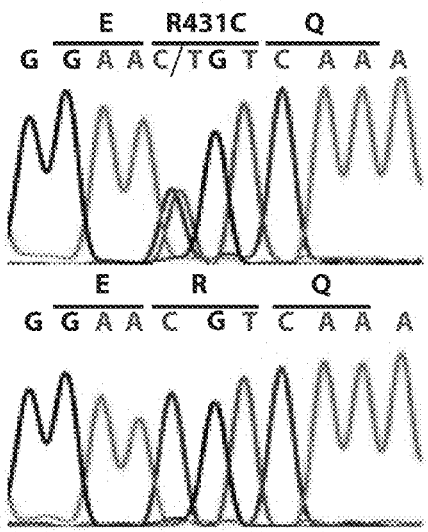

Figure 1E

```
SEQ ID NO 8   Human        405 ---KAIQERLFKQDTSSSTTHLAQQLKQERQKELACLRGRFDKGNIWSAE 451
SEQ ID NO 9   Chimpanzee   406 ---KAIQERLFKQDTSSSTTHLAQQLKQERQKELACLRGRFDKGNIWSAE 452
SEQ ID NO 10  wolfs        408 ---KAIQERLFKQNASSSTTHLAQQLKQERKELACLRGRFDKGNLWSAE 454
SEQ ID NO 11  Cattle       441 ---KAIQERLFRQNASSSTTHLAQQLKQERQKELACLRSRFDKGNLWSAE 487
SEQ ID NO 12  Mouse        400 ---KAIQERLFKQNTCSSTTHLAQQKLQEREKELACLRGRLDKGNLWSAE 446
SEQ ID NO 13  Rat          356 ---KAIQERLFKQNTCSSTTHLAQQLKQEREKELACLRGRFDKGSLWSAE 402
SEQ ID NO 14  Chicken      403 ---RTIQEKLLKQNENSSTANLALQLKQERERELACIRGRFDKGNLWSAE 449
SEQ ID NO 15  Zebra fish   457 PKFKLLQERLGGAQATSTTAALTEKQKMEREAELAQIRNRFQKGNML---- 503
```

FIGURE 2
Figure 2A
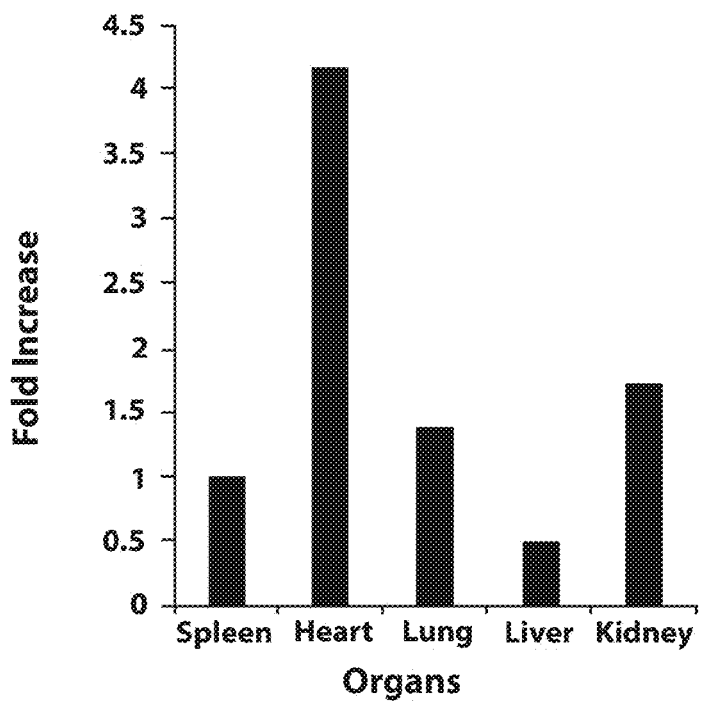
Figure 2B
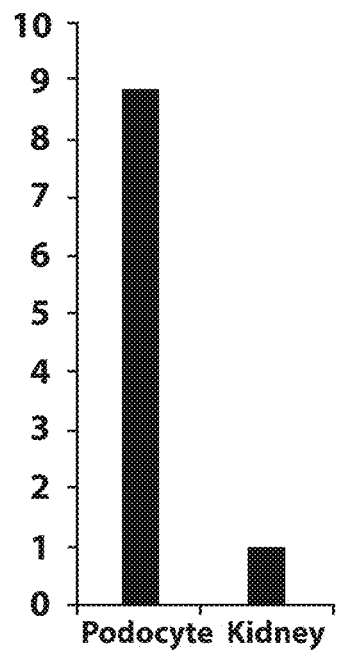

FIGURE 2, Cont.

Figure 4
Figure 4A
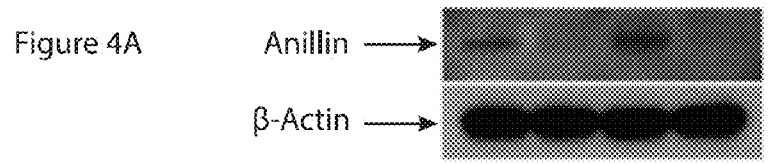
Figure 4B
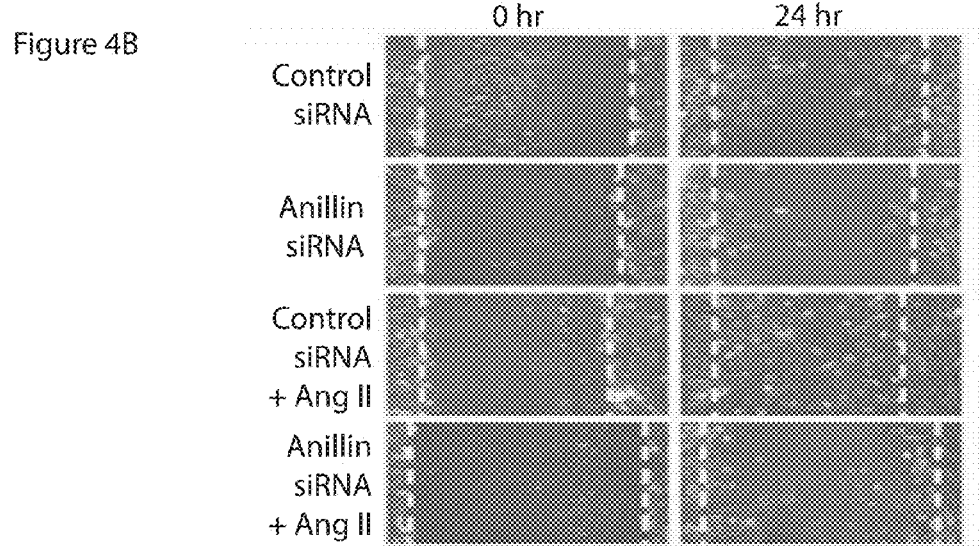
Figure 4C
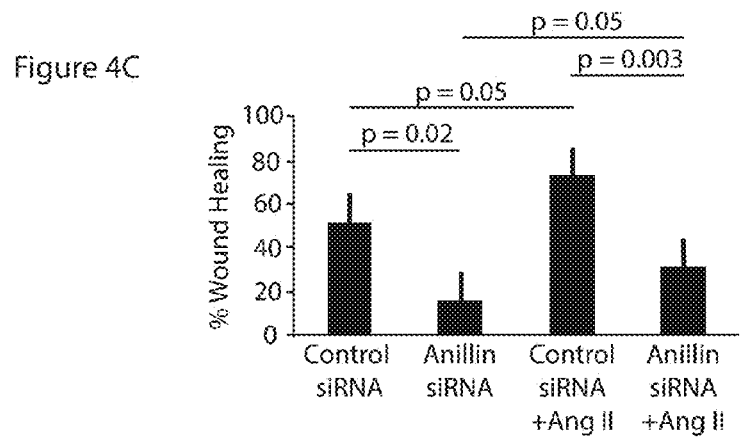

Figure 5
Figure 5A
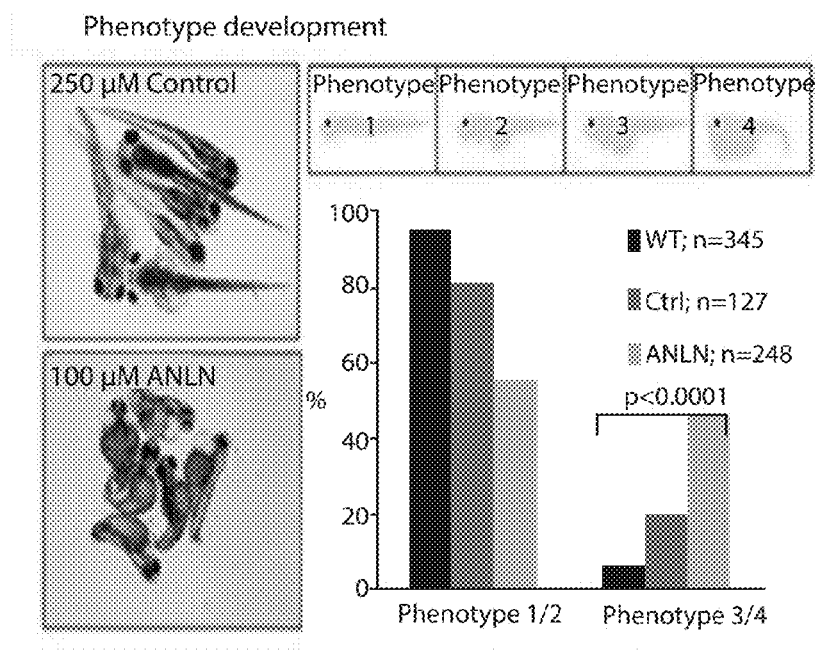
Figure 5B
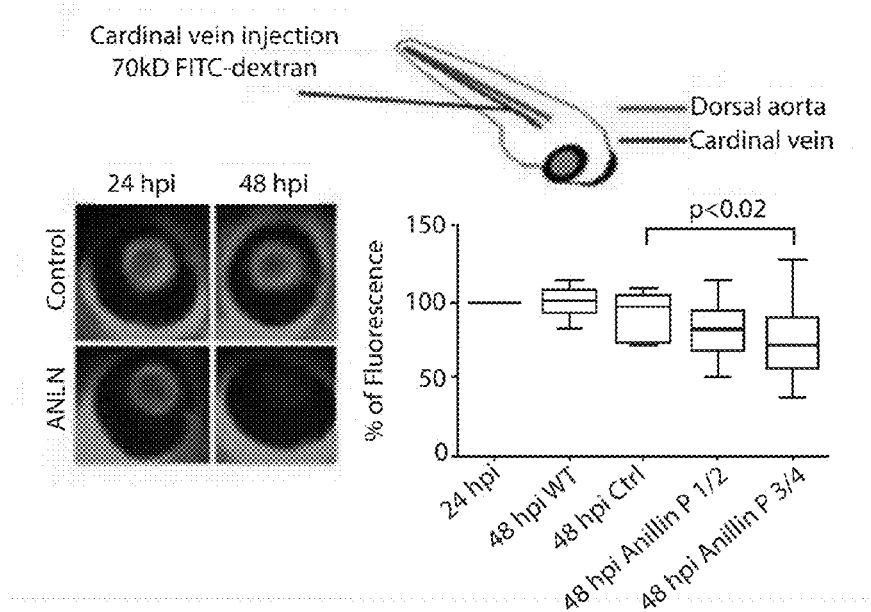

Figure 5, Cont.

Figure 6. Simplified Pedigree
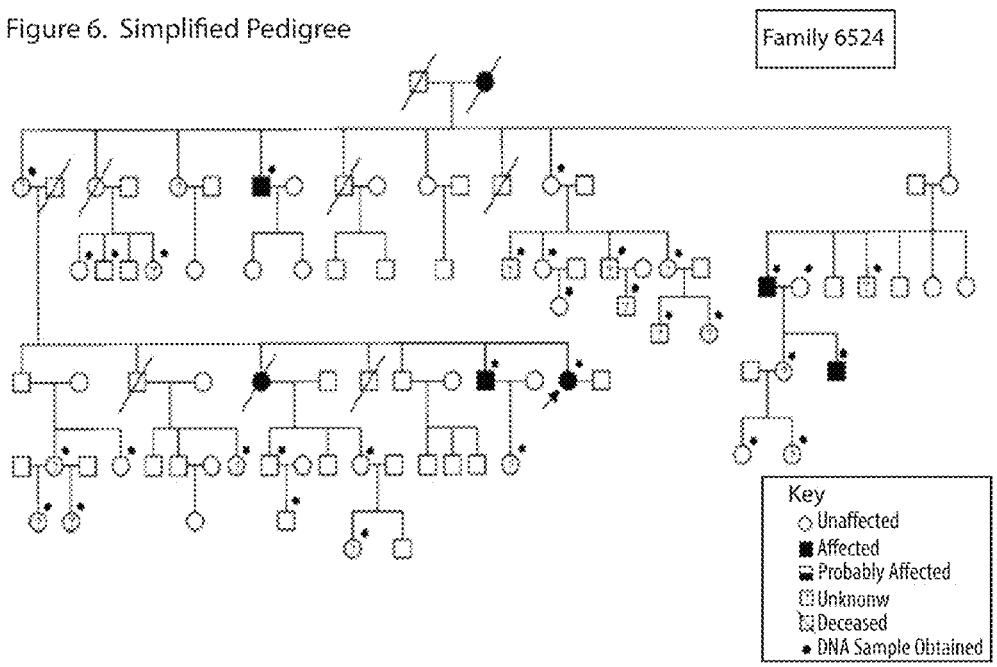
Figure 7. R458Q Mutation in Control (Top Panel) and Affected (Bottom Panel)
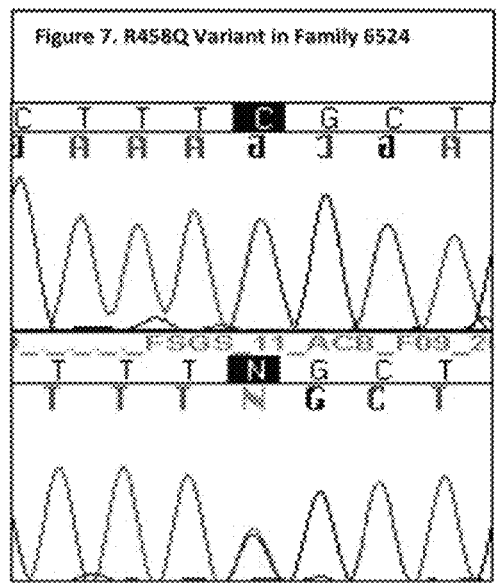

Figure 8: WT1 - Protein Structure
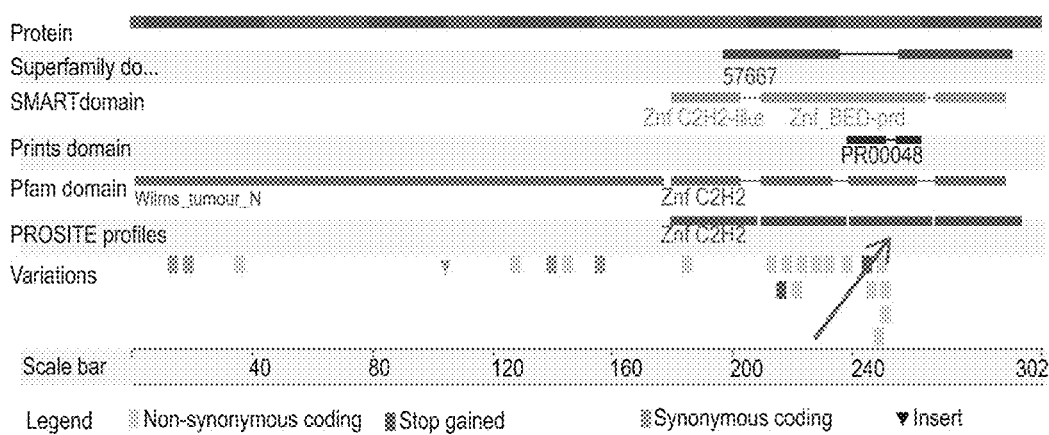
Figure 9: Conservation through Evolution of the WT1 R458Q Variant
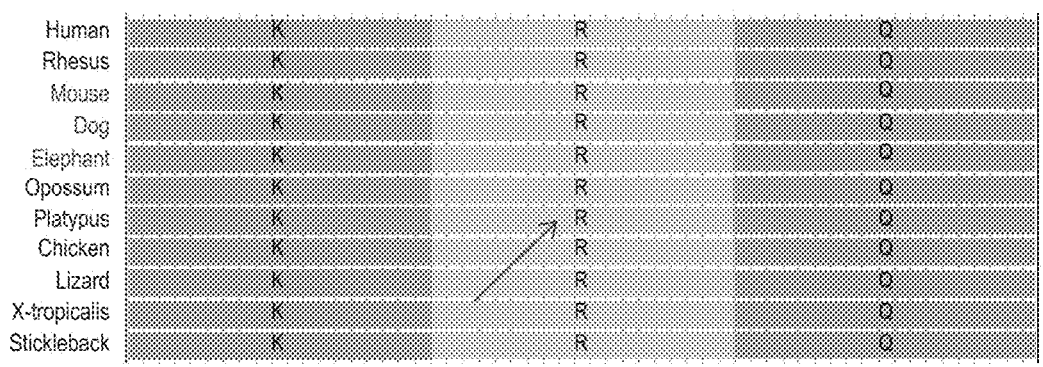

Figure 10: Protein Expression (Western)
Figure 10. Western Blot of WT1
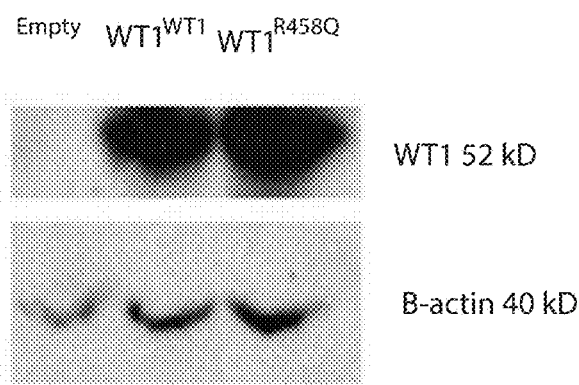
Figure 11: Immunofluorescence/Co-localization
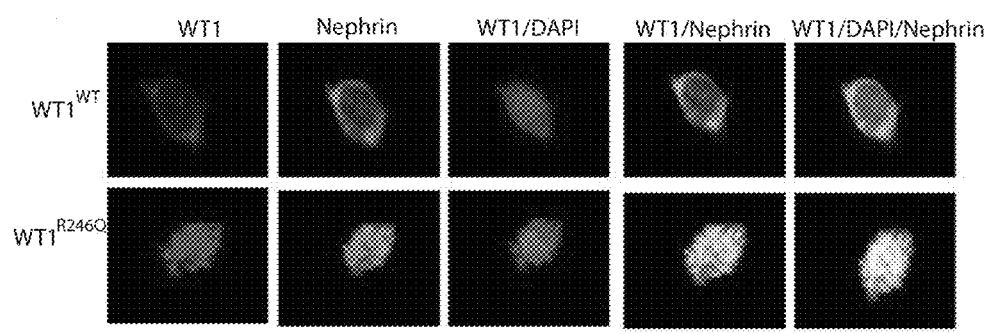

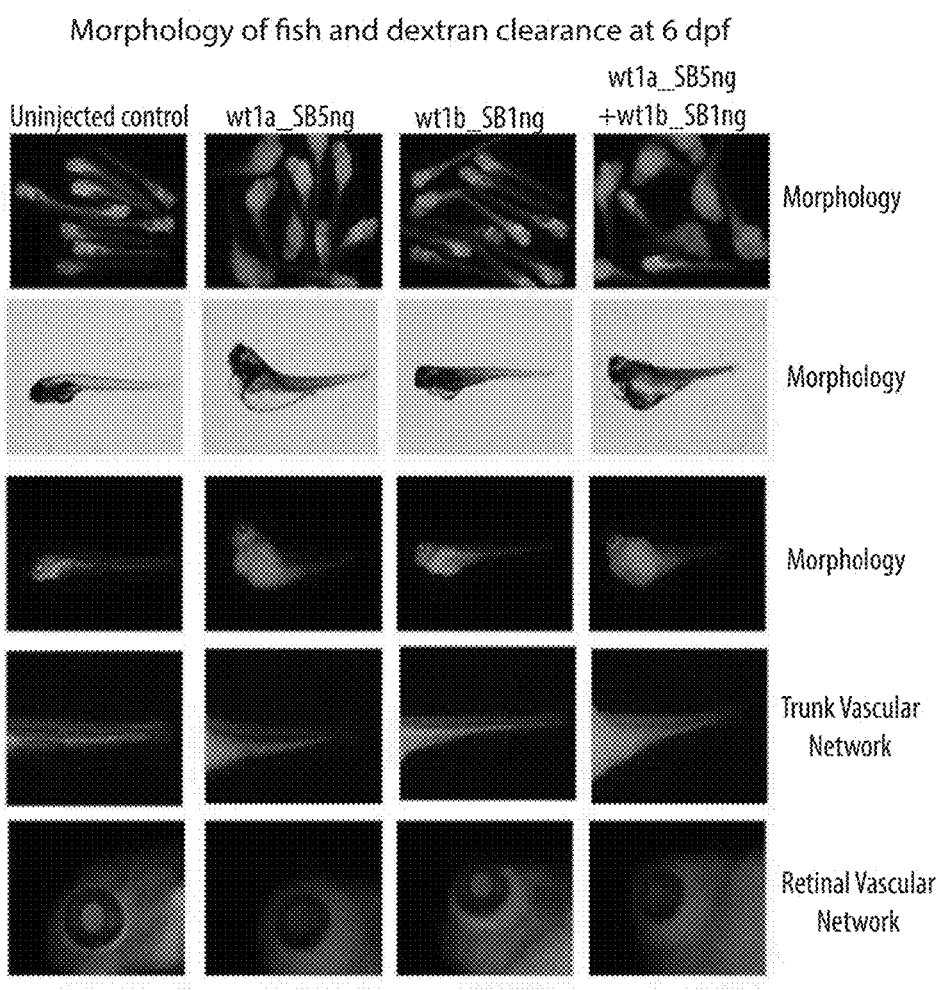
Figure 12: In vivo Modeling

Figure 13: Genome wide linkage studies in a family with hereditary VUR

Figure 13, Cont.

Figure14A: Missense mutations in TNXB as a cause of VUR

Figure 14, Cont.

```
SEQ ID NO 102 HUMAN
    GPFDSFMVQYKDAQGQPQAVPVAGDENEVTVPGLDPDRKYKMNLYGLRGRQRVGPESVVA 1345
SEQ ID NO 103 COW
    GSFDSFVVQYKDAQGRPQAVPVTGDENEVAIPGLEPDRKYKMNLYGLHGRQRVGPVSVVA 1266
SEQ ID NO 104 PIG
    GSFDSFTVQYKDAQGRPQVVPVKGDENEVTIPGLESDRKYRMNLYGLHGRQRVGPVSVVA 1336
SEQ ID NO 105 DOG
    GSFDSFVVQYKDAQGQPQAVPVRGDENEVTIPGLESHRKYKMNLYGLHGRQRVGPVSVVA 1429
SEQ ID NO 106 ELEPHANT
    GHFDYFMVQYRNGDGQPKAVRVPGHEDEVTILGLEPDQKYKMNLYGLHGGQRVGPISAIG 1212
SEQ ID NO 107 MOUSE
    GPFDSFVILYKDAQGQPQSVPIEGDENEVTVPGLESNRKYKMNLYGLRGRQRVGPVSVVA 1326
SEQ IS NO 108 GUINEA PIG
    GPFDSFVVQYKDAQGQPQAVPVGADQSELTVPGLEPNRKYKMNLYGLRGRQRVGPASVVA 975
SEQ ID NO 109 OPOSSUM
    GKFDSFVVQYKDKDGQSQVVPVEVGQNEVTISDLQPSRKYKMNLYGLQGKQRVGPISVIA 1306

SEQ ID 110 HUMAN
    LEPGRKYKMHLYGLHEGQRVGPVSTVG---------ITAPLPTPLPVEPRLGELAVAAVT 3274
SEQ ID 111 COW
    LEPGHKYKMHLYGLHGGRRVGPASTVG---------VTASLTTERPLAPRLGELAVAVVT 3088
SEQ ID 112 PIG
    LEPDHKYKMHLYGFHDGQRVGPVSTVG---------MTASMITEPPVAPRLGELATAAVT 3122
SEQ ID 113 DOG
    LEPGRKYKMHLYGLDRGRRMGPVSTVG---------LTASLSTPG--------------- 2883
SEQ ID 114 ELEPHANT
    LEPGRKYKLHLYGLHEGRRVGPVSAVG---------TIAPMPTEPPKEPRLGELSVAAVT 2187
SEQ ID 115 MOUSE
    LDPGRKYKMNLYGLHEGRRVGPVSTVG---------VTASLTTEPPIEPRLGELAAVEVT 3040
SEQ ID 116 GUINEA PIG
    LDAGRRYKMNLYGLHQAGRVGPVSTVA---------VTAPLPTWPAVDPRLGELAVAAVT 2848
SEQ ID 117 OPOSSUM
    LEPDHKYKMNLYGFHDGQRVGPVSVIGKTETPSPTVLTTEAPTEVSVKPQLGKLTVMKTT
```

Figure14B: Missense mutations in TNXB as a cause of VUR

Figure 15: Modeling of TNXB T3257I and G1331R predicted to cause structual changes in TNXB protein
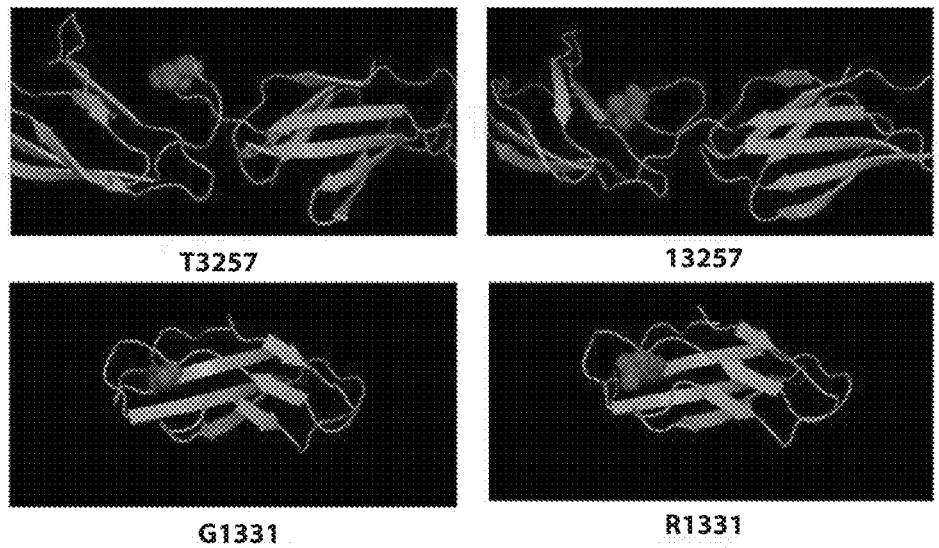
Figure 16: Delayed wound healing in T3257I fibroblast cell line
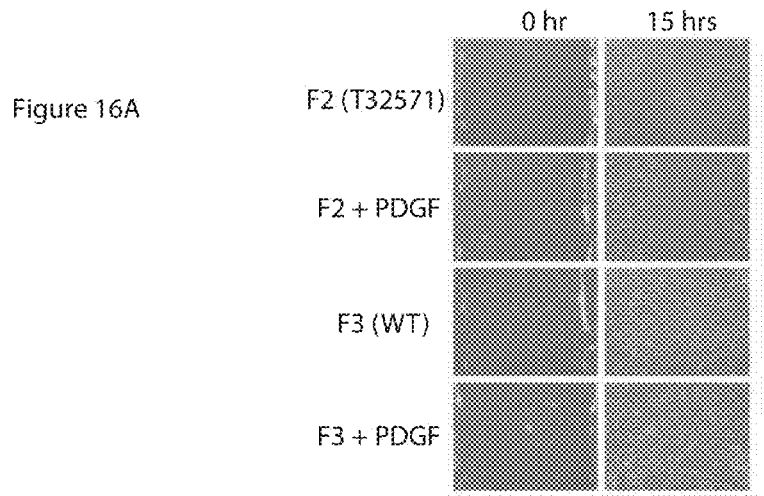
Figure 16A FIGURE 16, Cont.

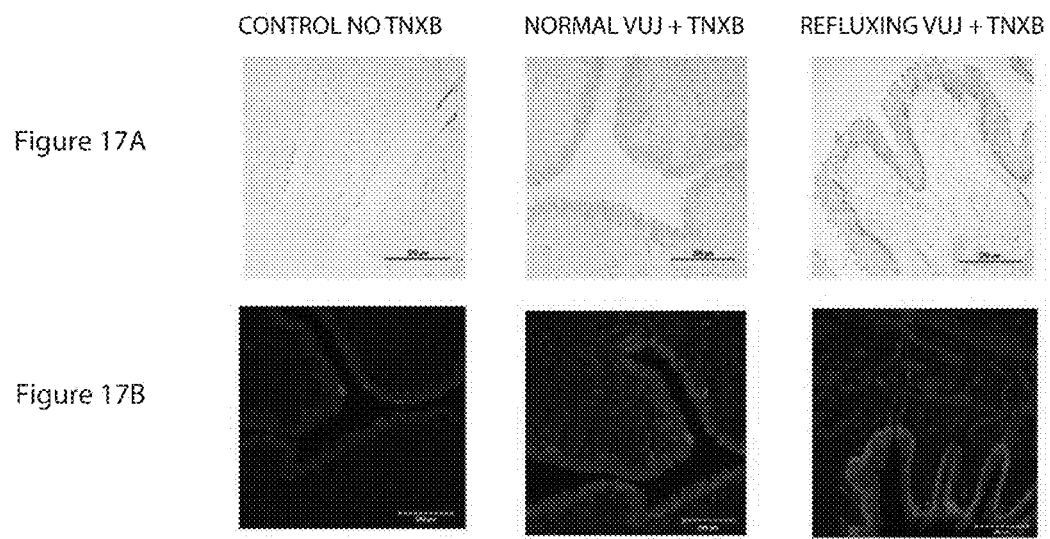
Figure 17: TNXB is expressed at vesicoureteric junction (VUJ) of refluxing and non-refluxing ureter Figure 18: Sequences referred to throughout the specification SEQ ID NO: 1-7 are human amino acid sequences from the indicated proteins

SEQ ID NO: 1 ANLN with mutation at position 431 (R431C)

MDPFTEKLLERTRARRENLQRKMAERPTAAPRSMTHAKRARQPLSEASNQQPLSGGEEKS
CTKPSPSKKRCSDNTEVEVSNLENKQPVESTSAKSCSPSPVSPQVQPQAADTISDSVAVP
ASLLGMRRGLNSRLEATAASSVKTRMQKLAEQRRRWDNDDMTDDIPESSLFSPMPSEEKA
ASPPRPLLSNASATPVGRRGRLANLAATICSWEDDVNHSFAKQNSVQEQPGTACLSKFSS
ASGASARINSSSVKQEATFCSQRDGDASLNKALSSSADDASLVNASISSSVKATSPVKST
TSITDAKSCEGQNPELLPKTPISPLKTGVSKPIVKSTLSQTVPSKGELSREICLQSQSKD
KSTTPGGTGIKPFLERFGERCQEHSKESPARSTPHRTPIITPNTKAIQERLFKQDTSSST
THLAQQLKQE░QKELACLRGRFDKGNIWSAEKGGNSKSKQLETKQETHCQSTPLKKHQGV
SKTQSLPVTEKVTENQIPAKNSSTEPKGFTECEMTKSSPLKITLFLEEDKSLKVTSDPKV
EQKIEVIREIEMSVDDDDINSSKVINDLFSDVLEEGELDMEKSQEEMDQALAESSEEQED
ALNISSMSLLAPLAQTVGVVSPESLVSTPRLELKDTSRSDESPKPGKFQRTRVPRAESGD
SLGSEDRDLLYSIDAYRSQRFKETERPSIKQVIVRKEDVTSKLDEKNNAFPCQVNIKQKM
QELNNEINMQQTVIYQASQALNCCVDEEHGKGSLEEAEAERLLLIATGKRTLLIDELNKL
KNEGPQRKNKASPQSEFMPSKGSVTLSEIRLPLKADFVCSTVQKPDAANYYYLIILKAGA
ENMVATPLASTSNSLNGDALTFTTTFTLQDVSNDFEINIEVYSLVQKKDPSGLDKKKKTS
KSKAITPKRLLTSITTKSNIHSSVMASPGGLSAVRTSNFALVGSYTLSLSSVGNTKFVLD
KVPFLSSLEGHIYLKIKCQVNSSVEERGFLTIFEDVSGFGAWHRRWCVLSGNCISYWTYP
DDEKRKNPIGRINLANCTSRQIEPANREFCARRNTFELITVRPQREDDRETLVSQCRDTL
CVTKNWLSADTKEERDLWMQKLNQVLVDIRLWQPDACYKPIGKP

SEQ ID NO: 2 ANLN wild-type sequence

MDPFTEKLLERTRARRENLQRKMAERPTAAPRSMTHAKRARQPLSEASNQQPLSGGEEKS
CTKPSPSKKRCSDNTEVEVSNLENKQPVESTSAKSCSPSPVSPQVQPQAADTISDSVAVP

Figure 18, Cont.

ASLLGMRRGLNSRLEATAASSVKTRMQKLAEQRRRWDNDDMTDDIPESSLFSPMPSEEKA
ASPPRPLLSNASATPVGRRGRLANLAATICSWEDDVNHSFAKQNSVQEQPGTACLSKFSS
ASGASARINSSSVKQEATFCSQRDGDASLNKALSSSADDASLVNASISSSVKATSPVKST
TSITDAKSCEGQNPELLPKTPISPLKTGVSKPIVKSTLSQTVPSKGELSREICLQSQSKD
KSTTPGGTGIKPFLERFGERCQEHSKESPARSTPHRTPIITPNTKAIQERLFKQDTSSST
THLAQQLKQE QKELACLRGRFDKGNIWSAEKGGNSKSKQLETKQETHCQSTPLKKHQGV
SKTQSLPVTEKVTENQIPAKNSSTEPKGFTECEMTKSSPLKITLFLEEDKSLKVTSDPKV
EQKIEVIREIEMSVDDDDINSSKVINDLFSDVLEEGELDMEKSQEEMDQALAESSEEQED
ALNISSMSLLAPLAQTVGVVSPESLVSTPRLELKDTSRSDESPKPGKFQRTRVPRAESGD
SLGSEDRDLLYSIDAYRSQRFKETERPSIKQVIVRKEDVTSKLDEKNNAFPCQVNIKQKM
QELNNEINMQQTVIYQASQALNCCVDEEHGKGSLEEAEAERLLLIATGKRTLLIDELNKL
KNEGPQRKNKASPQSEFMPSKGSVTLSEIRLPLKADFVCSTVQKPDAANYYYLIILKAGA
ENMVATPLASTSNSLNGDALTFTTTFTLQDVSNDFEINIEVYSLVQKKDPSGLDKKKKTS
KSKAITPKRLLTSITTKSNIHSSVMASPGGLSAVRTSNFALVGSYTLSLSSVGNTKFVLD
KVPFLSSLEGHIYLKIKCQVNSSVEERGFLTIFEDVSGFGAWHRRWCVLSGNCISYWTYP
DDEKRKNPIGRINLANCTSRQIEPANREFCARRNTFELITVRPQREDDRETLVSQCRDTL
CVTKNWLSADTKEERDLWMQKLNQVLVDIRLWQPDACYKPIGKP

SEQ ID NO: 3 WT1 with R458Q mutation
MQDPASTCVPEPASQHTLRSGPGCLQQPEQQGVRDPGGIWAKLG
  AAEASAERLQGRRSRGASGSEPQQMGSDVRDLNALLPAVPSLGGGGGCALPVSGAAQW
  APVLDFAPPGASAYGSLGGPAPPPAPPPPPPPPHSFIKQEPSWGGAEPHEEQCLSAF
  TVHFSGQFTGTAGACRYGPFGPPPPSQASSGQARMFPNAPYLPSCLESQPAIRNQGYS
  TVTFDGTPSYGHTPSHHAAQFPNHSFKHEDPMGQQGSLGEQQYSVPPPVYGCHTPTDS
  CTGSQALLLRTPYSSDNLYQMTSQLECMTWNQMNLGATLKGVAAGSSSSVKWTEGQSN

Figure 18, Cont.

HSTGYESDNHTTPILCGAQYRIHTHGVFRGIQDVRRVPGVAPTLVRSASETSEKRPFM
CAYPGCNKRYFKLSHLQMHSRKHTGEKPYQCDFKDCERRFSRSDQLKRHQRRHTGVKP
FQCKTCQ░KFSRSDHLKTHTRTHTGKTSEKPFSCRWPSCQKKFARSDELVRHHNMHQR
NMTKLQLAL

SEQ ID NO:4 wild-type WT1

MQDPASTCVPEPASQHTLRSGPGCLQQPEQQGVRDPGGIWAKLG
AAEASAERLQGRRSRGASGSEPQQMGSDVRDLNALLPAVPSLGGGGGCALPVSGAAQW
APVLDFAPPGASAYGSLGGPAPPPAPPPPPPPPHSFIKQEPSWGGAEPHEEQCLSAF
TVHFSGQFTGTAGACRYGPFGPPPPSQASSGQARMFPNAPYLPSCLESQPAIRNQGYS
TVTFDGTPSYGHTPSHHAAQFPNHSFKHEDPMGQQGSLGEQQYSVPPPVYGCHTPTDS
CTGSQALLLRTPYSSDNLYQMTSQLECMTWNQMNLGATLKGVAAGSSSSVKWTEGQSN
HSTGYESDNHTTPILCGAQYRIHTHGVFRGIQDVRRVPGVAPTLVRSASETSEKRPFM
CAYPGCNKRYFKLSHLQMHSRKHTGEKPYQCDFKDCERRFSRSDQLKRHQRRHTGVKP
FQCKTCQ░KFSRSDHLKTHTRTHTGKTSEKPFSCRWPSCQKKFARSDELVRHHNMHQR
NMTKLQLAL

SEQ ID NO:5 TNXB with T3257I mutation

MMPAQYALTSSLVLLVLLSTARAGPFSSRSNVTLPAPRPPPQPGGHTVGAGVGSPSSQLY
EHTVEGGEKQVVFTHRINLPPSTGCGCPPGTEPPVLASEVQALRVRLEILEELVKGLKEQ
CTGGCCPASAQAGTGQTDVRTLCSLHGVFDLSRCTCSCEPGWGGPTCSDPTDAEIPPSSP
PSASGSCPDDCNDQGRCVRGRCVCFPGYTGPSCGWPSCPGDCQGRGRCVQGVCVCRAGFS
GPDCSQRSCPRGCSQRGRCEGGRCVCDPGYTGDDCGMRSCPRGCSQRGRCENGRCVCNPG
YTGEDCGVRSCPRGCSQRGRCKDGRCVCDPGYTGEDCGTRSCPWDCGEGGRCVDGRCVCW
PGYTGEDCSTRTCPRDCRGRGRCEDGECICDTGYSGDDCGVRSCPGDCNQRGRCEDGRCV

Figure 18, Cont.

```
CWPGYTGTDCGSRACPRDCRGRGRCENGVCVCNAGYSGEDCGVRSCPGDCRGRGRCESGR
CMCWPGYTGRDCGTRACPGDCRGRGRCVDGRCVCNPGFTGEDCGSRRCPGDCRGHGLCED
GVCVCDAGYSGEDCSTRSCPGGCRGRGQCLDGRCVCEDGYSGEDCGVRQCPNDCSQHGVC
QDGVCICWEGYVSEDCSIRTCPSNCHGRGRCEEGRCLCDPGYTGPTCATRMCPADCRGRG
RCVQGVCLCHVGYGGEDCGQEEPPASACPGGCGPRELCRAGQCVCVEGFRGPDCAIQTCP
GDCRGRGECHDGSCVCKDGYAGEDCGEEVPTIEGMRMHLLEETTVRTEWTPAPGPVDAYE
IQFIPTTEGASPPFTARVPSSASAYDQRGLAPGQEYQVTVRALRGTSWGLPASKTITTMI
DGPQDLRVVAVTPTTLELGWLRPQAEVDRFVVSYVSAGNQRVRLEVPPEADGTLLTDLMP
GVEYVVTVTAERGRAVSYPASVRANTGSSPLGLLGTTDEPPPSGPSTTQGAQAPLLQQRP
QELGELRVLGRDETGRLRVVWTAQPDTFAYFQLRMRVPEGPGAHEEVLPGDVRQALVPPP
PPGTPYELSLHGVPPGGKPSDPIIYQGIMDKDEEKPGKSSGPPRLGELTVTDRTSDSLLL
RWTVPEGEFDSFVIQYKDRDGQPQVVPVEGPQRSAVITSLDPGRKYKFVLYGFVGKKRHG
PLVAEAKILPQSDPSPGTPPHLGNLWVTDPTPDSLHLSWTVPEGQFDTFMVQYRDRDGRP
QVVPVEGPERSFVVSSLDPDHKYRFTLFGIANKKRYGPLTADGTTAPERKEEPPRPEFLE
QPLLGELTVTGVTPDSLRLSWTVAQGPFDSFMVQYKDAQGQPQAVPVAGDENEVTVPGLD
PDRKYKMNLYLRGRQRVGPESVVAKTAPQEDVDETPSPTELGTEAPESPEEPLLGELTV
TGSSPDSLSLFWTVPQGSFDSFTVQYKDRDGRPRAVRVGGKESEVTVGGLEPGHKYKMHL
YGLHEGQRVGPVSAVGVTAPQQEETPPATESPLEPRLGELTVTDVTPNSVGLSWTVPEGQ
FDSFIVQYKDKDGQPQVVPVAADQREVTVYNLEPERKYKMNMYGLHDGQRMGPLSVVIVT
APLPPAPATEASKPPLEPRLGELTVTDITPDSVGLSWTVPEGEFDSFVVQYKDRDGQPQV
VPVAADQREVTIPDLEPSRKYKFLLFGIQDGKRRSPVSVEAKTVARGDASPGAPPRLGEL
WVTDPTPDSLRLSWTVPEGQFDSFVVQFKDKDGPQVVPVEGHERSVTVTPLDAGRKYRFL
LYGLLGKKRHGPLTADGTTEARSAMDDTGTKRPPKPRLGEELQVTTVTQNSVGLSWTVPE
GQFDSFVVQYKDRDGQPQVVPVEGSLREVSVPGLDPAHRYKLLLYGLHHGKRVGPISAVA
ITAGREETETETTAPTPPAPEPHLGELTVEEATSHTLHLSWMVTEGEFDSFEIQYTDRDG
```

Figure 18, Cont.

QLQMVRIGGDRNDITLSGLESDHRYLVTLYGFSDGKHVGPVHVEALTVPEEEKPSEPPTA
TPEPPIKPRLGELTVTDATPDSLSLSWTVPEGQFDHFLVQYRNGDGQPKAVRVPGHEEGV
TISGLEPDHKYKMNLYGFHGGQRMGPVSVVGVTAAEEETPSPTEPSMEAPEPAEEPLLGE
LTVTGSSPDSLSLSWTVPQGRFDSFTVQYKDRDGRPQVVRVGGEESEVTVGGLEPGRKYK
MHLYGLHEGRRVGPVSAVGVTAPEEESPDAPLAKLRLGQMTVRDITSDSLSLSWTVPEGQ
FDHFLVQFKNGDGQPKAVRVPGHEDGVTISGLEPDHKYKMNLYGFHGGQRVGPVSAVGLT
APGKDEEMAPASTEPPTPEPPIKPRLEELTVTDATPDSLSLSWTVPEGQFDHFLVQYKNG
DGQPKATRVPGHEDRVTISGLEPDNKYKMNLYGFHGGQRVGPVSAIGVTAAEEETPSPTE
PSMEAPEPPEEPLLGELTVTGSSPDSLSLSWTVPQGRFDSFTVQYKDRDGRPQVVRVGGE
ESEVTVGGLEPGRKYKMHLYGLHEGRRVGPVSTVGVTAPQEDVDETPSPTEPGTEAPGPP
EEPLLGELTVTGSSPDSLSLSWTVPQGRFDSFTVQYKDRDGRPQAVRVGGQESKVTVRGL
EPGRKYKMHLYGLHEGRRLGPVSAVGVTEDEAETTQAVPTMTPEPPIKPRLGELTMTDAT
PDSLSLSWTVPEGQFDHFLVQYRNGDGQPKAVRVPGHEDGVTISGLEPDHKYKMNLYGFH
GGQRVGPISVIGVTAAEEETPSPTELSTEAPEPPEEPLLGELTVTGSSPDSLSLSWTIPQ
GHFDSFTVQYKDRDGRPQVMRVRGEESEVTVGGLEPGRKYKMHLYGLHEGRRVGPVSTVG
VTAPEDEAETTQAVPTTTPEPPNKPRLGELTVTDATPDSLSLSWMVPEGQFDHFLVQYRN
GDGQPKVVRVPGHEDGVTISGLEPDHKYKMNLYGFHGGQRVGPISVIGVTAAEEETPAPT
EPSTEAPEPPEEPLLGELTVTGSSPDSLSLSWTIPQGRFDSFTVQYKDRDGRPQVVRVRG
EESEVTVGGLEPGCKYKMHLYGLHEGQRVGPVSAVGVTAPKDEAETTQAVPTMTPEPPIK
PRLGELTVTDATPDSLSLSWMVPEGQFDHFLVQYRNGDGQPKAVRVPGHEDGVTISGLEP
DHKYKMNLYGFHGGQRVGPVSAIGVTEEETPSPTEPSTEAPEAPEEPLLGELTVTGSSPD
SLSLSWTVPQGRFDSFTVQYKDRDGQPQVVRVRGEESEVTVGGLEPGRKYKMHLYGLHEG
QRVGPVSTVGITAPLP PLPVEPRLGELAVAAVTSDSVGLSWTVAQGPFDSFLVQYRDAQ
GQPQAVPVSGDLRAVAVSGLDPARKYKFLLFGLQNGKRHGPVFVEARTAPDTKPSPRLGE
LTVTDATPDSVGLSWTVPEGEFDSFVVQYKDKDGRLQVVPVAANQREVTVQGLEPSRKYR

Figure 18, Cont.

FLLYGLSGRKRLGPISADSTTAPLEKELPPHLGELTVAEETSSSLRLSWTVAQGPFDSFV
VQYRDTDGQPRAVPVAADQRTVTVEDLEPGKKYKFLLYGLLGGKRLGPVSALGMTAPEED
TPAPELAPEAPEPPEEPRLGVLTVTDTTPDSMRLSWSVAQGPFDSFVVQYEDTNGQPQAL
LVDGDQSKILISGLEPSTPYRFLLYGLHEGKRLGPLSAEGTTGLAPAGQTSEESRPRLSQ
LSVTDVTTSSLRLNWEAPPGAFDSFLLRFGVPSPSTLEPHPRPLLQRELMVPGTRHSAVL
RDLRSGTLYSLTLYGLRGPHKADSIQGTARTLSPVLESPRDLQFSEIRETSAKVNWMPPP
SRADSFKVSYQLADGGEPQSVQVDGQARTQKLQGLIPGARYEVTVVSVRGFEESEPLTGF
LTTVPDGPTQLRALNLTEGFAVLHWKPPQNPVDTYDVQVTAPGAPPLQAETPGSAVDYPL
HDLVLHTNYTATVRGLRGPNLTSPASITFTTGLEAPRDLEAKEVTPRTALLTWTEPPVRP
AGYLLSFHTPGGQNQEILLPGGITSHQLLGLFPSTSYNARLQAMWGQSLLPPVSTSFTTG
GLRIPFPRDCGEEMQNGAGASRTSTIFLNGNRERPLNVFCDMETDGGGWLVFQRRMDGQT
DFWRDWEDYAHGFGNISGEFWLGNEALHSLTQAGDYSMRVDLRAGDEAVFAQYDSFHVDS
AAEYYRLHLEGYHGTAGDSMSYHSGSVFSARDRDPNSLLISCAVSYRGAWWYRNCHYANL
NGLYGSTVDHQGVSWYHWKGFEFSVPFTEMKLRPRNFRSPAGGG

SEQ ID NO:6  Wild-type TNXB sequence

MMPAQYALTSSLVLLVLLSTARAGPFSSRSNVTLPAPRPPPQPGGHTVGAGVGSPSSQLY
EHTVEGGEKQVVFTHRINLPPSTGCGCPPGTEPPVLASEVQALRVRLEILEELVKGLKEQ
CTGGCCPASAQAGTGQTDVRTLCSLHGVFDLSRCTCSCEPGWGGPTCSDPTDAEIPPSSP
PSASGSCPDDCNDQGRCVRGRCVCFPGYTGPSCGWPSCPGDCQGRGRCVQGVCVCRAGFS
GPDCSQRSCPRGCSQRGRCEGGRCVCDPGYTGDDCGMRSCPRGCSQRGRCENGRCVCNPG
YTGEDCGVRSCPRGCSQRGRCKDGRCVCDPGYTGEDCGTRSCPWDCGEGGRCVDGRCVCW
PGYTGEDCSTRTCPRDCRGRGRCEDGECICDTGYSGDDCGVRSCPGDCNQRGRCEDGRCV
CWPGYTGTDCGSRACPRDCRGRGRCENGVCVCNAGYSGEDCGVRSCPGDCRGRGRCESGR
CMCWPGYTGRDCGTRACPGDCRGRGRCVDGRCVCNPGFTGEDCGSRRCPGDCRGHGLCED

Figure 18, Cont.

```
GVCVCDAGYSGEDCSTRSCPGGCRGRGQCLDGRCVCEDGYSGEDCGVRQCPNDCSQHGVC
QDGVCICWEGYVSEDCSIRTCPSNCHGRGRCEEGRCLCDPGYTGPTCATRMCPADCRGRG
RCVQGVCLCHVGYGGEDCGQEEPPASACPGGCGPRELCRAGQCVCVEGFRGPDCAIQTCP
GDCRGRGECHDGSCVCKDGYAGEDCGEEVPTIEGMRMHLLEETTVRTEWTPAPGPVDAYE
IQFIPTTEGASPPFTARVPSSASAYDQRGLAPGQEYQVTVRALRGTSWGLPASKTITTMI
DGPQDLRVVAVTPTTLELGWLRPQAEVDRFVVSYVSAGNQRVRLEVPPEADGTLLTDLMP
GVEYVVTVTAERGRAVSYPASVRANTGSSPLGLLGTTDEPPPSGPSTTQGAQAPLLQQRP
QELGELRVLGRDETGRLRVVWTAQPDTFAYFQLRMRVPEGPGAHEEVLPGDVRQALVPPP
PPGTPYELSLHGVPPGGKPSDPIIYQGIMDKDEEKPGKSSGPPRLGELTVIDRTSDSLLL
RWTVPEGEFDSFVIQYKDRDGQPQVVPVEGPQRSAVITSLDPGRKYKFVLYGFVGKKRHG
PLVAEAKILPQSDPSPGTPPHLGNLWVTDPTPDSLHLSWTVPEGQFDTFMVQYRDRDGRP
QVVPVEGPERSFVVSSLDPDHKYRFTLFGIANKKRYGPLTADGTTAPERKEEPPRPEFLE
QPLLGELTVTGVTPDSLRLSWTVAQGPFDSFMVQYKDAQGQPQAVPVAGDENEVTVPGLD
PDRKYKMNLYXLRGRQRVGPESVVAKTAPQEDVDETPSPTELGTEAPESPEEPLLGELTV
TGSSPDSLSLFWTVPQGSFDSFTVQYKDRDGRPRAVRVGGKESEVTVGGLEPGHKYKMHL
YGLHEGQRVGPVSAVGVTAPQQEETPPATESPLEPRLGELTVTDVTPNSVGLSWTVPEGQ
FDSFIVQYKDKDGQPQVVPVAADQREVTVYNLEPERKYKMNMYGLHDGQRMGPLSVVIVT
APLPPAPATEASKPPLEPRLGELTVTDITPDSVGLSWTVPEGEFDSFVVQYKDRDGQPQV
VPVAADQREVTIPDLEPSRKYKFLLFGIQDGKRRSPVSVEAKTVARGDASPGAPPRLGEL
WVTDPTPDSLRLSWTVPEGQFDSFVVQFKDKDGPQVVPVEGHERSVTVTPLDAGRKYRFL
LYGLLGKKRHGPLTADGTTEARSAMDDTGTKRPPKPRLGEELQVTTVTQNSVGLSWTVPE
GQFDSFVVQYKDRDGQPQVVPVEGSLREVSVPGLDPAHRYKLLLYGLHHGKRVGPISAVA
ITAGREETETETTAPTPPAPEPHLGELTVEEATSHTLHLSWMVTEGEFDSFEIQYTDRDG
QLQMVRIGGDRNDITLSGLESDHRYLVTLYGFSDGKHVGPVHVEALTVPEEEKPSEPPTA
TPEPPIKPRLGELTVTDATPDSLSLSWTVPEGQFDHFLVQYRNGDGQPKAVRVPGHEEGV
```

Figure 18, Cont.

TISGLEPDHKYKMNLYGFHGGQRMGPVSVVGVTAAEEETPSPTEPSMEAPEPAEEPLLGE
LTVTGSSPDSLSLSWTVPQGRFDSFTVQYKDRDGRPQVVRVGGEESEVTVGGLEPGRKYK
MHLYGLHEGRRVGPVSAVGVTAPEEESPDAPLAKLRLGQMTVRDITSDSLSLSWTVPEGQ
FDHFLVQFKNGDGQPKAVRVPGHEDGVTISGLEPDHKYKMNLYGFHGGQRVGPVSAVGLT
APGKDEEMAPASTEPPTPEPPIKPRLEELTVTDATPDSLSLSWTVPEGQFDHFLVQYKNG
DGQPKATRVPGHEDRVTISGLEPDNKYKMNLYGFHGGQRVGPVSAIGVTAAEEETPSPTE
PSMEAPEPPEEPLLGELTVTGSSPDSLSLSWTVPQGRFDSFTVQYKDRDGRPQVVRVGGE
ESEVTVGGLEPGRKYKMHLYGLHEGRRVGPVSTVGVTAPQEDVDETPSPTEPGTEAPGPP
EEPLLGELTVTGSSPDSLSLSWTVPQGRFDSFTVQYKDRDGRPQAVRVGGQESKVTVRGL
EPGRKYKMHLYGLHEGRRLGPVSAVGVTEDEAETTQAVPTMTPEPPIKPRLGELTMTDAT
PDSLSLSWTVPEGQFDHFLVQYRNGDGQPKAVRVPGHEDGVTISGLEPDHKYKMNLYGFH
GGQRVGPISVIGVTAAEEETPSPTELSTEAPEPPEEPLLGELTVTGSSPDSLSLSWTIPQ
GHFDSFTVQYKDRDGRPQVMRVRGEESEVTVGGLEPGRKYKMHLYGLHEGRRVGPVSTVG
VTAPEDEAETTQAVPTTTPEPPNKPRLGELTVTDATPDSLSLSWMVPEGQFDHFLVQYRN
GDGQPKVVRVPGHEDGVTISGLEPDHKYKMNLYGFHGGQRVGPISVIGVTAAEEETPAPT
EPSTEAPEPPEEPLLGELTVTGSSPDSLSLSWTIPQGRFDSFTVQYKDRDGRPQVVRVRG
EESEVTVGGLEPGCKYKMHLYGLHEGQRVGPVSAVGVTAPKDEAETTQAVPTMTPEPPIK
PRLGELTVTDATPDSLSLSWMVPEGQFDHFLVQYRNGDGQPKAVRVPGHEDGVTISGLEP
DHKYKMNLYGFHGGQRVGPVSAIGVTEEETPSPTEPSTEAPEAPEEPLLGELTVTGSSPD
SLSLSWTVPQGRFDSFTVQYKDRDGQPQVVRVRGEESEVTVGGLEPGRKYKMHLYGLHEG
QRVGPVSTVGITAPLPPLPVEPRLGELAVAAVTSDSVGLSWTVAQGPFDSFLVQYRDAQ
GQPQAVPVSGDLRAVAVSGLDPARKYKFLLFGLQNGKRHGPVPVEARTAPDTKPSPRLGE
LTVTDATPDSVGLSWTVPEGEFDSFVVQYKDKDGRLQVVPVAANQREVTVQGLEPSRKYR
FLLYGLSGRKRLGPISADSTTAPLEKELPPHLGELTVAEETSSSLRLSWTVAQGPFDSFV
VQYRDTDGQPRAVPVAADQRTVTVEDLEPGKKYKFLLYGLLGGKRLGPVSALGMTAPEED

Figure 18, Cont.

TPAPELAPEAPEPPEEPRLGVLTVTDTTPDSMRLSWSVAQGPFDSFVVQYEDTNGQPQAL
LVDGDQSKILISGLEPSTPYRFLLYGLHEGKRLGPLSAEGTTGLAPAGQTSEESRPRLSQ
LSVTDVTTSSLRLNWEAPPGAFDSFLLRFGVPSPSTLEPHPRPLLQRELMVPGTRHSAVL
RDLRSGTLYSLTLYGLRGPHKADSIQGTARTLSPVLESPRDLQFSEIRETSAKVNWMPPP
SRADSFKVSYQLADGGEPQSVQVDGQARTQKLQGLIPGARYEVTVVSVRGFEESEPLTGF
LTTVPDGPTQLRALNLTEGFAVLHWKPPQNPVDTYDVQVTAPGAPPLQAETPGSAVDYPL
HDLVLHTNYTATVRGLRGPNLTSPASITFTTGLEAPRDLEAKEVTPRTALLTWTEPPVRP
AGYLLSFHTPGGQNQEILLPGGITSHQLLGLFPSTSYNARLQAMWGQSLLPPVSTSFTTG
GLRIPFPRDCGEEMQNGAGASRTSTIFLNGNRERPLNVFCDMETDGGGWLVFQRRMDGQT
DFWRDWEDYAHGFGNISGEFWLGNEALHSLTQAGDYSMRVDLRAGDEAVFAQYDSFHVDS
AAEYYRLHLEGYHGTAGDSMSYHSGSVFSARDRDPNSLLISCAVSYRGAWWYRNCHYANL
NGLYGSTVDHQGVSWYHWKGFEFSVPFTEMKLRPRNFRSPAGGG

SEQ ID NO: 7 TNXB with G1331R mutation

MMPAQYALTSSLVLLVLLSTARAGPFSSRSNVTLPAPRPPPQPGGHTVGAGVGSPSSQLY
EHTVEGGEKQVVFTHRINLPPSTGCGCPPGTEPPVLASEVQALRVRLEILEELVKGLKEQ
CTGGCCPASAQAGTGQTDVRTLCSLHGVFDLSRCTCSCEPGWGGPTCSDPTDAEIPPSSP
PSASGSCPDDCNDQGRCVRGRCVCFPGYTGPSCGWPSCPGDCQGRGRCVQGVCVCRAGFS
GPDCSQRSCPRGCSQRGRCEGGRCVCDPGYTGDDCGMRSCPRGCSQRGRCENGRCVCNPG
YTGEDCGVRSCPRGCSQRGRCKDGRCVCDPGYTGEDCGTRSCPWDCGEGGRCVDGRCVCW
PGYTGEDCSTRTCPRDCRGRGRCEDGECICDTGYSGDDCGVRSCPGDCNQRGRCEDGRCV
CWPGYTGTDCGSRACPRDCRGRGRCENGVCVCNAGYSGEDCGVRSCPGDCRGRGRCESGR
CMCWPGYTGRDCGTRACPGDCRGRGRCVDGRCVCNPGFTGEDCGSRRCPGDCRGHGLCED
GVCVCDAGYSGEDCSTRSCPGGCRGRGQCLDGRCVCEDGYSGEDCGVRQCPNDCSQHGVC
QDGVCICWEGYVSEDCSIRTCPSNCHGRGRCEEGRCLCDPGYTGPTCATRMCPADCRGRG

Figure 18, Cont.

```
RCVQGVCLCHVGYGGEDCGQEEPPASACPGGCGPRELCRAGQCVCVEGFRGPDCAIQTCP
GDCRGRGECHDGSCVCKDGYAGEDCGEEVPTIEGMRMHLLEETTVRTEWTPAPGPVDAYE
IQFIPTTEGASPPFTARVPSSASAYDQRGLAPGQEYQVTVRALRGTSWGLPASKTITTMI
DGPQDLRVVAVTPTTLELGWLRPQAEVDRFVVSYVSAGNQRVRLEVPPEADGTLLTDLMP
GVEYVVTVTAERGRAVSYPASVRANTGSSPLGLLGTTDEPPPSGPSTTQGAQAPLLQQRP
QELGELRVLGRDETGRLRVVWTAQPDTFAYFQLRMRVPEGPGAHEEVLPGDVRQALVPPP
PPGTPYELSLHGVPPGGKPSDPIIYQGIMDKDEEKPGKSSGPPRLGELTVTDRTSDSLLL
RWTVPEGEFDSFVIQYKDRDGQPQVVPVEGPQRSAVITSLDPGRKYKFVLYGFVGKKRHG
PLVAEAKILPQSDPSPGTPPHLGNLWVTDPTPDSLHLSWTVPEGQFDTFMVQYRDRDGRP
QVVPVEGPERSFVVSSLDPDHKYRFTLFGIANKKRYGPLTADGTTAPERKEEPPRPEFLE
QPLLGELTVTGVTPDSLRLSWTVAQGPFDSFMVQYKDAQGQPQAVPVAGDENEVTVPGLD
PDRKYKMNLY█LRGRQRVGPESVVAKTAPQEDVDETPSPTELGTEAPESPEEPLLGELTV
TGSSPDSLSLFWTVPQGSFDSFTVQYKDRDGRPRAVRVGGKESEVTVGGLEPGHKYKMHL
YGLHEGQRVGPVSAVGVTAPQQEETPPATESPLEPRLGELTVIDVTPNSVGLSWTVPEGQ
FDSFIVQYKDKDGQPQVVPVAADQREVTVYNLEPERKYKMNMYGLHDGQRMGPLSVVIVT
APLPPAPATEASKPPLEPRLGELTVTDITPDSVGLSWTVPEGEFDSFVVQYKDRDGQPQV
VPVAADQREVTIPDLEPSRKYKFLLFGIQDGKRRSPVSVEAKTVARGDASPGAPPRLGEL
WVTDPTPDSLRLSWTVPEGQFDSFVVQFKDKDGPQVVPVEGHERSVTVTPLDAGRKYRFL
LYGLLGKKRHGPLTADGTTEARSAMDDTGTKRPPKPRLGEELQVTTVTQNSVGLSWTVPE
GQFDSFVVQYKDRDGQPQVVPVEGSLREVSVPGLDPAHRYKLLLYGLHHGKRVGPISAVA
ITAGREETETETTAPTPPAPEPHLGELTVEEATSHTLHLSWMVTEGEFDSFEIQYTDRDG
QLQMVRIGGDRNDITLSGLESDHRYLVTLYGFSDGKHVGPVHVEALTVPEEEKPSEPPTA
TPEPPIKPRLGELTVTDATPDSLSLSWTVPEGQFDHFLVQYRNGDGQPKAVRVPGHEEGV
TISGLEPDHKYKMNLYGFHGGQRMGPVSVVGVTAAEEETPSPTEPSMEAPEPAEEPLLGE
LTVTGSSPDSLSLSWTVPQGRFDSFTVQYKDRDGRPQVVRVGGEESEVTVGGLEPGRKYK
```

Figure 18, Cont.

MHLYGLHEGRRVGPVSAVGVTAPEEESPDAPLAKLRLGQMTVRDITSDSLSLSWTVPEGQ
FDHFLVQFKNGDGQPKAVRVPGHEDGVTISGLEPDHKYKMNLYGFHGGQRVGPVSAVGLT
APGKDEEMAPASTEPPTPEPPIKPRLEELTVTDATPDSLSLSWTVPEGQFDHFLVQYKNG
DGQPKATRVPGHEDRVTISGLEPDNKYKMNLYGFHGGQRVGPVSAIGVTAAEEETPSPTE
PSMEAPEPPEEPLLGELTVTGSSPDSLSLSWTVPQGRFDSFTVQYKDRDGRPQVVRVGGE
ESEVTVGGLEPGRKYKMHLYGLHEGRRVGPVSTVGVTAPQEDVDETPSPTEPGTEAPGPP
EEPLLGELTVTGSSPDSLSLSWTVPQGRFDSFTVQYKDRDGRPQAVRVGGQESKVTVRGL
EPGRKYKMHLYGLHEGRRLGPVSAVGVTEDEAETTQAVPTMTPEPPIKPRLGELTMTDAT
PDSLSLSWTVPEGQFDHFLVQYRNGDGQPKAVRVPGHEDGVTISGLEPDHKYKMNLYGFH
GGQRVGPISVIGVTAAEEETPSPTELSTEAPEPPEEPLLGELTVTGSSPDSLSLSWTIPQ
GHFDSFTVQYKDRDGRPQVMRVRGEESEVTVGGLEPGRKYKMHLYGLHEGRRVGPVSTVG
VTAPEDEAETTQAVPTTTPEPPNKPRLGELTVTDATPDSLSLSWMVPEGQFDHFLVQYRN
GDGQPKVVRVPGHEDGVTISGLEPDHKYKMNLYGFHGGQRVGPISVIGVTAAEEETPAPT
EPSTEAPEPPEEPLLGELTVTGSSPDSLSLSWTIPQGRFDSFTVQYKDRDGRPQVVRVRG
EESEVTVGGLEPGCKYKMHLYGLHEGQRVGPVSAVGVTAPKDEAETTQAVPTMTPEPPIK
PRLGELTVTDATPDSLSLSWMVPEGQFDHFLVQYRNGDGQPKAVRVPGHEDGVTISGLEP
DHKYKMNLYGFHGGQRVGPVSAIGVTEEETPSPTEPSTEAPEAPEEPLLGELTVTGSSPD
SLSLSWTVPQGRFDSFTVQYKDRDGQPQVVRVRGEESEVTVGGLEPGRKYKMHLYGLHEG
QRVGPVSTVGITAPLP PLPVEPRLGELAVAAVTSDSVGLSWTVAQGPFDSFLVQYRDAQ
GQPQAVPVSGDLRAVAVSGLDPARKYKFLLFGLQNGKRHGPVPVEARTAPDTKPSPRLGE
LTVTDATPDSVGLSWTVPEGEFDSFVVQYKDKDGRLQVVPVAANQREVTVQGLEPSRKYR
FLLYGLSGRKRLGPISADSTTAPLEKELPPHLGELTVAEETSSSLRLSWTVAQGPFDSFV
VQYRDTDGQPRAVPVAADQRTVTVEDLEPGKKYKFLLYGLLGGKRLGPVSALGMTAPEED
TPAPELAPEAPEPPEEPRLGVLTVTDTTPDSMRLSWSVAQGPFDSFVVQYEDTNGQPQAL
LVDGDQSKILISGLEPSTPYRFLLYGLHEGKRLGPLSAEGTTGLAPAGQTSEESRPRLSQ

Figure 18, Cont.

LSVTDVTTSSLRLNWEAPPGAFDSFLLRFGVPSPSTLEPHPRPLLQRELMVPGTRHSAVL

RDLRSGTLYSLTLYGLRGPHKADSIQGTARTLSPVLESPRDLQFSEIRETSAKVNWMPPP

SRADSFKVSYQLADGGEPQSVQVDGQARTQKLQGLIPGARYEVTVVSVRGFEESEPLTGF

LTTVPDGPTQLRALNLTEGFAVLHWKPPQNPVDTYDVQVTAPGAPPLQAETPGSAVDYPL

HDLVLHTNYTATVRGLRGPNLTSPASITFTTGLEAPRDLEAKEVTPRTALLTWTEPPVRP

AGYLLSFHTPGGQNQEILLPGGITSHQLLGLFPSTSYNARLQAMWGQSLLPPVSTSFTTG

GLRIPFPRDCGEEMQNGAGASRTSTIFLNGNRERPLNVFCDMETDGGGWLVFQRRMDGQT

DFWRDWEDYAHGFGNISGEFWLGNEALHSLTQAGDYSMRVDLRAGDEAVFAQYDSFHVDS

AAEYYRLHLEGYHGTAGDSMSYHSGSVFSARDRDPNSLLISCAVSYRGAWWYRNCHYANL

NGLYGSTVDHQGVSWYHWKGFEFSVPFTEMKLRPRNFRSPAGGG

SEQ ID NO: 210  Anillin wild-type cDNA sequence   Homo sapiens

```
   1 ggcttggcgc tgaaattcaa atttgaacgg ctgcagagcc cgagtccgtc actggaagcc
  61 gagaggagag gacagctggt tgtgggagag ttccccgcc tcagactcct ggtttttcc
 121 aggagacaca ctgagctgag actcactttt ctcttcctga atttgaacca ccgttccat
 181 cgtctcgtag tccgacgcct ggggcgatgg atccgtttac ggagaaactg ctggagcgaa
 241 cccgtgccag gcgagagaat cttcagagaa aaatggctga gaggcccaca gcagctccaa
 301 ggtctatgac tcatgctaag cgagctagac agccactttc agaagcaagt aaccagcagc
 361 ccctctctgg tggtgaagag aaatcttgta caaaccatc gccatcaaaa aaacgctgtt
 421 ctgacaacac tgaagtagaa gtttctaact tggaaaataa acaaccagtt gagtcgacat
 481 ctgcaaaatc ttgttctcca agtcctgtgt ctcctcaggt gcagccacaa gcagcagata
 541 ccatcagtga ttctgttgct gtccggcat cactgctggg catgaggaga gggctgaact
 601 caagattgga agcaactgca gcctcctcag ttaaaacacg tatgcaaaaa cttgcagagc
 661 aacggcgccg ttgggataat gatgatatga cagatgacat tcctgaaagc tcactcttct
 721 caccaatgcc atcagaggaa aaggctgctt ccctccag acctctgctt tcaaatgcct
 781 cggcaactcc agttggcaga aggggccgtc tggccaatct tgctgcaact atttgctcct
 841 gggaagatga tgtaaatcac tcatttgcaa aacaaaacag tgtacaagaa cagctggta
 901 ccgcttgttt atccaaattt tcctctgcaa gtggagcatc tgctaggatc aatagcagca
 961 gtgttaagca ggaagctaca ttctgttccc aaagggatgg cgatgcctct ttgaataaag
1021 ccctatcctc aagtgctgat gatgcgtctt tggttaatgc ctcaatttcc agctctgtga
1081 aagctacttc tccagtgaaa tctactacat ctatcactga tgctaaaagt tgtgagggac
1141 aaaatcctga gctacttcca aaaactccta ttagtcctct gaaaacgggg gtatcgaaac
1201 caattgtgaa gtcaacttta tcccagacag ttccatccaa gggagaatta agtagagaaa
1261 tttgtctgca atctcaatct aaagacaaat ctacgacacc aggaggaaca ggaattaagc
1321 ctttcctgga acgctttgga gagcgttgtc aagaacatag caaagaaagt ccagctcgta
1381 gcacacccca cagaacccc attattactc caaataaaa ggccatccaa gaaaaattat
1441 tcaagcaaga cacatcttca tctactaccc atttagcaca acagctcaag caggaacgtc
1501 aaaaagaact agcatgtctt cgtggccgat ttgacaaggg caatatatgg agtgcagaaa
1561 aaggcggaaa ctcaaaaagc aaacaactag aaaccaaaca ggaaactcac tgtcagagca
1621 ctccctcaa aaacaccaa ggtgtttcaa aaactcagtc acttccagta acagaaaagg
1681 tgaccgaaaa ccagatacca gccaaaatt ctagtacaga acctaaagaa gtgatacgtg
1741 aaattgagat gagtgtggat gatgatgata tcaatagttc gaaagtaatt aatgacctct
```

Figure 18, Cont.

```
1801 tcagtgatgt cctagaggaa ggtgaactag atatggagaa gagccaagag gagatggatc
1861 aagcattagc agaaagcagc gaagaacagg aagatgcact gaatatctcc tcaatgtctt
1921 tacttgcacc attggcacaa acagttggtg tggtaagtcc agagagttta gtgtccacac
1981 ctagactgga attgaaagac accagcagaa gtgatgaaag tccaaaacca ggaaaattcc
2041 aaagaactcg tgtccctcga gctgaatctg gtgatagcct tggttctgaa gatcgtgatc
2101 ttctttacag cattgatgca tatagatctc aaagattcaa agaaacagaa cgtccatcaa
2161 taaagcaggt gattgttcgg aaggaagatg ttacttcaaa actggatgaa aaaaataatg
2221 ccttttccttg tcaagttaat atcaaacaga aaatgcagga actcaataac gaaataaata
2281 tgcaacagac agtgatctat caagctagcc aggctcttaa ctgctgtgtt gatgaagaac
2341 atggaaaagg gtccctagaa gaagctgaag cagaaagact tcttctaatt gcaactggga
2401 agagaacact tttgattgat gaattgaata aattgaagaa cgaaggacct cagaggaaga
2461 ataaggctag tcccaaagt gaatttatgc catccaaagg atcagttact ttgtcagaaa
2521 tccgcttgcc tctaaaagca gatttttgtct gcagtacggt tcagaaacca gatgcagcaa
2581 attactatta cttaattata ctaaaagcag gagctgaaaa tatggtagcc acaccattag
2641 caagtacttc aaactctctt aacggtgatg ctctgacatt cactactaca tttactctgc
2701 aagatgtatc caatgacttt gaaataaata ttgaagttta cagcttggtg caaaagaaag
2761 atccctcagg ccttgataag aagaaaaaaa catccaagtc caaggctatt actccaaagc
2821 gactcctcac atctataacc acaaaaagca acattcattc ttcagtcatg gccagtccag
2881 gaggtcttag tgctgtgcga accagcaact tcgcccttgt tggatcttac acattatcat
2941 tgtcttcagt aggaaaatact aagtttgttc tggacaaggt ccccttttta tcttctttgg
3001 aaggtcatat ttatttaaaa ataaaatgtc aagtgaattc cagtgttgaa gaaagaggtt
3061 ttctaaccat atttgaagat gttagtggtt ttggtgcctg gcatcgaaga tggtgtgttc
3121 tttctggaaa ctgtatatct tattggactt atccagatga tgagaaacgc aagaatccca
3181 taggaaggat aaatctggct aattgtacca gtcgtcagat agaaccagcc aacagagaat
3241 tttgtgcaag acgcaacact tttgaattaa ttactgtccg accacaaaga gaagatgacc
3301 gagagactct tgtcagccaa tgcaggggaca cactctgtgt taccaagaac tggctgtctg
3361 cagatactaa agaagagcgg gatctctgga tgcaaaaact caatcaagtt cttgttgata
3421 ttcgcctctg gcaacctgat gcttgctaca aacctattgg aaagcttaa acgggaaat
3481 ttccatgcta tctagaggtt tttgatgtca tcttaagaaa cacacttaag agcatcagat
3541 ttactgattg catttatgc tttaagtacg aaagggtttg tgccaatatt cactacgtat
3601 tatgcagtat ttatatcttt tgtatgtaaa acttttaactg atttctgtca ttcatcaatg
3661 agtagaagta aatacattat agttgatttt gctaaatctt aatttaaaag cctcattttc
3721 ctagaaatct aattattcag ttattcatga caatatttttt ttaaaagtaa gaaattctga
3781 gttgtcttct tggagctgta ggtcttgaag cagcaacgtc tttcagggggt tggagacaga
3841 aacccattct ccaatctcag tagttttttc gaaaggctgt gatcatttat tgatcgtgat
3901 atgacttgtt actagggtac tgaaaaaaat gtctaaggcc tttacagaaa catttttagt
3961 aatgaggatg agaacttttt caaatagcaa atatatattg gcttaaagca tgaggctgtc
4021 ttcagaaaag tgatgtggac ataggaggca atgtgtgaga ctggggggtt caatatttta
4081 tatagaagag ttaataagca catggtttac atttactcag ctactatata tgcagtgtgg
4141 tgcacatttt cacagaattc tggttttcatt aagtacatta tttttgctgc gtagcttaca
4201 gacttagcat attagttttt tctactccta caagtgtaaa ttgaaaaatc tttatattaa
4261 aaaagtaaac tgttatgaag ctgctatgta ctaataatac tttgcttgcc aaagtgtttg
4321 ggttttgttg ttgtttgttt gtttgttttgt ttttggttca tgaacaacag tgtctagaaa
4381 cccattttga aagtggaaaa ttattaagtc acctatcacc tttaaacgcc ttttttaaa
4441 attataaaat attgtaaagc agggtctcaa cttttaaata cactttgaac ttcttctctg
4501 aattattaaa gttctttatg acctcattta taaacactaa attctgtcac ctcctgtcat
4561 tttattttttt attcattcaa atgtattttt tcttgtgcat attataaaaa tatattttat
4621 gagctcttac tcaaataaat acctgtaaat gtctaaagga aaaaaaaaaa aaaaa
```

SEQ ID NO: 211 Wilms Tumor 1 (WT1) wild-type cDNA Homo sapiens

```
agctggggta aggagttcaa ggcagcgccc acaccgggg gtctctcgca accgaccgc
  61 ctgtccgctc cccacttcc cgccctccct cccacctact cattcaccca cccacccacc
 121 cagagccggg acggcagccc aggcgcccgg gccgcgcgt ctcctcgccc cgatcctgga
 181 cttcctcttg ctgcaggacc cggcttccac gtgtgtcccg gagccggcgt ctcagcacac
```

Figure 18, Cont.

```
 241 gctccgctcc gggcctgggt gcctacagca gccagagcag cagggagtcc gggacccggg
 301 cggcatctgg gccaagttag gcgccgccga ggccagcgct gaacgtctcc agggccggag
 361 gagccgcggg gcgtccgggt ctgagccgca gcaaatgggc tccgacgtgc gggacctgaa
 421 cgcgctgctg cccgccgtcc cctccctggg tggcggcggc ggctgtgccc tgcctgtgag
 481 cggcgcggcg cagtgggcgc cggtgctgga ctttgcgccc ccgggcgctt cggcttacgg
 541 gtcgttgggc ggccccgcgc cgccaccggc tccgccgcca ccccgccgc cgccgcctca
 601 ctccttcatc aaacaggagc cgagctgggg cggcgcggag ccgcacgagg agcagtgcct
 661 gagcgccttc actgtccact tttccggcca gttcactggc acagccggag cctgtcgcta
 721 cgggcccttc ggtcctcctc cgcccagcca ggcgtcatcc ggccaggcca ggatgtttcc
 781 taacgcgccc tacctgccca gctgcctcga gagccagccc gctattcgca atcagggtta
 841 cagcacggtc acctcgacg ggacgcccag ctacggtcac acgccctcgc accatgcggc
 901 gcagttcccc aaccactcat tcaagcatga ggatcccatg ggccagcagg gctcgctggg
 961 tgagcagcag tactcggtgc cgccccggt ctatggctgc cacacccca ccgacagctg
1021 caccggcagc caggctttgc tgctgaggac gccctacagc agtgacaatt tataccaaat
1081 gacatcccag cttgaatgca tgacctggaa tcagatgaac ttaggagcca ccttaaaggg
1141 agttgctgct gggagctcca gctcagtgaa atggacagaa gggcagagca accacagcac
1201 agggtacgag agcgataacc acacaacgcc catcctctgc ggagcccaat acagaataca
1261 cacgcacggt gtcttcagag gcattcagga tgtgcgacgt gtgcctggag tagccccgac
1321 tcttgtacgg tcggcatctg agaccagtga gaaacgcccc ttcatgtgtg cttacccagg
1381 ctgcaataag agatatttta agctgtccca cttacagatg cacagcagga agcacactgg
1441 tgagaaacca taccagtgtg acttcaagga ctgtgaacga aggttttctc gttcagacca
1501 gctcaaaaga caccaaagga gacatacagg tgtgaaacca ttccagtgta aaacttgtca
1561 gcgaaagttc tcccggtccg accacctgaa gacccacacc aggactcata caggtaaaac
1621 aagtgaaaag cccttcagct gtcggtggcc aagttgtcag aaaaagtttg cccggtcaga
1681 tgaattagtc cgccatcaca acatgcatca gagaaacatg accaaactcc agctggcgct
1741 ttgaggggtc tccctcgggg accgttcagt gtcccaggca gcacagtgtg tgaactgctt
1801 tcaagtctga ctctccactc ctcctcacta aaaaggaaac ttcagttgat cttcttcatc
1861 caacttccaa gacaagatac cggtgcttct ggaaactacc aggtgtgcct ggaagagttg
1921 gtctctgccc tgcctacttt tagttgactc acaggccctg gagaagcagc taacaatgtc
1981 tggttagtta aaagcccatt gccatttggt gtggattttc tactgtaaga agagccatag
2041 ctgatcatgt cccctgacc cttcccttct ttttttatgc tcgttttcgc tggggatgga
2101 attattgtac cattttctat catggaatat ttataggcca gggcatgtgt atgtgtctgc
2161 taatgtaaac tttgtcatgg tttccattta ctaacagcaa cagcaagaaa taaatcagag
2221 agcaaggcat cggggggtgaa tcttgtctaa cattcccgag gtcagccagg ctgctaacct
2281 ggaaagcagg atgtagttct gccaggcaac ttttaaagct catgcatttc aagcagctga
2341 agaaaaaatc agaactaacc agtacctctg tatagaaatc taaaagaatt ttaccattca
2401 gttaattcaa tgtgaacact ggcacactgc tcttaagaaa ctatgaagat ctgagatttt
2461 tttgtgtatg tttttgactc ttttgagtgg taatcatatg tgtctttata gatgtacata
2521 cctccttgca caaatggagg ggaattcatt ttcatcactg gggagtgtcct tagtgtataa
2581 aaaccatgct ggtatatggc ttcaagttgt aaaaatgaaa gtgactttaa aagaaaatag
2641 gggatggtcc aggatctcca ctgataagac tgttttttaag taacttaagg acctttgggt
2701 ctacaagtat atgtgaaaaa aatgagactt actgggtgag gaaatccatt gtttaaagat
2761 ggtcgtgtgt gtgtgtgtgt gtgtgtgtgt gtgtgtgttg tgttgtgttt tgttttttaa
2821 gggagggaat ttattattta ccgttgcttg aaattactgt gtaaatatat gtctgataat
2881 gatttgctct ttgacaacta aaattaggac tgtataagta ctagatgcat cactgggtgt
2941 tgatcttaca agatattgat gataacactt aaaattgtaa cctgcatttt tcactttgct
3001 ctcaattaaa gtctattcaa aaggaaaaaa aaaaaa
```

SEQ ID NO: 211 Tenascin X (TNXB) wild-type cDNA Homo sapiens

```
tcctccccttt ctcctcccct gctcgctgca gactccctcc tcactgtcgc tgccgagatc
  61 cacagtcggt tgtggctcag cccctgttgc aggggacaag tgagggagac ttccctgtcc
 121 tgccctgaga cgccgccctc ccggggttgg ggacagagca ggtgcagagg cactgcagct
 181 gctcggttgc ccagcctcct gaatgatgcc agcccagtat gctctaacct ccagcctggt
 241 tctcctggtg ctgctgagca cagccagagc aggcccccttc tcttcacggt ccaatgtgac
```

Figure 18, Cont.

```
 301 actgccagcc ccccggcccc ctccccagcc aggggccac acagtgggg ctggagtggg
 361 aagcccctct tctcagcttt acgagcacac agtggaagga ggggagaagc aggtggtatt
 421 cacccaccgc attaacctgc cccttccac tggctgtggc tgtccccag gcaccgagcc
 481 cccagtcctt gcttcagagg tacaggccct gagggtccgt ctagagatcc tggaggagtt
 541 ggtgaagggg ctcaaggaac agtgcactgg gggatgttgt cctgcctctg cccaagctgg
 601 cacaggtcag acagatgtgc ggaccctctg cagtctccat ggtgtgtttg atctgagccg
 661 ctgcacctgt tcctgtgagc caggctgggg tgggcccacc tgctcagacc ccacagatgc
 721 tgagatccct ccctcttccc caccctcagc ctcggggtcc tgcccagatg actgcaatga
 781 tcagggtcgc tgtgtccgtg gtcgttgcgt gtgctttccc ggctacactg gcccagctg
 841 tggctggcca tcctgtcccg gggactgcca aggccgtggg cgctgcgtgc agggcgtgtg
 901 tgtgtgccgg gcaggcttct caggccccga ctgcagccag cgctcctgcc ctcgaggttg
 961 cagcagagg ggacgctgtg agggtgggcg ctgcgtgtgt gacccaggct acactggtga
1021 cgactgtggc atgaggagct gccctcgcg ttgcagtcag aggggggcgct gtgagaatgg
1081 gcgctgcgtg tgtaaccccg gctacactgg cgaggactgt gggggtgagga gctgccctcg
1141 gggctgcagc cagcgggac gctgcaagga cgggcgctgc gtgtgtgacc ccggctacac
1201 tggcgaggac tgtggtacgc ggagctgccc ctggagctgt ggcgaggggcg gggcgctgcgt
1261 ggacggccgc tgcgtgtgct ggcccgggta cacaggcgag gactgcagca cgcggacatg
1321 tccgagggac tgccggggcc gcgggcgctg cgaggacggc gaatgcattt gcgacacggg
1381 ctacagcggg gacgactgcg gcgtgcgcag ctgccctggc gactgcaacc aaagggggccg
1441 ctgcgaggac ggccgctgcg tgtgctgcc ggggtacact ggaaccgatt gcggctcgcg
1501 cgcctgccca cgcgactgta gaggtcgcgg gcgctgcgag aacggcgtgt gtgtttgcaa
1561 tgcgggctac agcggcgagg actgcggtgt gcgcagctgt cctggggact gtcgtggccg
1621 gggccgctgt gagagtggcc gctgcatgtg ttggccgggg tacacaggcc gggactgcgg
1681 cacgcgcgcc tgtcctggcg actgtcgcgg gcgcgggcgc tgcgtggatg gccgctgcgt
1741 gtgcaacccg ggcttcaccg gtgaggactg tgggagccgt cgctgtcccg gggactgccg
1801 tgggcacggc ctttgcgagg atggcgtgtg cgtgtgtgac gcaggctact caggggaaga
1861 ctgcagcacg cgcagctgcc ccggggggctg ccgaggccgc ggccagtgcc tagatgggcg
1921 gtgtgtgtgc gaggacggct actctggcga ggattgcggt gtgaggcagt gcccgaatga
1981 ctgcagccag cacggcgtgt gccaggacgg tgtgtgcatc tgttgggaag gctacgtgag
2041 tgaggactgc agcatccgca cctgccccctc caactgccac gggaggggcc gctgtgagga
2101 agggcgctgc ctgtgcgacc caggctacac cggccctacc tgtgccaccc gcatgtgccc
2161 ggctgactgc cggggacgtg ggcggtgtgt gcaaggagtg tgcctgtgcc acgtgggcta
2221 tggcggtgag gactgcgggc aggaagagcc tccagccagc gcctgccctg gaggctgcgg
2281 gccccgggaa ctgtgtgtgcc caggccagtg tgtgtgtgta gagggcttcc gaggccctga
2341 ctgtgccatc cagacatgcc cagggggactg ccgtggccga ggagagtgtc acgatggcag
2401 ctgtgtctgc aaagatgggt atgctggcga agactgcgga gaagaggtgc caaccattga
2461 gggcatgagg atgcatctct tggaggagac aacagttcgg acagagtgga ccccggctcc
2521 tggccccgtg gatgcctatg aaattcagtt catccccacg acagagggg cgagcccccc
2581 attcacagca cgggttccaa gctctgcctc agcctatgac cagagaggac tggcccctgg
2641 acaggagtac caggtcactg tccgagccct tcgagggcac agctgggcc ttcctgcctc
2701 caagaccatc accaccatga tcgatgggcc ccaggacctc cgagtggtgg ctgtgacacc
2761 gacaacactg gagcttggct ggctgcgtcc ccaggctgag gtggaccgat ttgtggtgtc
2821 ctacgtcagt gccggcaacc agaggtgag gctggaagtg ccccctgaag cagacgggac
2881 gctgctgact gacctgatgc caggcgtaga atatgtggtg actgtcacag cggagcgggg
2941 ccgggcagtc agctacccag cttctgtcag ggccaacaca gggtcctcac ccttgggcct
3001 cttgggggact accgatgagc ctcctccctc aggcccctcg acgacgcaag gggcccaggc
3061 tcctctcctg cagcagcgcc cccaggagct gggagagttg agggtgctgg gcagagatga
3121 gacagggcgc ctccgtgtgg tctggaccgc ccagcctgac acctttgcct acttccaact
3181 gcgcatgcgg gtgcccgagg ggccggggc acatgaggaa gtgctgccag gggacgtccg
3241 ccaggctctg gtgcctccac cccctcctgg aaccccgtat gagctgtcac ttcatgggt
3301 ccctcctggg ggcaagccct ctgaccccat catctaccaa ggcattatgg acaaggatga
3361 ggagaagcct gggaagtcct caggccacc acgcctgggt gagctgacgg tgacagacag
3421 gacctccgac tccttgctcc tgcgctggac ggtccccgag ggcgagtttg actccttcgt
3481 gatccagtac aaagacaggg acgggcagcc ccaggtggtg cccgtggaag acccccagcg
3541 ctcggccgtc atcacctccc tggatcctgg ccgcaagtac aaatttgtcc tgtatgggtt
3601 tgttggcaag aagaggcatg gtccgctggt ggctgaagcc aagatcttgc ctcagagtga
3661 cccaagtcca gggactccac cccacctggg aaacctgtgg gtgacagacc ctacccccaga
```

Figure 18, Cont.

```
3721 ttcactgcac ctctcctgga ctgtccctga gggccagttt gacaccttca tggtccagta
3781 cagggacagg gatggacggc cccaggtggt acctgtggaa gggcccgagc gttcattttgt
3841 tgtctcctca ctggaccctg accacaagta cagattcact ctgtttggaa ttgcgaacaa
3901 gaagcggtat ggcccctca cggccgatgg caccactgct ccagagagga aagaggagcc
3961 ccccgccct gagttcctgg agcagcccct cctggggaa ctgacagtga ccggcgtgac
4021 cccagactcc ttgcgtctct catggacagt ggcccagggc cccttcgact cattcatggt
4081 ccagtacaag gatgcacagg ggcagcccca ggcagtgcct gttgcggggg atgagaatga
4141 ggttactgtc cccggcctgg atcccgaccg gaagtataag atgaacctct acgggcttcg
4201 tggcaggcag cgtgtggggc ccgagtctgt ggtggccaag actgctcctc aggaggatgt
4261 ggacgagacc cccagcccca cagaactggg cacggaggcc ccggagtccc ccgaggagcc
4321 gctcctgggg gagctgacag tgacaggatc ctcccctgat tcgctgagcc tcttctggac
4381 cgtcccccag ggcagcttcg actctttcac cgtgcagtac aaggacaggg atgggcggcc
4441 ccgggcggtg cgtgttgggg gcaaggagag tgaggtcacc gtgggaggcc tagagcccgg
4501 gcacaagtac aagatgcacc tgtacgcct ccacgagggg cagcgcgtgg gcccggtgtc
4561 cgccgtgggc gtgacagccc cacaacaaga agagacccct ccagccactg agtcccgct
4621 ggagccacgc ctaggagagc tgacagtgac agatgtgacc cccaactctg tgggcctctc
4681 ctggacagtc cccgagggcc agtttgactc cttcatagtc cagtacaagg acaaggacgg
4741 gcagcccag gtggtgccgg tggcggcaga ccagcgagag gtcacagtct acaacctgga
4801 gcctgagaga aaatataaga tgaacatgta tggactacat gatgggcaac gcatgggccc
4861 cctgtctgtg gtcatcgtga cggctcccct cccaccagcc ccagccacag aggcctccaa
4921 gcctcccctg gagccacgcc taggggagct gacagtgacg gatataaccc ctgactctgt
4981 gggcctctca tggacagtcc ctgagggtga attcgactcc tttgtggttc agtacaagga
5041 cagggacggg cagcccagg tggtgccgt ggctgcagat cagcgggagg tcactatccc
5101 tgacctggaa ccctcccgca agtacaagtt cctgctcttt gggatccagg atgggaaacg
5161 acgcagccca gtctctgtgg aggcaaagac ggttgcccga ggtgacgcca gccagggc
5221 cccacccgc cttggggagc tgtgggtgac agaccccacc ccagactcac tgcgcctctc
5281 ctggacggtt cctgagggcc agttcgactc ttttgtggtc cagttcaagg acaaagacgg
5341 gcccaggtg gtgcccgtgg agggccatga gcgctctgtc actgtcaccc ctctggatgc
5401 cggccgcaag tacagattcc tcctctatgg cctcctgggc aagaagcgcc atggccctct
5461 cactgccgac ggcaccacgg aagcccggag tgctatggat gatactggaa caaagcgtcc
5521 cccaaaaccc cgtctggggg aggagctgca ggtgaccacc gtgacccaga actccgtggg
5581 cctctcctgg acagtccctg agggccagtt tgactccttt gtggtccagt acaaagacag
5641 ggacgggcag cccaggtgg tgccgtgaa gggcagcctc agggaggtca gcgtgccggg
5701 cctggaccct gcccacaggt acaagctgct gctctacggg ctgcaccacg gcaagcgtgt
5761 gggccccatc tcggccgtcg ccattactgc cggcagggaa gaaacggaaa ctgagaccac
5821 ggccccgacc cctccagcgc ctgagcccca cctcggggag ttgacagtgg aggaggccac
5881 gtcacacacc ctgcatctct cctggatggt gactgaggga gaatttgact ccttcgaaat
5941 ccagtacaca gatagagacg ggcaactcca aatggtccgc ataggaggtg accggaatga
6001 catcaccctc tctggcctgg aatccgacca cagatacctg gtgaccctgt atggtttcag
6061 tgatgggaag catgtaggtc ctgtccatgt cgaggccctg acagtccggg aggaggagaa
6121 gccttcagaa cctcccaccg caaccccga gccccatc aagcctcgcc tgggggagct
6181 gaccgtgaca gatgccaccc ctgactcct cagcctgtcc tggacagttc ccagggaca
6241 gttgaccac ttcctggtcc agtacaggaa tggagatggg cagccaaggg cagtgaggt
6301 gccagggcac gaggaagggg tcaccatctc gggcctggag ccagaccata aatacaagat
6361 gaacctgtac ggcttccacg gtggccagcg catgggccct gtgtctgtcg tcggggtgac
6421 agctgcagag gaagagaccc ccagccccac agaacccagc atggaggccc cggagcccgc
6481 tgaggagccg ctcctggggg agctaacagt gacaggatcc tcccctgact cgctgagcct
6541 ctcctggacc gtcccccagg gccgcttcga ctccttcacc gtgcagtaca aggacaggga
6601 cgggcggccc caggtggtgc gtgttggggg cgaggagagt gaagtcaccg tgggggcct
6661 ggagcctggg cgcaagtaca agatgcacct gtacggcctc acgagggc ggcgcgtggg
6721 cccagtgtct gctgtgggcg tcacggcccc cgaagaggag tcccctgatg ctcctcttgc
6781 aaagctgcgc ctagggcaga tgacagtgag agacatcacc tccgactccc tcagcctctc
6841 ctggacagtc cccgagggcc agtttaaga tgacagggac agtttaagaa atgggacgg
6901 gcagcccaag gcggtgcggg tgccgggaca cgaggatggg gtcaccatct cgggcctgga
6961 gccagaccac aagtacaaga tgaacctgta cggcttccac ggtggccagc gcgtgggccc
7021 cgtgtctgct gttggtttaa ctgccccagg aaaggatgaa gaaatgggcc cagcctcgac
7081 agaacctccc acccctgaac cccccatcaa gcctcgcctg gaggagctga ccgtgacaga
```

Figure 18, Cont.

```
7141 tgcgaccct gactcctca gcctgtcctg gacggttccc gagggacagt ttgaccactt
7201 cctggtccag tacaagaatg gggatgggca gcccaaggca acacgggtgc caggacatga
7261 ggacagggtc accatctccg gcctggagcc agacaacaag tacaagatga acctgtacgg
7321 cttccacggt ggccagcgtg tgggcccgt gtctgccatc ggggtgacag ctgcagagga
7381 agagacccc agcccacag aacccagcat ggaggcccg gagccctg aggagccgct
7441 cctggggag ctaacagtga caggatcctc cctgactcg ctgagcctct cctggaccgt
7501 ccccagggc cgcttcgact ccttcaccgt gcagtacaag gacagggacg ggcggcccca
7561 ggtggtgcgt gttggggcg aggagagcga ggtcaccgtg gggggcctgg agcctggcg
7621 caaataaag atgcacctgt atggcctcca cgagggggcg cgcgtgggcc cggtgtccac
7681 cgtgggcgtg actgccccac aagaggatgt ggacgagacc cccagccta cagaaccagg
7741 cacagaggcc ccagggccc ccgaggagcc tctcctgggg gagctgacag tgacaggatc
7801 ctcccctgac tcgctgagcc tttcctggac cgtccccag ggccgctttg actccttcac
7861 cgtgcagtac aaggacaggg acgggcggcc ccaggcgtg cgtgttgggg gccaggagag
7921 caaggtcact gtgagggcc tggagcctgg gcgcaagtac aagatgcacc tgtacggcct
7981 ccacgagggg cggcgctgg gccggtgtc tgccgtgggc gtcacagagg atgaagccga
8041 gaccaccaa gcagtgccta ccatgaccc tgagcccccc atcaagcctc gcctggggga
8101 gctgaccatg acagatgcca ccctgactc cctcagcctg tcctggacgg ttcccgaggg
8161 ccagtttgac cacttcctgg tccagtacag gaatgggat gggcagccca aggcggtgcg
8221 ggtgccgggg cacgaggacg ggtcaccat ctcaggcctg gagccagacc ataaatacaa
8281 gatgaacctg tacggcttcc acgtggcca gcgcgtgggc cccatctctg tcattgggt
8341 gacggctgca gaggaagaga cccccagccc cacggaactc agcactgagg cccggagcc
8401 cctgaggag ccgctcctgg gggagctgac agtgacagga tcctccctg actcgctgag
8461 cctctcctgg accatccccc agggccactt cgactccttc accgtgcagt acaaggacag
8521 ggacgggcgg ccccaggtga tcgtgtcag gggcgaggag agcgaggtca ccgtgggggg
8581 cctggagccc gggcgcaaat acaagatgca cctgtacggc ctccacgagg ggcggcgtgt
8641 gggcccggtg tccacgtgg tgtgacaga ggatgaagca gagaccaccc aagcagtgcc
8701 caccaccaac cctgagcccc caacaagcc tcgcctcggg gagctgaccg tgacagatgc
8761 caccctgac tccctcagcc tgtcctggat ggtcccgag ggccagtttg accacttcct
8821 ggtccagtac aggaatgggg atgggcagcc caaggtgtg cgggtgccgg ggcacgagga
8881 cgggtcacc atctcaggcc tggagccaga ccacaagtac aagatgaacc tgtacggctt
8941 ccacgtggc cagcgcgtgg gccccatctc tgtcattggg gtgacagctg cagaggaaga
9001 aactccccgcc cccacagaac ccagcacgga ggcccggag ccctgagg agccgctcct
9061 gggggagctg acagtgacag gatcctcccc tgactcgctg agcctctcct ggaccatccc
9121 ccaggccgc ttcgactcct tcactgtgca gtacaaggac agggacgggc ggccccaggt
9181 ggtgcgtgtc aggggcgagg agagcgaggt caccgtgggg ggcctggagc ccgggtgcaa
9241 atacaagatg cacctgtacg gcctccacga ggggcagcgc gtgggcccag tgtccgctgt
9301 gggtgtgaca gctccaaagg atgaagccga gaccacccaa gcagtgccta ccatgacccc
9361 tgagccccc atcaagcctc gcctggggga gctgaccgtg acagatgcca ccccgactc
9421 cctcagcctg tcctggatgt tcccgaggg ccagtttgac cacttcctgg tccagtacag
9481 gaatgggat gggcagccca aggcggtgcg ggtgccgggg cacgaggacg ggtcaccat
9541 ctcaggcctg gagccagacc ataaatacaa gatgaacctg tacggcttcc acgtggcca
9601 gcgcgtaggc cctgtgtctg ccattgggt gacggaggaa gagaccccca gccccacaga
9661 acccagcact gaggcccgg aggccctga ggagccgctc ctgggggagt tgacagtgac
9721 aggatcctcc cctgactcgc tgagcctctc ctggaccgtc cccagggcc gcttcgactc
9781 cttcaccgtg cagtacaag acagggacg gcagcccag gtggtgcgtg tcagggcga
9841 ggagagcgag gtcaccgtg ggggcctgga gccgggcgc aaatacaaga tgcatctgta
9901 cggcctccac gaggggcagc gcgtgggcc agtgtccacc gtgggcatca cggcgccct
9961 gcccaccca ctgccggtgg agccacgctg ggggagctg gcggtgccgg cgtgacctc
10021 ggactcagtg ggcctctcat ggacggtggc ccaggcccc tttgactcct tcctggtaca
10081 gtacaggac gcagggcc agcccaggc agtgctgtg agcggagacc tccagcggt
10141 cgccgtctcg gggctggacc cggcccgcaa gtacaagttc ctgctctttg gactccagaa
10201 tgggaaacgc cacggccag tcctgtggga ggcaggacc gccagaca ccaaaccgtc
10261 tcccgcctc ggggagctga ctgtgacaga tgcgaccct gactccgtgg gcctctcgtg
10321 gacggtcct gagggcgaat tcgactcctt cgtggtccag tacaaggata aggatggtcg
10381 gctccaggtg gtgccggtga cagcaacca gcgggagacc acagtccagg gcctggagcc
10441 cagtaggaaa tacaggttcc tgctctatgg tctgtcaggc aggaaacgac tgggccccat
10501 ctctgctgac agcaccacag ctccctgga gaaggagcta cctcccacc tggggaact
```

Figure 18, Cont.

```
10561 gaccgtggct gaggagacct ccagctctct gcgcctgtcc tggacggtag cccagggccc
10621 ctttgactcc ttcgtggtcc agtacaggga cacggacggg cagcccaggg cagtgcctgt
10681 ggccgcagac cagcgcacag tcaccgtaga ggacctggag cctggcaaga aatacaagtt
10741 tctgctctac gggctccttg ggggaaagcg cctggccccg gtctctgccc tgggaatgac
10801 agcccagaa gaggacacac cagcccaga gttagcccca gaggccctg agcctcctga
10861 agagcccgc ctaggagtgc tgacgtgac cgacacaacc ccagactcca tgcgcctctc
10921 gtggagcgtg gcccagggcc cctttgattc cttcgtggtc cagtatgagg acacgaacgg
10981 gcagcccag gccttgctcg tggacggcga ccagagcaag atcctcatct caggcctgga
11041 gcccagcacc cctacaggt tcctcctcta tggcctccat gaagggaagc gcctggggcc
11101 cctctcagct gagggcacca cagggctggc tcctgctggt cagacctcag aggagtcaag
11161 gccccgcctg tccagctgt ctgtgactga cgtgaccacc agttcactga ggctcaactg
11221 ggaggcccca cggggggcct tcgactcctt cctgctccgc tttggggttc catcaccaag
11281 cactctggag ccgcatccgc gtccactgct gcagcgcgag ctgatggtgc cggggacgcg
11341 gcactcggcc gtgctccggg acctgcgttc cgggactctg tacagcctga cactgtatgg
11401 gctgcgagga cccacaagg ccgacagcat ccaggaacc gcccgcaccc tcagcccagt
11461 tctggagagc cccgtgacc tccaattcag tgaaatcagg gagacctcag ccaaggtcaa
11521 ctggatgccc ccaccatccc gggcggacag cttcaaagtc tcctaccagc tggcggacgg
11581 aggggagcct cagagtgtgc aggtggatgg ccaggcccgg acccagaaac tccagggggct
11641 gatcccaggc gctcgctatg aggtgaccgt ggtctcggtc cgaggctttg aggagagtga
11701 gcctctcaca ggcttcctca ccacggttcc tgacggtccc acacagttgc gtgcactgaa
11761 cttgaccgag ggattcgccg tgctgcactg gaagcccccc cagaatcctg tggacaccta
11821 tgacgtccag gtcacagccc ctgggccc gcctctgcag gcggagaccc caggcagcgc
11881 ggtggactac cccctgcatg accttgtcct ccacaccaac tacaccgcca cagtgcgtgg
11941 cctgcggggc ccaaccctca cttccccagc cagcatcacc ttcaccacag ggctagaggc
12001 ccctcgggac ttggaggcca aggaagtgac ccccgcacc gccctgctca cttggactga
12061 gccccagtc cggccgcag gctacctgct cagcttccac acccctggtg gacagaacca
12121 ggagatcctg ctcccaggag ggatcacatc tcaccagctc cttggcctct ttccctccac
12181 ctcctacaat gcacggctcc aggccatgtg gggccagagc ctcctgccgc ccgtgtccac
12241 ctcttteacc acgggtgggc tgcggatccc cttccccagg gactgcgggg aggagatgca
12301 gaacggagcc ggtgcctcca ggaccagcac catcttcctc aacggcaacc gcgagcggcc
12361 cctgaacgtg ttttgcgaca tggagactga tggggcggc tggctggtgt tccagcgccg
12421 catggatgga cagacagact tctgagggga ctgggaggac tatgcccatg gttttgggaa
12481 catctctgga gagttctggc tgggcaatga ggccctgcac agcctgacac aggcaggtga
12541 ctactccatg cgcgtggacc tgcgggctgg ggacgaggct gtgttcgccc agtacgactc
12601 cttccacgta gactcggctg cggagtacta ccgcctccac ttggagggct accacggcac
12661 cgcagggac tccatgagct accacagcgg cagtgtcttc tctgcccgtg atcgggaccc
12721 caacagcttg ctcatctcct gcgctgtctc ctaccgaggg gcctgtggt acaggaactg
12781 ccactacgcc aacctcaacg ggctctacgg gagcacagtg gaccatcagg gagtgagctg
12841 gtaccactgg aagggcttcg agttctcggt gccttcacg gaaatgaagc tgagaccaag
12901 aaactttcgc tccccagcgg ggggaggctg agctgctgcc cacctctctc gcacccagt
12961 atgactgccg agcactgagg ggtcgcccg agagaagagc caggtccttc caccaccag
13021 ccgctggagg aagccttctc tgccagcgat ctcgcagcac tgtgtttaca ggggggaggg
13081 gaggggttcg tacgggagca ataaaggaga aactgaggta cccggaaaaa aaaaaaaaaa
13141 aaa
```

GENES CAUSING HEREDITARY KIDNEY DISEASE OR MALFORMATION OF THE URINARY TRACT

CROSS-REFERENCE TO RELATED APPLICATIONS

This patent application claims the benefit of priority of U.S. Provisional Patent Application No. 61/708,986, filed Oct. 2, 2012, which is incorporated herein by reference in its entirety.

STATEMENT REGARDING FEDERALLY SPONSORED RESEARCH

This invention was made with United States government support awarded by the National Institutes of Health grant number 5K08-DK082495. The United States has certain rights in this invention.

SEQUENCE LISTING

This application was filed electronically via EFS-Web and includes an electronically submitted Sequence Listing in .txt format. The .txt file contains a sequence listing entitled "2013-11-16_5667-00113_ST25_Sequence_Listing.txt" created on Dec. 3, 2013 and is 219,761 bytes in size. The Sequence Listing contained in this .txt file is part of the specification and is hereby incorporated by reference herein in its entirety.

INTRODUCTION

This invention relates to the area of genetic diseases and in particular kidney disease and congenital malformation of the urinary tract. It relates in particular to methods of screening for therapeutic agents capable of ameliorating these conditions and also to methods for diagnosing these conditions as well as other conditions caused by the genetic polymorphisms identified herein.

Focal and segmental glomerulosclerosis (FSGS) is a significant cause of end-stage renal disease world-wide and up to one-fifth of dialysis patients have this diagnosis. The prevalence of FSGS is increasing yearly and the incidence is particularly high in the black population. FSGS is a pathological entity in which the glomerulus is primarily targeted. Typical manifestations of FSGS include proteinuria, hypertension, nephrotic syndrome, renal insufficiency and eventual kidney failure. Our understanding of the pathogenesis of FSGS is incomplete and there are no consistently effective treatments.

Analysis of disease-causing mutations in hereditary FSGS and congenital nephrotic syndromes has provided striking new insights into the pathogenesis of nephrotic syndrome. The previous identification of at least three genes causing familial FSGS and hereditary nephrotic syndromes underscores the significant genetic heterogeneity in this disorder. These studies have highlighted the importance of abnormalities in the podocyte and the slit diaphragm of the glomerulus to the development of the severe proteinuria that characterizes the nephrotic syndrome.

Primary vesicoureteric reflux (PVUR) is the most common type of congenital anomaly of the kidney and the urinary tract (CAKUT). PVUR is characterized by retrograde flow of urine from the bladder to the ureter and the kidney due to an abnormal ureterovesical junction. PVUR is the single most important risk factor for pyelonephritis and renal parenchymal scarring (RPS) in children. RPS due to PVUR is a major cause of end stage kidney disease requiring dialysis and kidney transplantation in children. The pathogenesis of PVUR has not been fully elucidated; however, it is known that it is a developmental anomaly that is probably due to a defect in reciprocal interaction between primary kidney mesenchyme and the ureteric bud during kidney development. Few loci have been reported for PVUR and to date the genetic causes of PVUR are still elusive.

SUMMARY

Isolated polynucleotides encoding polypeptides comprising novel mutations associated with either FSGS or PVUR are provided and methods of identifying subjects at risk of developing or of passing on FSGS or PVUR are provided herein. An isolated polynucleotide encoding an anillin (ANLN) poly/peptide of SEQ ID NO:1 (comprising an R431C substitution), a Wilm's Tumor 1 protein (WT1) of SEQ ID NO: 3 (comprising an R458Q substitution), a Tenascin X (TNXB) protein of SEQ ID NO: 5 (comprising a T3257I substitution) or SEQ ID NO:7 (comprising a G1331R substitution) are provided. Polypeptides encoded by the polynucleotides provided herein are also provided.

In another aspect, oligonucleotide probes, antisense nucleotides, morpholinos or other inhibitory RNAs comprising at least 15 nucleotides, including nucleotides encoding at least one amino acid selected from amino acid 431 of SEQ ID NO:1, amino acid 458 of SEQ ID NO:3, amino acid 3257 of SEQ ID NO: 5, or amino acid 1331 of SEQ ID NO: 7 or complementary to such nucleotides and capable of binding to at least one strand of the polynucleotides described herein are also provided. Kits comprising the probes, nucleotides, inhibitory RNAs or primers are also provided. The primers may be primer pairs capable of amplifying a sequence comprising position 1291 of ANLN (position 1497 of SEQ ID NO: 210), position 1373 of WT1 (position 2088 of SEQ ID NO: 211), or position 9770 (position 9966 of SEQ ID NO: 212) or 3991 (position 4193 of SEQ ID NO: 212) of TNXB.

In still another aspect, cells transformed with the polynucleotides described herein and cells capable of expressing the polynucleotides and polypeptides are provided herein. Constructs comprising the polynucleotides are also provided.

In yet another aspect, antibodies capable of binding the polypeptides of SEQ ID NO: 1, SEQ IN NO: 3, SEQ ID NO: 5 or SEQ ID NO: 7 are also provided.

In still other aspects methods of identifying subjects at increased risk of developing focal and segmental glomerulosclerosis (FSGS) or primary vesicoureteric reflux (PVUR) are also provided. The methods include isolating nucleic acids from a sample from the subject being tested and analyzing the isolated nucleic acids at the positions noted herein. The analysis will then allow the risk of the subject for developing or passing on the risk of developing either FSGS or PVUR to be assessed. In one embodiment the subject is then administered an appropriate treatment based on the results of the analysis.

In still another aspect, methods of screening for candidate agents useful in treating either FSGS or PVUR are provided. The methods include contacting a cell transformed with a polynucleotide encoding the ANLN, WT1 or TNXB polypeptides comprising the mutations described herein with the candidate agent A phenotype is then compared in the cells to the phenotype in a control cell not containing the mutation. Candidate agents capable of reversing the phenotype or causing the phenotype in the contacted cells to be more similar to that of control cells is a candidate agent for treating FSGS or PVUR.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

FIG. 1A is a depiction of the pedigree of Family 6562.

FIG. 1B is a photograph of kidney morphology in an affected kidney.

FIG. 1C is a graph showing the chromosomal linkage analysis identifying chromosome 7 as harboring the genetic defect for the Family.

FIG. 1D is a chromatogram showing the nucleotide sequence of the Anillin gene in affected (top) and unaffected (bottom) family members identifying the mutation that results in the R431C mutation.

FIG. 1E is a sequence alignment of a portion of the Anillin amino acid sequence with the red box highlighting the conserved arginine at position 431 throughout the indicated species.

FIG. 2A is a graph showing the relative Anillin expression levels in the indicated organs of a mouse.

FIG. 2B is a graph showing the relative Anillin expression levels in the podocyte and the kidney as a whole.

FIG. 4A is a photograph of a Western blot showing the level of Anillin and β-actin expression in podocyte cultures treated with a control siRNA, an anillin siRNA, a control siRNA and AngII or the anillin siRNA and AngII (from left to right).

FIG. 4B is a set of photographs of the podocytes at the time of the scratch wounds and 24 hours later after the indicated treatments.

FIG. 4C is a graph showing the percentage of wound healing of the podocyte cells in each of the treatment conditions and shows the calculated probabilities above the graph.

FIG. 5A is a set of photographs, a cartoon depiction and a graph showing the effects of reducing anillin expression in zebrafish embryos at 120 hours post-fertilization.

FIG. 5B is a cartoon depicting the vein injection of FITC-dextran, a photograph of the zebrafish eye showing the fluorescence 24 and 48 hours after injection in control or anillin knockdown zebrafish and a graph showing the relative amount of fluorescence under the indicated treatment condition.

FIG. 6 is a depiction of the pedigree of FSGS in Family 6524.

FIG. 7 is a chromatogram of the nucleotide sequencing showing the wild-type sequence coding for an arginine on the top portion and of an FSGS affected subject showing a wild-type sequence coding for an arginine and a sequence coding for a glutamine.

FIG. 8 is a graph depicting the WT1 protein structure and showing the position of R458Q in exon 9 of the protein.

FIG. 9 is a sequence alignment of positions 457-459 of WT1 from various species showing conservation of the arginine at this position.

FIG. 10 is a photograph of a Western blot showing HEK293 cells transfected with an empty vector, WT1 wild-type or the WT1 R458Q variant. The abundance and motility of the mutant and wild-type WT1 proteins are comparable.

FIG. 11 is a set of photographs showing immunofluorescence and co-localization of WT1 wild-type and the WT1 R458Q variant with DAPI and Nephrin.

FIG. 12 is a set of photographs showing the effects of reducing WT1 expression in zebrafish embryos at 6 days post-fertilization. The left column shows uninjected control zebrafish, the next column to the right are zebrafish injected with a WT1 specific morpholino, the next column to the right are zebrafish injected with a control morpholino and the right hand column shows zebrafish injected with both morpholinos.

FIG. 15 is a set of models of the predicted structure of TNXB and the change to the structure of proteins comprising either the T3257I or G1331R mutations.

FIG. 16A is a set of photographs showing delayed wound healing of a fibroblast cell line from an affected subject with TNXB T3257I (F2) as compared to fibroblasts from a subject carrying the wild-type TNXB (F3).

FIG. 17 is a set of photographs showing that the TNXB protein is expressed in the human vesicoureteric junction in both normal and refluxing subjects.

FIG. 18 provides the amino acid sequences of ANLN, WT1 and TNXB for the Substitution mutations and wild-type sequences and the nucleotide sequences of the wild-type polynucleotides. FIG. 18A provides the amino acid sequence of ANLN with an R431C mutation of SEQ ID NO: 1. FIG 18B provides the amino acid sequence of ANLN wild-type of SEQ ID NO: 2. FIG. 18C provides the amino acid sequence of WT1 with the R458Q mutation of SEQ ID NO: 3. FIG. 18D provides the amino acid sequence of wild-type WT1 of SEQ ID NO: 4. FIG. 18E provides the amino acid sequence of TNXB with the T3257I mutation of SEQ ID NO: 5. FIG. 18F provides the wild-type TNXB sequence of SEQ ID NO: 6. FIG. 18G provides the amino acid sequence of TNXB with the G1331R mutation of SEQ ID NO:7. FIG 18H provides the wild-type Anillin cDNA sequence of SEQ ID NO: 210. FIG. 18I provides the wild-type WT1 cDNA sequence of SEQ ID NO: 211. FIG. 18J provides the wild-type TNXB cDNA sequence of SEQ ID NO: 212.

DETAILED DESCRIPTION

Figure 2C:
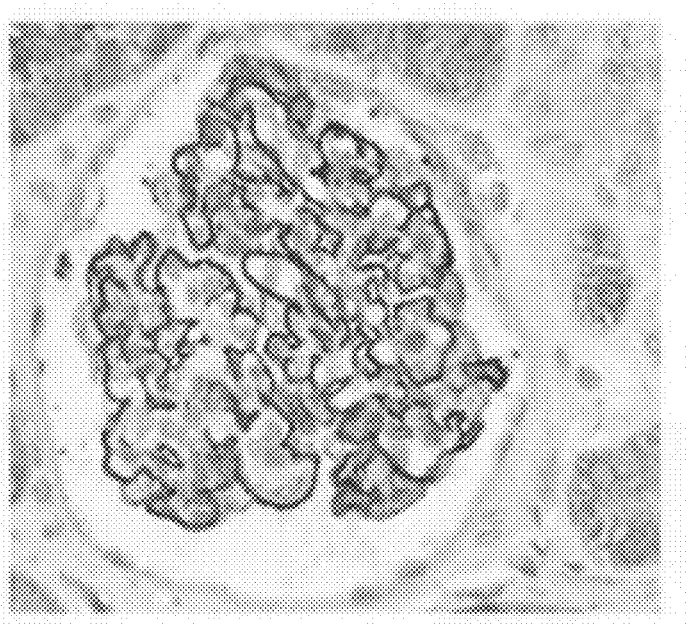
FIG. 2C is a photograph of normal kidney biopsy tissue stained for synaptopodin in brown and anillin in red.

Provided herein are isolated polynucleotides encoding polypeptides comprising novel mutations associated with either FSGS or congenital malformation of the urinary tract. The polynucleotides encode polypeptides comprising at least one of an R431C substitution of ANLN or an R458Q substitution of WT1, both of which are associated with familial forms of FSGS. The polynucleotides also include those that encode polypeptides comprising at least one of a G1331R substitution or a T3257I substitution of TNXB. Suitably the polynucleotides are at least 15, 20, 25, 30, 35, 40, 50, 75, 100, 150, 200, 250, 300, 350, 400, 450, 500 nucleotides long and include the nucleotide coding for the substitution. Suitably the polynucleotide encodes the full-length polypeptide. Polynucleotides encoding partial polypeptides comprising the site of the substitutions indicated are also provided.

The polypeptide sequences of the polypeptides comprising the mutations and the polynucleotide sequences of the wild-type genes encoding these polypeptides are provided in FIG. 18. The ANLN amino acid sequence comprising the substitution is SEQ ID NO: 1. The wild-type amino acid sequence is provided as SEQ ID NO: 2. The WT1 amino acid sequence comprising the R485Q mutation is provided as SEQ ID NO: 3 and the corresponding wild-type WT1 amino acid sequence is SEQ ID NO: 4. The TNXB amino acid sequence containing the T3257I substitution is SEQ ID NO: 5 and the TNXB amino acid sequence containing the G1331R substitution is provided as SEQ ID NO: 7 while the TNXB wild-type amino acid sequence is SEQ ID NO: 6. The polynucleotide encoding wild-type ANLN is provided in FIG. 18 and is SEQ ID NO: 210. The wild-type WT1 polynucleotide sequence is provided as SEQ ID NO: 211 and the wild-type TNXB polynucleotide sequence is provided as SEQ ID NO: 212.

Isolated polynucleotides homologous to the polynucleotides described herein are also provided. Those of skill in the art will appreciate that a relatively small number of amino acid changes, in particular conservative amino acid changes, may be incorporated into a polypeptide without affecting the function of the polypeptide Those of skill in the art also understand the degeneracy of the genetic code and that a variety of polynucleotides can encode the same polypeptide. Thus also included herein are polynucleotides encoding polypeptides that are homologous to those described above which contain the substitution mutations described above. The polypeptides may be 90%, 93%, 95%, 97%, 98%, or 99% identical to the polypeptide sequences provided herein. Conservative amino acid changes are those in which the amino acid side chains have a similar charge, polarity or over-all shape or size.

The polynucleotide may further include an origin of replication suitable to allow maintenance of the polynucleotide within a prokaryotic or eukaryotic host cell or within a viral nucleic acid. The polynucleotides may further include promoters or enhancers operably connected to the polynucleotides to allow for expression of the polynucleotide in an appropriate host cell. Such cells may not natively express the polynucleotide or polypeptide or may be knocked out for expression of the native protein. Alternatively, the cells may express a native copy and the copy of the polypeptide with the substitution mutation may have a dominant effect in the cell line. Thus polypeptides encoded by the polynucleotides provided herein are also provided as are cells transformed with the polynucleotide or otherwise made capable of expressing the polynucleotides provided herein.

The isolated polynucleotides or proteins provided herein may be prepared by methods available to those of skill in the art. Isolated indicates that the polynucleotides or proteins are not in their naturally occurring state. Notably each of the isolated polynucleotides claimed are cDNA molecules and as such do not occur in nature. Such preparations may be considered to be cell-free preparations. Typically, the polynucleotide or protein will be extracted from the cells by breaking the cell membrane and optionally removing non-desired components. For example, proteins or nucleic acids can be removed, if not desired, using enzymatic degradation. Alternatively, desired proteins or nucleic acids can be purified using sequence-specific reagents, including but not limited to oligonucleotide probes, primers, and antibodies. Lysozyme and/or detergents and/or pressure can be used to break cells, for example. Techniques for isolating cell-free preparations are well known in the art, and any that are convenient can be used.

The polypeptides comprising the mutations and their relationship to development of either FSGS or congenital malformation of the urinary tract is described more fully below in the Examples section. Each of the substitutions described herein is expected to alter the protein and affect its function and thus result in the indicated condition in subjects carrying a gene coding for the protein. In some cases the presence of the substitution is not tightly linked to the disease or does not represent a 100% occurrence of the disease. In these cases the presence of the substitution mutation, may indicate a likelihood of developing a kidney or urinary tract disease later in life or a risk of passing on such a disease or defect to one's children. The polynucleotides and polypeptides provided herein may be useful for understanding the etiology of the condition suffered by the subject, may be useful in screening for candidate therapeutic agents capable of treating or even reversing the condition in the subject and/or may be useful to diagnose individuals at risk of developing the condition or of passing a risk for developing the condition to their own children.

The polypeptides provided herein may be full-length polypeptides or may be fragments of the full-length polypeptide including the substitutions indicated above. Polypeptides may be useful for a variety of reasons. For example, polypeptides which contain, the substitutions noted above can be used inter alia for raising antibodies. Such polypeptides are typically less than full-length proteins. Preferably such residues are at least 6, 7, 8, 9, 10, 11, 12, 13, 14, 15, 17, 19, 21, 23, 25, 30, 40, 50 or more residues in length. As an example, if the polypeptide is 6 residues in length, than it can comprise residues including the substitution site (i.e. residue 431 of ANLN). Sufficient residues are desired to form a good immunogen or blocking antigen for use in assays. It may be desirable to conjugate or genetically fuse additional sequences to the polypeptide, for example, to boost immunogenicity, to enhance purification, to facilitate production or expression, or to facilitate detection. Any sequences as are convenient may be used for these or other purposes. The size of these additional sequences may vary greatly, but typically will be at least 2, 4, 6, or 8 amino acid residues in length. Suitably the additional sequences will be less than 100, 90, 80, 70, 60, 50, 40, 30, 20 or 10 amino acids in length.

The polypeptides may be used to make antibodies capable of binding to the polypeptide sequences provided herein. In other words, antibodies capable of binding to SEQ ID NO: 1, SEQ ID NO: 3, SEQ ID NO: 5 or SEQ ID NO: 7 are also provided. Suitably the antibodies recognize an epitope of the polypeptides that includes the substituted amino acid. Suitably, the antibodies have a higher affinity for the polypeptides provided herein (SEQ ID NO: 1, 3, 5 or 7) than for the wild-type polypeptides (SEQ ID NO: 2, 4, 6 or 6, respectively). Suitably the antibodies have at least two fold, three fold, four fold, five fold, seven fold, ten fold or even higher affinity for the substituted polypeptides described herein as compared to their wild-type counterparts. The affinity of antibodies for their targets can be measured using a variety of techniques known to those skilled in the art, Suitably the antibodies are IgGs. Suitably the antibodies are useful for differential detection of the substituted proteins described herein as compared to the wild-type so that the antibodies are useful in differential detection assays, such as immunofluourescence, FACS, ELISA, Western blotting or other antibody-based assays known to those skilled in the art.

While particular nucleotide sequences which are found in humans are disclosed herein any nucleotide sequences may be used which encode a desired form of the substituted polypeptides described herein. Thus non-naturally occurring sequences may be used. These may be desirable, for example, to enhance expression in heterologous expression systems of polypeptides or proteins. Computer programs for generating degenerate coding sequences are available and can be used for this purpose. Pencil, paper, the genetic code, and a human hand can also be used to generate degenerate coding sequences. For production purposes, it may be desirable to genetically engineer a coding sequence of a protein or polypeptide into an expression vector or other construct. Such vectors or constructs will typically contain an origin of replication, either of viral, plasmid, BAC or YAC origin. Such polynucleotides and/or vectors can be replicated and/or expressed in cell culture. Preferably the cultures will be of mammalian cells, and more preferably of human cells. However, other cell types may be advantageous for production, including but not limited to yeast cells, insect cells, and avian cells.

Antisense constructs, antisense oligonucleotides, RNA interference constructs, morpholinos or siRNA duplex RNA molecules can be used to interfere with expression of the polypeptides described herein. Typically at least 15, 17, 18, 19, or 21 nucleotides of the complement of mRNA sequences encoding the polypeptides are sufficient for an antisense molecule. Typically at least 18, 19, 21, 22, or 23 nucleotides are sufficient for an RNA interference molecule. Preferably an RNA interference molecule will have a 2 nucleotide 3' overhang. If the RNA interference molecule is expressed in a cell from a construct, for example from a hairpin molecule or from an inverted repeat of the desired sequence, then the endogenous cellular machinery will create the overhangs. siRNA molecules can be prepared by chemical synthesis, in vitro transcription, or digestion of long dsRNA by Rnase III or Dicer by methods known to those of skill in the art. Morpholinos are a type of antisense molecule using a backbone of 6 membered morpholine rings rather than ribose or deoxyribose and a non-ionic phosphorodiamidate linkage replacing the phosphodiester linkages of normal DNA or RNA. These can be introduced into cells by transfection, electroporation, or other methods known in the art. See Hannon, G J, 2002, RNA Interference, Nature 418: 244-251; Bernstein E et al., 2002, The rest is silence. RNA 7: 1509-1521; Hutvagner G et al., RNAi: Nature abhors a double-strand. Curr. Opin. Genetics & Development 12: 225-232; Brummelkamp, 2002, A system for stable expression of short interfering RNAs in mammalian cells. Science 296: 550-553; Lee N S, Dohjima T, Bauer G, Li H, Li M-J, Ehsani A, Salvaterra P, and Rossi J. (2002). Expression of small interfering RNAs targeted against HIV-1 rev transcripts in human cells. Nature Biotechnol. 20:500-505; Miyagishi M, and Taira K. (2002). U6-promoter-driven siRNAs with four uridine 3' overhangs efficiently suppress targeted gene expression in mammalian cells. Nature Biotechnol. 20:497-500; Paddison P J, Caudy A A, Bernstein E, Hannon G J, and Conklin D S. (2002). Short hairpin RNAs (shRNAs) induce sequence-specific silencing in mammalian cells. Genes & Dev, 16:948-958; Paul C P, Good P D, Winer I, and Engelke D R. (2002). Effective expression of small interfering RNA in human cells. Nature Biotechnol. 20:505-508; Sui G, Soohoo C, Affar E-B, Gay F, Shi Y, Forrester W C, and Shi Y. (2002). A DNA vector-based RNAi technology to suppress gene expression in mammalian cells. Proc. Natl. Acad. Sci. USA 99(6):5515-5520; Yu J-Y, DeRuiter S L, and Turner D L. (2002). RNA interference by expression of short-interfering RNAs and hairpin RNAs in mammalian cells. Proc. Natl. Acad. Sci. USA 99(9):6047-6052.

Antisense or RNA interference molecules can be delivered in vitro to cells or in vivo, e.g., to tumors of a mammal. Typical delivery means known in the art can be used. Description of delivery methods for morpholinos and inhibitory RNAs are provided in the Examples. For example, delivery to a diseased kidney can be accomplished by direct intrarenal injections. Other modes of delivery can be used without limitation, including: intravenous, intramuscular, intraperitoneal, intraarterial, local delivery during surgery, endoscopic, and subcutaneous. Vectors can be selected for desirable properties for any particular application. Vectors can be viral, plasmid or liposome based. Adenoviral vectors are useful in this regard. Tissue-specific, cell-type specific, or otherwise regulatable promoters can be used to control the transcription of the inhibitory polynucleotide molecules. Non-viral carriers such as liposomes or nanospheres can also be used. Suitably, the antisense or inhibitory RNA molecules provided herein are capable of inhibiting expression of the polypeptide in a cell. The inhibition may not be complete inhibition, but may down regulate expression of the protein by 2, 3, 5, 7, 10, 15, 20 or more fold. Rescue mRNA techniques may be used in conjunction with inhibitory RNA by transfecting cells with the inhibitory RNA to block or reduce expression of the mutated protein containing the identified substitution mutations in ANLN, WT1 or TNXB along with or followed by expression of the normal wild-type sequence through a genetic engineering or gene therapy approach.

Oligonucleotide probes capable of binding to at least one strand of the polynucleotides provided herein are also provided. The probes are suitably at least 15 nucleotides long and include the site of the substitution. The probe suitably includes the sequence encoding or complementary to the sequence encoding amino acid 431 of ANLN (nucleotide position 1291 of ANLN (position 1497 of SEQ ID NO: 210)), amino acid 458 of WT-1 (nucleotide position 1373 of WT-1 (position 2088 of SEQ ID NO: 211)) or amino acids 1331 (nucleotide position 3991 (position 4193 of SEQ ID NO: 212)) or 3257 (nucleotide position 9770 (position 9966 of SEQ ID NO: 212)) of TNXB. The probes may be single or double stranded DNA or RNA. The probes may be labeled to allow for easy detection of a binding interaction for use in a variety of assays known to those skilled in the art such as Northern or Southern blots, real-time PCR, in situ hybridization, melt-curve analysis as well as others. Convenient labels are known to those of skill in the art and include fluorescent or radiolabeled probes.

Kits for determining the nucleotide present at the substitution positions of the polynucleotides and polypeptides described herein within a sample from a subject are also provided. The kits may be used to perform the methods described herein. The kits may include a first oligonucleotide capable of binding to a target polynucleotide comprising the substitution. The oligonucleotide may be used as a probe, primer or combined with a second oligonucleotide capable of binding the complement to the target polynucleotide to amplify the target polynucleotide e.g., using PCR. For example, a kit may include a set of primers capable of amplifying a sequence comprising position 1291 of ANLN, position 1373 of WT1, or position 9770 or 3991 of TNXB. The primer pair may amplify a region comprising the substitutions identified herein or alternatively primers may be designed that will only amplify the genes comprising the mutation, such as by including the nucleotide change as the 3' end of one of the primers.

Methods of identifying subjects at increased risk of developing, or of having children at risk of developing focal and segmental glomerulosclerosis (FSGS) or congenital malformations of the urinary tract are also provided herein. The methods include obtaining a sample from the subject and isolating nucleic acids from the sample from the subject. The isolated nucleic acids can then be amplified, such as by using PCR using primers that are specific for or are capable of amplifying a sequence corresponding to position 1291 of the ANLN polynucleotide sequence or position 1373 the WT1 polynucleotide sequence for assessing the risk, of FSGS or alternatively position 3991 or 9770 of the TNXB polynucleotide sequence for assessing the risk of congenital malformation of the urinary tract. The amplification of the sequences allows for determination of the nucleotides present at the indicated positions of the ANLN, WT1 and TNXB genes. This determination then allows subjects at increased risk of developing FSGS or alternatively congenital malformation of the urinary tract to be identified. If the nucleotide of the subject at the position corresponding to position 1291 of ANLN is a thymine or the nucleotide at the position corresponding to 1373 of WT1 is a thymine on either allele in the subject, the subject is at risk of developing FSGS. If the nucleotide of the subject at the position corresponding to position 9770 of TNXB is a thymine or if the nucleotide at the position corresponding to position 3991 of TNXB is an adenine on either allele in the subject the subject and the subject's children are at risk of having a congenital malformation of the urinary tract.

The analysis of the polynucleotide sequence may be obtained by any method, including several known to those of skill in the art. For example, the analysis may include directly sequencing a DNA sample from the subject, restriction fragment length polymorphism (RFLP) analysis, differential amplification, primer extension or microarray analysis. The determining step may also include a step which requires formation of a duplex comprising the amplified nucleic acid and an oligonucleotide probe capable of binding to at least one strand of the amplified sequence comprising the substitutions in ANLN, WT1 and TNXB described herein. These duplexes can be characterized using a variety of methods known to those of skill in the art. For example, the probe may be labeled such that when it binds to the complementary sequence the probe fluorescence and the fluorescence can be an indicator of the presence of the substitution in the sample from the subject. Alternatively, the analysis may be done by an entity separate from the entity obtaining the sample or identifying the level of risk for the subject. For example the sequencing information can be obtained from a separate entity, such as an independent testing laboratory.

The single nucleotide polymorphisms (SNPs) identified herein all result in an amino acid change in the polypeptide encoded by the polynucleotide. These substitutions can be detected and information about the polynucleotide obtained by any method capable of detecting amino acid changes in a polypeptide as well, e.g., using protease digestion or Western blot analysis or other antibody based technique using for example the antibodies described above. In the Examples, the polynucleotides from individual subjects were amplified using polymerase chain reaction and nucleotide sequencing was used to determine the nucleotide at the particular position.

Sequences can be determined using any techniques which detect directly or indirectly a change in a protein or nucleic acid sequence. Thus, for example, if a mutation causes premature truncation, such a sequence feature can be detected by determining the size of the encoded mRNA or protein. Directly determining amino acid or nucleotide sequences can be used, and these techniques are well known in the art. Antibodies that are specific for a sequence can be used for probing mutant proteins. Probes and or primers that hybridize to wild-type or a particular mutation can be used. Any technique which detects such hybridization or the lack thereof can be used without limitation. Some of these are descried more fully below.

A sample useful for practicing the methods described herein can be any biological sample of a subject, typically a human subject. Suitably, the sample contains nucleic acid molecules, including portions of the gene sequences to be examined, or corresponding encoded polypeptides, depending on the particular method used. The sample can be a cell, tissue or organ sample, or can be a sample of a biological material such as a body fluid, for example blood, milk, semen, saliva or a biopsy. A nucleic acid sample useful for practicing the methods provided herein may be DNA or RNA. The nucleic acid sample generally is a DNA sample, suitably genomic DNA. A cDNA sample or amplification product thereof can also be used. The SNPs described herein are in coding regions of a gene and result in polypeptides containing different amino acids at the positions corresponding to the SNPs due to a change to a codon encoding a distinct amino acid as demonstrated in the Examples. The methods described herein can also be practiced using a sample containing polypeptides of the subject.

Any suitable method may be used to determine the nucleotide for a particular SNP in a sample, including any of numerous methods available to those of skill in the art. Such methods can utilize one or more oligonucleotide probes or primers, including, for example, an amplification primer pair that selectively hybridizes to a target polynucleotide that includes one or more of the SNPs described herein. Oligonucleotide probes useful in practicing the methods can include, for example, an oligonucleotide that is complementary to a portion of the target polynucleotide, including the position of the SNP, wherein the presence of a specific nucleotide at the position (i.e., the SNP) is detected by the presence or absence of selective hybridization of the probe. Such a method can include contacting the target polynucleotide and hybridized oligonucleotide with an endonuclease, and detecting the presence or absence of a cleavage product of the probe, depending on whether the nucleotide at the SNP site is complementary to the corresponding nucleotide of the probe.

An oligonucleotide ligation assay may be used to identify nucleotide at a polymorphic position. In this assay, a pair of probes that selectively hybridize upstream and adjacent to and downstream and adjacent to the site of the SNP are used. One of the probes includes a terminal nucleotide (3'-nucleotide) complementary to a nucleotide occurrence of the SNP. Where the terminal nucleotide of the probe is complementary to the nucleotide, selective hybridization includes the terminal nucleotide such that, in the presence of a ligase, the upstream and downstream oligonucleotides are ligated. The presence or absence of a ligation product is indicative of the nucleotide occurrence at the SNP site.

An oligonucleotide also can be useful as a primer, for example, for a primer extension reaction, wherein the product (or absence of a product) of the extension reaction is indicative of the nucleotide present at the site. In addition, a primer pair useful for amplifying (i.e. by PCR) a portion of the target polynucleotide including the SNP site can be useful. In this assay, the amplification product is examined, i.e. via sequencing, to determine the nucleotide at the SNP site. Particularly useful methods include those that are readily adaptable to a high throughput format, to a multiplex format, or to both. The primer extension or amplification product can be detected directly or indirectly and/or can be sequenced using various methods known in the art. Amplification products which span a SNP locus can be sequenced using traditional sequencing methodologies. Alternatively, the products may be analyzed by RFLP analysis by treating the amplification products with restriction endonucleases which will differentially digest the products based on the nucleotide present at the SNP site.

Methods of the invention can identify nucleotides at SNPs using genome-wide sequencing or "microsequencing" methods, Whole-genome sequencing of individuals identifies all SNP genotypes in a single analysis. Microsequencing methods determine the identity of only a single nucleotide at a "predetermined" site. Such methods have particular utility in determining the presence and identity of SNPs in a target polynucleotide. Such microsequencing methods, as well as other methods for determining the nucleotide at a SNP locus are available to those skilled in the art.

The nucleotide present at a SNP can also be identified using an immunoassay specific for one or more of the nucleotides at the SNP site. The SNP can also be identified by contacting polynucleotides in the sample or polynucleotides derived from the sample, with a specific binding pair member that selectively hybridizes to a polynucleotide region comprising the SNP, under conditions wherein the binding pair member specifically binds at or near the SNP. The specific binding pair member can be an antibody or a complementary polynucleotide.

The nucleotide present at a SNP can be identified by other methods as well as those discussed above. For example, sequencing methods such as mass spectrometry, scanning electron microscopy, or methods in which a polynucleotide flows past a sorting device that can detect the sequence of the polynucleotide. The occurrence of a SNP can be identified using electrochemical detection devices as well. Other formats include melting curve analysis using fluorescently labeled hybridization probes, or intercalating dyes.

The methods of identifying the nucleotide present at a SNP may also utilize selective hybridization such as a microarray. Selective hybridization refers to hybridization under moderately stringent or highly stringent conditions such that a nucleotide sequence preferentially associates with a selected nucleotide sequence over unrelated nucleotide sequences to a large enough extent to be useful in identifying the nucleotide at a SNP. The nucleotide may be detected by comparing the amount of labeled oligonucleotide that binds to target nucleic acid molecule as compared to a nucleic acid molecule other than the target molecule, particularly a substantially similar (i.e., homologous) nucleic acid molecule other than the target nucleic acid molecule. Conditions that allow for selective hybridization can be determined empirically, or can be estimated based, for example, on the relative GC:AT content of the hybridizing oligonucleotide and the sequence to which it is to hybridize, the length of the hybridizing oligonucleotide, and the number of mismatches between the oligonucleotide and sequence to which it is to hybridize.

Methods of screening for candidate agents useful for treating FSGS or congenital malformation of the urinary tract are also provided. These methods include contacting a cell transformed with a polynucleotide encoding a WT1, ANLN or TNXB polypeptide comprising the mutations described herein with a candidate agent and comparing a phenotype of the contacted cells to that of control cells. The control cells may be cells expressing only a wild-type form of the indicated polypeptide. The cells may be transformed with an empty or control vector or a vector with a polynucleotide encoding wild-type polypeptide.

The phenotype observed and measured will differ depending on the polypeptide being tested. For WT1 the phenotype is selected from nephrin expression, synaptopodin expression, edema and percentage of cells undergoing either death or apoptosis. In the Examples these phenotypes are shown in cells (or zebrafish) expressing the R458Q form of WT1. Thus a candidate agent capable of reversing these phenotypic effects of transformation with R458Q WT1 is a candidate agent for treating FSGS. For ANLN the phenotype is selected from edema, dextran uptake by cells, or motility. In the Examples these phenotypes are shown in cells (and zebrafish) expressing the R431C form of ANLN. Thus a candidate agent capable of reversing these phenotypic effects of transformation with R431C ANLN in a cell is a candidate agent for treating FSGS. For TNXB, the phenotype is selected from wound healing, motility, adhesion and altered phosphorylation of focal adhesion kinase (FAK). In the Examples these phenotypes are noted in cells expressing at least one of the G1331R or T3257I form of TNXB. Thus a candidate agent capable of reversing these phenotypic effects of transformation with either G1331R or T3257I TNXB is a candidate agent for treating congenital malformations of the urinary tract.

Methods of diagnosing FSGS or PVUR in a subject or whether the subject is a carrier for FSGS or PVUR are also provided. The methods include requesting a test to determine whether the subject comprises a mutation in ANLN, WT1 or TNXB selected from a R431C substitution in ANLN, an R458Q substitution in WT1 or a T3257I or G1331R substitution in TNXB and then determining whether the subject is a carrier of or at risk for developing FSGS or PVUR. If the subject has or is at risk of developing FSGS or PVUR then a treatment for FSGS or PVUR as appropriate is administered to the subject.

Methods of diagnosing FSGS or PVUR in a subject by analyzing a sample obtained from the subject for the presence of mutations including a R431C substitution in ANLN, an R458Q substitution in WT1 or a T3257I or G1331R substitution in TNXB. Subjects having one of these substitutions in WT1 or ANLN in either allele can be diagnosed as having or being susceptible to FSGS and subjects having one of the substitutions in TNXB on either allele can be diagnosed as having or being susceptible to PVUR.

Cells may be contacted with the agent directly or indirectly in vivo, in vitro, or ex vivo. Contacting encompasses administration to or co-culture with a cell, tissue, mammal, patient, or human. Further, contacting a cell includes adding an agent to a cell culture. Other suitable methods may include introducing or administering an agent to a cell, tissue, mammal, or patient using appropriate procedures and routes of administration.

Treating a disease includes, but is not limited to, reducing progression of a disease, reducing symptoms of the disease, slowing progression of the disease or reversing the disease pathology in the subject. Treating a subject as used herein refers to any type of treatment that imparts a benefit to a subject afflicted with a disease or at risk of developing the disease, including improvement in the condition of the subject (e.g., in one or more symptoms), delay in the progression of the disease, delay the onset of symptoms or slow the progression of symptoms, etc.

The following examples are meant only to be illustrative and are not meant as limitations on the scope of the invention or of the appended claims. All references cited herein are hereby incorporated by reference in their entireties.

EXAMPLES

Example 1

Anillin (ANLN) Substitution Associated with FSGS

We have identified the cause of the genetic mutation in the US kindred (Duke Family 6562). ANLN is the gene encoding the F-actin binding protein anillin having the wild-type nucleic acid sequence of SEQ ID NO: 210 and the corresponding amino acid sequence of SEQ ID NO: 2. Anillin is important in cytokinesis and also regulates cell growth by its interaction with the pro-migratory and pro-survival phosphoinositide 3 kinase/AKT (protein kinase B) PI3K/AKT (PKB) pathway. Anillin is strongly expressed in immortalized podocytes and interacts with CD2AP, nephrin, INF2, and RhoA. ANLN appears to be important in maintaining the podocyte actin cytoskeleton. These findings re-emphasize the importance of aberrant proliferation of the podocyte, cell survival pathways, cell migration and filopodia formation in the pathogenesis of FSGS.

The ailing gene was found to be expressed in kidney, brain, heart, lung, liver, spleen and cultured podocyte via rtPCR analysis. All exons were sequenced in affected and control subjects as shown in the pedigree in FIG. 1A of Family 6562 (see methods section below). FIG. 1B shows the kidney morphology in affected individuals. FIG. 1C shows the linkage analysis and the subsequent identification of the mutation associated with FSGS in Family 6562 as being located on chromosome 7, We further believe this to be the genetic mutation causing FSGS in this family based on the following data. As shown in the chromatograms of FIG. 1D, a $^{1291}C \rightarrow T$ nucleotide change was found in exon 7 in affected individuals and segregated with the disease in family 6562 (see FIG. 1D). This causes a significant amino acid change of an arginine to a cysteine (R431C) (see FIG. 1E and SEQ ID NO: 1 and 2). No evidence of the variant was found in greater than 1600 control chromosomes. A search of all available public SNP (single nucleotide polymorphisms) databases did not reveal evidence of this being a previously known polymorphism. The arginine at position 431 is conserved throughout evolution (including man, chimp, wolf, cattle, mouse, rat, chicken and zebrafish (see FIG. 1E). The R431C variant was found to be probably damaging via in silico modeling with a SIFT score of 0.91.

Anillin is a 124 kDa protein with a nuclear domain, an F-actin binding domain, a coiled coil domain and a pleckstrin homology (PH) domain among others. It functions as a scaffold protein that links RhoA and mDia2 (mouse formin 2) with actin and myosin in cellular cleavage furrows during cytokinesis and cellularization, in addition it binds and bundles F-actin in vitro. The R431C mutation is in the F-actin binding domain of the protein suggesting that the change may affect the actin cytoskeleton architecture.

Figure 2D:
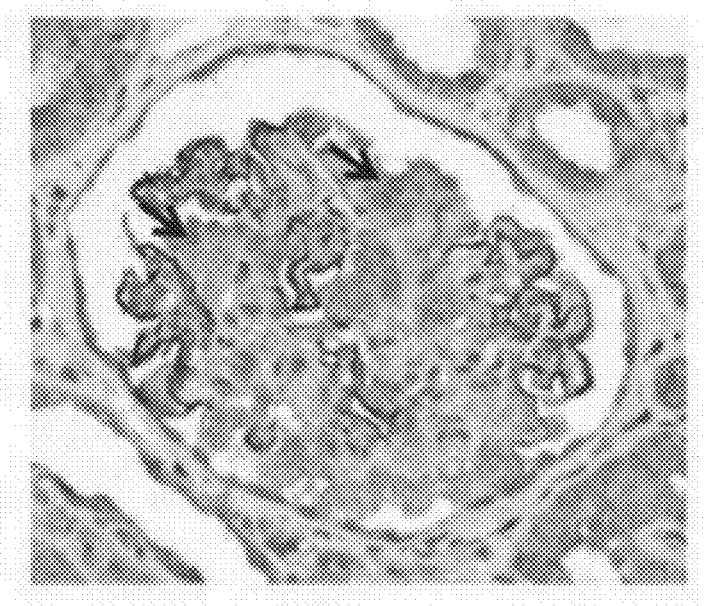
FIG. 2D is a photograph of kidney tissue from an FSGS subject with the R431C mutation in anillin stained for synaptopodin in brown and anillin in red.

As shown in FIG. 2A, anillin is ubiquitously expressed in all organs including the kidney. All values were normalized for expression in the spleen. FIG. 2B shows that anillin expression in mouse podocyte is approximately 9× higher than whole kidney. FIG. 2C shows normal kidney biopsy tissue after double staining for synaptopodin with anti-human mouse monoclonal antibody with brown DAB chromogen and anillin anti-human rabbit polyclonal antibody with fast red stain. Synaptopodin is strongly expressed in the glomerulus and the podocyte and the expression of anillin is mainly in the tubules. FIG. 2D shows double staining for synaptopodin and anillin in a similar sample from an affected subject showed patchy expression of synaptopodin in the glomerulus and significant upregulation of anillin expression in the glomerulus and the reactive podocyte (black arrow) compared with normal kidney tissue.

Figure 3:
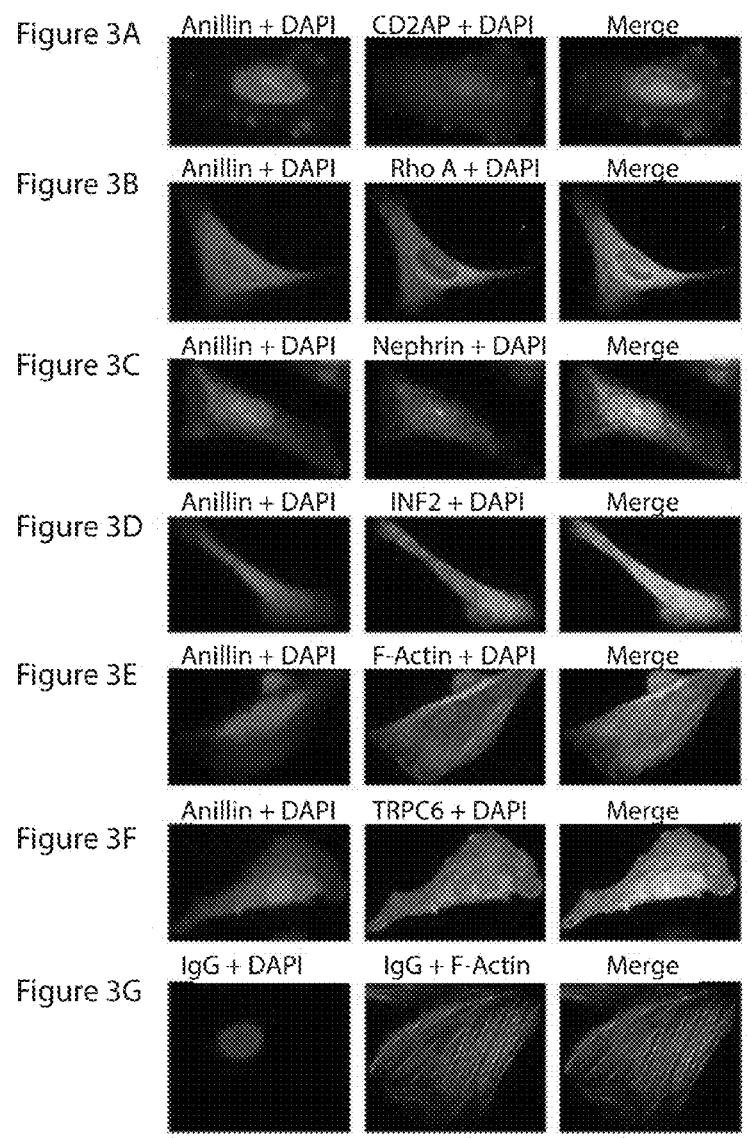
FIG. 3 shows a set of photographs showing the subcellular localization of endogenous anillin in a podocyte cell line with anillin shown in red, cell nuclei stained blue using DAPI and the indicated marker shown in green such that co-localization appears yellow in the right hand photograph. The markers shown are CD2 AP (A), RhoA (B), Nephrin (C), INF2 (D), F-actin (F), TRPC6 (F), and F-actin with an IgG control (G).

FIG. 3 shows subcellular localization of endogenous anillin in an immortalized podocyte cell line. Endogenous anillin protein staining is shown in red. Co-immunolabeling for anti-CD2AP (A) anti-RhoA (B), anti-nephrin (C) anti-INF2 (D) and anti-F-actin are shown in green. Cell nuclei are stained with DAPI (blue). Anillin is strongly expressed in both the nucleus and cytoplasm and co-localizes with CD2AP, RhoA, nephrin, INF2, F-actin and TRPC6, in cultured immortalized human podocytes. IgG served as the control antibody (G).

FIG. 4 shows siRNA-mediated ANLN gene silencing impairs Ang II-induced podocyte migration. Targeted silencing of ANLN gene expression in immortalized human podocytes attenuates Ang II-induced podocytes relative to control (p=0.003). Knockdown of ANLN expression in transfected podocytes is confirmed by immunoblot in control and ANLN siRNA transfected cell lysates.

Figure 5C:
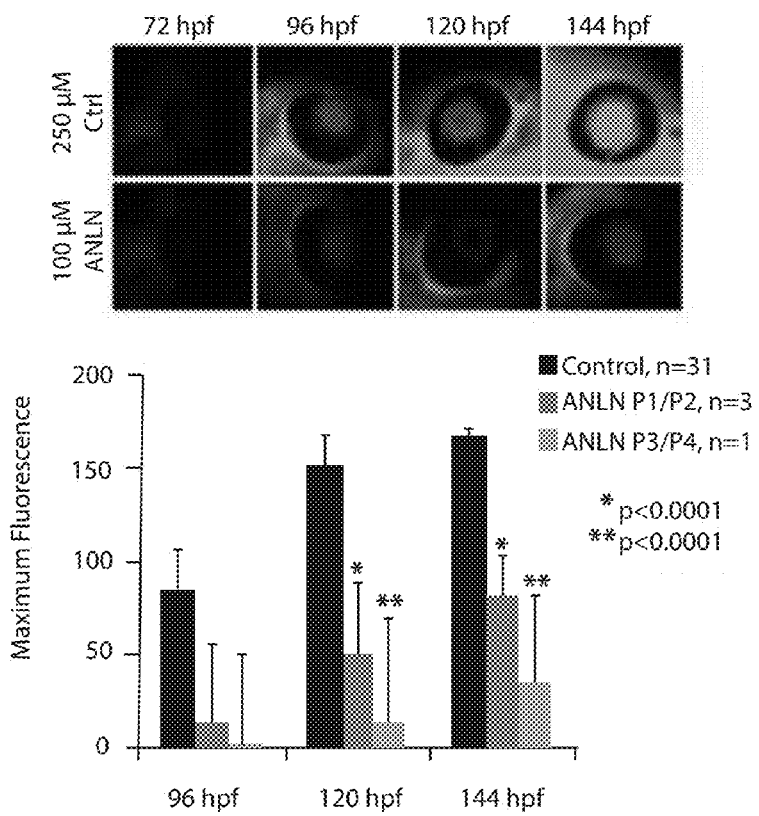
FIG. 5C is a set of photographs and corresponding graphic representation comparing fluorescence in control and anillin knockdown transgenic zebrafish (1-FABP:DBP-EGFP) at the indicated times post-anillin knockdown by injection of the morpholinos.
Figure 13A:
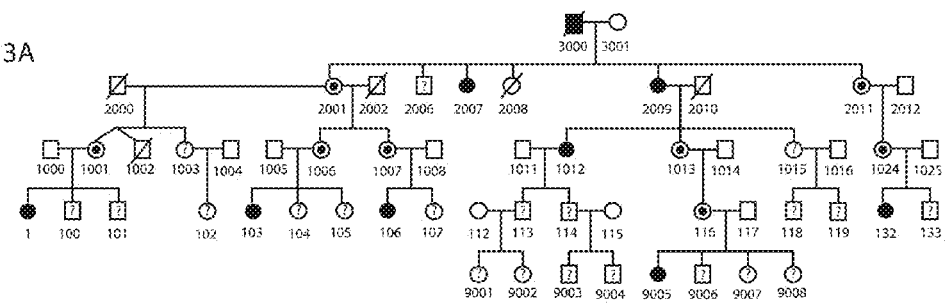
FIG. 13A is a depiction of the pedigree of Family 6606.
Figure 13B:
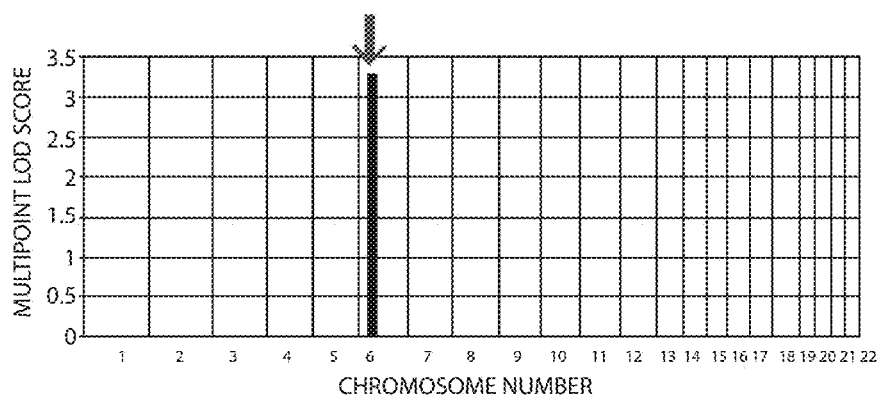
FIG. 13B shows the linkage analysis pointing to a mutation on chromosome 6.
Figure 13C:
FIG. 13C shows images of normal and affected individual's ureterovesical junction.
Figure 13D:
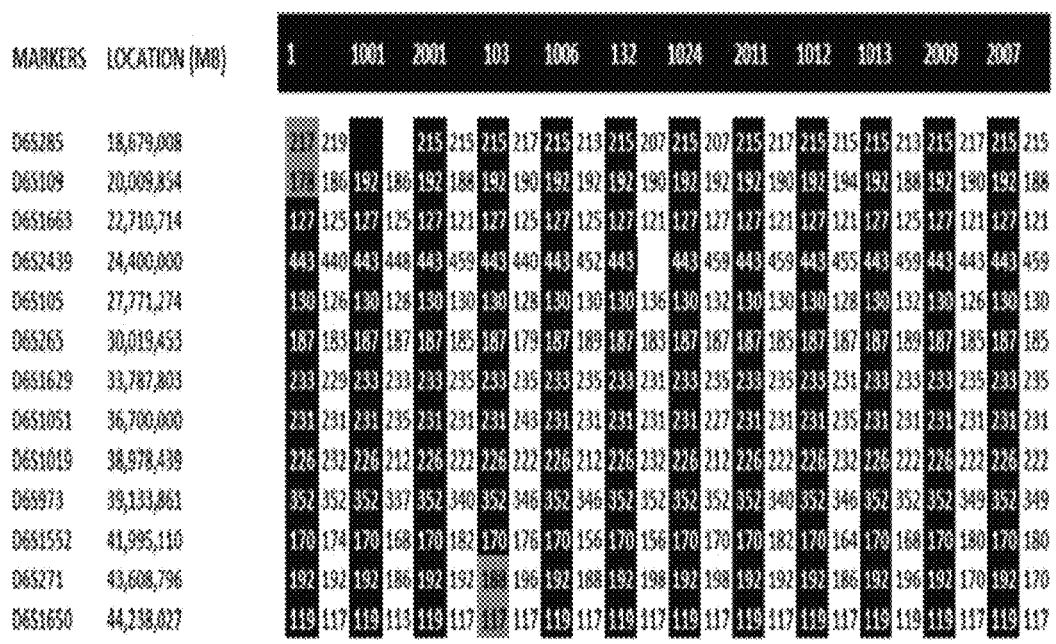
FIG. 13D is a graph showing the markers and their location on chromosome 6 in the affected individuals identified by number and in relation to the pedigree depicted in FIG. 13A.

FIG. 5A shows ANLN-knockdown leads to an edema phenotype in zebrafish. Fertilized eggs were injected with a control or Anillin specific morpholino and phenotypes were scored at 120 hours post fertilization (hpf). Edema development was graded as P1=no phenotype, P2=mild phenotype, P3=moderate/severe and P4=severe phenotype. FIG. 5B shows Anillin-knockdown leads to loss of injected high molecular weight dextran. Zebrafish larvae 48 hrs post injection of no (WT), control-morpholino (Ctrl) or Anillin-morpholino were anesthetized and injected with a FITC-labeled 70-kDa dextran. The amount of systemic fluorescence was assessed post injection by measurement of fluorescence intensity in the retinal blood vessel plexus at baseline and 24 hrs later in individual fish. Loss of systemic fluorescence indicates systemic loss of high molecular weight proteins from the circulation especially in fish with a severe edema phenotype (P3/P4), FIG. 5C shows Anillin-knockdown leads to loss of systemic fluorescence in Tg (1-fabp: DBP-EGFP) zebrafish. Tg(1-fabp:DBP-EGFP) develop from 72hpf until 144hpf increasing systemic fluorescence by increasing amounts of circulating EGFP labeled Vitamin-D binding protein (MW ~64 kDa). Anillin-knockdown causes a significant reduction in systemic fluorescence in mild and severely affected knockdown fish indicating again systemic loss of high molecular weight proteins.

Little is known about the pathogenesis of familial FSGS and nephrotic syndromes. There are several known genes which cause hereditary FSGS and nephrotic syndromes (nephrin, podocin, ACTN4, TRPC6, PLCE1, INF2, CD2AP, etc). ANLN as a cause for familial FSGS is completely novel. The knowledge that this gene is a cause of familial FSGS may help further elucidate the origin and development of this pathological entity. Furthermore, specific molecular targets may eventually be identified to aid in the treatment of FSGS.

In regards to the possible pathogenetic mechanisms by which mutations in ANLN causes FSGS, this is not yet clear, however overexpression of ANLN in kidney biopsies from subjects with collapsing FSGS may cause the disease by aberrant reentry of terminally differentiated podocytes into the cell cycle. Furthermore the findings that anillin interacts with key podocyte genes may point to a critical role for anillin in maintaining the actin cytoskeleton. A podocyte cell line treated with anillin siRNA showed reduced motility. Additionally, the interaction of anillin with INF2 advances the notion that cell migration and filopodia formation are important in the pathogenesis of FSGS. Anillin also plays a significant role in the P13k/AKT pathway, a pathway that regulates cell growth, proliferation and migration and may therefore affect podocyte endowment during development. In addition the pathway can be easily targeted by small molecule kinases and may therefore represent a possible therapeutic target for FSGS.

Methods:

Case ascertainment: Institutional Review Board approval was obtained from Duke University Medical Center (Durham, N.C., USA). Families with FSGS were identified through the International Collaborative Group on Familial FSGS. Inclusion criteria and determination of affection status are as previously reported. Briefly, inclusion in this analysis required at least one individual with biopsy-proven FSGS and a second family member with FSGS and/or ESKD. Clinical evaluation of these kindreds included a full family history, physical examination, urinalysis with qualitative or quantitative proteinuria and serum creatinine assay when appropriate. Renal pathology reports and slides were reviewed when available for affected individuals. Individuals were classified as follows: Affected: If they required dialysis, had undergone renal transplantation, had 2+ to 4+ proteinuria by qualitative urinalysis ≥500 mg/24 hours on quantitative urinalysis or had a renal biopsy demonstrating FSGS without evidence of other systemic diseases known to cause FSGS or chronic renal failure. Probably affected: If they had trace to 1+ proteinuria on qualitative urinalysis. These individuals were categorized as unknown in the linkage analysis. Unaffected: Individuals who had no detectable proteinuria on qualitative urinalysis and unrelated married-in spouses. We excluded mutation in known FSGS genes (NPHS1, NPHS2, PLCE1, ACTN4, TRPC6, and INF2) in all the affected individuals.

Linkage analysis: A genuine-wide linkage scan was performed using the Illumina Infinum II HumanLinkage-24 genotyping beadchip assay (Illumina Inc., San Diego, Calif.). This assay contained over 5000 single nucleotide polymorphisms (SNPs) with an average, genetic distance of 0.58 cM and call rate >99%, Genotyping was performed on 12 most informative individuals from the family comprising of six affected individuals and six unaffected individuals. Two-point LOD scores were calculated for all the 5000 SNP markers. A LOD score (the logarithm of the odds of linkage) of ≥3.0 is considered significant evidence for linkage and ≤−2.0 is significant evidence for exclusion of linkage to the region. Values between these are classified as "suggestive" LOD score. A rare dominant model was assumed. A conservative low-penetrance "affecteds-only" analysis was performed to ensure that results obtained were not due to asymptomatic individuals who were non-penetrant carriers of the FSGS gene.

Whole exome sequencing and podocyte exome sequencing: We performed whole exome sequencing on the proband. DNA was fragmented using the E220 ultrasonicator to obtain fragment size between 350-450 bases. The library was prepared with the Illumina Truseq library according to the manufacturer's instruction. Truseq exome enrichment kit was used according to the protocol provided by Illumina. The sample from the proband was hybridized to biotin labeled probes, which binds the region of interest in complementary fashion. The targeted region was then enriched with streptavidin beads, and the product was eluted from the beads. The captured region was sequenced using one lane of Hiseq 2000 sequencer. We target >60 fold reads and machine error was monitored with Hiseq control software (HCS 1.1.37.19). The output was analyzed with the Illumina real time analysis (RTA 1.7.48) software. The reads that passed the quality control test were aligned with the Human Reference genome (HG 19) using the BWA software. SAMtools software was used to merge the sequence reads into consensus genotypes. Variants from the cleaned alignment were called with SAMtools software.

Sanger sequencing: All the potential disease causing variants that were identified genome-wide by both bid chips were confirmed by Sanger sequencing. Briefly both strands of all the variants were sequenced using exon flanking primers. In addition, both strands of all the coding exons of ANLN were sequenced in 100 families with FSGS using the same method, exon primer sequences and CDNA are listed in Tables 1 and 2. All sequences were analyzed with Sequencher software (Gene Codes Corp., Ann Arbor, Mich.).

TABLE 1

ANLN exon primers

| Primer Name | Primer Sequence | SEQ ID NO: |
|---|---|---|
| ANLN-1F | CACTTTTCTCTTCCTGAATTTGAAC | 16 |
| ANLN-1R | TGACAGAGGAAGGTGGGTG | 17 |
| ANLN-2F | AAATTTGTGGCCGTTAAAAATC | 18 |
| ANLN-2R | AATGAAATGTTTGGGGCTTG | 19 |
| ANLN-3F | TTTAAAAGAATAGGGAGGGGTG | 20 |
| ANLN-3R | ATGCAAGCAAAGGATACTCAAC | 21 |
| ANLN-4F | ATTCAGCATAGAGTGATCCTGGT | 22 |
| ANLN-4R | CCATCCACCTGCACATACAC | 23 |
| ANLN-5F | GGACTTGAATTGTTTGTTATAGGAC | 24 |
| ANLN-5R | CAAATCATTGCTGTACCATTCA | 25 |
| ANLN-6F | CAAAGCATTTGAAGCTGTAATG | 26 |
| ANLN-6R | GGCATCAGAACCCATTTTG | 27 |
| ANLN-7F | TCAGACAAGATTGGGCACAT | 28 |
| ANLN-7R | CGAAAAGTGACAGAGTTAATTGGA | 29 |
| ANLN-8F | CACTATCTCTTTGGTTCTAAGGAAAC | 30 |
| ANLN-8R | AGAACAAACAAATCCAGCAAAG | 31 |
| ANLN-9F | AAGAGAGGACAGGTGTTCAGG | 32 |
| ANLN-9R | CCCTGTCAAAGTCAGTGAGG | 33 |
| ANLN-10F | TTGAAGCTGAAGATTTTCTTGG | 34 |
| ANLN-10R | AGGTCTGCAAAATTCCCTTG | 35 |
| ANLN-11F | GGAGAATTCATTGATTTTCACAGA | 36 |
| ANLN-11R | TGTCAATCTAAACCATGACCCTTA | 37 |
| ANLN-12F | GGATAGTGCTCAGTGTGTTGC | 38 |
| ANLN-12R | AGCTCACAGCCTAGTGCAAG | 39 |
| ANLN-13F | TTTTGGTGCATAGTCGAGAAAC | 40 |
| ANLN-13R | TCCACTGGAACAGATGACTAGG | 41 |
| ANLN-14F | TTTGCTCTCATTAGAAACAGTTACG | 42 |
| ANLN-14R | ACAATTCAATCTAGGTGAGGTTCA | 43 |
| ANLN-15F | TTTGTGTCTGGAAAGTTGATTTTAG | 44 |
| ANLN-15R | GTGCATAAGGCGTTTCAAAG | 45 |
| ANLN-16.17F | AAATATTTTGGACTTGCATTATAGGG | 46 |
| ANLN-16.17R | AAATTGGAACATGAAACTGATCC | 47 |
| ANLN-18.19F | GGTTGGATAGTTTTACTTTCTGAGAC | 48 |
| ANLN-18.19R | TGCAAGTGCTTAATTCCTTACC | 49 |
| ANLN-20F | TTCTACTGGGATGGGGTGAG | 50 |
| ANLN-20R | AAAAGCATTGTGGCATTTCC | 51 |
| ANLN-21F | TGCTCTGTTTTCAAGTTGTAATAGTC | 52 |
| ANLN-21R | AACAAGTCTGTATTTCACAAAATGG | 53 |

TABLE 1-continued

ANLN exon primers

| Primer Name | Primer Sequence | SEQ ID NO: |
|---|---|---|
| ANLN-22F | CAGCATTTCATTGTTAGGACATTT | 54 |
| ANLN-22R | CAGAGGGAACATTTGCATGA | 55 |
| ANLN-23F | AAATGCTGCTTAATGCTTACTGAC | 56 |
| ANLN-23R | AGTGGTAAGTACATAGTGGGCAATC | 57 |
| ANLN-24F | TCCCTAGCAAGAGTACATGGG | 58 |
| ANLN-24R | TGCAATCAGTAAATCTGATGCTC | 59 |

TABLE 2

Anillin cDNA primers

| Primer Name | Primer Sequence | SEQ ID NO: |
|---|---|---|
| VP1.5-F | GGACTTTCCAAAATGTCG | 60 |
| ANLNcdna-1R | AGACACAGGACTTGGAGAAC | 61 |
| ANLNcdna-2F | ACGCTGTTCTGACAACACTGA | 62 |
| ANLNcdna-2R | TCCCTTTGGGAACAGAATGT | 63 |
| ANLNcdna-3F | ATTTGCTCCTGGGAAGATGA | 64 |
| ANLNcdna-3R | GGATGGCCTTTGTATTTGGA | 65 |
| ANLNcdna-4F | TCTGCAATCTCAATCTAAAGACAAA | 66 |
| ANLNcdna-4R | ACTGAGTTTTTGAAACACCTTGG | 67 |
| ANLNcdna-5F | GAAAAAGGCGGAAACTCAAA | 68 |
| ANLNcdna-5R | GTGCCAATGGTGCAAGTAAA | 69 |
| ANLNcdna-6F | AGCCAAGAGGAGATGGATCA | 70 |
| ANLNcdna-6R | AAAGTGTTCTCTTCCCAGTTGC | 71 |
| ANLNcdna-7F | TCTATCAAGCTAGCCAGGCTCT | 72 |
| ANLNcdna-7R | GTGAGGAGTCGCTTTGGAGT | 73 |
| ANLNcdna-8F | ACAGCTTGGTGCAAAAGAAAG | 74 |
| ANLNcdna-8R | TGCATTGGCTGACAAGAGTC | 75 |
| ANLNcdna-9F | CGCAAGAATCCCATAGGAAG | 76 |
| ANLNcdna-9R | GTTGTTGATGGCGTGCAG | 77 |
| ANLNcdna-10F | CTTCTACCACTTCGGCACCT | 78 |
| ANLNcdna-10R | CCTAGTCAGACAAAATGATGCAA | 79 |

In silico prediction of impact of amino acid substitution: The R431C variant in ANLN gene was entered into Polyphen 2 software to examine the predicted damaging effect of the amino acid substitution to the function of ANLN. The Hum Var-trained version was used which is optimal for Mendelian disorders as it distinguishes mutations with drastic effects from all the remaining human variation, including abundant mildly deleterious alleles. PolyPhen-2 calculates a Naïve Bayes posterior probability that any mutation is damaging and this is represented with a score ranging from 0-1. A mutation was also appraised qualitatively, as benign, possibly damaging, or probably damaging based on the model's false positive rate.

Primary podocyte culture and mRNA extraction Primary podocyte culture was established as previously described (J Am Sac Nephrol 2011; 22:526-535). Wild-type mice (sv129) were sacrificed and kidneys were harvested under sterile conditions. Decapsulated glomeruli were isolated from kidneys of individual mice by sequential washing with ice cold phosphate buffer solution (PBS) through 180 µM, 100 µM and 71 µM sieves (Retsch Inc., Newtown, Pa.). After washing in ice cold PBS, the glomerulus concentrated pellet (71 µM sieves product) was resuspended in RPMI medium supplemented with FBS (Fetal Bovine Serum) and liquid penicillin-streptomycin (Invitrogen, Carlsbad, Calif.) and cultured ma type I collagen flask for 3 to 5 days. Products were isolated by passing trypsinized outgrowing cells from the glomeruli through a 40 µM nylon cell strainer (Fisher Scientific, Norcross, Ga.), and were then cultured in RPMI supplemented medium in a type I collagen flask. Podocytes were split upon reaching 95% confluency. The identity of the podocytes was routinely confirmed by Wilms' Tumor-1 (WT1) antibody staining (Santa Cruz Biotechnology, Santa Cruz, Calif., USA). Experimental studies were conducted within the first 3 to 4 passages of the podocyte subculture.

Total RNA was manually extracted from freshly cultured podocytes, whole kidney, brain, heart, liver, lung and spleen tissues from WT mice using an RNeasy® Mini kit (Qiagen; Valencia, Calif.). Tissue was stabilized in RNAlater® solution (AMBION, Inc.; Austin, Tex.) immediately after sacrifice of the mouse. Subsequently, 0.5 µg of total RNA was reverse transcribed into complementary DNA (cDNA) utilizing the reverse transcription system (Promega Corporation; Madison, Wis.) with oligo(dT) primers, according to the manufacturer's protocol. The cDNA was diluted 2.5 fold for the real-time PCR reaction. Quantification of mRNA by real-time PCR was performed using the ABI 7900 HT system (Applied Biosystems; Foster City, Calif.). PCR reactions for β-Actin and ANLN, TRPC6, NPHS2, NPHS1, and WT1 were performed in a final volume of 10 µL, consisting of 2 µL cDNA, 2.5 µL RNAse and DNAse free water, 0.5 µL of 20× Taqman® Gene Expression Assays (Table 1.) and 5 µL, of Taqman® 2×PCR Mastermix (both Applied Biosystems; Foster City, Calif.). The target DNA was amplified during 40 cycles of 50° C. for 2 minutes, 95° C. for 10 minutes, 15 seconds, and 60° C. for 1 minute. Each individual experiment was performed three times, in duplicate. Relative expression of the target genes was analyzed by normalizing to the housekeeping gene β-Actin and selected results are shown in FIG. 2.

Immunohistochemistry: Single label immunohistochemistry was performed on formalin-fixed, paraffin embedded tissue sections using mouse monoclonal synaptopodin antibody clone G1D4 at 1:80 dilution (Acris Antibodies, San Diego, Calif.) and anillin rabbit polyclonal antibody at 1:100 and 1:200 (Bethyl Laboratories, Inc, Montgomery Tex.)), Four micrometer formalin-fixed, paraffin embedded tissue sections were programmed and processed on the Bond III automated slide stainer (Leica Microsystems, Buffalo Grove Ill.) including paraffin removal, heat induced epitope retrieval (Epitope Retrieval Solution number two for 20 minutes) and application of the primary antibody. Detection of the bound antibody was accomplished with the use of Bond Refine horseradish peroxidase labeled detection system (Leica Microsystems). Prior to the application of chromogen, the tissue sections were treated with hydrogen peroxide to block endogenous peroxidase activity. The bound immune complex was visualized with the on-line application of diaminobenzidine (DAB) and subsequently counter-stained with hematoxylin. Completed slides were dehydrated with alcohol, cleared with xylene and cover slipped with a permanent mounting media. Double stain immune-histochemistry was manually performed on formalin-fixed, paraffin embedded tissue sections by preparing antibody cocktails of synaptopodin (1:80 dilution) and anillin (1:100 dilution). Following paraffin removal, clearing, quenching of endogenous peroxidase activity and hydration, tissue sections were pretreated for twenty minutes in 99° C. Tris/EDTA epitope retrieval solution. Anillin/synaptopodin antibody cocktails were prepared, applied to the tissue sections and incubated for sixty minutes at room temperature. Detection of the bound antibodies was accomplished by applying Mach 2 Kit #1 or Mach 2 Kit #2 (Biocare Medical, Concord Calif.). Mach 2 Kit #1 is a cocktail of HRP labeled anti-rabbit IgG and alkaline phosphatase labeled anti-mouse Ig's while Mach 2 Kit #2 consists of HRP labeled anti-mouse and AP labeled anti-rabbit. Comparative color combinations of tissue sections for anillin/synaptopodin double stain IHC was performed in order to obtain the best color combination. The labeled antibody complex was detected by sequential application of chromogenic substrates DAB and Fast Red. Tissue sections were counter stained with hematoxylin and air dried prior to cover slipping with a permanent mounting medium and results are depicted in FIGS. 2C and 2D.

Subcellular Localization of Anillin in Immortalized Podocytes

Immunofluorescence: Immortalized human podocytes were cultured on collagen I-coated coverslips (BD Biosciences) and treated as indicated. Cells were then fixed with 4% paraformaldehyde in PBS (Sigma). Podocytes were then washed twice with ice cold PBS prior to permeabilization with 0.1% Triton X-100 in PBS. Cells were then washed with ice cold PBS twice and blocked with buffer containing 5% goat serum prior to incubation with rabbit polyclonal Anillin antibody (Bethyl Laboratories, Montgomery, Tex.), mouse monoclonal Rho A antibody (Abeam), mouse monoclonal nephrin antibody (Abgent, Inc, San Diego, Calif.), and mouse polyclonal CD2AP antibody (Santa Cruz Biotechnologies, Santa Cruz, Calif.) overnight at 4° C. Cells were then washed with ice cold PBS and secondary Alexa Flora 488 antibody was applied (Invitrogen) at a concentration of 1:1,000 for 1 hour at room temperature. Cells were then washed 4 times with room temperature PBS prior to addition of DAN stain at a concentration of 1:10,000 diluted in PBS. Podocyte immunofluorescence imaging was performed using a Zeiss AxioImager and the MetaMorph® Bioimaging Software. Representative photographs are shown in FIG. 3.

Wound Healing Assay siRNA Transfections: Conditionally immortalized human podocytes were transfected with Signal Silence® siRNA for Anillin (Applied Biosystems, Carlsbad, Calif.) using Lipofectamine RNAiMax™ (Invitrogen) per manufacturer's protocol. Briefly, siRNA/RNAiMax complexes were formed by incubation in a 1:3 ratio for 20 minutes at room temperature. Cultured podocytes were trypsinized with 0.05% trypsin/EDTA solution (Invitrogen) for 5 minutes at 37° C. Cells were the centrifuged at 1500 rpm for 5 min and resuspended in supplemented RPMI 1640 maintenance media. Podocytes were then mixed with siRNA/RNAiMax complexes and plated at 37° C. for 24 hours. Culture media was then changed and cells were treated and harvested within 48 hours. FIG. 4A shows the levels of Anillin as compared to β-actin in treated and untreated cells.

Scratch Wound Healing Assay: Conditionally immortalized human podocyte cultures were treated with inhibitors as indicated 2 hours prior to wound creation. Cell monolayers were then washed and scratch wounds were applied using 1000 μL pipet tip. Podocytes were then washed once again before treatment with inhibitors and agonists were applied as indicated. Podocytes were then imaged using an EVOS® microscope at time 0 immediately after wound creation. Cells were then returned to growth restrictive conditions for 24 hours prior to final imaging of wound healing. Results are shown in FIGS. 4B and 4C.

Zebrafish stocks and injections: Zebrafish (AB) were grown and mated at 28.5° C., and embryos were kept and handled in standard E3 solution as previously described. Morpholinos were injected in fertilized eggs in the one to four-cell stage using a Nanoject II injection device (Drummond Scientific, Broomall, Pa.). The following morpholinos were designed and ordered from GeneTools (Philomath, Oreg.) control, 5'-CCTCTTACCTCAGTTACAATTTATA-3' (SEQ ID NO: 208) and Anillin, 5'-GGCCCCT-GAAAACAGTTGTATAGAT-3' (SEQ ID NO: 209). Morpholino injections were carried out with concentrations ranging from 50 to 100 μM with an injection volume of 4.6 nl in injection buffer (100 mM KCl, 0.1% phenol red). Embryos were monitored for the development of phenotype until 120 h post fertilization (hpf). Phenotype was scored 1 to 4, relative to the amount of edema present.

Eye Assays: Two types of Eye Assays were performed to assess proteinuria. At 50-55 h post morpholino injection, remaining chorions were manually removed from all embryos. For one group, cardinal vein injections were performed as described by Hentschel et al., 2007 Am J Physiol Renal Physiol 293: F1746-50. Briefly, 4.6 μL, FITC-labeled 70-kDa dextran (Molecular Probes, Eugene, Oreg.) was injected into the cardiac venous sinus. For this injection, zebrafish were anesthetized in a 1:20 to 1:100 dilution of 4 mg/ml Tricaine (MESAB: ethyl-m-aminobenzoate methanesulfonate, 1% Na2HPO4, pH 7.0) (Sigma-Aldrich) and positioned on their backs in a 1% agarose injection mold. After the injection, fish were returned to egg water, where they quickly regained motility. The results are shown in FIG. 5B.

A second assay was performed measuring endogenous fluorescent intensity of retinal blood vessels in Tg (1-fabp: DBP-EGFP) zebrafish (gift from J. Xie and B. Anand-Apte, Cleveland, Ohio) at 96, 120 and 144 hrs post morpholino injection. These animal protocols were approved by the Mount Desert Island Biological Laboratory (MDIBL) Animal Care Committee. Results are shown in FIG. 5C.

Image analysis. For eye assay measurements zebrafish larvae were transferred into individual wells of a 96-well plate (Fisher, Pittsburgh, Pa.). Fish were anesthetized with Tricane and sequential images of live fish were generated using a Zeiss inverted microscope (Axiovert 200) connected to an AxioCam MRm charge-coupled device camera, and images were taken with fixed exposure times and gain using the Axio Vision release 4.5 SP1 software package. The maximum fluorescence intensities of images of the pupil of the fish were measured using NIH's ImageJ application and reported in relative units of brightness.

Example 2

Wilms Tumor 1 (WT1) Substitution Associated with FSGS

We have identified the cause of the genetic mutation in the US kindred (Duke Family 6524—FIG. 6). WT1 is the gene encoding for the Wilms' Tumor 1 protein (the nucleotide sequence of wild-type WT-1 is provided in SEQ ID NO: 211 and the wild-type amino acid sequence is provided in SEQ ID NO: 4). We found an R458Q mutation in Duke Family 6524 on chromosome 11p13 (FIG. 7); transcript variant D, NM_024426.3. The R458Q (C1373T) variant is located in exon 9 which is the 3rd zinc-finger motif of WT1 (FIG. 8, red arrow, from http://useast.ensembl.org—transcript variant D, NM_024426.3).

Wilms' Tumor or nephroblastoma was first described by Max Wilms in 1899. It accounts for ~7.5% of all childhood tumors and occurs in 1:10,000 children. WT1 tumors are also associated with a number of congenital syndromes such as Denys-Drash, Frasier and Beckwith-Wiedemann syndrome. Homozygous mutations in the WT1 gene have been found to account for Wilms' tumor in 5-10% of cases. WT1 has between 24 and 36 isoforms. While the exon 5, +/− KTS (an insertion/deletion variant), in-frame CTG start site and internal ATG start codon isoforms are best known, there appear to be many others. WT1 is a transcription factor and has an essential role in the normal development of the urogenital system as well as cellular development, survival and apoptosis. It is thought to be integral during kidney development for mesenchymal-epithelial transformation. It contains four zinc-finger motifs at the C-terminus and a proline/glutamine-rich DNA-binding domain at the N-terminus. WT1 appears to have many functions, including acting as a tumor suppressor, an oncogene, transcriptional regulator, involved in RNA metabolism as well as pro-vs. anti-differentiation. In the kidney, WT1 is a podocyte-specific gene. WT1 is upregulated in the kidney and is upregulated during podocyte differentiation and enhances expression of podocyte differentiation markers such as nephrin and podocalyxin and the cell cycle regulator p21 and represses expression of PAX2 and egr-1 (early growth response element-1) resulting in growth suppression and inhibition of proliferation. Mice that lack WT1 lack kidneys, gonads and spleens and die at mid-gestation.

We believe this R458Q alteration to be the genetic mutation causing FSGS in this family. The variant was not found in >1600 control chromosomes. A search of all available public SNP (single nucleotide polymorphisms) databases did not reveal evidence of this being a previously known polymorphism. The R458Q variant segregates with disease in Family 6524. The arginine of interest is conserved from human to Stickleback (FIG. 9—from http://genome.cse.ucsc.edu). Additionally, it was found to be probably damaging by PolyPhen in silica modeling with a score of 0947/1.00.

Little is known about the pathogenesis of familial FSGS and nephrotic syndromes. There are several known genes which cause hereditary FSGS and nephrotic syndromes (nephrin, podocin, ACTN4, TRPC6, PLCE1, INF2, CD2AP, etc). This WT1 R458Q mutation as a cause for familial FSGS is completely novel. The knowledge that this gene is a cause of familial FSGS may help further elucidate the origin and development of this pathological entity. Furthermore, specific molecular targets may eventually be identified to aid in the treatment of FSGS.

To further analyze the effects of the WT1 R458Q variant on WT1 function and begin to understand its role in development of FSGS in this family. Human embryonic kidney cells (HEK293) were transfected with human wild-type WT1 or mutagenized WT1 R458Q. The wild-type WT1 was cloned from a human kidney cDNA library. The Western blot showing the relative protein expression and mobility is shown in FIG. 10 and β-actin served as a loading control.

The abundance and mobility of the WT1$^{R458Q}$ were comparable to those of the WT1$^{WT}$.

The transfected HEK293 cells were then subjected to immunofluorescence analysis. To assess the spatial distribution of WT1 and associated podocyte proteins, immunofluorescence and colocalization studies of transfected HEK293 cells were performed using antibodies to WT1, F-actin, TRPC6, CD2AP and nephrin. There was no evidence of mislocalization of these proteins between mutated or wild-type cells, except with nephrin (FIG. 11). There appears to be mislocalization of both WT1 and nephrin to the nucleus in the mutated cells as opposed to the wild-type. These results suggest that the WT1$^{R458Q}$ mutation caused mislocalization of nephrin.

To further investigate the transformed HEK293 cells, mRNA expression of various transcripts was assessed by rtPCR. As shown in Table 3 below, there was evidence for changes in various important podocyte gene mRNA transcription in HEK293 cells transfected with either WT1$^{R458Q}$ or WT1$^{WT}$. RNA was isolated from HEK293 cells transfected with either wild-type or mutated WT1 at 48 hours and subjected to rtPCR as previously described. There was no difference in mRNA expression of WT1$^{R458Q}$ or WT1$^{WT}$ in HEK293 cells at 48 hours. There was also no difference in TRPC6 or CD2AP expression; however, there was a significant difference in nephrin and synaptopodin mRNA expression and expression of both was downregulated in the R458Q expressing HEK293 cell. We also compared the levels of apoptosis and cell death in the transfected HEK293 cells. There was an increase in apoptosis and cell death in the R458Q mutated HEK293 cells vs. the wild-type cells.

TABLE 3 mRNA Expression (rtPCR)

|  | WT | R458Q | P value |
| --- | --- | --- | --- |
| TRPC6 | 0.73 | 0.84 | 0.89 |
| Nephrin | 11.92 | 7.25 | 0.011 |
| Synaptopodin | 6.7 | 3.31 | 0.00072 |
| CD2AP | 1.61 | 1.82 | 0.19 |

TABLE 4

Apoptosis/Cell Death

| Table 2. WT1 WT vs. Mut FACS analysis | Mean | Standard Deviation | Sample Size | SEM | P Value |
| --- | --- | --- | --- | --- | --- |
| WT1 - WT Apoptosis | 6.86 | 1.3 | 15 | 0.34 | <0.01 |
| WT1 - Mut Apoptosis | 9.22 | 2.45 | 11 | 0.74 |  |
| WT1 - WT Dead | 8.27 | 1.39 | 15 | 0.36 | <0.001 |
| WT1 - Mut Dead | 11.48 | 2.49 | 11 | 0.75 |  |

To further characterize the WT1 R458Q mutation, a WT1 knockdown experiment was performed in zebrafish. The experiments were carried out as described below and results are shown in FIG. 12, Reduced WT1 expression during zebrafish development led to significant cardiac yolk edema, increased dextran extravasation in the trunk vascular network, as well as increased dextran dispersion in the retinal vascular network. These data suggest that WT1 knockdown causes glomerular filtration defects in the zebrafish.

Methods

Case ascertainment: Institutional Review Board approval was obtained from Duke University Medical Center (Durham, N.C., USA). Families with FSGS were identified through the international Collaborative Group on Familial FSGS. Inclusion in this analysis required at least one individual with biopsy-proven FSGS and a second family member with FSGS and/or ESKD. Clinical evaluation of these kindreds included a full family history, physical examination, urinalysis with qualitative or quantitative proteinuria and serum creatinine assay when appropriate. Renal pathology reports and slides were reviewed when available for affected individuals. Individuals were classified as follows: Affected: If they required dialysis, had undergone renal transplantation, had 2+ to 4+ proteinuria by qualitative urinalysis ≥500 mg/24 hours on quantitative urinalysis or had a renal biopsy demonstrating FSGS without evidence of other systemic diseases known to cause FSGS or chronic renal failure. Probably affected: If they had trace to 1+ proteinuria on qualitative urinalysis. These individuals were categorized as unknown in the linkage analysis. Unaffected: Individuals who had no detectable proteinuria on qualitative urinalysis and unrelated married-in spouses, We excluded mutations in known FSGS genes (NPHS1, NPHS2, PLCE1, ACTN4, TRPC6, and INF2) in all the affected individuals.

Linkage analysis: A genome-wide linkage scan was performed using the Illumina Infinum II HumanLinkage-24 genotyping beadchip assay (Illumina Inc., San Diego, Calif.). This assay contained over 5000 single nucleotide polymorphisms (SNPs) with an average genetic distance of 0.58 cM and call rate >99%. Two-point LOD scores were calculated for all the 5000 SNP markers. A LOD score (the logarithm of the odds of linkage) of ≥3.0 is considered significant evidence for linkage and ≤−2.0 is significant evidence for exclusion of linkage to the region, Values between these are classified as "suggestive" LOD scores. A rare dominant model was assumed. A conservative low-penetrance "affecteds-only" analysis was performed to ensure that results obtained were not due to asymptomatic individuals who were non-penetrant carriers of the FSGS gene. The linkage analysis suggested the gene was on chromosome 11.

Whole exome sequencing: We performed whole exome sequencing on the proband. DNA was fragmented using the E220 ultrasonicator to obtain fragment size between 350-450 bases. The library was prepared with the Illumina Truseq library according to the manufacturer's instruction. Truseq exome enrichment kit was used according to the protocol provided by Illumina. The sample from the proband was hybridized to biotin labeled probes, which binds the region of interest in complementary fashion. The targeted region was then enriched with streptavidin beads, and the product was eluted from the beads. The captured region was sequenced using one lane of Hiseq 2000 sequencer. We target >60 fold reads and machine error was monitored with Hiseq control software (HCS 1.1.37.19). The output was analyzed with the Illumina real time analysis (RTA 1.7.48) software. The reads that passed the quality control test were aligned with the Human Reference genome (HG 19) using the BWA software, SAMtools software was used to merge the sequence reads into consensus genotypes. Variants from the cleaned alignment were called with SAMtools software.

Sanger sequencing: All the potential disease causing variants that were identified genome-wide by both bid chips were confirmed by Sanger sequencing. See FIG. 7 which shows an exemplary chromatogram for affected and unaffected subjects. Briefly both strands of all the variants were sequenced using exon flanking primers. In addition, both strands of all the coding exons of WT1 were sequenced in 100 families with FSGS using the same method and exon primer sequences are listed in Table 5. AU sequences were analyzed with Sequencher software (Gene Codes Corp Ann Arbor, Mich.).

TABLE 5

WT1 Primers

| Primer Name | Primer Sequence | Amplicon | SEQ ID NO: |
|---|---|---|---|
| WT1Exon1-1F | attcacccacccacccac | 507 | 80 |
| WT1Exon1-1R | TGAAGGAGTGAggcggc | | 81 |
| WT1Exon1-2F | TGTGCCCTGCCTGTGAG | 475 | 82 |
| WT1Exon1-2R | TAAGAGCTGCGGTCAAAAGG | | 83 |
| WT1Exon2F | TGGTTCAGACCCACTGCC | 252 | 84 |
| WT1Exon2R | GGAGAGGAGGATAGCACGG | | 85 |
| WT1Exon3F | GGCTCAGGATCTCGTGTCTC | 324 | 86 |
| WT1Exon3R | GTGCCTCCAAGACCCTGC | | 87 |
| WT1Exon4F | TCCATTGCTTTTGAAGAAACAG | 217 | 88 |
| WT1Exon4R | CTTTGAAATGGTTCAAACAGG | | 89 |
| WT1Exon5F | CACTGGATTCTGGGATCTGG | 186 | 90 |
| WT1Exon5R | GCCAGTCAGCAAGGCCTAC | | 91 |
| WT1Exon6F | ATTTCCAAATGGCGACTGTG | 217 | 92 |
| WT1Exon6R | GGCCGGTAAGTAGGAAGAGG | | 93 |
| WT1Exon7F | CAGTGCTCACTCTCCCTCAAG | 289 | 94 |
| WT1Exon7R | CTGGAAAAGGAGCTCTTGAAC | | 95 |
| WT1Exon8F | TTGCCTTTAATGAGATCCCC | 215 | 96 |
| WT1Exon8R | CATGAAATCAACCCTAGCCC | | 97 |
| WT1Exon9F | TGTGGGCCTCACTGTGC | 226 | 98 |
| WT1Exon9R | CTCTCATCACAATTTCATTCCAC | | 99 |
| WT1Exon10F | AATTCAGAGTGGGTGCCTTG | 305 | 100 |
| WT1Exon10R | GAGGAGTGGAGAGTCAGACTTG | | 101 |

In silico prediction of impact of amino acid substitution: The R458Q variant in the WT1 gene was entered into Polyphen 2 software to examine the predicted damaging effect of the amino acid substitution to the function of WT1. The Hum Var-trained version was used which is optimal for Mendelian disorders as it distinguishes mutations with drastic effects from all the remaining human variation, including abundant mildly deleterious alleles. PolyPhen-2 calculates a Naïve Bayes posterior probability that any mutation is damaging and this is represented with a score ranging from 0-1. A mutation was also appraised qualitatively, as benign, possibly damaging, or probably damaging based on the model's false positive rate.

Immunofluorescence and mRNA extraction were performed as described above.

Zebrafish stocks and injections: Zebrafish (AB) were grown and mated at 28.5° C., and embryos were kept and handled in standard E3 solution as previously described. Morpholinos were injected in fertilized eggs in the one- to four-cell stage using a Nanoject II injection device (Drummond Scientific, Broomall, Pa.). Morpholino injections were carried out with concentrations ranging from 50 to 100 µM in injection buffer (100 mM KCl, 0.1% phenol red). Embryos were monitored for the development of phenotype until 6 days post fertilization (hpf). Photographs showing exemplary morphology of the zebrafish receiving the different treatments are shown in FIG. 12. These animal protocols were approved by the Mount Desert Island Biological Laboratory (MDIBL) Animal Care Committee.

Example 3

Tenascin X (TNXB) Substitutions Associated with Congenital Malformation of the Urinary Tract We have also identified the cause of the genetic mutation in the US kindred (Duke Family 6606), We performed whole exome sequencing on two affected members of the family and identified a deleterious heterozygous mutation in Tenascin X (TNXB) that segregates with the disease in the family. We screened eleven additional families and found another deleterious mutation. The wild-type nucleotide sequence is provided as SEQ ID NO: 212 and the wild-type amino acid sequence is provided at SEQ ID NO: 6.

Tenascins are a family of large extracellular matrix proteins. Members of the family include tenascin-XB (TNXB), tenascin-C (TNC), and tenascin-R (TNCR). They all have similar structure and are characterized by four main domains, namely the N terminal assembly domain, EGF like repeats, multiple fibronectin III domains and C-terminal fibrinogen like domain. The fibronectin domains of most tenascins seems to have anti-adhesive properties, thus their activity during development and cell proliferation seems to be their ability to control cell adhesion and migration. TNXB is expressed throughout development in kidney and other organs and also in adult tissues.

Figure 14:
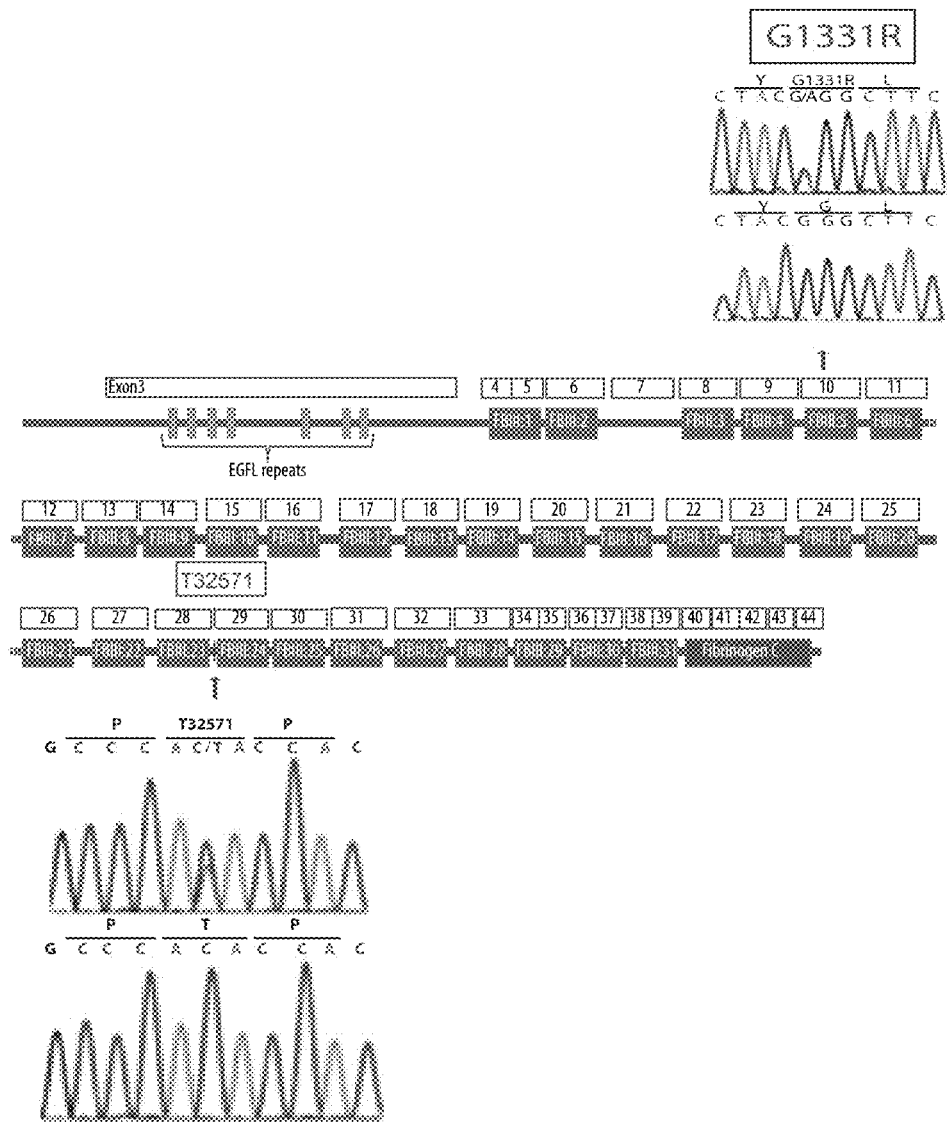
FIG. 14 is a depiction of the genetic sequence of TNXB showing the location of the exons and the identified mutations. The top half of FIG. 14B contains a sequence alignment showing the wild-type sequence at position 1331 is highly conserved between opossum and human and on FIG. 14A the chromatogram of the nucleotide sequence in this area in an affected subject having the G1331R mutation is shown on top of the chromatogram from an unaffected subject. The bottom half of FIG. 14B contains a sequence alignment showing the wild-type sequence at position 3257 which is also highly conserved between opossum and humans. The chromatograms on the bottom of FIG. 14A shows the nucleotide sequence from an affected individual encoding the T3257I mutation as compared to the sequence of an unaffected subject with the wild-type sequence on the bottom.

We believe this is the cause of PVUR in this family based on the following data Exon 29 at position 9770 of TNXB of affected individuals has a C>T nucleotide change. The mutation was found in all affected individuals and segregated with the disease in family 6606 (see FIG. 13). This causes a significant amino acid change of a threonine to an isoleucine (T3257I). En a limited screening of eleven more families with PVUR, we found another change in exon 10 at position 3991 of TNXB a G>A nucleotide change causing a deleterious amino acid change of glycine to an arginine (G1331R) was found. This data suggested that the mutation in TNXB may be a hitherto unrecognized common cause of PVUR. No evidence of the variant was found in greater than 1600 control chromosomes. A search of all available public SNP (single nucleotide polymorphisms) databases did not reveal evidence of the two changes being previously known polymorphisms. The two wild-type amino acids are conserved evolutionarily (FIG. 14). Both changes were found to be probably damaging via in silico modeling with polyphen score of 0.99 out of a maximum damaging score of 1.

Affected family members have asymptomatic joint hypermobility, a finding previously associated with defects in TNXB, but not with PVUR. In silk° modeling, shows that the T3257I mutation is likely to be functionally important due to its location in the linker region between two FnIII domains (FIGS. 14 and 15). The G1331R mutation is located at the end of beta sheet "F", the highly non-conservative amino acid substitution is therefore likely to perturb the positioning of the following loop, and possibly the entire secondary structure of neighboring fibronectin domain (FIGS. 14 and 15).

Figure 16B:
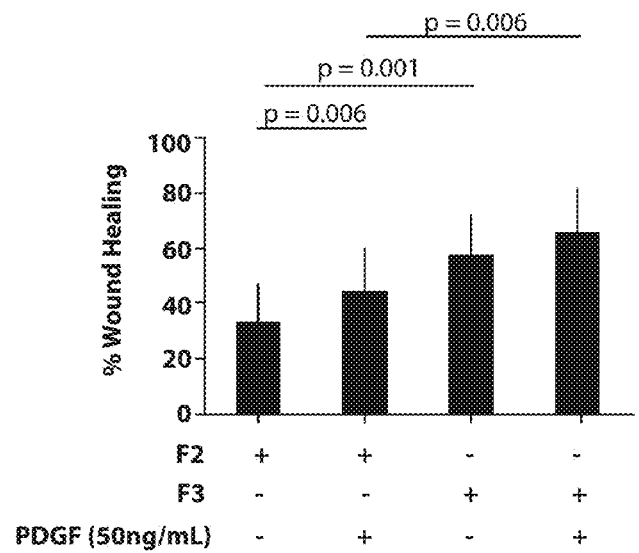
FIG. 16B is a graph showing the quantified results of the photographs of FIG. 16A showing delayed wound healing in affected cells.
Figure 16C:
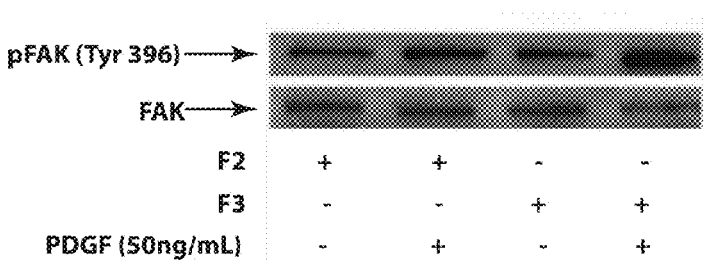
FIG. 16C is photograph showing that the levels of focal adhesion kinase (FAK) and phosphorylated FAK in the cells from affected (TNXB T3257I) cells (F2) and unaffected wild-type TNXB cells (F3). The levels are diminished in the affected cells.

FIG. 16 shows a fibroblast cell culture from an affected individual demonstrated reduced wound healing and motility compared with the cell line from an unaffected individual. Furthermore an assay of phosphorylated Focal adhesion kinase (PFAK) an anti-adhesion and pro motility kinase showed a low level expression in the cell line from affected individual compared with the unaffected person.

FIG. 17 shows that TNXB protein is expressed in human vesicoureteric junction (VUJ) from a normal individual and individual with reflux suggesting that TNXB is important in the development of the VUJ and reflux. TN XB has not been shown to be involved in either of these before.

Methods

Clinical ascertainment: Institutional Review Board approval was obtained from Duke University Medical Center (Durham, N.C., USA). Families were identified from the Pediatric Nephrology and Urology clinic. Family members were classified as follows: Affected: Family members were considered "affected" if they have vesicoureteric reflux on voiding cystourethrogram (VCUG) or reflux nephropathy on intravenous urogram (IVU) (See FIG. 13C). Supportive evidence includes history of recurrent UTI and abnormal findings on renal ultrasonography. Unaffected: Family members were classified as unaffected if they have no detectable VUR on screening VCUG/IVU performed as part of routine clinical care or if they are married ins. Unknown: Vesicoureteric reflux may be asymptomatic, and low grade reflux may also resolve spontaneously. In order to avoid misclassifications, family members who are asymptomatic and those with history of UTI but with no radiological investigations were classified as "unknown". Clinical evaluation of the families included history of UTI, full family history, and physical examination. Radiological studies such as renal utlrasonography, voiding cystourethrogram, intravenous urogram and DMSA scan were reviewed. See FIG. 13A.

Genome Wide Linkage Studies and Fine Mapping: A genome-wide linkage scan was performed using the 10,000 SNP linkage panel (mean marker information 95%) from Illumina Infinum 2.5 million genotyping beadchip assay (Illumina Inc San Diego, Calif.), We used autosomal dominant affecteds-only model in which only affected individuals contributed to the LOD score. We assumed a disease causing allele frequency of 0.01, and we ran simulations assuming the parametric linkage analysis for a dominant model under assumptions of both complete and reduced penetrance. Two-point and multipoint LOD scores were calculated for all 10,000 informative SNPS using the Vitesse statistical program. A LOD score (the logarithm of the odds of linkage) of >3.0 is considered significant evidence for linkage and ≤−2.0 is significant evidence for exclusion of linkage to the region. Values between these are inconclusive and additional data are needed before a conclusion can be reached. For two-point LOD scores >3.0; a 1-lod-unit-down support interval was calculated as an approximation to a 95% confidence interval. A rare dominant model was assumed. A conservative low-penetrance "affecteds-only" analysis was performed to ensure that results obtained were not due to asymptomatic individuals who were non-penetrant carriers of the PVUR gene. Microsatellite markers were identified in the chromosome op region. See FIGS. 13B and 13D. Primers were designed for the microsatellites. The forward primers were pre-labeled with fluorescent dye and a standard PCR reaction was carried out. Genotyping was performed on ABI 3730 Genetic analyzer (Applied Biosystems, Foster, Calif.) at the Center for Human Genetics Duke University sequencing core. Haplotype analysis was carried out as previously described to identify critical recombination events by visual inspection and was confirmed by using SIMWALK software. Under a rare dominant model with reduced penetrance, all affected individuals in a family will share at least one haplotype in common. Thus a candidate interval was excluded when two affected individuals within the pedigree inherited different haplotypes.

Whole Exome Sequencing: We perform whole exome sequencing on the proband and her affected great auntie. DNA was fragmented using the E220 ultrasonicator to obtain fragment size between 350-450 bases. The library was prepared with the Illumina Truseq library according to the manufacturer's instruction. Truseq exome enrichment kit was used according to the protocol provided by Illumina. The samples from the two affected individuals were hybridized to biotin labeled probes, which binds the region of interest in complementary fashion. The targeted regions were then enriched with streptavidin beads, and the product was eluted from the beads. The captured region was sequenced using one lane of Hiseq 2000 sequencer. We target >60 fold reads and machine error was monitored with Hiseq control software (HCS 1.1.37.19). The output was analyzed with the Illumina real time analysis (RTA 1.7.48) software. The reads that passed the quality control test were aligned with the Human Reference genome (HG 19) using the BWA software. SAMtools software was used to merge the sequence reads into consensus genotypes. Variants from the cleaned alignment were called with SAMtools software.

Sanger sequencing: All the potential disease causing variants and exons of TNXB were sequenced by Sanger method. Briefly both strands of all the variants and coding exons of TNXB were sequenced using exon flanking primers. Primer sequences are listed in Table 6. All sequences were analyzed with the Sequencher software (Gene Codes Corp Ann Arbor, Mich.). See FIG. 14.

TABLE 6

Primer sequences for TNXB

| Primer Name | Primer Sequence | SEQ ID NO: |
|---|---|---|
| TNXB-2F | CCTCATGGTGAGGAAGGAGT | 118 |
| TNXB-2R | TCTCCTTTTTGAAGCTGCTCT | 119 |
| TNXB-3.1F | ATGCCACAGTCGTCACCA | 120 |
| TNXB-3.1R | AGAGCAGAGCTGGGCTACAT | 121 |
| TNXB-3.2F | GCAATCGGTTCCAGTGTACC | 122 |
| TNXB-3.2R | GGTCGTTGCGTGTGCTTT | 123 |
| TNXB-3.3F | GCAGTCTTCCCCTGAGTAGC | 124 |
| TNXB-3.3R | GAATGCATTTGCGACACG | 125 |
| TNXB-3.4F | AGGCACACTCCTTGCACAC | 126 |
| TNXB-3.4R | GAGAACGGCGTGTGTGTTT | 127 |
| TNXB-3.5F | TCTTCCTCAGGCTCAGGTCT | 128 |
| TNXB-3.5R | AGGCTACGTGAGTGAGGACTG | 129 |
| TNXB-3.5(2)F | CATGTCTGGATGGCACAGTC | 130 |
| TNXB-3.5(2)R | CTAGATGGGCGGTGTGTGT | 131 |
| TNXB-3.5(3)F | CCCTCTACACACACACACTGG | 132 |
| TNXB-3.5(3)R | GGAAGGCTACGTGAGTGAGG | 133 |
| TNXB-3.6F | CATGCTCTCCCTCCACTCTT | 134 |
| TNXB-3.6R | GTGCAAGGAGTCTTGCCTGT | 135 |
| TNXB-4F | GCCATCTGGACTCAACCAAT | 136 |
| TNXB-4R | CTGAGTAAAAGGGGCTGTGG | 137 |
| TNXB-5F | GGCAGATTCCCTCTCTAGTCC | 138 |
| TNXB-5R | GAGATAAGGGGGATTGAGCA | 139 |
| TNXB-6F | CCAGAAGCATTCAGAGGAGTC | 140 |

TABLE 6-continued

Primer sequences for TNXB

| Primer Name | Primer Sequence | SEQ ID NO: |
|---|---|---|
| TNXB-6R | TGGACTAGAGAGGGAATCTGC | 141 |
| TNXB-7F | CCAATAACCCCAGCTCCTC | 142 |
| TNXB-7R | GGACTGGGGATTCCTTTCTAGT | 143 |
| TNXB-8F | CCCAAAGCACTGAGAAAACC | 144 |
| TNXB-8R | ATCCAGGATGGAGTGAGGTG | 145 |
| TNXB-9F | CTGACACAGCCAGGGTATGA | 146 |
| TNXB-9R | CCTATGTGGGATTTGGCTTC | 147 |
| TNXB-10F | GGCAAAATGAGCTGAGAAGG | 148 |
| TNXB-10R | TGTCAGGCTTCCCAGAAGTT | 149 |
| TNXB-11F | CTGGAGCAAGGAGAGCAACT | 150 |
| TNXB-11R | TTTCCATGGCTGTCATCTGT | 151 |
| TNXB-12F | GGAGGAGTAAAGGGGTCAGG | 152 |
| TNXB-12R | GGTGACAGCGAGACTCCATC | 153 |
| TNXB-13F | CAGGTGGACAAAGGGAAGAC | 154 |
| TNXB-13R | CCCCATCTCAGTTCACAGC | 155 |
| TNXB-14F | CTGGGGCCAAATAATGGTAA | 156 |
| TNXB-14R | GCAGTTCTGGGTTTTTCCAG | 157 |
| TNXB-15F | AAAGGGGCACAAGGAAACTT | 158 |
| TNXB-15R | CCCAGTCTTCCAGAAACAGC | 159 |
| TNXB-16F | TTCTGAAGGCTTCTCCTCCTC | 160 |
| TNXB-16R | TTTCGATTGCTGACTGCTTG | 161 |
| TNXB-17F | ACCAAAGAGCAAGAGGGTGA | 162 |
| TNXB-17R | CTTTCAGATGGCTGGGAGAG | 163 |
| TNXB-18F | AGGAGATGCTGGAGGCTGTA | 164 |
| TNXB-18R | CCAGTCATAGCCTTGGCTTC | 165 |
| TNXB-19F | AGTGAAGGCACCAGCAGAA | 166 |
| TNXB-19R | CCTCAACACCTCCTTGCAG | 167 |
| TNXB-20F | ACCAAAGAGCAAGAGGGTGA | 168 |
| TNXB-20R | GCACCAGCATCCAGACTGT | 169 |
| TNXB-21F | GGTACCCATGAGGGAAAGGT | 170 |
| TNXB-21R | CCACGACGTAAGCACATCC | 171 |
| TNXB-22F | ACTGTGAGCCCCATCAAGAC | 172 |
| TNXB-22R | AGCAAAGCAAGTTGCCCTTA | 173 |
| TNXB-23F | ACCAAAGAGCAAGAGGGTGA | 174 |
| TNXB-23R | GGGCACTTTGTGTTTTGTGA | 175 |
| TNXB-24F | CATGGAAACGTGCAAAAGAA | 176 |
| TNXB-24R | CTTGAAGACCTGAGCACATCC | 177 |
| TNXB-25F | GTCAGTCCTCAGGGAAGTGG | 178 |
| TNXB-25R | AACAAAAGATGGCGAGGAGA | 179 |
| TNXB-26F | CGAAGACTGGAGAGACAGCA | 180 |
| TNXB-26R | CCTTCCTCACAAGACCCAAG | 181 |
| TNXB-27F | CCACCAGTCATCACCAAAGA | 182 |
| TNXB-27R | GTCCTGTTCTTGGGCACTTT | 183 |
| TNXB-28F | AAGAGGTGCCAAGATCCAAA | 184 |
| TNXB-28R | CCAGTCATAGCCTTGGCTTC | 185 |
| TNXB-29F | ATCAGTGGGTGCTGAGGACT | 186 |
| TNXB-29R | GCCGCTAAGAAATGCTCACT | 187 |
| TNXB-30F | GAGGGACTCACTTTCGGAGTT | 188 |
| TNXB-30R | ATAGCAGCCCAGGAAGCTC | 189 |
| TNXB-31F | TTGTCTTCAGCCCAAATGC | 190 |
| TNXB-31R | CTCGATCACAGCAGGGAAG | 191 |
| TNXB-32F | GGCAGAGCTAAAGGCCACT | 192 |
| TNXB-32R | GCCAAGCCTGGAAGATAAAA | 193 |
| TNXB-33F | CCCCGTGAAGTACAAAGACC | 194 |
| TNXB-33R | CAAGCTGGTGTGCTTCTGTC | 195 |
| TNXB-34.35F | CCCTCCTCGTTCTCTCTCAA | 196 |
| TNXB-34.35R | ATCTGCAGAGCGACTTCCAT | 197 |
| TNXB-36.37F | AGGGAAAGCAGGAAGAGGAG | 198 |
| TNXB-36.37R | GAGAGAACGAGGAGGGTGAA | 199 |
| TNXB-38.39F | ATGTCGCAAAACACGTTCAG | 200 |
| TNXB-38.39R | GTAGGGTCTGTGGGGTGTGT | 201 |
| TNXB-40.41F | ACGCGCATGGAGTAGTCAC | 202 |
| TNXB-40.41R | CGTGTCCACCTCTTTCACC | 203 |
| TNXB-42.43F | CTGTTACACTGTGGGGCTGA | 204 |
| TNXB-42.43R | CACAGGGACTGGGGAACTAC | 205 |
| TNXB-44F | AAGGACCCTGGCTCTTCTCT | 206 |
| TNXB-44R | CAGAGGGAGCTGGAGTTGAT | 207 |

In silico prediction of impact of amino acid substitution: The variants in TNXB gene were entered into Polyphen 2 software to examine the predicted damaging effect of the amino acid substitution to the function of TNXB. The HumVar-trained version was used which is optimal for Mendelian disorders as it distinguishes mutations with drastic effects from all the remaining human variation, including abundant mildly deleterious alleles. PolyPhen-2 calculates a Naïve Bayes posterior probability that any mutation is damaging and this is represented with a score ranging from 0-1. A mutation was also appraised qualitatively, as benign, possibly damaging, or probably damaging based on the model's false positive rate.

Structures of the 23rd, 24th and 4th Fibronectin III (FnIII) domains of TNXB were modeled by the I-TASSER server (http://zhanglab.ccmb.med.umich.edu/I-TASSER/). The models of FnIII 4 and 23/24 contain amino acids 1261 to 1350 and 2741 to 3330 of TNXB (E7EPZ9) respectively. See FIG. 15. The TM and the C-score of the predicted model was evaluated. The TM score is between 0 and 1, and is a measure of the difference between the predicted model and the likely native structure. A TM score >0.5 indicates a model of correct topology while a score of <0.17 indicates random similarity. The C-score estimates the quality of the predicted model based on the threading template alignments and structure refinement. C-scores fall between 2 and −5, with higher scores indicating higher confidence; C-scores of 0.5, 1, and 1.5 have an I-TASSER prediction success rate of 94, 97 and 98% respectively. Models were manipulated using PyMOL, (PyMOL Molecular Graphics System, DeLano Scientific, San Carlos, Calif.).

Wound healing assay: Fibroblast cell lines were established by culturing skin biopsy samples in modified DMEM. Cells were harvested and passage once they reach confluence. Confluent fibroblast cell lines were trypsinized and suspended in DMEM growth media. Fibroblast cell lines were treated with platelet derived growth factors for two hours prior to wound creation. Cell monolayers were then washed and scratch wounds were applied using 1000 μL pipet tip. Fibroblasts were then washed and imaged using an EVOS® microscope at time 0 immediately after wound creation. Cells were then returned to growth restrictive conditions for 15 hours prior to final imaging of wound healing as shown in FIG. 16.

Immunohistochemistry: Sections of vesicoureteric junction (VUJ) tissues were obtained from humans with VUR who were undergoing reimplantation and VUJ sections from autopsy samples served as normal controls. Single label immunohistochemistry was performed on formalin-fixed, paraffin embedded tissue sections using rabbit polyclonal TNX antibody at 1:50 dilution. Four micrometer formalin-fixed, paraffin embedded tissue sections were programmed and processed on the Bond III automated slide stainer (Leica Microsystems, Buffalo Grove Ill.) including paraffin removal, heat induced epitope retrieval (Epitope Retrieval Solution number two for 20 minutes) and application, of the primary antibody. Detection of the bound antibody was accomplished with the use of Bond Refine horseradish peroxidase labeled detection system (Leica Microsystems). Prior to the application of chromogen, the tissue sections were treated with hydrogen peroxide to block endogenous peroxidase activity. The bound immune complex was visualized with the on-line application of diaminobenzidine (DAB) and subsequently counter-stained with hematoxylin. Completed slides were dehydrated with alcohol, cleared with xylene and cover slipped with a permanent mounting media. See FIG. 17.

We claim:

1. An isolated polynucleotide comprising a cDNA encoding an anillin (ANLN) polypeptide of SEQ ID NO:1 (comprises R431C substitution).

2. The isolated polynucleotide of claim 1, further comprising an origin of replication.

3. A cell transformed with the polynucleotide of claim 1.

4. A construct comprising the polynucleotide of claim 1.

5. The construct of claim 4, further comprising a promoter operably connected to the polynucleotide.

* * * * *

SEQUENCE LISTING

```
<160> NUMBER OF SEQ ID NOS: 212

<210> SEQ ID NO 1
<211> LENGTH: 1124
<212> TYPE: PRT
<213> ORGANISM: Homo sapiens
<220> FEATURE:
<221> NAME/KEY: misc_feature
<222> LOCATION: (1)..(1124)
<223> OTHER INFORMATION: ANLN with mutation at position 431 (R431C)

<400> SEQUENCE: 1

Met Asp Pro Phe Thr Glu Lys Leu Leu Glu Arg Thr Arg Ala Arg Arg
1               5                   10                  15

Glu Asn Leu Gln Arg Lys Met Ala Glu Arg Pro Thr Ala Ala Pro Arg
            20                  25                  30

Ser Met Thr His Ala Lys Arg Ala Arg Gln Pro Leu Ser Glu Ala Ser
        35                  40                  45

Asn Gln Gln Pro Leu Ser Gly Gly Glu Glu Lys Ser Cys Thr Lys Pro
    50                  55                  60

Ser Pro Ser Lys Lys Arg Cys Ser Asp Asn Thr Glu Val Glu Val Ser
65                  70                  75                  80

Asn Leu Glu Asn Lys Gln Pro Val Glu Ser Thr Ser Ala Lys Ser Cys
                85                  90                  95

Ser Pro Ser Pro Val Ser Pro Gln Val Gln Pro Gln Ala Ala Asp Thr
            100                 105                 110

Ile Ser Asp Ser Val Ala Val Pro Ala Ser Leu Leu Gly Met Arg Arg
        115                 120                 125

Gly Leu Asn Ser Arg Leu Glu Ala Thr Ala Ala Ser Ser Val Lys Thr
    130                 135                 140

Arg Met Gln Lys Leu Ala Glu Gln Arg Arg Trp Asp Asn Asp
145                 150                 155                 160
```

-continued

```
Met Thr Asp Asp Ile Pro Glu Ser Ser Leu Phe Ser Pro Met Pro Ser
                165                 170                 175
Glu Glu Lys Ala Ala Ser Pro Pro Arg Pro Leu Leu Ser Asn Ala Ser
            180                 185                 190
Ala Thr Pro Val Gly Arg Arg Gly Arg Leu Ala Asn Leu Ala Ala Thr
        195                 200                 205
Ile Cys Ser Trp Glu Asp Asp Val Asn His Ser Phe Ala Lys Gln Asn
    210                 215                 220
Ser Val Gln Glu Gln Pro Gly Thr Ala Cys Leu Ser Lys Phe Ser Ser
225                 230                 235                 240
Ala Ser Gly Ala Ser Ala Arg Ile Asn Ser Ser Val Lys Gln Glu
                245                 250                 255
Ala Thr Phe Cys Ser Gln Arg Asp Gly Asp Ala Ser Leu Asn Lys Ala
            260                 265                 270
Leu Ser Ser Ser Ala Asp Asp Ala Ser Leu Val Asn Ala Ser Ile Ser
        275                 280                 285
Ser Ser Val Lys Ala Thr Ser Pro Val Lys Ser Thr Thr Ser Ile Thr
    290                 295                 300
Asp Ala Lys Ser Cys Glu Gly Gln Asn Pro Glu Leu Leu Pro Lys Thr
305                 310                 315                 320
Pro Ile Ser Pro Leu Lys Thr Gly Val Ser Lys Pro Ile Val Lys Ser
                325                 330                 335
Thr Leu Ser Gln Thr Val Pro Ser Lys Gly Leu Ser Arg Glu Ile
            340                 345                 350
Cys Leu Gln Ser Gln Ser Lys Asp Lys Ser Thr Thr Pro Gly Gly Thr
        355                 360                 365
Gly Ile Lys Pro Phe Leu Glu Arg Phe Gly Glu Arg Cys Gln Glu His
    370                 375                 380
Ser Lys Glu Ser Pro Ala Arg Ser Thr Pro His Arg Thr Pro Ile Ile
385                 390                 395                 400
Thr Pro Asn Thr Lys Ala Ile Gln Glu Arg Leu Phe Lys Gln Asp Thr
                405                 410                 415
Ser Ser Ser Thr Thr His Leu Ala Gln Gln Leu Lys Gln Glu Cys Gln
            420                 425                 430
Lys Glu Leu Ala Cys Leu Arg Gly Arg Phe Asp Lys Gly Asn Ile Trp
        435                 440                 445
Ser Ala Glu Lys Gly Gly Asn Ser Lys Ser Lys Gln Leu Glu Thr Lys
    450                 455                 460
Gln Glu Thr His Cys Gln Ser Thr Pro Leu Lys Lys His Gln Gly Val
465                 470                 475                 480
Ser Lys Thr Gln Ser Leu Pro Val Thr Glu Lys Val Thr Glu Asn Gln
                485                 490                 495
Ile Pro Ala Lys Asn Ser Ser Thr Glu Pro Lys Gly Phe Thr Glu Cys
            500                 505                 510
Glu Met Thr Lys Ser Ser Pro Leu Lys Ile Thr Leu Phe Leu Glu Glu
        515                 520                 525
Asp Lys Ser Leu Lys Val Thr Ser Asp Pro Lys Val Glu Gln Lys Ile
    530                 535                 540
Glu Val Ile Arg Glu Ile Glu Met Ser Val Asp Asp Asp Ile Asn
545                 550                 555                 560
Ser Ser Lys Val Ile Asn Asp Leu Phe Ser Asp Val Leu Glu Glu Gly
                565                 570                 575
Glu Leu Asp Met Glu Lys Ser Gln Glu Glu Met Asp Gln Ala Leu Ala
```

-continued

```
                580                 585                 590
Glu Ser Ser Glu Glu Gln Glu Asp Ala Leu Asn Ile Ser Ser Met Ser
            595                 600                 605

Leu Leu Ala Pro Leu Ala Gln Thr Val Gly Val Val Ser Pro Glu Ser
            610                 615                 620

Leu Val Ser Thr Pro Arg Leu Glu Leu Lys Asp Thr Ser Arg Ser Asp
625                 630                 635                 640

Glu Ser Pro Lys Pro Gly Lys Phe Gln Arg Thr Arg Val Pro Arg Ala
            645                 650                 655

Glu Ser Gly Asp Ser Leu Gly Ser Glu Asp Arg Asp Leu Leu Tyr Ser
            660                 665                 670

Ile Asp Ala Tyr Arg Ser Gln Arg Phe Lys Glu Thr Glu Arg Pro Ser
            675                 680                 685

Ile Lys Gln Val Ile Val Arg Lys Glu Asp Val Thr Ser Lys Leu Asp
            690                 695                 700

Glu Lys Asn Asn Ala Phe Pro Cys Gln Val Asn Ile Lys Gln Lys Met
705                 710                 715                 720

Gln Glu Leu Asn Asn Glu Ile Asn Met Gln Gln Thr Val Ile Tyr Gln
            725                 730                 735

Ala Ser Gln Ala Leu Asn Cys Cys Val Asp Glu Glu His Gly Lys Gly
            740                 745                 750

Ser Leu Glu Glu Ala Glu Ala Glu Arg Leu Leu Leu Ile Ala Thr Gly
            755                 760                 765

Lys Arg Thr Leu Leu Ile Asp Glu Leu Asn Lys Leu Lys Asn Glu Gly
            770                 775                 780

Pro Gln Arg Lys Asn Lys Ala Ser Pro Gln Ser Glu Phe Met Pro Ser
785                 790                 795                 800

Lys Gly Ser Val Thr Leu Ser Glu Ile Arg Leu Pro Leu Lys Ala Asp
            805                 810                 815

Phe Val Cys Ser Thr Val Gln Lys Pro Asp Ala Ala Asn Tyr Tyr Tyr
            820                 825                 830

Leu Ile Ile Leu Lys Ala Gly Ala Glu Asn Met Val Ala Thr Pro Leu
            835                 840                 845

Ala Ser Thr Ser Asn Ser Leu Asn Gly Asp Ala Leu Thr Phe Thr Thr
            850                 855                 860

Thr Phe Thr Leu Gln Asp Val Ser Asn Asp Phe Glu Ile Asn Ile Glu
865                 870                 875                 880

Val Tyr Ser Leu Val Gln Lys Lys Asp Pro Ser Gly Leu Asp Lys Lys
            885                 890                 895

Lys Lys Thr Ser Lys Ser Lys Ala Ile Thr Pro Lys Arg Leu Leu Thr
            900                 905                 910

Ser Ile Thr Thr Lys Ser Asn Ile His Ser Ser Val Met Ala Ser Pro
            915                 920                 925

Gly Gly Leu Ser Ala Val Arg Thr Ser Asn Phe Ala Leu Val Gly Ser
            930                 935                 940

Tyr Thr Leu Ser Leu Ser Ser Val Gly Asn Thr Lys Phe Val Leu Asp
945                 950                 955                 960

Lys Val Pro Phe Leu Ser Ser Leu Glu Gly His Ile Tyr Leu Lys Ile
            965                 970                 975

Lys Cys Gln Val Asn Ser Ser Val Glu Glu Arg Gly Phe Leu Thr Ile
            980                 985                 990

Phe Glu Asp Val Ser Gly Phe Gly Ala Trp His Arg Arg Trp Cys Val
            995                 1000                1005
```

```
Leu Ser Gly Asn Cys Ile Ser Tyr Trp Thr Tyr Pro Asp Asp Glu
    1010            1015                1020

Lys Arg Lys Asn Pro Ile Gly Arg Ile Asn Leu Ala Asn Cys Thr
    1025            1030                1035

Ser Arg Gln Ile Glu Pro Ala Asn Arg Glu Phe Cys Ala Arg Arg
    1040            1045                1050

Asn Thr Phe Glu Leu Ile Thr Val Arg Pro Gln Arg Glu Asp Asp
    1055            1060                1065

Arg Glu Thr Leu Val Ser Gln Cys Arg Asp Thr Leu Cys Val Thr
    1070            1075                1080

Lys Asn Trp Leu Ser Ala Asp Thr Lys Glu Glu Arg Asp Leu Trp
    1085            1090                1095

Met Gln Lys Leu Asn Gln Val Leu Val Asp Ile Arg Leu Trp Gln
    1100            1105                1110

Pro Asp Ala Cys Tyr Lys Pro Ile Gly Lys Pro
    1115            1120

<210> SEQ ID NO 2
<211> LENGTH: 1124
<212> TYPE: PRT
<213> ORGANISM: Homo sapiens
<220> FEATURE:
<221> NAME/KEY: misc_feature
<222> LOCATION: (1)..(1124)
<223> OTHER INFORMATION: ANLN wild-type sequence

<400> SEQUENCE: 2

Met Asp Pro Phe Thr Glu Lys Leu Leu Glu Arg Thr Arg Ala Arg Arg
1               5                   10                  15

Glu Asn Leu Gln Arg Lys Met Ala Glu Arg Pro Thr Ala Pro Arg
            20                  25                  30

Ser Met Thr His Ala Lys Arg Ala Arg Gln Pro Leu Ser Glu Ala Ser
            35                  40                  45

Asn Gln Gln Pro Leu Ser Gly Gly Glu Glu Lys Ser Cys Thr Lys Pro
    50                  55                  60

Ser Pro Ser Lys Lys Arg Cys Ser Asp Asn Thr Glu Val Glu Val Ser
65                  70                  75                  80

Asn Leu Glu Asn Lys Gln Pro Val Glu Ser Thr Ser Ala Lys Ser Cys
                85                  90                  95

Ser Pro Ser Pro Val Ser Pro Gln Val Gln Pro Gln Ala Ala Asp Thr
            100                 105                 110

Ile Ser Asp Ser Val Ala Val Pro Ala Ser Leu Leu Gly Met Arg Arg
        115                 120                 125

Gly Leu Asn Ser Arg Leu Glu Ala Thr Ala Ala Ser Ser Val Lys Thr
    130                 135                 140

Arg Met Gln Lys Leu Ala Glu Gln Arg Arg Trp Asp Asn Asp Asp
145                 150                 155                 160

Met Thr Asp Asp Ile Pro Glu Ser Ser Leu Phe Ser Pro Met Pro Ser
                165                 170                 175

Glu Glu Lys Ala Ala Ser Pro Pro Arg Pro Leu Leu Ser Asn Ala Ser
            180                 185                 190

Ala Thr Pro Val Gly Arg Arg Gly Arg Leu Ala Asn Leu Ala Ala Thr
        195                 200                 205

Ile Cys Ser Trp Glu Asp Asp Val Asn His Ser Phe Ala Lys Gln Asn
    210                 215                 220
```

-continued

Ser Val Gln Glu Gln Pro Gly Thr Ala Cys Leu Ser Lys Phe Ser Ser
225                 230                 235                 240

Ala Ser Gly Ala Ser Ala Arg Ile Asn Ser Ser Val Lys Gln Glu
        245                 250                 255

Ala Thr Phe Cys Ser Gln Arg Asp Gly Asp Ala Ser Leu Asn Lys Ala
            260                 265                 270

Leu Ser Ser Ser Ala Asp Asp Ala Ser Leu Val Asn Ala Ser Ile Ser
                275                 280                 285

Ser Ser Val Lys Ala Thr Ser Pro Val Lys Ser Thr Ser Ile Thr
290                 295                 300

Asp Ala Lys Ser Cys Glu Gly Gln Asn Pro Glu Leu Leu Pro Lys Thr
305                 310                 315                 320

Pro Ile Ser Pro Leu Lys Thr Gly Val Ser Lys Pro Ile Val Lys Ser
                325                 330                 335

Thr Leu Ser Gln Thr Val Pro Ser Lys Gly Leu Ser Arg Glu Ile
                340                 345                 350

Cys Leu Gln Ser Gln Ser Lys Asp Lys Ser Thr Pro Gly Gly Thr
        355                 360                 365

Gly Ile Lys Pro Phe Leu Glu Arg Phe Gly Glu Arg Cys Gln Glu His
370                 375                 380

Ser Lys Glu Ser Pro Ala Arg Ser Thr Pro His Arg Thr Pro Ile Ile
385                 390                 395                 400

Thr Pro Asn Thr Lys Ala Ile Gln Glu Arg Leu Phe Lys Gln Asp Thr
                405                 410                 415

Ser Ser Ser Thr Thr His Leu Ala Gln Gln Leu Lys Gln Glu Arg Gln
                420                 425                 430

Lys Glu Leu Ala Cys Leu Arg Gly Arg Phe Asp Lys Gly Asn Ile Trp
        435                 440                 445

Ser Ala Glu Lys Gly Gly Asn Ser Lys Ser Lys Gln Leu Glu Thr Lys
        450                 455                 460

Gln Glu Thr His Cys Gln Ser Thr Pro Leu Lys Lys His Gln Gly Val
465                 470                 475                 480

Ser Lys Thr Gln Ser Leu Pro Val Thr Glu Lys Val Thr Glu Asn Gln
                485                 490                 495

Ile Pro Ala Lys Asn Ser Ser Thr Glu Pro Lys Gly Phe Thr Glu Cys
                500                 505                 510

Glu Met Thr Lys Ser Ser Pro Leu Lys Ile Thr Leu Phe Leu Glu Glu
            515                 520                 525

Asp Lys Ser Leu Lys Val Thr Ser Asp Pro Lys Val Glu Gln Lys Ile
530                 535                 540

Glu Val Ile Arg Glu Ile Glu Met Ser Val Asp Asp Asp Ile Asn
545                 550                 555                 560

Ser Ser Lys Val Ile Asn Asp Leu Phe Ser Asp Val Leu Glu Glu Gly
                565                 570                 575

Glu Leu Asp Met Glu Lys Ser Gln Glu Glu Met Asp Gln Ala Leu Ala
            580                 585                 590

Glu Ser Ser Glu Glu Gln Glu Asp Ala Leu Asn Ile Ser Ser Met Ser
        595                 600                 605

Leu Leu Ala Pro Leu Ala Gln Thr Val Gly Val Ser Pro Glu Ser
        610                 615                 620

Leu Val Ser Thr Pro Arg Leu Glu Leu Lys Asp Thr Ser Arg Ser Asp
625                 630                 635                 640

Glu Ser Pro Lys Pro Gly Lys Phe Gln Arg Thr Arg Val Pro Arg Ala

-continued

```
              645                 650                 655
Glu Ser Gly Asp Ser Leu Gly Ser Glu Asp Arg Asp Leu Leu Tyr Ser
              660                 665                 670
Ile Asp Ala Tyr Arg Ser Gln Arg Phe Lys Glu Thr Glu Arg Pro Ser
              675                 680                 685
Ile Lys Gln Val Ile Val Arg Lys Glu Asp Val Thr Ser Lys Leu Asp
              690                 695                 700
Glu Lys Asn Asn Ala Phe Pro Cys Gln Val Asn Ile Lys Gln Lys Met
705                 710                 715                 720
Gln Glu Leu Asn Asn Glu Ile Asn Met Gln Gln Thr Val Ile Tyr Gln
                  725                 730                 735
Ala Ser Gln Ala Leu Asn Cys Cys Val Asp Glu Glu His Gly Lys Gly
                  740                 745                 750
Ser Leu Glu Glu Ala Glu Ala Glu Arg Leu Leu Leu Ile Ala Thr Gly
                  755                 760                 765
Lys Arg Thr Leu Leu Ile Asp Glu Leu Asn Lys Leu Lys Asn Glu Gly
770                 775                 780
Pro Gln Arg Lys Asn Lys Ala Ser Pro Gln Ser Glu Phe Met Pro Ser
785                 790                 795                 800
Lys Gly Ser Val Thr Leu Ser Glu Ile Arg Leu Pro Leu Lys Ala Asp
                  805                 810                 815
Phe Val Cys Ser Thr Val Gln Lys Pro Asp Ala Ala Asn Tyr Tyr Tyr
                  820                 825                 830
Leu Ile Ile Leu Lys Ala Gly Ala Glu Asn Met Val Ala Thr Pro Leu
              835                 840                 845
Ala Ser Thr Ser Asn Ser Leu Asn Gly Asp Ala Leu Thr Phe Thr Thr
850                 855                 860
Thr Phe Thr Leu Gln Asp Val Ser Asn Asp Phe Glu Ile Asn Ile Glu
865                 870                 875                 880
Val Tyr Ser Leu Val Gln Lys Lys Asp Pro Ser Gly Leu Asp Lys Lys
                  885                 890                 895
Lys Lys Thr Ser Lys Ser Lys Ala Ile Thr Pro Lys Arg Leu Leu Thr
                  900                 905                 910
Ser Ile Thr Thr Lys Ser Asn Ile His Ser Ser Val Met Ala Ser Pro
              915                 920                 925
Gly Gly Leu Ser Ala Val Arg Thr Ser Asn Phe Ala Leu Val Gly Ser
              930                 935                 940
Tyr Thr Leu Ser Leu Ser Ser Val Gly Asn Thr Lys Phe Val Leu Asp
945                 950                 955                 960
Lys Val Pro Phe Leu Ser Ser Leu Glu Gly His Ile Tyr Leu Lys Ile
                  965                 970                 975
Lys Cys Gln Val Asn Ser Ser Val Glu Glu Arg Gly Phe Leu Thr Ile
                  980                 985                 990
Phe Glu Asp Val Ser Gly Phe Gly Ala Trp His Arg Arg Trp Cys Val
                  995                 1000                1005
Leu Ser  Gly Asn Cys Ile Ser  Tyr Trp Thr Tyr Pro  Asp Asp Glu
     1010                 1015                1020
Lys Arg  Lys Asn Pro Ile Gly  Arg Ile Asn Leu Ala  Asn Cys Thr
     1025                 1030                1035
Ser Arg  Gln Ile Glu Pro Ala  Asn Arg Glu Phe Cys  Ala Arg Arg
     1040                 1045                1050
Asn Thr  Phe Glu Leu Ile Thr  Val Arg Pro Gln Arg  Glu Asp Asp
     1055                 1060                1065
```

-continued

```
Arg Glu Thr Leu Val Ser Gln Cys Arg Asp Thr Leu Cys Val Thr
    1070            1075                1080

Lys Asn Trp Leu Ser Ala Asp Thr Lys Glu Glu Arg Asp Leu Trp
    1085            1090                1095

Met Gln Lys Leu Asn Gln Val Leu Val Asp Ile Arg Leu Trp Gln
    1100            1105                1110

Pro Asp Ala Cys Tyr Lys Pro Ile Gly Lys Pro
    1115            1120

<210> SEQ ID NO 3
<211> LENGTH: 517
<212> TYPE: PRT
<213> ORGANISM: Homo sapiens
<220> FEATURE:
<221> NAME/KEY: misc_feature
<222> LOCATION: (1)..(517)
<223> OTHER INFORMATION: WT1 with R458Q mutation

<400> SEQUENCE: 3

Met Gln Asp Pro Ala Ser Thr Cys Val Pro Glu Pro Ala Ser Gln His
1               5                   10                  15

Thr Leu Arg Ser Gly Pro Gly Cys Leu Gln Gln Pro Glu Gln Gln Gly
            20                  25                  30

Val Arg Asp Pro Gly Gly Ile Trp Ala Lys Leu Gly Ala Ala Glu Ala
        35                  40                  45

Ser Ala Glu Arg Leu Gln Gly Arg Arg Ser Arg Gly Ala Ser Gly Ser
    50                  55                  60

Glu Pro Gln Gln Met Gly Ser Asp Val Arg Asp Leu Asn Ala Leu Leu
65                  70                  75                  80

Pro Ala Val Pro Ser Leu Gly Gly Gly Gly Cys Ala Leu Pro Val
                85                  90                  95

Ser Gly Ala Ala Gln Trp Ala Pro Val Leu Asp Phe Ala Pro Pro Gly
            100                 105                 110

Ala Ser Ala Tyr Gly Ser Leu Gly Gly Pro Ala Pro Pro Pro Ala Pro
        115                 120                 125

Pro Pro Pro Pro Pro Pro Pro His Ser Phe Ile Lys Gln Glu Pro
    130                 135                 140

Ser Trp Gly Gly Ala Glu Pro His Glu Glu Gln Cys Leu Ser Ala Phe
145                 150                 155                 160

Thr Val His Phe Ser Gly Gln Phe Thr Gly Thr Ala Gly Ala Cys Arg
                165                 170                 175

Tyr Gly Pro Phe Gly Pro Pro Pro Ser Gln Ala Ser Ser Gly Gln
            180                 185                 190

Ala Arg Met Phe Pro Asn Ala Pro Tyr Leu Pro Ser Cys Leu Glu Ser
        195                 200                 205

Gln Pro Ala Ile Arg Asn Gln Gly Tyr Ser Thr Val Thr Phe Asp Gly
    210                 215                 220

Thr Pro Ser Tyr Gly His Thr Pro Ser His His Ala Ala Gln Phe Pro
225                 230                 235                 240

Asn His Ser Phe Lys His Glu Asp Pro Met Gly Gln Gln Gly Ser Leu
                245                 250                 255

Gly Glu Gln Gln Tyr Ser Val Pro Pro Val Tyr Gly Cys His Thr
            260                 265                 270

Pro Thr Asp Ser Cys Thr Gly Ser Gln Ala Leu Leu Leu Arg Thr Pro
        275                 280                 285
```

```
Tyr Ser Ser Asp Asn Leu Tyr Gln Met Thr Ser Gln Leu Glu Cys Met
    290                 295                 300

Thr Trp Asn Gln Met Asn Leu Gly Ala Thr Leu Lys Gly Val Ala Ala
305                 310                 315                 320

Gly Ser Ser Ser Val Lys Trp Thr Glu Gly Gln Ser Asn His Ser
                325                 330                 335

Thr Gly Tyr Glu Ser Asp Asn His Thr Thr Pro Ile Leu Cys Gly Ala
            340                 345                 350

Gln Tyr Arg Ile His Thr His Gly Val Phe Arg Gly Ile Gln Asp Val
        355                 360                 365

Arg Arg Val Pro Gly Val Ala Pro Thr Leu Val Arg Ser Ala Ser Glu
370                 375                 380

Thr Ser Glu Lys Arg Pro Phe Met Cys Ala Tyr Pro Gly Cys Asn Lys
385                 390                 395                 400

Arg Tyr Phe Lys Leu Ser His Leu Gln Met His Ser Arg Lys His Thr
                405                 410                 415

Gly Glu Lys Pro Tyr Gln Cys Asp Phe Lys Asp Cys Glu Arg Arg Phe
            420                 425                 430

Ser Arg Ser Asp Gln Leu Lys Arg His Gln Arg Arg His Thr Gly Val
        435                 440                 445

Lys Pro Phe Gln Cys Lys Thr Cys Gln Gln Lys Phe Ser Arg Ser Asp
450                 455                 460

His Leu Lys Thr His Thr Arg Thr His Thr Gly Lys Thr Ser Glu Lys
465                 470                 475                 480

Pro Phe Ser Cys Arg Trp Pro Ser Cys Gln Lys Lys Phe Ala Arg Ser
                485                 490                 495

Asp Glu Leu Val Arg His His Asn Met His Gln Arg Asn Met Thr Lys
            500                 505                 510

Leu Gln Leu Ala Leu
        515

<210> SEQ ID NO 4
<211> LENGTH: 517
<212> TYPE: PRT
<213> ORGANISM: Homo sapiens
<220> FEATURE:
<221> NAME/KEY: misc_feature
<222> LOCATION: (1)..(517)
<223> OTHER INFORMATION: wild-type WT1

<400> SEQUENCE: 4

Met Gln Asp Pro Ala Ser Thr Cys Val Pro Glu Pro Ala Ser Gln His
1               5                   10                  15

Thr Leu Arg Ser Gly Pro Gly Cys Leu Gln Gln Pro Glu Gln Gln Gly
            20                  25                  30

Val Arg Asp Pro Gly Gly Ile Trp Ala Lys Leu Gly Ala Ala Glu Ala
        35                  40                  45

Ser Ala Glu Arg Leu Gln Gly Arg Ser Arg Gly Ala Ser Gly Ser
    50                  55                  60

Glu Pro Gln Gln Met Gly Ser Asp Val Arg Asp Leu Asn Ala Leu Leu
65                  70                  75                  80

Pro Ala Val Pro Ser Leu Gly Gly Gly Gly Cys Ala Leu Pro Val
                85                  90                  95

Ser Gly Ala Ala Gln Trp Ala Pro Val Leu Asp Phe Ala Pro Pro Gly
            100                 105                 110

Ala Ser Ala Tyr Gly Ser Leu Gly Gly Pro Ala Pro Pro Pro Ala Pro
```

```
              115                 120                 125
        Pro Pro Pro Pro Pro Pro Pro His Ser Phe Ile Lys Gln Glu Pro
            130                 135                 140

Ser Trp Gly Gly Ala Glu Pro His Glu Glu Gln Cys Leu Ser Ala Phe
        145                 150                 155                 160

Thr Val His Phe Ser Gly Gln Phe Thr Thr Ala Gly Ala Cys Arg
                        165                 170                 175

Tyr Gly Pro Phe Gly Pro Pro Pro Ser Gln Ala Ser Ser Gly Gln
                    180                 185                 190

Ala Arg Met Phe Pro Asn Ala Pro Tyr Leu Pro Ser Cys Leu Glu Ser
                    195                 200                 205

Gln Pro Ala Ile Arg Asn Gln Gly Tyr Ser Thr Val Thr Phe Asp Gly
                    210                 215                 220

Thr Pro Ser Tyr Gly His Thr Pro Ser His His Ala Ala Gln Phe Pro
        225                 230                 235                 240

Asn His Ser Phe Lys His Glu Asp Pro Met Gly Gln Gln Gly Ser Leu
                        245                 250                 255

Gly Glu Gln Gln Tyr Ser Val Pro Pro Val Tyr Gly Cys His Thr
                    260                 265                 270

Pro Thr Asp Ser Cys Thr Gly Ser Gln Ala Leu Leu Leu Arg Thr Pro
                    275                 280                 285

Tyr Ser Ser Asp Asn Leu Tyr Gln Met Thr Ser Gln Leu Glu Cys Met
        290                 295                 300

Thr Trp Asn Gln Met Asn Leu Gly Ala Thr Leu Lys Gly Val Ala Ala
        305                 310                 315                 320

Gly Ser Ser Ser Val Lys Trp Thr Glu Gly Gln Ser Asn His Ser
                        325                 330                 335

Thr Gly Tyr Glu Ser Asp Asn His Thr Thr Pro Ile Leu Cys Gly Ala
                    340                 345                 350

Gln Tyr Arg Ile His Thr His Gly Val Phe Arg Gly Ile Gln Asp Val
                    355                 360                 365

Arg Arg Val Pro Gly Val Ala Pro Thr Leu Val Arg Ser Ala Ser Glu
                    370                 375                 380

Thr Ser Glu Lys Arg Pro Phe Met Cys Ala Tyr Pro Gly Cys Asn Lys
        385                 390                 395                 400

Arg Tyr Phe Lys Leu Ser His Leu Gln Met His Ser Arg Lys His Thr
                        405                 410                 415

Gly Glu Lys Pro Tyr Gln Cys Asp Phe Lys Asp Cys Glu Arg Arg Phe
                    420                 425                 430

Ser Arg Ser Asp Gln Leu Lys Arg His Gln Arg Arg His Thr Gly Val
                    435                 440                 445

Lys Pro Phe Gln Cys Lys Thr Cys Gln Arg Lys Phe Ser Arg Ser Asp
                    450                 455                 460

His Leu Lys Thr His Thr Arg Thr His Thr Gly Lys Thr Ser Glu Lys
        465                 470                 475                 480

Pro Phe Ser Cys Arg Trp Pro Ser Cys Gln Lys Phe Ala Arg Ser
                        485                 490                 495

Asp Glu Leu Val Arg His His Asn Met His Gln Arg Asn Met Thr Lys
                    500                 505                 510

Leu Gln Leu Ala Leu
                    515

<210> SEQ ID NO 5
```

-continued

```
<211> LENGTH: 4244
<212> TYPE: PRT
<213> ORGANISM: Homo sapiens
<220> FEATURE:
<221> NAME/KEY: misc_feature
<222> LOCATION: (1)..(4244)
<223> OTHER INFORMATION: TNXB with T3257I mutation

<400> SEQUENCE: 5
```

Met Met Pro Ala Gln Tyr Ala Leu Thr Ser Ser Leu Val Leu Leu Val
1               5                   10                  15

Leu Leu Ser Thr Ala Arg Ala Gly Pro Phe Ser Ser Arg Ser Asn Val
            20                  25                  30

Thr Leu Pro Ala Pro Arg Pro Pro Gln Pro Gly Gly His Thr Val
        35                  40                  45

Gly Ala Gly Val Gly Ser Pro Ser Ser Gln Leu Tyr Glu His Thr Val
50                  55                  60

Glu Gly Gly Glu Lys Gln Val Val Phe Thr His Arg Ile Asn Leu Pro
65                  70                  75                  80

Pro Ser Thr Gly Cys Gly Cys Pro Pro Gly Thr Glu Pro Pro Val Leu
                85                  90                  95

Ala Ser Glu Val Gln Ala Leu Arg Val Arg Leu Glu Ile Leu Glu Glu
            100                 105                 110

Leu Val Lys Gly Leu Lys Glu Gln Cys Thr Gly Gly Cys Cys Pro Ala
        115                 120                 125

Ser Ala Gln Ala Gly Thr Gly Gln Thr Asp Val Arg Thr Leu Cys Ser
130                 135                 140

Leu His Gly Val Phe Asp Leu Ser Arg Cys Thr Cys Ser Cys Glu Pro
145                 150                 155                 160

Gly Trp Gly Gly Pro Thr Cys Ser Asp Pro Thr Asp Ala Glu Ile Pro
                165                 170                 175

Pro Ser Ser Pro Pro Ser Ala Ser Gly Ser Cys Pro Asp Asp Cys Asn
            180                 185                 190

Asp Gln Gly Arg Cys Val Arg Gly Arg Cys Val Cys Phe Pro Gly Tyr
        195                 200                 205

Thr Gly Pro Ser Cys Gly Trp Pro Ser Cys Pro Gly Asp Cys Gln Gly
210                 215                 220

Arg Gly Arg Cys Val Gln Gly Val Cys Val Cys Arg Ala Gly Phe Ser
225                 230                 235                 240

Gly Pro Asp Cys Ser Gln Arg Ser Cys Pro Arg Gly Cys Ser Gln Arg
                245                 250                 255

Gly Arg Cys Glu Gly Gly Arg Cys Val Cys Asp Pro Gly Tyr Thr Gly
            260                 265                 270

Asp Asp Cys Gly Met Arg Ser Cys Pro Arg Gly Cys Ser Gln Arg Gly
        275                 280                 285

Arg Cys Glu Asn Gly Arg Cys Val Cys Asn Pro Gly Tyr Thr Gly Glu
290                 295                 300

Asp Cys Gly Val Arg Ser Cys Pro Arg Gly Cys Ser Gln Arg Gly Arg
305                 310                 315                 320

Cys Lys Asp Gly Arg Cys Val Cys Asp Pro Gly Tyr Thr Gly Glu Asp
                325                 330                 335

Cys Gly Thr Arg Ser Cys Pro Trp Asp Cys Gly Glu Gly Gly Arg Cys
            340                 345                 350

Val Asp Gly Arg Cys Val Cys Trp Pro Gly Tyr Thr Gly Glu Asp Cys
        355                 360                 365

-continued

```
Ser Thr Arg Thr Cys Pro Arg Asp Cys Arg Gly Arg Gly Arg Cys Glu
370                 375                 380

Asp Gly Glu Cys Ile Cys Asp Thr Gly Tyr Ser Gly Asp Asp Cys Gly
385                 390                 395                 400

Val Arg Ser Cys Pro Gly Asp Cys Asn Gln Arg Gly Arg Cys Glu Asp
            405                 410                 415

Gly Arg Cys Val Cys Trp Pro Gly Tyr Thr Gly Thr Asp Cys Gly Ser
        420                 425                 430

Arg Ala Cys Pro Arg Asp Cys Arg Gly Arg Gly Arg Cys Glu Asn Gly
            435                 440                 445

Val Cys Val Cys Asn Ala Gly Tyr Ser Gly Glu Asp Cys Gly Val Arg
450                 455                 460

Ser Cys Pro Gly Asp Cys Arg Gly Arg Gly Arg Cys Glu Ser Gly Arg
465                 470                 475                 480

Cys Met Cys Trp Pro Gly Tyr Thr Gly Arg Asp Cys Gly Thr Arg Ala
                485                 490                 495

Cys Pro Gly Asp Cys Arg Gly Arg Gly Arg Cys Val Asp Gly Arg Cys
            500                 505                 510

Val Cys Asn Pro Gly Phe Thr Gly Glu Asp Cys Gly Ser Arg Arg Cys
        515                 520                 525

Pro Gly Asp Cys Arg Gly His Gly Leu Cys Glu Asp Gly Val Cys Val
    530                 535                 540

Cys Asp Ala Gly Tyr Ser Gly Glu Asp Cys Ser Thr Arg Ser Cys Pro
545                 550                 555                 560

Gly Gly Cys Arg Gly Arg Gly Gln Cys Leu Asp Gly Arg Cys Val Cys
                565                 570                 575

Glu Asp Gly Tyr Ser Gly Glu Asp Cys Gly Val Arg Gln Cys Pro Asn
            580                 585                 590

Asp Cys Ser Gln His Gly Val Cys Gln Asp Gly Val Cys Ile Cys Trp
        595                 600                 605

Glu Gly Tyr Val Ser Glu Asp Cys Ser Ile Arg Thr Cys Pro Ser Asn
    610                 615                 620

Cys His Gly Arg Gly Arg Cys Glu Glu Gly Arg Cys Leu Cys Asp Pro
625                 630                 635                 640

Gly Tyr Thr Gly Pro Thr Cys Ala Thr Arg Met Cys Pro Ala Asp Cys
                645                 650                 655

Arg Gly Arg Gly Arg Cys Val Gln Gly Val Cys Leu Cys His Val Gly
            660                 665                 670

Tyr Gly Gly Glu Asp Cys Gly Gln Glu Pro Pro Ala Ser Ala Cys
        675                 680                 685

Pro Gly Gly Cys Gly Pro Arg Glu Leu Cys Arg Ala Gly Gln Cys Val
    690                 695                 700

Cys Val Glu Gly Phe Arg Gly Pro Asp Cys Ala Ile Gln Thr Cys Pro
705                 710                 715                 720

Gly Asp Cys Arg Gly Arg Gly Cys His Asp Gly Ser Cys Val Cys
            725                 730                 735

Lys Asp Gly Tyr Ala Gly Glu Asp Cys Gly Glu Glu Val Pro Thr Ile
        740                 745                 750

Glu Gly Met Arg Met His Leu Leu Glu Glu Thr Thr Val Arg Thr Glu
    755                 760                 765

Trp Thr Pro Ala Pro Gly Pro Val Asp Ala Tyr Glu Ile Gln Phe Ile
770                 775                 780

Pro Thr Thr Glu Gly Ala Ser Pro Pro Phe Thr Ala Arg Val Pro Ser
```

-continued

```
            785                 790                 795                 800
Ser Ala Ser Ala Tyr Asp Gln Arg Gly Leu Ala Pro Gly Gln Glu Tyr
                805                 810                 815

Gln Val Thr Val Arg Ala Leu Arg Gly Thr Ser Trp Gly Leu Pro Ala
                820                 825                 830

Ser Lys Thr Ile Thr Thr Met Ile Asp Gly Pro Gln Asp Leu Arg Val
                835                 840                 845

Val Ala Val Thr Pro Thr Thr Leu Glu Leu Gly Trp Leu Arg Pro Gln
        850                 855                 860

Ala Glu Val Asp Arg Phe Val Val Ser Tyr Val Ser Ala Gly Asn Gln
    865                 870                 875                 880

Arg Val Arg Leu Glu Val Pro Pro Glu Ala Asp Gly Thr Leu Leu Thr
                885                 890                 895

Asp Leu Met Pro Gly Val Glu Tyr Val Val Thr Val Thr Ala Glu Arg
                900                 905                 910

Gly Arg Ala Val Ser Tyr Pro Ala Ser Val Arg Ala Asn Thr Gly Ser
                915                 920                 925

Ser Pro Leu Gly Leu Leu Gly Thr Thr Asp Glu Pro Pro Ser Gly
        930                 935                 940

Pro Ser Thr Thr Gln Gly Ala Gln Ala Pro Leu Leu Gln Arg Pro
945                 950                 955                 960

Gln Glu Leu Gly Glu Leu Arg Val Leu Gly Arg Asp Glu Thr Gly Arg
                965                 970                 975

Leu Arg Val Val Trp Thr Ala Gln Pro Asp Thr Phe Ala Tyr Phe Gln
                980                 985                 990

Leu Arg Met Arg Val Pro Glu Gly  Pro Gly Ala His Glu  Glu Val Leu
                995                 1000                1005

Pro Gly  Asp Val Arg Gln Ala  Leu Val Pro Pro  Pro Pro Gly
        1010                1015                1020

Thr Pro  Tyr Glu Leu Ser Leu  His Gly Val Pro  Gly Gly Lys
        1025                1030                1035

Pro Ser  Asp Pro Ile Ile Tyr  Gln Gly Ile Met Asp  Lys Asp Glu
        1040                1045                1050

Glu Lys  Pro Gly Lys Ser Ser  Gly Pro Pro Arg Leu  Gly Glu Leu
        1055                1060                1065

Thr Val  Thr Asp Arg Thr Ser  Asp Ser Leu Leu Leu  Arg Trp Thr
        1070                1075                1080

Val Pro  Glu Gly Glu Phe Asp  Ser Phe Val Ile Gln  Tyr Lys Asp
        1085                1090                1095

Arg Asp  Gly Gln Pro Gln Val  Val Pro Val Glu Gly  Pro Gln Arg
        1100                1105                1110

Ser Ala  Val Ile Thr Ser Leu  Asp Pro Gly Arg Lys  Tyr Lys Phe
        1115                1120                1125

Val Leu  Tyr Gly Phe Val Gly  Lys Lys Arg His Gly  Pro Leu Val
        1130                1135                1140

Ala Glu  Ala Lys Ile Leu Pro  Gln Ser Asp Pro Ser  Pro Gly Thr
        1145                1150                1155

Pro Pro  His Leu Gly Asn Leu  Trp Val Thr Asp Pro  Thr Pro Asp
        1160                1165                1170

Ser Leu  His Leu Ser Trp Thr  Val Pro Glu Gly Gln  Phe Asp Thr
        1175                1180                1185

Phe Met  Val Gln Tyr Arg Asp  Arg Asp Gly Arg Pro  Gln Val Val
        1190                1195                1200
```

```
Pro Val Glu Gly Pro Glu Arg Ser Phe Val Ser  Ser Leu Asp
1205              1210                1215

Pro Asp His Lys Tyr Arg Phe Thr Leu Phe Gly Ile  Ala Asn Lys
1220              1225                1230

Lys Arg Tyr Gly Pro Leu Thr Ala Asp Gly Thr Thr  Ala Pro Glu
1235              1240                1245

Arg Lys Glu Glu Pro Pro Arg Pro Glu Phe Leu Glu  Gln Pro Leu
1250              1255                1260

Leu Gly Glu Leu Thr Val Thr Gly Val Thr Pro Asp  Ser Leu Arg
1265              1270                1275

Leu Ser Trp Thr Val Ala Gln Gly Pro Phe Asp Ser  Phe Met Val
1280              1285                1290

Gln Tyr Lys Asp Ala Gln Gly Gln Pro Gln Ala Val  Pro Val Ala
1295              1300                1305

Gly Asp Glu Asn Glu Val Thr Val Pro Gly Leu Asp  Pro Asp Arg
1310              1315                1320

Lys Tyr Lys Met Asn Leu Tyr Gly Leu Arg Gly Arg  Gln Arg Val
1325              1330                1335

Gly Pro Glu Ser Val Val Ala Lys Thr Ala Pro Gln  Glu Asp Val
1340              1345                1350

Asp Glu Thr Pro Ser Pro Thr Glu Leu Gly Thr Glu  Ala Pro Glu
1355              1360                1365

Ser Pro Glu Glu Pro Leu Leu Gly Glu Leu Thr Val  Thr Gly Ser
1370              1375                1380

Ser Pro Asp Ser Leu Ser Leu Phe Trp Thr Val Pro  Gln Gly Ser
1385              1390                1395

Phe Asp Ser Phe Thr Val Gln Tyr Lys Asp Arg Asp  Gly Arg Pro
1400              1405                1410

Arg Ala Val Arg Val Gly Gly Lys Glu Ser Glu Val  Thr Val Gly
1415              1420                1425

Gly Leu Glu Pro Gly His Lys Tyr Lys Met His Leu  Tyr Gly Leu
1430              1435                1440

His Glu Gly Gln Arg Val Gly Pro Val Ser Ala Val  Gly Val Thr
1445              1450                1455

Ala Pro Gln Gln Glu Glu Thr Pro Pro Ala Thr Glu  Ser Pro Leu
1460              1465                1470

Glu Pro Arg Leu Gly Glu Leu Thr Val Thr Asp Val  Thr Pro Asn
1475              1480                1485

Ser Val Gly Leu Ser Trp Thr Val Pro Glu Gly Gln  Phe Asp Ser
1490              1495                1500

Phe Ile Val Gln Tyr Lys Asp Lys Asp Gly Gln Pro  Gln Val Val
1505              1510                1515

Pro Val Ala Ala Asp Gln Arg Glu Val Thr Val Tyr  Asn Leu Glu
1520              1525                1530

Pro Glu Arg Lys Tyr Lys Met Asn Met Tyr Gly Leu  His Asp Gly
1535              1540                1545

Gln Arg Met Gly Pro Leu Ser Val Val Ile Val Thr  Ala Pro Leu
1550              1555                1560

Pro Pro Ala Pro Ala Thr Glu Ala Ser Lys Pro Pro  Leu Glu Pro
1565              1570                1575

Arg Leu Gly Glu Leu Thr Val Thr Asp Ile Thr Pro  Asp Ser Val
1580              1585                1590
```

```
Gly Leu Ser Trp Thr Val Pro Glu Gly Glu Phe Asp Ser Phe Val
    1595                1600                1605

Val Gln Tyr Lys Asp Arg Asp Gly Gln Pro Gln Val Val Pro Val
    1610                1615                1620

Ala Ala Asp Gln Arg Glu Val Thr Ile Pro Asp Leu Glu Pro Ser
    1625                1630                1635

Arg Lys Tyr Lys Phe Leu Leu Phe Gly Ile Gln Asp Gly Lys Arg
    1640                1645                1650

Arg Ser Pro Val Ser Val Glu Ala Lys Thr Val Ala Arg Gly Asp
    1655                1660                1665

Ala Ser Pro Gly Ala Pro Pro Arg Leu Gly Glu Leu Trp Val Thr
    1670                1675                1680

Asp Pro Thr Pro Asp Ser Leu Arg Leu Ser Trp Thr Val Pro Glu
    1685                1690                1695

Gly Gln Phe Asp Ser Phe Val Val Gln Phe Lys Asp Lys Asp Gly
    1700                1705                1710

Pro Gln Val Val Pro Val Glu Gly His Glu Arg Ser Val Thr Val
    1715                1720                1725

Thr Pro Leu Asp Ala Gly Arg Lys Tyr Arg Phe Leu Leu Tyr Gly
    1730                1735                1740

Leu Leu Gly Lys Lys Arg His Gly Pro Leu Thr Ala Asp Gly Thr
    1745                1750                1755

Thr Glu Ala Arg Ser Ala Met Asp Asp Thr Gly Thr Lys Arg Pro
    1760                1765                1770

Pro Lys Pro Arg Leu Gly Glu Leu Gln Val Thr Thr Val Thr
    1775                1780                1785

Gln Asn Ser Val Gly Leu Ser Trp Thr Val Pro Glu Gly Gln Phe
    1790                1795                1800

Asp Ser Phe Val Val Gln Tyr Lys Asp Arg Asp Gly Gln Pro Gln
    1805                1810                1815

Val Val Pro Val Glu Gly Ser Leu Arg Glu Val Ser Val Pro Gly
    1820                1825                1830

Leu Asp Pro Ala His Arg Tyr Lys Leu Leu Leu Tyr Gly Leu His
    1835                1840                1845

His Gly Lys Arg Val Gly Pro Ile Ser Ala Val Ala Ile Thr Ala
    1850                1855                1860

Gly Arg Glu Glu Thr Glu Thr Glu Thr Thr Ala Pro Thr Pro Pro
    1865                1870                1875

Ala Pro Glu Pro His Leu Gly Glu Leu Thr Val Glu Glu Ala Thr
    1880                1885                1890

Ser His Thr Leu His Leu Ser Trp Met Val Thr Glu Gly Glu Phe
    1895                1900                1905

Asp Ser Phe Glu Ile Gln Tyr Thr Asp Arg Asp Gly Gln Leu Gln
    1910                1915                1920

Met Val Arg Ile Gly Gly Asp Arg Asn Asp Ile Thr Leu Ser Gly
    1925                1930                1935

Leu Glu Ser Asp His Arg Tyr Leu Val Thr Leu Tyr Gly Phe Ser
    1940                1945                1950

Asp Gly Lys His Val Gly Pro Val His Val Glu Ala Leu Thr Val
    1955                1960                1965

Pro Glu Glu Glu Lys Pro Ser Glu Pro Pro Thr Ala Thr Pro Glu
    1970                1975                1980

Pro Pro Ile Lys Pro Arg Leu Gly Glu Leu Thr Val Thr Asp Ala
```

```
            1985                1990                1995
Thr  Pro  Asp  Ser  Leu  Ser  Leu  Ser  Trp  Thr  Val  Pro  Glu  Gly  Gln
            2000                2005                2010

Phe  Asp  His  Phe  Leu  Val  Gln  Tyr  Arg  Asn  Gly  Asp  Gly  Gln  Pro
            2015                2020                2025

Lys  Ala  Val  Arg  Val  Pro  Gly  His  Glu  Glu  Gly  Val  Thr  Ile  Ser
            2030                2035                2040

Gly  Leu  Glu  Pro  Asp  His  Lys  Tyr  Lys  Met  Asn  Leu  Tyr  Gly  Phe
            2045                2050                2055

His  Gly  Gly  Gln  Arg  Met  Gly  Pro  Val  Ser  Val  Gly  Val  Thr
            2060                2065                2070

Ala  Ala  Glu  Glu  Glu  Thr  Pro  Ser  Pro  Thr  Glu  Pro  Ser  Met  Glu
            2075                2080                2085

Ala  Pro  Glu  Pro  Ala  Glu  Glu  Pro  Leu  Leu  Gly  Glu  Leu  Thr  Val
            2090                2095                2100

Thr  Gly  Ser  Ser  Pro  Asp  Ser  Leu  Ser  Leu  Ser  Trp  Thr  Val  Pro
            2105                2110                2115

Gln  Gly  Arg  Phe  Asp  Ser  Phe  Thr  Val  Gln  Tyr  Lys  Asp  Arg  Asp
            2120                2125                2130

Gly  Arg  Pro  Gln  Val  Val  Arg  Val  Gly  Gly  Glu  Glu  Ser  Glu  Val
            2135                2140                2145

Thr  Val  Gly  Gly  Leu  Glu  Pro  Gly  Arg  Lys  Tyr  Lys  Met  His  Leu
            2150                2155                2160

Tyr  Gly  Leu  His  Glu  Gly  Arg  Arg  Val  Gly  Pro  Val  Ser  Ala  Val
            2165                2170                2175

Gly  Val  Thr  Ala  Pro  Glu  Glu  Glu  Ser  Pro  Asp  Ala  Pro  Leu  Ala
            2180                2185                2190

Lys  Leu  Arg  Leu  Gly  Gln  Met  Thr  Val  Arg  Asp  Ile  Thr  Ser  Asp
            2195                2200                2205

Ser  Leu  Ser  Leu  Ser  Trp  Thr  Val  Pro  Glu  Gly  Gln  Phe  Asp  His
            2210                2215                2220

Phe  Leu  Val  Gln  Phe  Lys  Asn  Gly  Asp  Gly  Gln  Pro  Lys  Ala  Val
            2225                2230                2235

Arg  Val  Pro  Gly  His  Glu  Asp  Gly  Val  Thr  Ile  Ser  Gly  Leu  Glu
            2240                2245                2250

Pro  Asp  His  Lys  Tyr  Lys  Met  Asn  Leu  Tyr  Gly  Phe  His  Gly  Gly
            2255                2260                2265

Gln  Arg  Val  Gly  Pro  Val  Ser  Ala  Val  Gly  Leu  Thr  Ala  Pro  Gly
            2270                2275                2280

Lys  Asp  Glu  Glu  Met  Ala  Pro  Ala  Ser  Thr  Glu  Pro  Pro  Thr  Pro
            2285                2290                2295

Glu  Pro  Pro  Ile  Lys  Pro  Arg  Leu  Glu  Glu  Leu  Thr  Val  Thr  Asp
            2300                2305                2310

Ala  Thr  Pro  Asp  Ser  Leu  Ser  Leu  Ser  Trp  Thr  Val  Pro  Glu  Gly
            2315                2320                2325

Gln  Phe  Asp  His  Phe  Leu  Val  Gln  Tyr  Lys  Asn  Gly  Asp  Gly  Gln
            2330                2335                2340

Pro  Lys  Ala  Thr  Arg  Val  Pro  Gly  His  Glu  Asp  Arg  Val  Thr  Ile
            2345                2350                2355

Ser  Gly  Leu  Glu  Pro  Asp  Asn  Lys  Tyr  Lys  Met  Asn  Leu  Tyr  Gly
            2360                2365                2370

Phe  His  Gly  Gly  Gln  Arg  Val  Gly  Pro  Val  Ser  Ala  Ile  Gly  Val
            2375                2380                2385
```

```
Thr Ala Ala Glu Glu Glu Thr Pro Ser Pro Thr Glu Pro Ser Met
    2390            2395            2400

Glu Ala Pro Glu Pro Pro Glu Glu Pro Leu Leu Gly Glu Leu Thr
    2405            2410            2415

Val Thr Gly Ser Ser Pro Asp Ser Leu Ser Leu Ser Trp Thr Val
    2420            2425            2430

Pro Gln Gly Arg Phe Asp Ser Phe Thr Val Gln Tyr Lys Asp Arg
    2435            2440            2445

Asp Gly Arg Pro Gln Val Val Arg Val Gly Gly Glu Glu Ser Glu
    2450            2455            2460

Val Thr Val Gly Gly Leu Glu Pro Gly Arg Lys Tyr Lys Met His
    2465            2470            2475

Leu Tyr Gly Leu His Glu Gly Arg Arg Val Gly Pro Val Ser Thr
    2480            2485            2490

Val Gly Val Thr Ala Pro Gln Glu Asp Val Asp Glu Thr Pro Ser
    2495            2500            2505

Pro Thr Glu Pro Gly Thr Glu Ala Pro Gly Pro Pro Glu Glu Pro
    2510            2515            2520

Leu Leu Gly Glu Leu Thr Val Thr Gly Ser Ser Pro Asp Ser Leu
    2525            2530            2535

Ser Leu Ser Trp Thr Val Pro Gln Gly Arg Phe Asp Ser Phe Thr
    2540            2545            2550

Val Gln Tyr Lys Asp Arg Asp Gly Arg Pro Gln Ala Val Arg Val
    2555            2560            2565

Gly Gly Gln Glu Ser Lys Val Thr Val Arg Gly Leu Glu Pro Gly
    2570            2575            2580

Arg Lys Tyr Lys Met His Leu Tyr Gly Leu His Glu Gly Arg Arg
    2585            2590            2595

Leu Gly Pro Val Ser Ala Val Gly Val Thr Glu Asp Glu Ala Glu
    2600            2605            2610

Thr Thr Gln Ala Val Pro Thr Met Thr Pro Glu Pro Pro Ile Lys
    2615            2620            2625

Pro Arg Leu Gly Glu Leu Thr Met Thr Asp Ala Thr Pro Asp Ser
    2630            2635            2640

Leu Ser Leu Ser Trp Thr Val Pro Glu Gly Gln Phe Asp His Phe
    2645            2650            2655

Leu Val Gln Tyr Arg Asn Gly Asp Gly Gln Pro Lys Ala Val Arg
    2660            2665            2670

Val Pro Gly His Glu Asp Gly Val Thr Ile Ser Gly Leu Glu Pro
    2675            2680            2685

Asp His Lys Tyr Lys Met Asn Leu Tyr Gly Phe His Gly Gly Gln
    2690            2695            2700

Arg Val Gly Pro Ile Ser Val Ile Gly Val Thr Ala Ala Glu Glu
    2705            2710            2715

Glu Thr Pro Ser Pro Thr Glu Leu Ser Thr Glu Ala Pro Glu Pro
    2720            2725            2730

Pro Glu Glu Pro Leu Leu Gly Glu Leu Thr Val Thr Gly Ser Ser
    2735            2740            2745

Pro Asp Ser Leu Ser Leu Ser Trp Thr Ile Pro Gln Gly His Phe
    2750            2755            2760

Asp Ser Phe Thr Val Gln Tyr Lys Asp Arg Asp Gly Arg Pro Gln
    2765            2770            2775
```

-continued

| | | | | | | | | | | | |
|---|---|---|---|---|---|---|---|---|---|---|---|
| Val | Met 2780 | Arg | Val | Arg | Gly 2785 | Glu | Ser | Glu | Val 2790 | Thr | Val | Gly | Gly |
| Leu | Glu 2795 | Pro | Gly | Arg | Lys 2800 | Tyr | Lys | Met | His 2805 | Leu | Tyr | Gly | Leu | His |
| Glu | Gly 2810 | Arg | Arg | Val | Gly 2815 | Pro | Val | Ser | Thr 2820 | Val | Gly | Val | Thr | Ala |
| Pro | Glu 2825 | Asp | Glu | Ala | Glu 2830 | Thr | Thr | Gln | Ala 2835 | Val | Pro | Thr | Thr | Thr |
| Pro | Glu 2840 | Pro | Pro | Asn | Lys 2845 | Pro | Arg | Leu | Gly 2850 | Glu | Leu | Thr | Val | Thr |
| Asp | Ala 2855 | Thr | Pro | Asp | Ser 2860 | Leu | Ser | Leu | Ser 2865 | Trp | Met | Val | Pro | Glu |
| Gly | Gln 2870 | Phe | Asp | His | Phe 2875 | Leu | Val | Gln | Tyr 2880 | Arg | Asn | Gly | Asp | Gly |
| Gln | Pro 2885 | Lys | Val | Val | Arg 2890 | Val | Pro | Gly | His 2895 | Glu | Asp | Gly | Val | Thr |
| Ile | Ser 2900 | Gly | Leu | Glu | Pro 2905 | Asp | His | Lys | Tyr 2910 | Lys | Met | Asn | Leu | Tyr |
| Gly | Phe 2915 | His | Gly | Gly | Gln 2920 | Arg | Val | Gly | Pro 2925 | Ile | Ser | Val | Ile | Gly |
| Val | Thr 2930 | Ala | Ala | Glu | Glu 2935 | Thr | Pro | Ala | Pro 2940 | Thr | Glu | Pro | Ser |
| Thr | Glu 2945 | Ala | Pro | Glu | Pro 2950 | Pro | Glu | Glu | Pro 2955 | Leu | Leu | Gly | Glu | Leu |
| Thr | Val 2960 | Thr | Gly | Ser | Ser 2965 | Pro | Asp | Ser | Leu 2970 | Ser | Leu | Ser | Trp | Thr |
| Ile | Pro 2975 | Gln | Gly | Arg | Phe 2980 | Asp | Ser | Phe | Thr 2985 | Val | Gln | Tyr | Lys | Asp |
| Arg | Asp 2990 | Gly | Arg | Pro | Gln 2995 | Val | Val | Arg | Val 3000 | Arg | Gly | Glu | Glu | Ser |
| Glu | Val 3005 | Thr | Val | Gly | Gly 3010 | Leu | Glu | Pro | Gly 3015 | Cys | Lys | Tyr | Lys | Met |
| His | Leu 3020 | Tyr | Gly | Leu | His 3025 | Glu | Gly | Gln | Arg 3030 | Val | Gly | Pro | Val | Ser |
| Ala | Val 3035 | Gly | Val | Thr | Ala 3040 | Pro | Lys | Asp | Glu 3045 | Ala | Glu | Thr | Thr | Gln |
| Ala | Val 3050 | Pro | Thr | Met | Thr 3055 | Pro | Glu | Pro | Pro 3060 | Ile | Lys | Pro | Arg | Leu |
| Gly | Glu 3065 | Leu | Thr | Val | Thr 3070 | Asp | Ala | Thr | Pro 3075 | Asp | Ser | Leu | Ser | Leu |
| Ser | Trp 3080 | Met | Val | Pro | Glu 3085 | Gly | Gln | Phe | Asp 3090 | His | Phe | Leu | Val | Gln |
| Tyr | Arg 3095 | Asn | Gly | Asp | Gly 3100 | Gln | Pro | Lys | Ala 3105 | Val | Arg | Val | Pro | Gly |
| His | Glu 3110 | Asp | Gly | Val | Thr 3115 | Ile | Ser | Gly | Leu 3120 | Glu | Pro | Asp | His | Lys |
| Tyr | Lys 3125 | Met | Asn | Leu | Tyr 3130 | Gly | Phe | His | Gly 3135 | Gly | Gln | Arg | Val | Gly |
| Pro | Val 3140 | Ser | Ala | Ile | Gly 3145 | Val | Thr | Glu | Glu 3150 | Glu | Thr | Pro | Ser | Pro |
| Thr | Glu 3155 | Pro | Ser | Thr | Glu 3160 | Ala | Pro | Glu | Ala 3165 | Pro | Glu | Glu | Pro | Leu |
| Leu | Gly | Glu | Leu | Thr | Val | Thr | Gly | Ser | Ser | Pro | Asp | Ser | Leu | Ser |

```
                3170                3175                3180
Leu Ser Trp Thr Val Pro Gln Gly Arg Phe Asp Ser Phe Thr Val
        3185                3190                3195
Gln Tyr Lys Asp Arg Asp Gly Gln Pro Gln Val Val Arg Val Arg
        3200                3205                3210
Gly Glu Glu Ser Glu Val Thr Val Gly Gly Leu Glu Pro Gly Arg
        3215                3220                3225
Lys Tyr Lys Met His Leu Tyr Gly Leu His Glu Gly Gln Arg Val
        3230                3235                3240
Gly Pro Val Ser Thr Val Gly Ile Thr Ala Pro Leu Pro Ile Pro
        3245                3250                3255
Leu Pro Val Glu Pro Arg Leu Gly Glu Leu Ala Val Ala Ala Val
        3260                3265                3270
Thr Ser Asp Ser Val Gly Leu Ser Trp Thr Val Ala Gln Gly Pro
        3275                3280                3285
Phe Asp Ser Phe Leu Val Gln Tyr Arg Asp Ala Gln Gly Gln Pro
        3290                3295                3300
Gln Ala Val Pro Val Ser Gly Asp Leu Arg Ala Val Ala Val Ser
        3305                3310                3315
Gly Leu Asp Pro Ala Arg Lys Tyr Lys Phe Leu Leu Phe Gly Leu
        3320                3325                3330
Gln Asn Gly Lys Arg His Gly Pro Val Pro Val Glu Ala Arg Thr
        3335                3340                3345
Ala Pro Asp Thr Lys Pro Ser Pro Arg Leu Gly Glu Leu Thr Val
        3350                3355                3360
Thr Asp Ala Thr Pro Asp Ser Val Gly Leu Ser Trp Thr Val Pro
        3365                3370                3375
Glu Gly Glu Phe Asp Ser Phe Val Val Gln Tyr Lys Asp Lys Asp
        3380                3385                3390
Gly Arg Leu Gln Val Val Pro Val Ala Ala Asn Gln Arg Glu Val
        3395                3400                3405
Thr Val Gln Gly Leu Glu Pro Ser Arg Lys Tyr Arg Phe Leu Leu
        3410                3415                3420
Tyr Gly Leu Ser Gly Arg Lys Arg Leu Gly Pro Ile Ser Ala Asp
        3425                3430                3435
Ser Thr Thr Ala Pro Leu Glu Lys Glu Leu Pro Pro His Leu Gly
        3440                3445                3450
Glu Leu Thr Val Ala Glu Glu Thr Ser Ser Ser Leu Arg Leu Ser
        3455                3460                3465
Trp Thr Val Ala Gln Gly Pro Phe Asp Ser Phe Val Val Gln Tyr
        3470                3475                3480
Arg Asp Thr Asp Gly Gln Pro Arg Ala Val Pro Val Ala Ala Asp
        3485                3490                3495
Gln Arg Thr Val Thr Val Glu Asp Leu Glu Pro Gly Lys Lys Tyr
        3500                3505                3510
Lys Phe Leu Leu Tyr Gly Leu Leu Gly Gly Lys Arg Leu Gly Pro
        3515                3520                3525
Val Ser Ala Leu Gly Met Thr Ala Pro Glu Glu Asp Thr Pro Ala
        3530                3535                3540
Pro Glu Leu Ala Pro Glu Ala Pro Glu Pro Pro Glu Glu Pro Arg
        3545                3550                3555
Leu Gly Val Leu Thr Val Thr Asp Thr Thr Pro Asp Ser Met Arg
        3560                3565                3570
```

-continued

```
Leu Ser Trp Ser Val Ala Gln Gly Pro Phe Asp Ser Phe Val Val
3575                3580                3585

Gln Tyr Glu Asp Thr Asn Gly Gln Pro Gln Ala Leu Leu Val Asp
3590                3595                3600

Gly Asp Gln Ser Lys Ile Leu Ile Ser Gly Leu Glu Pro Ser Thr
3605                3610                3615

Pro Tyr Arg Phe Leu Leu Tyr Gly Leu His Glu Gly Lys Arg Leu
3620                3625                3630

Gly Pro Leu Ser Ala Glu Gly Thr Thr Gly Leu Ala Pro Ala Gly
3635                3640                3645

Gln Thr Ser Glu Glu Ser Arg Pro Arg Leu Ser Gln Leu Ser Val
3650                3655                3660

Thr Asp Val Thr Thr Ser Ser Leu Arg Leu Asn Trp Glu Ala Pro
3665                3670                3675

Pro Gly Ala Phe Asp Ser Phe Leu Leu Arg Phe Gly Val Pro Ser
3680                3685                3690

Pro Ser Thr Leu Glu Pro His Pro Arg Pro Leu Leu Gln Arg Glu
3695                3700                3705

Leu Met Val Pro Gly Thr Arg His Ser Ala Val Leu Arg Asp Leu
3710                3715                3720

Arg Ser Gly Thr Leu Tyr Ser Leu Thr Leu Tyr Gly Leu Arg Gly
3725                3730                3735

Pro His Lys Ala Asp Ser Ile Gln Gly Thr Ala Arg Thr Leu Ser
3740                3745                3750

Pro Val Leu Glu Ser Pro Arg Asp Leu Gln Phe Ser Glu Ile Arg
3755                3760                3765

Glu Thr Ser Ala Lys Val Asn Trp Met Pro Pro Ser Arg Ala
3770                3775                3780

Asp Ser Phe Lys Val Ser Tyr Gln Leu Ala Asp Gly Gly Glu Pro
3785                3790                3795

Gln Ser Val Gln Val Asp Gly Gln Ala Arg Thr Gln Lys Leu Gln
3800                3805                3810

Gly Leu Ile Pro Gly Ala Arg Tyr Glu Val Thr Val Val Ser Val
3815                3820                3825

Arg Gly Phe Glu Glu Ser Glu Pro Leu Thr Gly Phe Leu Thr Thr
3830                3835                3840

Val Pro Asp Gly Pro Thr Gln Leu Arg Ala Leu Asn Leu Thr Glu
3845                3850                3855

Gly Phe Ala Val Leu His Trp Lys Pro Pro Gln Asn Pro Val Asp
3860                3865                3870

Thr Tyr Asp Val Gln Val Thr Ala Pro Gly Ala Pro Pro Leu Gln
3875                3880                3885

Ala Glu Thr Pro Gly Ser Ala Val Asp Tyr Pro Leu His Asp Leu
3890                3895                3900

Val Leu His Thr Asn Tyr Thr Ala Thr Val Arg Gly Leu Arg Gly
3905                3910                3915

Pro Asn Leu Thr Ser Pro Ala Ser Ile Thr Phe Thr Thr Gly Leu
3920                3925                3930

Glu Ala Pro Arg Asp Leu Glu Ala Lys Glu Val Thr Pro Arg Thr
3935                3940                3945

Ala Leu Leu Thr Trp Thr Glu Pro Pro Val Arg Pro Ala Gly Tyr
3950                3955                3960
```

```
Leu Leu Ser Phe His Thr Pro Gly Gly Gln Asn Gln Glu Ile Leu
    3965                3970                3975

Leu Pro Gly Gly Ile Thr Ser His Gln Leu Leu Gly Leu Phe Pro
    3980                3985                3990

Ser Thr Ser Tyr Asn Ala Arg Leu Gln Ala Met Trp Gly Gln Ser
    3995                4000                4005

Leu Leu Pro Pro Val Ser Thr Ser Phe Thr Thr Gly Gly Leu Arg
    4010                4015                4020

Ile Pro Phe Pro Arg Asp Cys Gly Glu Glu Met Gln Asn Gly Ala
    4025                4030                4035

Gly Ala Ser Arg Thr Ser Thr Ile Phe Leu Asn Gly Asn Arg Glu
    4040                4045                4050

Arg Pro Leu Asn Val Phe Cys Asp Met Glu Thr Asp Gly Gly Gly
    4055                4060                4065

Trp Leu Val Phe Gln Arg Arg Met Asp Gly Gln Thr Asp Phe Trp
    4070                4075                4080

Arg Asp Trp Glu Asp Tyr Ala His Gly Phe Gly Asn Ile Ser Gly
    4085                4090                4095

Glu Phe Trp Leu Gly Asn Glu Ala Leu His Ser Leu Thr Gln Ala
    4100                4105                4110

Gly Asp Tyr Ser Met Arg Val Asp Leu Arg Ala Gly Asp Glu Ala
    4115                4120                4125

Val Phe Ala Gln Tyr Asp Ser Phe His Val Asp Ser Ala Ala Glu
    4130                4135                4140

Tyr Tyr Arg Leu His Leu Glu Gly Tyr His Gly Thr Ala Gly Asp
    4145                4150                4155

Ser Met Ser Tyr His Ser Gly Ser Val Phe Ser Ala Arg Asp Arg
    4160                4165                4170

Asp Pro Asn Ser Leu Leu Ile Ser Cys Ala Val Ser Tyr Arg Gly
    4175                4180                4185

Ala Trp Trp Tyr Arg Asn Cys His Tyr Ala Asn Leu Asn Gly Leu
    4190                4195                4200

Tyr Gly Ser Thr Val Asp His Gln Gly Val Ser Trp Tyr His Trp
    4205                4210                4215

Lys Gly Phe Glu Phe Ser Val Pro Phe Thr Glu Met Lys Leu Arg
    4220                4225                4230

Pro Arg Asn Phe Arg Ser Pro Ala Gly Gly Gly
    4235                4240
```

<210> SEQ ID NO 6
<211> LENGTH: 4244
<212> TYPE: PRT
<213> ORGANISM: Homo sapiens
<220> FEATURE:
<221> NAME/KEY: misc_feature
<222> LOCATION: (1)..(4244)
<223> OTHER INFORMATION: Wild-type TNXB sequence

<400> SEQUENCE: 6

```
Met Met Pro Ala Gln Tyr Ala Leu Thr Ser Ser Leu Val Leu Val
1               5                   10                  15

Leu Leu Ser Thr Ala Arg Ala Gly Pro Phe Ser Ser Arg Ser Asn Val
                20                  25                  30

Thr Leu Pro Ala Pro Arg Pro Pro Gln Pro Gly Gly His Thr Val
            35                  40                  45

Gly Ala Gly Val Gly Ser Pro Ser Ser Gln Leu Tyr Glu His Thr Val
```

```
            50                  55                  60
Glu Gly Gly Glu Lys Gln Val Val Phe Thr His Arg Ile Asn Leu Pro
65                  70                  75                  80

Pro Ser Thr Gly Cys Gly Cys Pro Pro Gly Thr Glu Pro Pro Val Leu
                85                  90                  95

Ala Ser Glu Val Gln Ala Leu Arg Val Arg Leu Glu Ile Leu Glu Glu
            100                 105                 110

Leu Val Lys Gly Leu Lys Glu Gln Cys Thr Gly Gly Cys Cys Pro Ala
        115                 120                 125

Ser Ala Gln Ala Gly Thr Gly Gln Thr Asp Val Arg Thr Leu Cys Ser
130                 135                 140

Leu His Gly Val Phe Asp Leu Ser Arg Cys Thr Cys Ser Cys Glu Pro
145                 150                 155                 160

Gly Trp Gly Gly Pro Thr Cys Ser Asp Pro Thr Asp Ala Glu Ile Pro
                165                 170                 175

Pro Ser Ser Pro Pro Ser Ala Ser Gly Ser Cys Pro Asp Asp Cys Asn
            180                 185                 190

Asp Gln Gly Arg Cys Val Arg Gly Arg Cys Val Cys Phe Pro Gly Tyr
        195                 200                 205

Thr Gly Pro Ser Cys Gly Trp Pro Ser Cys Pro Gly Asp Cys Gln Gly
210                 215                 220

Arg Gly Arg Cys Val Gln Gly Val Cys Val Cys Arg Ala Gly Phe Ser
225                 230                 235                 240

Gly Pro Asp Cys Ser Gln Arg Ser Cys Pro Arg Gly Cys Ser Gln Arg
            245                 250                 255

Gly Arg Cys Glu Gly Gly Arg Cys Val Cys Asp Pro Gly Tyr Thr Gly
        260                 265                 270

Asp Asp Cys Gly Met Arg Ser Cys Pro Arg Gly Cys Ser Gln Arg Gly
        275                 280                 285

Arg Cys Glu Asn Gly Arg Cys Val Cys Asn Pro Gly Tyr Thr Gly Glu
        290                 295                 300

Asp Cys Gly Val Arg Ser Cys Pro Arg Gly Cys Ser Gln Arg Gly Arg
305                 310                 315                 320

Cys Lys Asp Gly Arg Cys Val Cys Asp Pro Gly Tyr Thr Gly Glu Asp
            325                 330                 335

Cys Gly Thr Arg Ser Cys Pro Trp Asp Cys Gly Glu Gly Gly Arg Cys
        340                 345                 350

Val Asp Gly Arg Cys Val Cys Trp Pro Gly Tyr Thr Gly Glu Asp Cys
        355                 360                 365

Ser Thr Arg Thr Cys Pro Arg Asp Cys Arg Gly Arg Gly Arg Cys Glu
370                 375                 380

Asp Gly Glu Cys Ile Cys Asp Thr Gly Tyr Ser Gly Asp Asp Cys Gly
385                 390                 395                 400

Val Arg Ser Cys Pro Gly Asp Cys Asn Gln Arg Gly Arg Cys Glu Asp
            405                 410                 415

Gly Arg Cys Val Cys Trp Pro Gly Tyr Thr Gly Thr Asp Cys Gly Ser
        420                 425                 430

Arg Ala Cys Pro Arg Asp Cys Arg Gly Arg Gly Arg Cys Glu Asn Gly
        435                 440                 445

Val Cys Val Cys Asn Ala Gly Tyr Ser Gly Glu Asp Cys Gly Val Arg
        450                 455                 460

Ser Cys Pro Gly Asp Cys Arg Gly Arg Gly Arg Cys Glu Ser Gly Arg
465                 470                 475                 480
```

-continued

Cys Met Cys Trp Pro Gly Tyr Thr Gly Arg Asp Cys Gly Thr Arg Ala
            485                 490                 495

Cys Pro Gly Asp Cys Arg Gly Arg Gly Arg Cys Val Asp Gly Arg Cys
            500                 505                 510

Val Cys Asn Pro Gly Phe Thr Gly Glu Asp Cys Gly Ser Arg Arg Cys
            515                 520                 525

Pro Gly Asp Cys Arg Gly His Gly Leu Cys Glu Asp Gly Val Cys Val
            530                 535                 540

Cys Asp Ala Gly Tyr Ser Gly Glu Asp Cys Ser Thr Arg Ser Cys Pro
545                 550                 555                 560

Gly Gly Cys Arg Gly Arg Gly Gln Cys Leu Asp Gly Arg Cys Val Cys
            565                 570                 575

Glu Asp Gly Tyr Ser Gly Glu Asp Cys Gly Val Arg Gln Cys Pro Asn
            580                 585                 590

Asp Cys Ser Gln His Gly Val Cys Gln Asp Gly Val Cys Ile Cys Trp
            595                 600                 605

Glu Gly Tyr Val Ser Glu Asp Cys Ser Ile Arg Thr Cys Pro Ser Asn
            610                 615                 620

Cys His Gly Arg Gly Arg Cys Glu Glu Gly Arg Cys Leu Cys Asp Pro
625                 630                 635                 640

Gly Tyr Thr Gly Pro Thr Cys Ala Thr Arg Met Cys Pro Ala Asp Cys
            645                 650                 655

Arg Gly Arg Gly Arg Cys Val Gln Gly Val Cys Leu Cys His Val Gly
            660                 665                 670

Tyr Gly Gly Glu Asp Cys Gly Gln Glu Pro Ala Ser Ala Cys
            675                 680                 685

Pro Gly Gly Cys Gly Pro Arg Glu Leu Cys Arg Ala Gly Gln Cys Val
            690                 695                 700

Cys Val Glu Gly Phe Arg Gly Pro Asp Cys Ala Ile Gln Thr Cys Pro
705                 710                 715                 720

Gly Asp Cys Arg Gly Arg Gly Glu Cys His Asp Gly Ser Cys Val Cys
            725                 730                 735

Lys Asp Gly Tyr Ala Gly Glu Asp Cys Gly Glu Glu Val Pro Thr Ile
            740                 745                 750

Glu Gly Met Arg Met His Leu Leu Glu Glu Thr Thr Val Arg Thr Glu
            755                 760                 765

Trp Thr Pro Ala Pro Gly Pro Val Asp Ala Tyr Glu Ile Gln Phe Ile
            770                 775                 780

Pro Thr Thr Glu Gly Ala Ser Pro Pro Phe Thr Ala Arg Val Pro Ser
785                 790                 795                 800

Ser Ala Ser Ala Tyr Asp Gln Arg Gly Leu Ala Pro Gly Gln Glu Tyr
            805                 810                 815

Gln Val Thr Val Arg Ala Leu Arg Gly Thr Ser Trp Gly Leu Pro Ala
            820                 825                 830

Ser Lys Thr Ile Thr Thr Met Ile Asp Gly Pro Gln Asp Leu Arg Val
            835                 840                 845

Val Ala Val Thr Pro Thr Thr Leu Glu Leu Gly Trp Leu Arg Pro Gln
850                 855                 860

Ala Glu Val Asp Arg Phe Val Val Ser Tyr Val Ser Ala Gly Asn Gln
865                 870                 875                 880

Arg Val Arg Leu Glu Val Pro Pro Glu Ala Asp Gly Thr Leu Leu Thr
            885                 890                 895

-continued

Asp Leu Met Pro Gly Val Glu Tyr Val Val Thr Val Thr Ala Glu Arg
            900                 905                 910

Gly Arg Ala Val Ser Tyr Pro Ala Ser Val Arg Ala Asn Thr Gly Ser
        915                 920                 925

Ser Pro Leu Gly Leu Leu Gly Thr Thr Asp Glu Pro Pro Ser Gly
    930                 935                 940

Pro Ser Thr Thr Gln Gly Ala Gln Ala Pro Leu Leu Gln Gln Arg Pro
945                 950                 955                 960

Gln Glu Leu Gly Glu Leu Arg Val Leu Gly Arg Asp Glu Thr Gly Arg
                965                 970                 975

Leu Arg Val Val Trp Thr Ala Gln Pro Asp Thr Phe Ala Tyr Phe Gln
            980                 985                 990

Leu Arg Met Arg Val Pro Glu Gly Pro Gly Ala His Glu Glu Val Leu
            995                 1000                1005

Pro Gly Asp Val Arg Gln Ala Leu Val Pro Pro Pro Pro Gly
    1010                1015                1020

Thr Pro Tyr Glu Leu Ser Leu His Gly Val Pro Gly Gly Lys
    1025                1030                1035

Pro Ser Asp Pro Ile Ile Tyr Gln Gly Ile Met Asp Lys Asp Glu
    1040                1045                1050

Glu Lys Pro Gly Lys Ser Ser Gly Pro Pro Arg Leu Gly Glu Leu
    1055                1060                1065

Thr Val Thr Asp Arg Thr Ser Asp Ser Leu Leu Leu Arg Trp Thr
    1070                1075                1080

Val Pro Glu Gly Glu Phe Asp Ser Phe Val Ile Gln Tyr Lys Asp
    1085                1090                1095

Arg Asp Gly Gln Pro Gln Val Val Pro Val Glu Gly Pro Gln Arg
    1100                1105                1110

Ser Ala Val Ile Thr Ser Leu Asp Pro Gly Arg Lys Tyr Lys Phe
    1115                1120                1125

Val Leu Tyr Gly Phe Val Gly Lys Lys Arg His Gly Pro Leu Val
    1130                1135                1140

Ala Glu Ala Lys Ile Leu Pro Gln Ser Asp Pro Ser Pro Gly Thr
    1145                1150                1155

Pro Pro His Leu Gly Asn Leu Trp Val Thr Asp Pro Thr Pro Asp
    1160                1165                1170

Ser Leu His Leu Ser Trp Thr Val Pro Glu Gly Gln Phe Asp Thr
    1175                1180                1185

Phe Met Val Gln Tyr Arg Asp Arg Asp Gly Arg Pro Gln Val Val
    1190                1195                1200

Pro Val Glu Gly Pro Glu Arg Ser Phe Val Val Ser Ser Leu Asp
    1205                1210                1215

Pro Asp His Lys Tyr Arg Phe Thr Leu Phe Gly Ile Ala Asn Lys
    1220                1225                1230

Lys Arg Tyr Gly Pro Leu Thr Ala Asp Gly Thr Thr Ala Pro Glu
    1235                1240                1245

Arg Lys Glu Glu Pro Pro Arg Pro Glu Phe Leu Glu Gln Pro Leu
    1250                1255                1260

Leu Gly Glu Leu Thr Val Thr Gly Val Thr Pro Asp Ser Leu Arg
    1265                1270                1275

Leu Ser Trp Thr Val Ala Gln Gly Pro Phe Asp Ser Phe Met Val
    1280                1285                1290

Gln Tyr Lys Asp Ala Gln Gly Gln Pro Gln Ala Val Pro Val Ala

-continued

```
                1295                1300                1305

Gly Asp Glu Asn Glu Val Thr Val Pro Gly Leu Asp Pro Asp Arg
    1310                1315                1320

Lys Tyr Lys Met Asn Leu Tyr Gly Leu Arg Gly Arg Gln Arg Val
1325                1330                1335

Gly Pro Glu Ser Val Val Ala Lys Thr Ala Pro Gln Glu Asp Val
1340                1345                1350

Asp Glu Thr Pro Ser Pro Thr Glu Leu Gly Thr Glu Ala Pro Glu
1355                1360                1365

Ser Pro Glu Glu Pro Leu Leu Gly Glu Leu Thr Val Thr Gly Ser
1370                1375                1380

Ser Pro Asp Ser Leu Ser Leu Phe Trp Thr Val Pro Gln Gly Ser
1385                1390                1395

Phe Asp Ser Phe Thr Val Gln Tyr Lys Asp Arg Asp Gly Arg Pro
1400                1405                1410

Arg Ala Val Arg Val Gly Gly Lys Glu Ser Glu Val Thr Val Gly
1415                1420                1425

Gly Leu Glu Pro Gly His Lys Tyr Lys Met His Leu Tyr Gly Leu
1430                1435                1440

His Glu Gly Gln Arg Val Gly Pro Val Ser Ala Val Gly Val Thr
1445                1450                1455

Ala Pro Gln Gln Glu Glu Thr Pro Pro Ala Thr Glu Ser Pro Leu
1460                1465                1470

Glu Pro Arg Leu Gly Glu Leu Thr Val Thr Asp Val Thr Pro Asn
1475                1480                1485

Ser Val Gly Leu Ser Trp Thr Val Pro Glu Gly Gln Phe Asp Ser
1490                1495                1500

Phe Ile Val Gln Tyr Lys Asp Lys Asp Gly Gln Pro Gln Val Val
1505                1510                1515

Pro Val Ala Ala Asp Gln Arg Glu Val Thr Val Tyr Asn Leu Glu
1520                1525                1530

Pro Glu Arg Lys Tyr Lys Met Asn Met Tyr Gly Leu His Asp Gly
1535                1540                1545

Gln Arg Met Gly Pro Leu Ser Val Val Ile Val Thr Ala Pro Leu
1550                1555                1560

Pro Pro Ala Pro Ala Thr Glu Ala Ser Lys Pro Pro Leu Glu Pro
1565                1570                1575

Arg Leu Gly Glu Leu Thr Val Thr Asp Ile Thr Pro Asp Ser Val
1580                1585                1590

Gly Leu Ser Trp Thr Val Pro Glu Gly Glu Phe Asp Ser Phe Val
1595                1600                1605

Val Gln Tyr Lys Asp Arg Asp Gly Gln Pro Gln Val Val Pro Val
1610                1615                1620

Ala Ala Asp Gln Arg Glu Val Thr Ile Pro Asp Leu Glu Pro Ser
1625                1630                1635

Arg Lys Tyr Lys Phe Leu Leu Phe Gly Ile Gln Asp Gly Lys Arg
1640                1645                1650

Arg Ser Pro Val Ser Val Glu Ala Lys Thr Val Ala Arg Gly Asp
1655                1660                1665

Ala Ser Pro Gly Ala Pro Pro Arg Leu Gly Glu Leu Trp Val Thr
1670                1675                1680

Asp Pro Thr Pro Asp Ser Leu Arg Leu Ser Trp Thr Val Pro Glu
1685                1690                1695
```

-continued

```
Gly Gln Phe Asp Ser Phe Val Val Gln Phe Lys Asp Lys Asp Gly
    1700                1705                1710
Pro Gln Val Val Pro Val Glu Gly His Glu Arg Ser Val Thr Val
    1715                1720                1725
Thr Pro Leu Asp Ala Gly Arg Lys Tyr Arg Phe Leu Leu Tyr Gly
    1730                1735                1740
Leu Leu Gly Lys Lys Arg His Gly Pro Leu Thr Ala Asp Gly Thr
    1745                1750                1755
Thr Glu Ala Arg Ser Ala Met Asp Asp Thr Gly Thr Lys Arg Pro
    1760                1765                1770
Pro Lys Pro Arg Leu Gly Glu Leu Gln Val Thr Thr Val Thr
    1775                1780                1785
Gln Asn Ser Val Gly Leu Ser Trp Thr Val Pro Glu Gly Gln Phe
    1790                1795                1800
Asp Ser Phe Val Val Gln Tyr Lys Asp Arg Asp Gly Gln Pro Gln
    1805                1810                1815
Val Val Pro Val Glu Gly Ser Leu Arg Glu Val Ser Val Pro Gly
    1820                1825                1830
Leu Asp Pro Ala His Arg Tyr Lys Leu Leu Leu Tyr Gly Leu His
    1835                1840                1845
His Gly Lys Arg Val Gly Pro Ile Ser Ala Val Ala Ile Thr Ala
    1850                1855                1860
Gly Arg Glu Glu Thr Glu Thr Glu Thr Thr Ala Pro Thr Pro Pro
    1865                1870                1875
Ala Pro Glu Pro His Leu Gly Glu Leu Thr Val Glu Glu Ala Thr
    1880                1885                1890
Ser His Thr Leu His Leu Ser Trp Met Val Thr Glu Gly Glu Phe
    1895                1900                1905
Asp Ser Phe Glu Ile Gln Tyr Thr Asp Arg Asp Gly Gln Leu Gln
    1910                1915                1920
Met Val Arg Ile Gly Gly Asp Arg Asn Asp Ile Thr Leu Ser Gly
    1925                1930                1935
Leu Glu Ser Asp His Arg Tyr Leu Val Thr Leu Tyr Gly Phe Ser
    1940                1945                1950
Asp Gly Lys His Val Gly Pro Val His Val Glu Ala Leu Thr Val
    1955                1960                1965
Pro Glu Glu Glu Lys Pro Ser Glu Pro Pro Thr Ala Thr Pro Glu
    1970                1975                1980
Pro Pro Ile Lys Pro Arg Leu Gly Glu Leu Thr Val Thr Asp Ala
    1985                1990                1995
Thr Pro Asp Ser Leu Ser Leu Ser Trp Thr Val Pro Glu Gly Gln
    2000                2005                2010
Phe Asp His Phe Leu Val Gln Tyr Arg Asn Gly Asp Gly Gln Pro
    2015                2020                2025
Lys Ala Val Arg Val Pro Gly His Glu Glu Gly Val Thr Ile Ser
    2030                2035                2040
Gly Leu Glu Pro Asp His Lys Tyr Lys Met Asn Leu Tyr Gly Phe
    2045                2050                2055
His Gly Gly Gln Arg Met Gly Pro Val Ser Val Val Gly Val Thr
    2060                2065                2070
Ala Ala Glu Glu Glu Thr Pro Ser Pro Thr Glu Pro Ser Met Glu
    2075                2080                2085
```

-continued

```
Ala Pro Glu Pro Ala Glu Glu Pro Leu Leu Gly Glu Leu Thr Val
2090            2095                2100

Thr Gly Ser Ser Pro Asp Ser Leu Ser Leu Ser Trp Thr Val Pro
2105            2110                2115

Gln Gly Arg Phe Asp Ser Phe Thr Val Gln Tyr Lys Asp Arg Asp
2120            2125                2130

Gly Arg Pro Gln Val Val Arg Val Gly Gly Glu Glu Ser Glu Val
2135            2140                2145

Thr Val Gly Gly Leu Glu Pro Gly Arg Lys Tyr Lys Met His Leu
2150            2155                2160

Tyr Gly Leu His Glu Gly Arg Val Gly Pro Val Ser Ala Val
2165            2170                2175

Gly Val Thr Ala Pro Glu Glu Ser Pro Asp Ala Pro Leu Ala
2180            2185                2190

Lys Leu Arg Leu Gly Gln Met Thr Val Arg Asp Ile Thr Ser Asp
2195            2200                2205

Ser Leu Ser Leu Ser Trp Thr Val Pro Glu Gly Gln Phe Asp His
2210            2215                2220

Phe Leu Val Gln Phe Lys Asn Gly Asp Gly Gln Pro Lys Ala Val
2225            2230                2235

Arg Val Pro Gly His Glu Asp Gly Val Thr Ile Ser Gly Leu Glu
2240            2245                2250

Pro Asp His Lys Tyr Lys Met Asn Leu Tyr Gly Phe His Gly Gly
2255            2260                2265

Gln Arg Val Gly Pro Val Ser Ala Val Gly Leu Thr Ala Pro Gly
2270            2275                2280

Lys Asp Glu Glu Met Ala Pro Ala Ser Thr Glu Pro Pro Thr Pro
2285            2290                2295

Glu Pro Pro Ile Lys Pro Arg Leu Glu Leu Thr Val Thr Asp
2300            2305                2310

Ala Thr Pro Asp Ser Leu Ser Leu Ser Trp Thr Val Pro Glu Gly
2315            2320                2325

Gln Phe Asp His Phe Leu Val Gln Tyr Lys Asn Gly Asp Gly Gln
2330            2335                2340

Pro Lys Ala Thr Arg Val Pro Gly His Glu Asp Arg Val Thr Ile
2345            2350                2355

Ser Gly Leu Glu Pro Asp Asn Lys Tyr Lys Met Asn Leu Tyr Gly
2360            2365                2370

Phe His Gly Gly Gln Arg Val Gly Pro Val Ser Ala Ile Gly Val
2375            2380                2385

Thr Ala Ala Glu Glu Glu Thr Pro Ser Pro Thr Glu Pro Ser Met
2390            2395                2400

Glu Ala Pro Glu Pro Pro Glu Pro Leu Leu Gly Glu Leu Thr
2405            2410                2415

Val Thr Gly Ser Ser Pro Asp Ser Leu Ser Leu Ser Trp Thr Val
2420            2425                2430

Pro Gln Gly Arg Phe Asp Ser Phe Thr Val Gln Tyr Lys Asp Arg
2435            2440                2445

Asp Gly Arg Pro Gln Val Val Arg Val Gly Gly Glu Glu Ser Glu
2450            2455                2460

Val Thr Val Gly Gly Leu Glu Pro Gly Arg Lys Tyr Lys Met His
2465            2470                2475

Leu Tyr Gly Leu His Glu Gly Arg Arg Val Gly Pro Val Ser Thr
```

-continued

Val Gly Val Thr Ala Pro Gln Glu Asp Val Asp Glu Thr Pro Ser
2495                2500                2505

Pro Thr Glu Pro Gly Thr Glu Ala Pro Gly Pro Pro Glu Glu Pro
2510                2515                2520

Leu Leu Gly Glu Leu Thr Val Thr Gly Ser Ser Pro Asp Ser Leu
2525                2530                2535

Ser Leu Ser Trp Thr Val Pro Gln Gly Arg Phe Asp Ser Phe Thr
2540                2545                2550

Val Gln Tyr Lys Asp Arg Asp Gly Arg Pro Gln Ala Val Arg Val
2555                2560                2565

Gly Gly Gln Glu Ser Lys Val Thr Val Arg Gly Leu Glu Pro Gly
2570                2575                2580

Arg Lys Tyr Lys Met His Leu Tyr Gly Leu His Glu Gly Arg Arg
2585                2590                2595

Leu Gly Pro Val Ser Ala Val Gly Val Thr Glu Asp Glu Ala Glu
2600                2605                2610

Thr Thr Gln Ala Val Pro Thr Met Thr Pro Glu Pro Pro Ile Lys
2615                2620                2625

Pro Arg Leu Gly Glu Leu Thr Met Thr Asp Ala Thr Pro Asp Ser
2630                2635                2640

Leu Ser Leu Ser Trp Thr Val Pro Glu Gly Gln Phe Asp His Phe
2645                2650                2655

Leu Val Gln Tyr Arg Asn Gly Asp Gly Gln Pro Lys Ala Val Arg
2660                2665                2670

Val Pro Gly His Glu Asp Gly Val Thr Ile Ser Gly Leu Glu Pro
2675                2680                2685

Asp His Lys Tyr Lys Met Asn Leu Tyr Gly Phe His Gly Gly Gln
2690                2695                2700

Arg Val Gly Pro Ile Ser Val Ile Gly Val Thr Ala Ala Glu Glu
2705                2710                2715

Glu Thr Pro Ser Pro Thr Glu Leu Ser Thr Glu Ala Pro Glu Pro
2720                2725                2730

Pro Glu Glu Pro Leu Leu Gly Glu Leu Thr Val Thr Gly Ser Ser
2735                2740                2745

Pro Asp Ser Leu Ser Leu Ser Trp Thr Ile Pro Gln Gly His Phe
2750                2755                2760

Asp Ser Phe Thr Val Gln Tyr Lys Asp Arg Asp Gly Arg Pro Gln
2765                2770                2775

Val Met Arg Val Arg Gly Glu Glu Ser Glu Val Thr Val Gly Gly
2780                2785                2790

Leu Glu Pro Gly Arg Lys Tyr Lys Met His Leu Tyr Gly Leu His
2795                2800                2805

Glu Gly Arg Arg Val Gly Pro Val Ser Thr Val Gly Val Thr Ala
2810                2815                2820

Pro Glu Asp Glu Ala Glu Thr Thr Gln Ala Val Pro Thr Thr Thr
2825                2830                2835

Pro Glu Pro Pro Asn Lys Pro Arg Leu Gly Glu Leu Thr Val Thr
2840                2845                2850

Asp Ala Thr Pro Asp Ser Leu Ser Leu Ser Trp Met Val Pro Glu
2855                2860                2865

Gly Gln Phe Asp His Phe Leu Val Gln Tyr Arg Asn Gly Asp Gly
2870                2875                2880

-continued

```
Gln Pro Lys Val Val Arg Val Pro Gly His Glu Asp Gly Val Thr
2885                2890                2895

Ile Ser Gly Leu Glu Pro Asp His Lys Tyr Lys Met Asn Leu Tyr
2900                2905                2910

Gly Phe His Gly Gly Gln Arg Val Gly Pro Ile Ser Val Ile Gly
2915                2920                2925

Val Thr Ala Ala Glu Glu Thr Pro Ala Pro Thr Glu Pro Ser
2930                2935                2940

Thr Glu Ala Pro Glu Pro Pro Glu Glu Pro Leu Leu Gly Glu Leu
2945                2950                2955

Thr Val Thr Gly Ser Ser Pro Asp Ser Leu Ser Leu Ser Trp Thr
2960                2965                2970

Ile Pro Gln Gly Arg Phe Asp Ser Phe Thr Val Gln Tyr Lys Asp
2975                2980                2985

Arg Asp Gly Arg Pro Gln Val Val Arg Val Arg Gly Glu Glu Ser
2990                2995                3000

Glu Val Thr Val Gly Gly Leu Glu Pro Gly Cys Lys Tyr Lys Met
3005                3010                3015

His Leu Tyr Gly Leu His Glu Gly Gln Arg Val Gly Pro Val Ser
3020                3025                3030

Ala Val Gly Val Thr Ala Pro Lys Asp Glu Ala Glu Thr Thr Gln
3035                3040                3045

Ala Val Pro Thr Met Thr Pro Glu Pro Pro Ile Lys Pro Arg Leu
3050                3055                3060

Gly Glu Leu Thr Val Thr Asp Ala Thr Pro Asp Ser Leu Ser Leu
3065                3070                3075

Ser Trp Met Val Pro Glu Gly Gln Phe Asp His Phe Leu Val Gln
3080                3085                3090

Tyr Arg Asn Gly Asp Gly Gln Pro Lys Ala Val Arg Val Pro Gly
3095                3100                3105

His Glu Asp Gly Val Thr Ile Ser Gly Leu Glu Pro Asp His Lys
3110                3115                3120

Tyr Lys Met Asn Leu Tyr Gly Phe His Gly Gly Gln Arg Val Gly
3125                3130                3135

Pro Val Ser Ala Ile Gly Val Thr Glu Glu Glu Thr Pro Ser Pro
3140                3145                3150

Thr Glu Pro Ser Thr Glu Ala Pro Glu Ala Pro Glu Glu Pro Leu
3155                3160                3165

Leu Gly Glu Leu Thr Val Thr Gly Ser Ser Pro Asp Ser Leu Ser
3170                3175                3180

Leu Ser Trp Thr Val Pro Gln Gly Arg Phe Asp Ser Phe Thr Val
3185                3190                3195

Gln Tyr Lys Asp Arg Asp Gly Gln Pro Gln Val Val Arg Val Arg
3200                3205                3210

Gly Glu Glu Ser Glu Val Thr Val Gly Gly Leu Glu Pro Gly Arg
3215                3220                3225

Lys Tyr Lys Met His Leu Tyr Gly Leu His Glu Gly Gln Arg Val
3230                3235                3240

Gly Pro Val Ser Thr Val Gly Ile Thr Ala Pro Leu Pro Thr Pro
3245                3250                3255

Leu Pro Val Glu Pro Arg Leu Gly Glu Leu Ala Val Ala Ala Val
3260                3265                3270
```

```
Thr Ser Asp Ser Val Gly Leu Ser Trp Thr Val Ala Gln Gly Pro
3275                3280                3285

Phe Asp Ser Phe Leu Val Gln Tyr Arg Asp Ala Gln Gly Gln Pro
3290                3295                3300

Gln Ala Val Pro Val Ser Gly Asp Leu Arg Ala Val Ala Val Ser
3305                3310                3315

Gly Leu Asp Pro Ala Arg Lys Tyr Lys Phe Leu Leu Phe Gly Leu
3320                3325                3330

Gln Asn Gly Lys Arg His Gly Pro Val Pro Val Glu Ala Arg Thr
3335                3340                3345

Ala Pro Asp Thr Lys Pro Ser Pro Arg Leu Gly Glu Leu Thr Val
3350                3355                3360

Thr Asp Ala Thr Pro Asp Ser Val Gly Leu Ser Trp Thr Val Pro
3365                3370                3375

Glu Gly Glu Phe Asp Ser Phe Val Val Gln Tyr Lys Asp Lys Asp
3380                3385                3390

Gly Arg Leu Gln Val Val Pro Val Ala Ala Asn Gln Arg Glu Val
3395                3400                3405

Thr Val Gln Gly Leu Glu Pro Ser Arg Lys Tyr Arg Phe Leu Leu
3410                3415                3420

Tyr Gly Leu Ser Gly Arg Lys Arg Leu Gly Pro Ile Ser Ala Asp
3425                3430                3435

Ser Thr Thr Ala Pro Leu Glu Lys Glu Leu Pro Pro His Leu Gly
3440                3445                3450

Glu Leu Thr Val Ala Glu Glu Thr Ser Ser Ser Leu Arg Leu Ser
3455                3460                3465

Trp Thr Val Ala Gln Gly Pro Phe Asp Ser Phe Val Val Gln Tyr
3470                3475                3480

Arg Asp Thr Asp Gly Gln Pro Arg Ala Val Pro Val Ala Ala Asp
3485                3490                3495

Gln Arg Thr Val Thr Val Glu Asp Leu Glu Pro Gly Lys Lys Tyr
3500                3505                3510

Lys Phe Leu Leu Tyr Gly Leu Leu Gly Gly Lys Arg Leu Gly Pro
3515                3520                3525

Val Ser Ala Leu Gly Met Thr Ala Pro Glu Glu Asp Thr Pro Ala
3530                3535                3540

Pro Glu Leu Ala Pro Glu Ala Pro Glu Pro Pro Glu Glu Pro Arg
3545                3550                3555

Leu Gly Val Leu Thr Val Thr Asp Thr Thr Pro Asp Ser Met Arg
3560                3565                3570

Leu Ser Trp Ser Val Ala Gln Gly Pro Phe Asp Ser Phe Val Val
3575                3580                3585

Gln Tyr Glu Asp Thr Asn Gly Gln Pro Gln Ala Leu Leu Val Asp
3590                3595                3600

Gly Asp Gln Ser Lys Ile Leu Ile Ser Gly Leu Glu Pro Ser Thr
3605                3610                3615

Pro Tyr Arg Phe Leu Leu Tyr Gly Leu His Glu Gly Lys Arg Leu
3620                3625                3630

Gly Pro Leu Ser Ala Glu Gly Thr Thr Gly Leu Ala Pro Ala Gly
3635                3640                3645

Gln Thr Ser Glu Glu Ser Arg Pro Arg Leu Ser Gln Leu Ser Val
3650                3655                3660

Thr Asp Val Thr Thr Ser Ser Leu Arg Leu Asn Trp Glu Ala Pro
```

-continued

| | | 3665 | | | 3670 | | | 3675 | | | |
|---|---|---|---|---|---|---|---|---|---|---|---|
| Pro | Gly | Ala | Phe | Asp | Ser | Phe | Leu | Leu | Arg | Phe | Gly | Val | Pro | Ser |
| | | 3680 | | | 3685 | | | 3690 | | | |
| Pro | Ser | Thr | Leu | Glu | Pro | His | Pro | Arg | Pro | Leu | Leu | Gln | Arg | Glu |
| | | 3695 | | | 3700 | | | 3705 | | | |
| Leu | Met | Val | Pro | Gly | Thr | Arg | His | Ser | Ala | Val | Leu | Arg | Asp | Leu |
| | | 3710 | | | 3715 | | | 3720 | | | |
| Arg | Ser | Gly | Thr | Leu | Tyr | Ser | Leu | Thr | Leu | Tyr | Gly | Leu | Arg | Gly |
| | | 3725 | | | 3730 | | | 3735 | | | |
| Pro | His | Lys | Ala | Asp | Ser | Ile | Gln | Gly | Thr | Ala | Arg | Thr | Leu | Ser |
| | | 3740 | | | 3745 | | | 3750 | | | |
| Pro | Val | Leu | Glu | Ser | Pro | Arg | Asp | Leu | Gln | Phe | Ser | Glu | Ile | Arg |
| | | 3755 | | | 3760 | | | 3765 | | | |
| Glu | Thr | Ser | Ala | Lys | Val | Asn | Trp | Met | Pro | Pro | Ser | Arg | Ala |
| | | 3770 | | | 3775 | | | 3780 | | | |
| Asp | Ser | Phe | Lys | Val | Ser | Tyr | Gln | Leu | Ala | Asp | Gly | Gly | Glu | Pro |
| | | 3785 | | | 3790 | | | 3795 | | | |
| Gln | Ser | Val | Gln | Val | Asp | Gly | Gln | Ala | Arg | Thr | Gln | Lys | Leu | Gln |
| | | 3800 | | | 3805 | | | 3810 | | | |
| Gly | Leu | Ile | Pro | Gly | Ala | Arg | Tyr | Glu | Val | Thr | Val | Val | Ser | Val |
| | | 3815 | | | 3820 | | | 3825 | | | |
| Arg | Gly | Phe | Glu | Glu | Ser | Glu | Pro | Leu | Thr | Gly | Phe | Leu | Thr | Thr |
| | | 3830 | | | 3835 | | | 3840 | | | |
| Val | Pro | Asp | Gly | Pro | Thr | Gln | Leu | Arg | Ala | Leu | Asn | Leu | Thr | Glu |
| | | 3845 | | | 3850 | | | 3855 | | | |
| Gly | Phe | Ala | Val | Leu | His | Trp | Lys | Pro | Pro | Gln | Asn | Pro | Val | Asp |
| | | 3860 | | | 3865 | | | 3870 | | | |
| Thr | Tyr | Asp | Val | Gln | Val | Thr | Ala | Pro | Gly | Ala | Pro | Pro | Leu | Gln |
| | | 3875 | | | 3880 | | | 3885 | | | |
| Ala | Glu | Thr | Pro | Gly | Ser | Ala | Val | Asp | Tyr | Pro | Leu | His | Asp | Leu |
| | | 3890 | | | 3895 | | | 3900 | | | |
| Val | Leu | His | Thr | Asn | Tyr | Thr | Ala | Thr | Val | Arg | Gly | Leu | Arg | Gly |
| | | 3905 | | | 3910 | | | 3915 | | | |
| Pro | Asn | Leu | Thr | Ser | Pro | Ala | Ser | Ile | Thr | Phe | Thr | Thr | Gly | Leu |
| | | 3920 | | | 3925 | | | 3930 | | | |
| Glu | Ala | Pro | Arg | Asp | Leu | Glu | Ala | Lys | Glu | Val | Thr | Pro | Arg | Thr |
| | | 3935 | | | 3940 | | | 3945 | | | |
| Ala | Leu | Leu | Thr | Trp | Thr | Glu | Pro | Pro | Val | Arg | Pro | Ala | Gly | Tyr |
| | | 3950 | | | 3955 | | | 3960 | | | |
| Leu | Leu | Ser | Phe | His | Thr | Pro | Gly | Gly | Gln | Asn | Gln | Glu | Ile | Leu |
| | | 3965 | | | 3970 | | | 3975 | | | |
| Leu | Pro | Gly | Gly | Ile | Thr | Ser | His | Gln | Leu | Leu | Gly | Leu | Phe | Pro |
| | | 3980 | | | 3985 | | | 3990 | | | |
| Ser | Thr | Ser | Tyr | Asn | Ala | Arg | Leu | Gln | Ala | Met | Trp | Gly | Gln | Ser |
| | | 3995 | | | 4000 | | | 4005 | | | |
| Leu | Leu | Pro | Pro | Val | Ser | Thr | Ser | Phe | Thr | Thr | Gly | Gly | Leu | Arg |
| | | 4010 | | | 4015 | | | 4020 | | | |
| Ile | Pro | Phe | Pro | Arg | Asp | Cys | Gly | Glu | Glu | Met | Gln | Asn | Gly | Ala |
| | | 4025 | | | 4030 | | | 4035 | | | |
| Gly | Ala | Ser | Arg | Thr | Ser | Thr | Ile | Phe | Leu | Asn | Gly | Asn | Arg | Glu |
| | | 4040 | | | 4045 | | | 4050 | | | |
| Arg | Pro | Leu | Asn | Val | Phe | Cys | Asp | Met | Glu | Thr | Asp | Gly | Gly | Gly |
| | | 4055 | | | 4060 | | | 4065 | | | |

```
Trp Leu Val Phe Gln Arg Arg Met Asp Gly Gln Thr Asp Phe Trp
    4070                4075                4080

Arg Asp Trp Glu Asp Tyr Ala His Gly Phe Gly Asn Ile Ser Gly
    4085                4090                4095

Glu Phe Trp Leu Gly Asn Glu Ala Leu His Ser Leu Thr Gln Ala
    4100                4105                4110

Gly Asp Tyr Ser Met Arg Val Asp Leu Arg Ala Gly Asp Glu Ala
    4115                4120                4125

Val Phe Ala Gln Tyr Asp Ser Phe His Val Asp Ser Ala Ala Glu
    4130                4135                4140

Tyr Tyr Arg Leu His Leu Glu Gly Tyr His Gly Thr Ala Gly Asp
    4145                4150                4155

Ser Met Ser Tyr His Ser Gly Ser Val Phe Ser Ala Arg Asp Arg
    4160                4165                4170

Asp Pro Asn Ser Leu Leu Ile Ser Cys Ala Val Ser Tyr Arg Gly
    4175                4180                4185

Ala Trp Trp Tyr Arg Asn Cys His Tyr Ala Asn Leu Asn Gly Leu
    4190                4195                4200

Tyr Gly Ser Thr Val Asp His Gln Gly Val Ser Trp Tyr His Trp
    4205                4210                4215

Lys Gly Phe Glu Phe Ser Val Pro Phe Thr Glu Met Lys Leu Arg
    4220                4225                4230

Pro Arg Asn Phe Arg Ser Pro Ala Gly Gly Gly
    4235                4240

<210> SEQ ID NO 7
<211> LENGTH: 4244
<212> TYPE: PRT
<213> ORGANISM: Homo sapiens
<220> FEATURE:
<221> NAME/KEY: misc_feature
<222> LOCATION: (1)..(4244)
<223> OTHER INFORMATION: TNXB with G1331R mutation

<400> SEQUENCE: 7

Met Met Pro Ala Gln Tyr Ala Leu Thr Ser Ser Leu Val Leu Val
1               5                   10                  15

Leu Leu Ser Thr Ala Arg Ala Gly Pro Phe Ser Ser Arg Ser Asn Val
                20                  25                  30

Thr Leu Pro Ala Pro Arg Pro Pro Gln Pro Gly Gly His Thr Val
            35                  40                  45

Gly Ala Gly Val Gly Ser Pro Ser Ser Gln Leu Tyr Glu His Thr Val
        50                  55                  60

Glu Gly Gly Glu Lys Gln Val Val Phe Thr His Arg Ile Asn Leu Pro
65                  70                  75                  80

Pro Ser Thr Gly Cys Gly Cys Pro Pro Gly Thr Glu Pro Val Leu
                85                  90                  95

Ala Ser Glu Val Gln Ala Leu Arg Val Arg Leu Glu Ile Glu Glu
            100                 105                 110

Leu Val Lys Gly Leu Lys Glu Gln Cys Thr Gly Gly Cys Cys Pro Ala
        115                 120                 125

Ser Ala Gln Ala Gly Thr Gly Gln Thr Asp Val Arg Thr Leu Cys Ser
    130                 135                 140

Leu His Gly Val Phe Asp Leu Ser Arg Cys Thr Cys Ser Cys Glu Pro
145                 150                 155                 160
```

-continued

```
Gly Trp Gly Gly Pro Thr Cys Ser Asp Pro Thr Asp Ala Glu Ile Pro
                165                 170                 175

Pro Ser Ser Pro Pro Ser Ala Ser Gly Ser Cys Pro Asp Asp Cys Asn
            180                 185                 190

Asp Gln Gly Arg Cys Val Arg Gly Arg Cys Val Cys Phe Pro Gly Tyr
        195                 200                 205

Thr Gly Pro Ser Cys Gly Trp Pro Ser Cys Pro Gly Asp Cys Gln Gly
    210                 215                 220

Arg Gly Arg Cys Val Gln Gly Val Cys Val Cys Arg Ala Gly Phe Ser
225                 230                 235                 240

Gly Pro Asp Cys Ser Gln Arg Ser Cys Pro Arg Gly Cys Ser Gln Arg
                245                 250                 255

Gly Arg Cys Glu Gly Gly Arg Cys Val Cys Asp Pro Gly Tyr Thr Gly
            260                 265                 270

Asp Asp Cys Gly Met Arg Ser Cys Pro Arg Gly Cys Ser Gln Arg Gly
        275                 280                 285

Arg Cys Glu Asn Gly Arg Cys Val Cys Asn Pro Gly Tyr Thr Gly Glu
    290                 295                 300

Asp Cys Gly Val Arg Ser Cys Pro Arg Gly Cys Ser Gln Arg Gly Arg
305                 310                 315                 320

Cys Lys Asp Gly Arg Cys Val Cys Asp Pro Gly Tyr Thr Gly Glu Asp
                325                 330                 335

Cys Gly Thr Arg Ser Cys Pro Trp Asp Cys Gly Glu Gly Gly Arg Cys
            340                 345                 350

Val Asp Gly Arg Cys Val Cys Trp Pro Gly Tyr Thr Gly Glu Asp Cys
        355                 360                 365

Ser Thr Arg Thr Cys Pro Arg Asp Cys Arg Gly Arg Gly Arg Cys Glu
    370                 375                 380

Asp Gly Glu Cys Ile Cys Asp Thr Gly Tyr Ser Gly Asp Asp Cys Gly
385                 390                 395                 400

Val Arg Ser Cys Pro Gly Asp Cys Asn Gln Arg Gly Arg Cys Glu Asp
                405                 410                 415

Gly Arg Cys Val Cys Trp Pro Gly Tyr Thr Gly Thr Asp Cys Gly Ser
            420                 425                 430

Arg Ala Cys Pro Arg Asp Cys Arg Gly Arg Gly Arg Cys Glu Asn Gly
        435                 440                 445

Val Cys Val Cys Asn Ala Gly Tyr Ser Gly Glu Asp Cys Gly Val Arg
    450                 455                 460

Ser Cys Pro Gly Asp Cys Arg Gly Arg Gly Arg Cys Glu Ser Gly Arg
465                 470                 475                 480

Cys Met Cys Trp Pro Gly Tyr Thr Gly Arg Asp Cys Gly Thr Arg Ala
                485                 490                 495

Cys Pro Gly Asp Cys Arg Gly Arg Gly Arg Cys Val Asp Gly Arg Cys
            500                 505                 510

Val Cys Asn Pro Gly Phe Thr Gly Glu Asp Cys Gly Ser Arg Arg Cys
        515                 520                 525

Pro Gly Asp Cys Arg Gly His Gly Leu Cys Glu Asp Gly Val Cys Val
    530                 535                 540

Cys Asp Ala Gly Tyr Ser Gly Glu Asp Cys Ser Thr Arg Ser Cys Pro
545                 550                 555                 560

Gly Gly Cys Arg Gly Arg Gly Gln Cys Leu Asp Gly Arg Cys Val Cys
                565                 570                 575

Glu Asp Gly Tyr Ser Gly Glu Asp Cys Gly Val Arg Gln Cys Pro Asn
```

```
              580             585             590
Asp Cys Ser Gln His Gly Val Cys Gln Asp Gly Val Cys Ile Cys Trp
            595             600             605
Glu Gly Tyr Val Ser Glu Asp Cys Ser Ile Arg Thr Cys Pro Ser Asn
            610             615             620
Cys His Gly Arg Gly Arg Cys Glu Glu Gly Arg Cys Leu Cys Asp Pro
625             630             635             640
Gly Tyr Thr Gly Pro Thr Cys Ala Thr Arg Met Cys Pro Ala Asp Cys
            645             650             655
Arg Gly Arg Gly Arg Cys Val Gln Gly Val Cys Leu Cys His Val Gly
            660             665             670
Tyr Gly Gly Glu Asp Cys Gly Gln Glu Glu Pro Pro Ala Ser Ala Cys
            675             680             685
Pro Gly Gly Cys Gly Pro Arg Glu Leu Cys Arg Ala Gly Gln Cys Val
            690             695             700
Cys Val Glu Gly Phe Arg Gly Pro Asp Cys Ala Ile Gln Thr Cys Pro
705             710             715             720
Gly Asp Cys Arg Gly Arg Gly Glu Cys His Asp Gly Ser Cys Val Cys
                725             730             735
Lys Asp Gly Tyr Ala Gly Glu Asp Cys Gly Glu Val Pro Thr Ile
            740             745             750
Glu Gly Met Arg Met His Leu Leu Glu Glu Thr Thr Val Arg Thr Glu
            755             760             765
Trp Thr Pro Ala Pro Gly Pro Val Asp Ala Tyr Glu Ile Gln Phe Ile
            770             775             780
Pro Thr Thr Glu Gly Ala Ser Pro Pro Phe Thr Ala Arg Val Pro Ser
785             790             795             800
Ser Ala Ser Ala Tyr Asp Gln Arg Gly Leu Ala Pro Gly Gln Glu Tyr
                805             810             815
Gln Val Thr Val Arg Ala Leu Arg Gly Thr Ser Trp Gly Leu Pro Ala
            820             825             830
Ser Lys Thr Ile Thr Thr Met Ile Asp Gly Pro Gln Asp Leu Arg Val
            835             840             845
Val Ala Val Thr Pro Thr Thr Leu Glu Leu Gly Trp Leu Arg Pro Gln
850             855             860
Ala Glu Val Asp Arg Phe Val Val Ser Tyr Val Ser Ala Gly Asn Gln
865             870             875             880
Arg Val Arg Leu Glu Val Pro Pro Glu Ala Asp Gly Thr Leu Leu Thr
                885             890             895
Asp Leu Met Pro Gly Val Glu Tyr Val Val Thr Val Thr Ala Glu Arg
                900             905             910
Gly Arg Ala Val Ser Tyr Pro Ala Ser Val Arg Ala Asn Thr Gly Ser
            915             920             925
Ser Pro Leu Gly Leu Gly Thr Thr Asp Glu Pro Pro Ser Gly
            930             935             940
Pro Ser Thr Thr Gln Gly Ala Gln Ala Pro Leu Leu Gln Arg Pro
945             950             955             960
Gln Glu Leu Gly Glu Leu Arg Val Leu Gly Arg Asp Glu Thr Gly Arg
                965             970             975
Leu Arg Val Val Trp Thr Ala Gln Pro Asp Thr Phe Ala Tyr Phe Gln
                980             985             990
Leu Arg Met Arg Val Pro Glu Gly Pro Gly Ala His Glu Glu Val Leu
            995             1000            1005
```

-continued

Pro Gly Asp Val Arg Gln Ala Leu Val Pro Pro Pro Gly
    1010            1015            1020

Thr Pro Tyr Glu Leu Ser Leu His Gly Val Pro Gly Gly Lys
    1025            1030            1035

Pro Ser Asp Pro Ile Ile Tyr Gln Gly Ile Met Asp Lys Asp Glu
    1040            1045            1050

Glu Lys Pro Gly Lys Ser Ser Gly Pro Pro Arg Leu Gly Glu Leu
    1055            1060            1065

Thr Val Thr Asp Arg Thr Ser Asp Ser Leu Leu Leu Arg Trp Thr
    1070            1075            1080

Val Pro Glu Gly Glu Phe Asp Ser Phe Val Ile Gln Tyr Lys Asp
    1085            1090            1095

Arg Asp Gly Gln Pro Gln Val Val Pro Val Glu Gly Pro Gln Arg
    1100            1105            1110

Ser Ala Val Ile Thr Ser Leu Asp Pro Gly Arg Lys Tyr Lys Phe
    1115            1120            1125

Val Leu Tyr Gly Phe Val Gly Lys Lys Arg His Gly Pro Leu Val
    1130            1135            1140

Ala Glu Ala Lys Ile Leu Pro Gln Ser Asp Pro Ser Pro Gly Thr
    1145            1150            1155

Pro Pro His Leu Gly Asn Leu Trp Val Thr Asp Pro Thr Pro Asp
    1160            1165            1170

Ser Leu His Leu Ser Trp Thr Val Pro Glu Gly Gln Phe Asp Thr
    1175            1180            1185

Phe Met Val Gln Tyr Arg Asp Arg Asp Gly Arg Pro Gln Val Val
    1190            1195            1200

Pro Val Glu Gly Pro Glu Arg Ser Phe Val Val Ser Ser Leu Asp
    1205            1210            1215

Pro Asp His Lys Tyr Arg Phe Thr Leu Phe Gly Ile Ala Asn Lys
    1220            1225            1230

Lys Arg Tyr Gly Pro Leu Thr Ala Asp Gly Thr Thr Ala Pro Glu
    1235            1240            1245

Arg Lys Glu Glu Pro Pro Arg Pro Glu Phe Leu Glu Gln Pro Leu
    1250            1255            1260

Leu Gly Glu Leu Thr Val Thr Gly Val Thr Pro Asp Ser Leu Arg
    1265            1270            1275

Leu Ser Trp Thr Val Ala Gln Gly Pro Phe Asp Ser Phe Met Val
    1280            1285            1290

Gln Tyr Lys Asp Ala Gln Gly Gln Pro Gln Ala Val Pro Val Ala
    1295            1300            1305

Gly Asp Glu Asn Glu Val Thr Val Pro Gly Leu Asp Pro Asp Arg
    1310            1315            1320

Lys Tyr Lys Met Asn Leu Tyr Arg Leu Arg Gly Arg Gln Arg Val
    1325            1330            1335

Gly Pro Glu Ser Val Val Ala Lys Thr Ala Pro Gln Glu Asp Val
    1340            1345            1350

Asp Glu Thr Pro Ser Pro Thr Glu Leu Gly Thr Glu Ala Pro Glu
    1355            1360            1365

Ser Pro Glu Glu Pro Leu Leu Gly Glu Leu Thr Val Thr Gly Ser
    1370            1375            1380

Ser Pro Asp Ser Leu Ser Leu Phe Trp Thr Val Pro Gln Gly Ser
    1385            1390            1395

-continued

```
Phe Asp Ser Phe Thr Val Gln Tyr Lys Asp Arg Asp Gly Arg Pro
    1400                1405                1410

Arg Ala Val Arg Val Gly Gly Lys Glu Ser Glu Val Thr Val Gly
    1415                1420                1425

Gly Leu Glu Pro Gly His Lys Tyr Lys Met His Leu Tyr Gly Leu
    1430                1435                1440

His Glu Gly Gln Arg Val Gly Pro Val Ser Ala Val Gly Val Thr
    1445                1450                1455

Ala Pro Gln Gln Glu Glu Thr Pro Pro Ala Thr Glu Ser Pro Leu
    1460                1465                1470

Glu Pro Arg Leu Gly Glu Leu Thr Val Thr Asp Val Thr Pro Asn
    1475                1480                1485

Ser Val Gly Leu Ser Trp Thr Val Pro Glu Gly Gln Phe Asp Ser
    1490                1495                1500

Phe Ile Val Gln Tyr Lys Asp Lys Asp Gly Gln Pro Gln Val Val
    1505                1510                1515

Pro Val Ala Ala Asp Gln Arg Glu Val Thr Val Tyr Asn Leu Glu
    1520                1525                1530

Pro Glu Arg Lys Tyr Lys Met Asn Met Tyr Gly Leu His Asp Gly
    1535                1540                1545

Gln Arg Met Gly Pro Leu Ser Val Val Ile Val Thr Ala Pro Leu
    1550                1555                1560

Pro Pro Ala Pro Ala Thr Glu Ala Ser Lys Pro Pro Leu Glu Pro
    1565                1570                1575

Arg Leu Gly Glu Leu Thr Val Thr Asp Ile Thr Pro Asp Ser Val
    1580                1585                1590

Gly Leu Ser Trp Thr Val Pro Glu Gly Glu Phe Asp Ser Phe Val
    1595                1600                1605

Val Gln Tyr Lys Asp Arg Asp Gly Gln Pro Gln Val Val Pro Val
    1610                1615                1620

Ala Ala Asp Gln Arg Glu Val Thr Ile Pro Asp Leu Glu Pro Ser
    1625                1630                1635

Arg Lys Tyr Lys Phe Leu Leu Phe Gly Ile Gln Asp Gly Lys Arg
    1640                1645                1650

Arg Ser Pro Val Ser Val Glu Ala Lys Thr Val Ala Arg Gly Asp
    1655                1660                1665

Ala Ser Pro Gly Ala Pro Pro Arg Leu Gly Glu Leu Trp Val Thr
    1670                1675                1680

Asp Pro Thr Pro Asp Ser Leu Arg Leu Ser Trp Thr Val Pro Glu
    1685                1690                1695

Gly Gln Phe Asp Ser Phe Val Gln Phe Lys Asp Lys Asp Gly
    1700                1705                1710

Pro Gln Val Val Pro Val Glu Gly His Glu Arg Ser Val Thr Val
    1715                1720                1725

Thr Pro Leu Asp Ala Gly Arg Lys Tyr Arg Phe Leu Leu Tyr Gly
    1730                1735                1740

Leu Leu Gly Lys Lys Arg His Gly Pro Leu Thr Ala Asp Gly Thr
    1745                1750                1755

Thr Glu Ala Arg Ser Ala Met Asp Asp Thr Gly Thr Lys Arg Pro
    1760                1765                1770

Pro Lys Pro Arg Leu Gly Glu Glu Leu Gln Val Thr Thr Val Thr
    1775                1780                1785

Gln Asn Ser Val Gly Leu Ser Trp Thr Val Pro Glu Gly Gln Phe
```

-continued

```
             1790                1795                1800
Asp Ser Phe Val Val Gln Tyr Lys Asp Arg Asp Gly Gln Pro Gln
     1805                1810                1815

Val Val Pro Val Glu Gly Ser Leu Arg Glu Val Ser Val Pro Gly
     1820                1825                1830

Leu Asp Pro Ala His Arg Tyr Lys Leu Leu Leu Tyr Gly Leu His
     1835                1840                1845

His Gly Lys Arg Val Gly Pro Ile Ser Ala Val Ala Ile Thr Ala
     1850                1855                1860

Gly Arg Glu Glu Thr Glu Thr Glu Thr Thr Ala Pro Thr Pro Pro
     1865                1870                1875

Ala Pro Glu Pro His Leu Gly Glu Leu Thr Val Glu Glu Ala Thr
     1880                1885                1890

Ser His Thr Leu His Leu Ser Trp Met Val Thr Glu Gly Glu Phe
     1895                1900                1905

Asp Ser Phe Glu Ile Gln Tyr Thr Asp Arg Asp Gly Gln Leu Gln
     1910                1915                1920

Met Val Arg Ile Gly Gly Asp Arg Asn Asp Ile Thr Leu Ser Gly
     1925                1930                1935

Leu Glu Ser Asp His Arg Tyr Leu Val Thr Leu Tyr Gly Phe Ser
     1940                1945                1950

Asp Gly Lys His Val Gly Pro Val His Val Glu Ala Leu Thr Val
     1955                1960                1965

Pro Glu Glu Glu Lys Pro Ser Glu Pro Pro Thr Ala Thr Pro Glu
     1970                1975                1980

Pro Pro Ile Lys Pro Arg Leu Gly Glu Leu Thr Val Thr Asp Ala
     1985                1990                1995

Thr Pro Asp Ser Leu Ser Leu Ser Trp Thr Val Pro Glu Gly Gln
     2000                2005                2010

Phe Asp His Phe Leu Val Gln Tyr Arg Asn Gly Asp Gly Gln Pro
     2015                2020                2025

Lys Ala Val Arg Val Pro Gly His Glu Glu Gly Val Thr Ile Ser
     2030                2035                2040

Gly Leu Glu Pro Asp His Lys Tyr Lys Met Asn Leu Tyr Gly Phe
     2045                2050                2055

His Gly Gly Gln Arg Met Gly Pro Val Ser Val Val Gly Val Thr
     2060                2065                2070

Ala Ala Glu Glu Glu Thr Pro Ser Pro Thr Glu Pro Ser Met Glu
     2075                2080                2085

Ala Pro Glu Pro Ala Glu Glu Pro Leu Leu Gly Glu Leu Thr Val
     2090                2095                2100

Thr Gly Ser Ser Pro Asp Ser Leu Ser Leu Ser Trp Thr Val Pro
     2105                2110                2115

Gln Gly Arg Phe Asp Ser Phe Thr Val Gln Tyr Lys Asp Arg Asp
     2120                2125                2130

Gly Arg Pro Gln Val Val Arg Val Gly Gly Glu Glu Ser Glu Val
     2135                2140                2145

Thr Val Gly Gly Leu Glu Pro Gly Arg Lys Tyr Lys Met His Leu
     2150                2155                2160

Tyr Gly Leu His Glu Gly Arg Arg Val Gly Pro Val Ser Ala Val
     2165                2170                2175

Gly Val Thr Ala Pro Glu Glu Glu Ser Pro Asp Ala Pro Leu Ala
     2180                2185                2190
```

-continued

```
Lys Leu Arg Leu Gly Gln Met Thr Val Arg Asp Ile Thr Ser Asp
2195                2200                2205

Ser Leu Ser Leu Ser Trp Thr Val Pro Glu Gly Gln Phe Asp His
2210                2215                2220

Phe Leu Val Gln Phe Lys Asn Gly Asp Gly Gln Pro Lys Ala Val
2225                2230                2235

Arg Val Pro Gly His Glu Asp Gly Val Thr Ile Ser Gly Leu Glu
2240                2245                2250

Pro Asp His Lys Tyr Lys Met Asn Leu Tyr Gly Phe His Gly Gly
2255                2260                2265

Gln Arg Val Gly Pro Val Ser Ala Val Gly Leu Thr Ala Pro Gly
2270                2275                2280

Lys Asp Glu Glu Met Ala Pro Ala Ser Thr Glu Pro Pro Thr Pro
2285                2290                2295

Glu Pro Pro Ile Lys Pro Arg Leu Glu Glu Leu Thr Val Thr Asp
2300                2305                2310

Ala Thr Pro Asp Ser Leu Ser Leu Ser Trp Thr Val Pro Glu Gly
2315                2320                2325

Gln Phe Asp His Phe Leu Val Gln Tyr Lys Asn Gly Asp Gly Gln
2330                2335                2340

Pro Lys Ala Thr Arg Val Pro Gly His Glu Asp Arg Val Thr Ile
2345                2350                2355

Ser Gly Leu Glu Pro Asp Asn Lys Tyr Lys Met Asn Leu Tyr Gly
2360                2365                2370

Phe His Gly Gly Gln Arg Val Gly Pro Val Ser Ala Ile Gly Val
2375                2380                2385

Thr Ala Ala Glu Glu Glu Thr Pro Ser Pro Thr Glu Pro Ser Met
2390                2395                2400

Glu Ala Pro Glu Pro Pro Glu Glu Pro Leu Leu Gly Glu Leu Thr
2405                2410                2415

Val Thr Gly Ser Ser Pro Asp Ser Leu Ser Leu Ser Trp Thr Val
2420                2425                2430

Pro Gln Gly Arg Phe Asp Ser Phe Thr Val Gln Tyr Lys Asp Arg
2435                2440                2445

Asp Gly Arg Pro Gln Val Val Arg Val Gly Gly Glu Glu Ser Glu
2450                2455                2460

Val Thr Val Gly Gly Leu Glu Pro Gly Arg Lys Tyr Lys Met His
2465                2470                2475

Leu Tyr Gly Leu His Glu Gly Arg Arg Val Gly Pro Val Ser Thr
2480                2485                2490

Val Gly Val Thr Ala Pro Gln Glu Asp Val Asp Glu Thr Pro Ser
2495                2500                2505

Pro Thr Glu Pro Gly Thr Glu Ala Pro Gly Pro Pro Glu Glu Pro
2510                2515                2520

Leu Leu Gly Glu Leu Thr Val Thr Gly Ser Ser Pro Asp Ser Leu
2525                2530                2535

Ser Leu Ser Trp Thr Val Pro Gln Gly Arg Phe Asp Ser Phe Thr
2540                2545                2550

Val Gln Tyr Lys Asp Arg Asp Gly Arg Pro Gln Ala Val Arg Val
2555                2560                2565

Gly Gly Gln Glu Ser Lys Val Thr Val Arg Gly Leu Glu Pro Gly
2570                2575                2580
```

-continued

```
Arg Lys Tyr Lys Met His Leu Tyr Gly Leu His Glu Gly Arg Arg
    2585                2590                2595
Leu Gly Pro Val Ser Ala Val Gly Val Thr Glu Asp Glu Ala Glu
    2600                2605                2610
Thr Thr Gln Ala Val Pro Thr Met Thr Pro Glu Pro Pro Ile Lys
    2615                2620                2625
Pro Arg Leu Gly Glu Leu Thr Met Thr Asp Ala Thr Pro Asp Ser
    2630                2635                2640
Leu Ser Leu Ser Trp Thr Val Pro Glu Gly Gln Phe Asp His Phe
    2645                2650                2655
Leu Val Gln Tyr Arg Asn Gly Asp Gly Gln Pro Lys Ala Val Arg
    2660                2665                2670
Val Pro Gly His Glu Asp Gly Val Thr Ile Ser Gly Leu Glu Pro
    2675                2680                2685
Asp His Lys Tyr Lys Met Asn Leu Tyr Gly Phe His Gly Gly Gln
    2690                2695                2700
Arg Val Gly Pro Ile Ser Val Ile Gly Val Thr Ala Ala Glu Glu
    2705                2710                2715
Glu Thr Pro Ser Pro Thr Glu Leu Ser Thr Glu Ala Pro Glu Pro
    2720                2725                2730
Pro Glu Glu Pro Leu Leu Gly Glu Leu Thr Val Thr Gly Ser Ser
    2735                2740                2745
Pro Asp Ser Leu Ser Leu Ser Trp Thr Ile Pro Gln Gly His Phe
    2750                2755                2760
Asp Ser Phe Thr Val Gln Tyr Lys Asp Arg Asp Gly Arg Pro Gln
    2765                2770                2775
Val Met Arg Val Arg Gly Glu Glu Ser Glu Val Thr Val Gly Gly
    2780                2785                2790
Leu Glu Pro Gly Arg Lys Tyr Lys Met His Leu Tyr Gly Leu His
    2795                2800                2805
Glu Gly Arg Arg Val Gly Pro Val Ser Thr Val Gly Val Thr Ala
    2810                2815                2820
Pro Glu Asp Glu Ala Glu Thr Thr Gln Ala Val Pro Thr Thr Thr
    2825                2830                2835
Pro Glu Pro Pro Asn Lys Pro Arg Leu Gly Glu Leu Thr Val Thr
    2840                2845                2850
Asp Ala Thr Pro Asp Ser Leu Ser Leu Ser Trp Met Val Pro Glu
    2855                2860                2865
Gly Gln Phe Asp His Phe Leu Val Gln Tyr Arg Asn Gly Asp Gly
    2870                2875                2880
Gln Pro Lys Val Val Arg Val Pro Gly His Glu Asp Gly Val Thr
    2885                2890                2895
Ile Ser Gly Leu Glu Pro Asp His Lys Tyr Lys Met Asn Leu Tyr
    2900                2905                2910
Gly Phe His Gly Gly Gln Arg Val Gly Pro Ile Ser Val Ile Gly
    2915                2920                2925
Val Thr Ala Ala Glu Glu Thr Pro Ala Pro Thr Glu Pro Ser
    2930                2935                2940
Thr Glu Ala Pro Glu Pro Pro Glu Glu Pro Leu Leu Gly Glu Leu
    2945                2950                2955
Thr Val Thr Gly Ser Ser Pro Asp Ser Leu Ser Leu Ser Trp Thr
    2960                2965                2970
Ile Pro Gln Gly Arg Phe Asp Ser Phe Thr Val Gln Tyr Lys Asp
```

```
            2975                2980                2985

Arg Asp Gly Arg Pro Gln Val Val Arg Val Arg Gly Glu Glu Ser
    2990                2995                3000

Glu Val Thr Val Gly Gly Leu Glu Pro Gly Cys Lys Tyr Lys Met
    3005                3010                3015

His Leu Tyr Gly Leu His Glu Gly Gln Arg Val Gly Pro Val Ser
    3020                3025                3030

Ala Val Gly Val Thr Ala Pro Lys Asp Glu Ala Glu Thr Thr Gln
    3035                3040                3045

Ala Val Pro Thr Met Thr Pro Glu Pro Pro Ile Lys Pro Arg Leu
    3050                3055                3060

Gly Glu Leu Thr Val Thr Asp Ala Thr Pro Asp Ser Leu Ser Leu
    3065                3070                3075

Ser Trp Met Val Pro Glu Gly Gln Phe Asp His Phe Leu Val Gln
    3080                3085                3090

Tyr Arg Asn Gly Asp Gly Gln Pro Lys Ala Val Arg Val Pro Gly
    3095                3100                3105

His Glu Asp Gly Val Thr Ile Ser Gly Leu Glu Pro Asp His Lys
    3110                3115                3120

Tyr Lys Met Asn Leu Tyr Gly Phe His Gly Gly Gln Arg Val Gly
    3125                3130                3135

Pro Val Ser Ala Ile Gly Val Thr Glu Glu Thr Pro Ser Pro
    3140                3145                3150

Thr Glu Pro Ser Thr Glu Ala Pro Glu Ala Pro Glu Glu Pro Leu
    3155                3160                3165

Leu Gly Glu Leu Thr Val Thr Gly Ser Ser Pro Asp Ser Leu Ser
    3170                3175                3180

Leu Ser Trp Thr Val Pro Gln Gly Arg Phe Asp Ser Phe Thr Val
    3185                3190                3195

Gln Tyr Lys Asp Arg Asp Gly Gln Pro Gln Val Val Arg Val Arg
    3200                3205                3210

Gly Glu Glu Ser Glu Val Thr Val Gly Gly Leu Glu Pro Gly Arg
    3215                3220                3225

Lys Tyr Lys Met His Leu Tyr Gly Leu His Glu Gly Gln Arg Val
    3230                3235                3240

Gly Pro Val Ser Thr Val Gly Ile Thr Ala Pro Leu Pro Thr Pro
    3245                3250                3255

Leu Pro Val Glu Pro Arg Leu Gly Glu Leu Ala Val Ala Ala Val
    3260                3265                3270

Thr Ser Asp Ser Val Gly Leu Ser Trp Thr Val Ala Gln Gly Pro
    3275                3280                3285

Phe Asp Ser Phe Leu Val Gln Tyr Arg Asp Ala Gln Gly Gln Pro
    3290                3295                3300

Gln Ala Val Pro Val Ser Gly Asp Leu Arg Ala Val Ala Val Ser
    3305                3310                3315

Gly Leu Asp Pro Ala Arg Lys Tyr Lys Phe Leu Leu Phe Gly Leu
    3320                3325                3330

Gln Asn Gly Lys Arg His Gly Pro Val Pro Val Glu Ala Arg Thr
    3335                3340                3345

Ala Pro Asp Thr Lys Pro Ser Pro Arg Leu Gly Glu Leu Thr Val
    3350                3355                3360

Thr Asp Ala Thr Pro Asp Ser Val Gly Leu Ser Trp Thr Val Pro
    3365                3370                3375
```

```
Glu Gly Glu Phe Asp Ser Phe Val Val Gln Tyr Lys Asp Lys Asp
    3380            3385                3390

Gly Arg Leu Gln Val Val Pro Val Ala Ala Asn Gln Arg Glu Val
    3395            3400                3405

Thr Val Gln Gly Leu Glu Pro Ser Arg Lys Tyr Arg Phe Leu Leu
    3410            3415                3420

Tyr Gly Leu Ser Gly Arg Lys Arg Leu Gly Pro Ile Ser Ala Asp
    3425            3430                3435

Ser Thr Thr Ala Pro Leu Glu Lys Glu Leu Pro His Leu Gly
    3440            3445                3450

Glu Leu Thr Val Ala Glu Glu Thr Ser Ser Leu Arg Leu Ser
    3455            3460                3465

Trp Thr Val Ala Gln Gly Pro Phe Asp Ser Phe Val Val Gln Tyr
    3470            3475                3480

Arg Asp Thr Asp Gly Gln Pro Arg Ala Val Pro Val Ala Ala Asp
    3485            3490                3495

Gln Arg Thr Val Thr Val Glu Asp Leu Glu Pro Gly Lys Lys Tyr
    3500            3505                3510

Lys Phe Leu Leu Tyr Gly Leu Leu Gly Lys Arg Leu Gly Pro
    3515            3520                3525

Val Ser Ala Leu Gly Met Thr Ala Pro Glu Glu Asp Thr Pro Ala
    3530            3535                3540

Pro Glu Leu Ala Pro Glu Ala Pro Glu Pro Pro Glu Glu Pro Arg
    3545            3550                3555

Leu Gly Val Leu Thr Val Thr Asp Thr Thr Pro Asp Ser Met Arg
    3560            3565                3570

Leu Ser Trp Ser Val Ala Gln Gly Pro Phe Asp Ser Phe Val Val
    3575            3580                3585

Gln Tyr Glu Asp Thr Asn Gly Gln Pro Gln Ala Leu Leu Val Asp
    3590            3595                3600

Gly Asp Gln Ser Lys Ile Leu Ile Ser Gly Leu Glu Pro Ser Thr
    3605            3610                3615

Pro Tyr Arg Phe Leu Leu Tyr Gly Leu His Glu Gly Lys Arg Leu
    3620            3625                3630

Gly Pro Leu Ser Ala Glu Gly Thr Thr Gly Leu Ala Pro Ala Gly
    3635            3640                3645

Gln Thr Ser Glu Glu Ser Arg Pro Arg Leu Ser Gln Leu Ser Val
    3650            3655                3660

Thr Asp Val Thr Thr Ser Ser Leu Arg Leu Asn Trp Glu Ala Pro
    3665            3670                3675

Pro Gly Ala Phe Asp Ser Phe Leu Leu Arg Phe Gly Val Pro Ser
    3680            3685                3690

Pro Ser Thr Leu Glu Pro His Pro Arg Pro Leu Leu Gln Arg Glu
    3695            3700                3705

Leu Met Val Pro Gly Thr Arg His Ser Ala Val Leu Arg Asp Leu
    3710            3715                3720

Arg Ser Gly Thr Leu Tyr Ser Leu Thr Leu Tyr Gly Leu Arg Gly
    3725            3730                3735

Pro His Lys Ala Asp Ser Ile Gln Gly Thr Ala Arg Thr Leu Ser
    3740            3745                3750

Pro Val Leu Glu Ser Pro Arg Asp Leu Gln Phe Ser Glu Ile Arg
    3755            3760                3765
```

```
Glu Thr Ser Ala Lys Val Asn Trp Met Pro Pro Ser Arg Ala
3770             3775            3780

Asp Ser Phe Lys Val Ser Tyr Gln Leu Ala Asp Gly Gly Glu Pro
3785             3790            3795

Gln Ser Val Gln Val Asp Gly Gln Ala Arg Thr Gln Lys Leu Gln
3800             3805            3810

Gly Leu Ile Pro Gly Ala Arg Tyr Glu Val Thr Val Val Ser Val
3815             3820            3825

Arg Gly Phe Glu Glu Ser Glu Pro Leu Thr Gly Phe Leu Thr Thr
3830             3835            3840

Val Pro Asp Gly Pro Thr Gln Leu Arg Ala Leu Asn Leu Thr Glu
3845             3850            3855

Gly Phe Ala Val Leu His Trp Lys Pro Pro Gln Asn Pro Val Asp
3860             3865            3870

Thr Tyr Asp Val Gln Val Thr Ala Pro Gly Ala Pro Pro Leu Gln
3875             3880            3885

Ala Glu Thr Pro Gly Ser Ala Val Asp Tyr Pro Leu His Asp Leu
3890             3895            3900

Val Leu His Thr Asn Tyr Thr Ala Thr Val Arg Gly Leu Arg Gly
3905             3910            3915

Pro Asn Leu Thr Ser Pro Ala Ser Ile Thr Phe Thr Thr Gly Leu
3920             3925            3930

Glu Ala Pro Arg Asp Leu Glu Ala Lys Glu Val Thr Pro Arg Thr
3935             3940            3945

Ala Leu Leu Thr Trp Thr Glu Pro Pro Val Arg Pro Ala Gly Tyr
3950             3955            3960

Leu Leu Ser Phe His Thr Pro Gly Gly Gln Asn Gln Glu Ile Leu
3965             3970            3975

Leu Pro Gly Gly Ile Thr Ser His Gln Leu Leu Gly Leu Phe Pro
3980             3985            3990

Ser Thr Ser Tyr Asn Ala Arg Leu Gln Ala Met Trp Gly Gln Ser
3995             4000            4005

Leu Leu Pro Pro Val Ser Thr Ser Phe Thr Thr Gly Gly Leu Arg
4010             4015            4020

Ile Pro Phe Pro Arg Asp Cys Gly Glu Glu Met Gln Asn Gly Ala
4025             4030            4035

Gly Ala Ser Arg Thr Ser Thr Ile Phe Leu Asn Gly Asn Arg Glu
4040             4045            4050

Arg Pro Leu Asn Val Phe Cys Asp Met Glu Thr Asp Gly Gly Gly
4055             4060            4065

Trp Leu Val Phe Gln Arg Arg Met Asp Gly Gln Thr Asp Phe Trp
4070             4075            4080

Arg Asp Trp Glu Asp Tyr Ala His Gly Phe Gly Asn Ile Ser Gly
4085             4090            4095

Glu Phe Trp Leu Gly Asn Glu Ala Leu His Ser Leu Thr Gln Ala
4100             4105            4110

Gly Asp Tyr Ser Met Arg Val Asp Leu Arg Ala Gly Asp Glu Ala
4115             4120            4125

Val Phe Ala Gln Tyr Asp Ser Phe His Val Asp Ser Ala Ala Glu
4130             4135            4140

Tyr Tyr Arg Leu His Leu Glu Gly Tyr His Gly Thr Ala Gly Asp
4145             4150            4155

Ser Met Ser Tyr His Ser Gly Ser Val Phe Ser Ala Arg Asp Arg
```

```
              4160                4165                4170

Asp Pro Asn Ser Leu Leu Ile Ser Cys Ala Val Ser Tyr Arg Gly
    4175                4180                4185

Ala Trp Trp Tyr Arg Asn Cys His Tyr Ala Asn Leu Asn Gly Leu
    4190                4195                4200

Tyr Gly Ser Thr Val Asp His Gln Gly Val Ser Trp Tyr His Trp
    4205                4210                4215

Lys Gly Phe Glu Phe Ser Val Pro Phe Thr Glu Met Lys Leu Arg
    4220                4225                4230

Pro Arg Asn Phe Arg Ser Pro Ala Gly Gly Gly
    4235                4240

<210> SEQ ID NO 8
<211> LENGTH: 47
<212> TYPE: PRT
<213> ORGANISM: Homo sapiens
<220> FEATURE:
<221> NAME/KEY: misc_feature
<222> LOCATION: (1)..(47)
<223> OTHER INFORMATION: Human ANLN  segment

<400> SEQUENCE: 8

Lys Ala Ile Gln Glu Arg Leu Phe Lys Gln Asp Thr Ser Ser Ser Thr
1               5                   10                  15

Thr His Leu Ala Gln Gln Leu Lys Gln Glu Arg Gln Lys Glu Leu Ala
                20                  25                  30

Cys Leu Arg Gly Arg Phe Asp Lys Gly Asn Ile Trp Ser Ala Glu
            35                  40                  45

<210> SEQ ID NO 9
<211> LENGTH: 47
<212> TYPE: PRT
<213> ORGANISM: Chimpanzee
<220> FEATURE:
<221> NAME/KEY: misc_feature
<222> LOCATION: (1)..(47)
<223> OTHER INFORMATION: Chimpanzee ANLN segment

<400> SEQUENCE: 9

Lys Ala Ile Gln Glu Arg Leu Phe Lys Gln Asp Thr Ser Ser Ser Thr
1               5                   10                  15

Thr His Leu Ala Gln Gln Leu Lys Gln Glu Arg Gln Lys Glu Leu Ala
                20                  25                  30

Cys Leu Arg Gly Arg Phe Asp Lys Gly Asn Ile Trp Ser Ala Glu
            35                  40                  45

<210> SEQ ID NO 10
<211> LENGTH: 47
<212> TYPE: PRT
<213> ORGANISM: Wolf
<220> FEATURE:
<221> NAME/KEY: misc_feature
<222> LOCATION: (1)..(47)
<223> OTHER INFORMATION: Wolf ANLN segment

<400> SEQUENCE: 10

Lys Ala Ile Gln Glu Arg Leu Phe Lys Gln Asn Ala Ser Ser Ser Thr
1               5                   10                  15

Thr His Leu Ala Gln Gln Leu Lys Gln Glu Arg Glu Lys Glu Leu Ala
                20                  25                  30

Cys Leu Arg Gly Arg Phe Asp Lys Gly Asn Leu Trp Ser Ala Glu
            35                  40                  45
```

<210> SEQ ID NO 11
<211> LENGTH: 47
<212> TYPE: PRT
<213> ORGANISM: Cattle
<220> FEATURE:
<221> NAME/KEY: misc_feature
<222> LOCATION: (1)..(47)
<223> OTHER INFORMATION: Cattle ANLN segment

<400> SEQUENCE: 11

Lys Ala Ile Gln Glu Arg Leu Phe Arg Gln Asn Ala Ser Ser Ser Thr
1               5                   10                  15

Thr His Leu Ala Gln Gln Leu Lys Gln Glu Arg Gln Lys Glu Leu Ala
            20                  25                  30

Cys Leu Arg Ser Arg Phe Asp Lys Gly Asn Leu Trp Ser Ala Glu
        35                  40                  45

<210> SEQ ID NO 12
<211> LENGTH: 47
<212> TYPE: PRT
<213> ORGANISM: Mouse
<220> FEATURE:
<221> NAME/KEY: misc_feature
<222> LOCATION: (1)..(47)
<223> OTHER INFORMATION: Mouse ANLN segment

<400> SEQUENCE: 12

Lys Ala Ile Gln Glu Arg Leu Phe Lys Gln Asn Thr Cys Ser Ser Thr
1               5                   10                  15

Thr His Leu Ala Gln Gln Leu Lys Gln Glu Arg Glu Lys Glu Leu Ala
            20                  25                  30

Cys Leu Arg Gly Arg Leu Asp Lys Gly Asn Leu Trp Ser Ala Glu
        35                  40                  45

<210> SEQ ID NO 13
<211> LENGTH: 47
<212> TYPE: PRT
<213> ORGANISM: Rat
<220> FEATURE:
<221> NAME/KEY: misc_feature
<222> LOCATION: (1)..(47)
<223> OTHER INFORMATION: Rat ANLN segment

<400> SEQUENCE: 13

Lys Ala Ile Gln Glu Arg Leu Phe Lys Gln Asn Thr Cys Ser Ser Thr
1               5                   10                  15

Thr His Leu Ala Gln Gln Leu Lys Gln Glu Arg Glu Lys Glu Leu Ala
            20                  25                  30

Cys Leu Arg Gly Arg Phe Asp Lys Gly Ser Leu Trp Ser Ala Glu
        35                  40                  45

<210> SEQ ID NO 14
<211> LENGTH: 47
<212> TYPE: PRT
<213> ORGANISM: Chicken
<220> FEATURE:
<221> NAME/KEY: misc_feature
<222> LOCATION: (1)..(47)
<223> OTHER INFORMATION: Chicken ANLN segment

<400> SEQUENCE: 14

Arg Thr Ile Gln Glu Lys Leu Leu Lys Gln Asn Glu Asn Ser Ser Thr
1               5                   10                  15

Ala Asn Leu Ala Leu Gln Leu Lys Gln Glu Arg Glu Arg Glu Leu Ala
            20                  25                  30

Cys Ile Arg Gly Arg Phe Asp Lys Gly Asn Leu Trp Ser Ala Glu
        35                  40                  45

<210> SEQ ID NO 15
<211> LENGTH: 47
<212> TYPE: PRT
<213> ORGANISM: Zebra Fish
<220> FEATURE:
<221> NAME/KEY: misc_feature
<222> LOCATION: (1)..(47)
<223> OTHER INFORMATION: Zebra Fish ANLN segment

<400> SEQUENCE: 15

Pro Lys Phe Lys Leu Leu Gln Glu Arg Leu Gly Gly Ala Gln Ala Thr
1               5                   10                  15

Ser Thr Thr Ala Ala Leu Thr Glu Lys Gln Lys Met Glu Arg Glu Ala
            20                  25                  30

Glu Leu Ala Gln Ile Arg Asn Arg Phe Gln Lys Gly Asn Met Leu
        35                  40                  45

<210> SEQ ID NO 16
<211> LENGTH: 25
<212> TYPE: DNA
<213> ORGANISM: Artificial Sequence
<220> FEATURE:
<223> OTHER INFORMATION: Synthetic primer: ANLN-1F

<400> SEQUENCE: 16
cacttttctc ttcctgaatt tgaac                                         25

<210> SEQ ID NO 17
<211> LENGTH: 19
<212> TYPE: DNA
<213> ORGANISM: Artificial Sequence
<220> FEATURE:
<223> OTHER INFORMATION: Synthetic primer: ANLN-1R

<400> SEQUENCE: 17
tgacagagga aggtgggtg                                                19

<210> SEQ ID NO 18
<211> LENGTH: 22
<212> TYPE: DNA
<213> ORGANISM: Artificial Sequence
<220> FEATURE:
<223> OTHER INFORMATION: Synthetic primer: ANLN-2F

<400> SEQUENCE: 18
aaatttgtgg ccgttaaaaa tc                                            22

<210> SEQ ID NO 19
<211> LENGTH: 20
<212> TYPE: DNA
<213> ORGANISM: Artificial Sequence
<220> FEATURE:
<223> OTHER INFORMATION: Synthetic primer: ANLN-2R

<400> SEQUENCE: 19
aatgaaatgt ttggggcttg                                               20

<210> SEQ ID NO 20
<211> LENGTH: 22
<212> TYPE: DNA

```
<213> ORGANISM: Artificial Sequence
<220> FEATURE:
<223> OTHER INFORMATION: Synthetic primer: ANLN-3F

<400> SEQUENCE: 20
tttaaaagaa tagggagggg tg                                           22

<210> SEQ ID NO 21
<211> LENGTH: 22
<212> TYPE: DNA
<213> ORGANISM: Artificial Sequence
<220> FEATURE:
<223> OTHER INFORMATION: Synthetic primer: ANLN-3R

<400> SEQUENCE: 21
atgcaagcaa aggatactca ac                                           22

<210> SEQ ID NO 22
<211> LENGTH: 23
<212> TYPE: DNA
<213> ORGANISM: Artificial Sequence
<220> FEATURE:
<223> OTHER INFORMATION: Synthetic primer: ANLN-4F

<400> SEQUENCE: 22
attcagcata gagtgatcct ggt                                          23

<210> SEQ ID NO 23
<211> LENGTH: 20
<212> TYPE: DNA
<213> ORGANISM: Artificial Sequence
<220> FEATURE:
<223> OTHER INFORMATION: Synthetic primer: ANLN-4R

<400> SEQUENCE: 23
ccatccacct gcacatacac                                              20

<210> SEQ ID NO 24
<211> LENGTH: 26
<212> TYPE: DNA
<213> ORGANISM: Artificial Sequence
<220> FEATURE:
<223> OTHER INFORMATION: Synthetic primer: ANLN-5F

<400> SEQUENCE: 24
ggacttgaat tgttttgtta taggac                                       26

<210> SEQ ID NO 25
<211> LENGTH: 22
<212> TYPE: DNA
<213> ORGANISM: Artificial Sequence
<220> FEATURE:
<223> OTHER INFORMATION: Synthetic primer: ANLN-5R

<400> SEQUENCE: 25
caaatcattg ctgtaccatt ca                                           22

<210> SEQ ID NO 26
<211> LENGTH: 23
<212> TYPE: DNA
<213> ORGANISM: Artificial Sequence
<220> FEATURE:
<223> OTHER INFORMATION: Synthetic primer: ANLN-6F

<400> SEQUENCE: 26
caaagcattt tgaagctgta atg                                          23
```

<210> SEQ ID NO 27
<211> LENGTH: 19
<212> TYPE: DNA
<213> ORGANISM: Artificial Sequence
<220> FEATURE:
<223> OTHER INFORMATION: Synthetic primer: ANLN-6R

<400> SEQUENCE: 27
ggcatcagaa cccattttg                                               19

<210> SEQ ID NO 28
<211> LENGTH: 20
<212> TYPE: DNA
<213> ORGANISM: Artificial Sequence
<220> FEATURE:
<223> OTHER INFORMATION: Synthetic primer: ANLN-7F

<400> SEQUENCE: 28
tcagacaaga ttgggcacat                                              20

<210> SEQ ID NO 29
<211> LENGTH: 24
<212> TYPE: DNA
<213> ORGANISM: Artificial Sequence
<220> FEATURE:
<223> OTHER INFORMATION: Synthetic primer: ANLN-7R

<400> SEQUENCE: 29
cgaaaagtga cagagttaat tgga                                         24

<210> SEQ ID NO 30
<211> LENGTH: 26
<212> TYPE: DNA
<213> ORGANISM: Artificial Sequence
<220> FEATURE:
<223> OTHER INFORMATION: Synthetic primer: ANLN-8F

<400> SEQUENCE: 30
cactatctct ttggttctaa ggaaac                                       26

<210> SEQ ID NO 31
<211> LENGTH: 22
<212> TYPE: DNA
<213> ORGANISM: Artificial Sequence
<220> FEATURE:
<223> OTHER INFORMATION: Synthetic primer: ANLN-8R

<400> SEQUENCE: 31
agaacaaaca aatccagcaa ag                                           22

<210> SEQ ID NO 32
<211> LENGTH: 21
<212> TYPE: DNA
<213> ORGANISM: Artificial Sequence
<220> FEATURE:
<223> OTHER INFORMATION: Synthetic primer: ANLN-9F

<400> SEQUENCE: 32
aagagaggac aggtgttcag g                                            21

<210> SEQ ID NO 33
<211> LENGTH: 20
<212> TYPE: DNA
<213> ORGANISM: Artificial Sequence
<220> FEATURE:

-continued

```
<223> OTHER INFORMATION: Synthetic primer: ANLN-9R

<400> SEQUENCE: 33
ccctgtcaaa gtcagtgagg                                               20

<210> SEQ ID NO 34
<211> LENGTH: 22
<212> TYPE: DNA
<213> ORGANISM: Artificial Sequence
<220> FEATURE:
<223> OTHER INFORMATION: Synthetic primer: ANLN-10F

<400> SEQUENCE: 34
ttgaagctga agattttctt gg                                            22

<210> SEQ ID NO 35
<211> LENGTH: 20
<212> TYPE: DNA
<213> ORGANISM: Artificial Sequence
<220> FEATURE:
<223> OTHER INFORMATION: Synthetic primer: ANLN-10R

<400> SEQUENCE: 35
aggtctgcaa aattcccttg                                               20

<210> SEQ ID NO 36
<211> LENGTH: 24
<212> TYPE: DNA
<213> ORGANISM: Artificial Sequence
<220> FEATURE:
<223> OTHER INFORMATION: Synthetic primer: ANLN-11F

<400> SEQUENCE: 36
ggagaattca ttgattttca caga                                          24

<210> SEQ ID NO 37
<211> LENGTH: 24
<212> TYPE: DNA
<213> ORGANISM: Artificial Sequence
<220> FEATURE:
<223> OTHER INFORMATION: Synthetic primer: ANLN-11R

<400> SEQUENCE: 37
tgtcaatcta aaccatgacc ctta                                          24

<210> SEQ ID NO 38
<211> LENGTH: 21
<212> TYPE: DNA
<213> ORGANISM: Artificial Sequence
<220> FEATURE:
<223> OTHER INFORMATION: Synthetic primer: ANLN-12F

<400> SEQUENCE: 38
ggatagtgct cagtgtgttg c                                             21

<210> SEQ ID NO 39
<211> LENGTH: 20
<212> TYPE: DNA
<213> ORGANISM: Artificial Sequence
<220> FEATURE:
<223> OTHER INFORMATION: Synthetic primer: ANLN-12R

<400> SEQUENCE: 39
agctcacagc ctagtgcaag                                               20
```

```
<210> SEQ ID NO 40
<211> LENGTH: 22
<212> TYPE: DNA
<213> ORGANISM: Artificial Sequence
<220> FEATURE:
<223> OTHER INFORMATION: Synthetic primer: ANLN-13F

<400> SEQUENCE: 40
ttttggtgca tagtcgagaa ac                                              22

<210> SEQ ID NO 41
<211> LENGTH: 22
<212> TYPE: DNA
<213> ORGANISM: Artificial Sequence
<220> FEATURE:
<223> OTHER INFORMATION: Synthetic primer: ANLN-13R

<400> SEQUENCE: 41
tccactggaa cagatgacta gg                                              22

<210> SEQ ID NO 42
<211> LENGTH: 25
<212> TYPE: DNA
<213> ORGANISM: Artificial Sequence
<220> FEATURE:
<223> OTHER INFORMATION: Synthetic primer: ANLN-14F

<400> SEQUENCE: 42
tttgctctca ttagaaacag ttacg                                           25

<210> SEQ ID NO 43
<211> LENGTH: 24
<212> TYPE: DNA
<213> ORGANISM: Artificial Sequence
<220> FEATURE:
<223> OTHER INFORMATION: Synthetic primer: ANLN-14R

<400> SEQUENCE: 43
acaattcaat ctaggtgagg ttca                                            24

<210> SEQ ID NO 44
<211> LENGTH: 25
<212> TYPE: DNA
<213> ORGANISM: Artificial Sequence
<220> FEATURE:
<223> OTHER INFORMATION: Synthetic primer: ANLN-15F

<400> SEQUENCE: 44
tttgtgtctg gaaagttgat tttag                                           25

<210> SEQ ID NO 45
<211> LENGTH: 20
<212> TYPE: DNA
<213> ORGANISM: Artificial Sequence
<220> FEATURE:
<223> OTHER INFORMATION: Synthetic primer: ANLN-15R

<400> SEQUENCE: 45
gtgcataagg cgtttcaaag                                                 20

<210> SEQ ID NO 46
<211> LENGTH: 26
<212> TYPE: DNA
<213> ORGANISM: Artificial Sequence
<220> FEATURE:
<223> OTHER INFORMATION: Synthetic primer: ANLN-16.17F
```

<400> SEQUENCE: 46
aaatattttg gacttgcatt ataggg                                        26

<210> SEQ ID NO 47
<211> LENGTH: 23
<212> TYPE: DNA
<213> ORGANISM: Artificial Sequence
<220> FEATURE:
<223> OTHER INFORMATION: Synthetic primer: ANLN-16.17R

<400> SEQUENCE: 47
aaattggaac atgaaactga tcc                                           23

<210> SEQ ID NO 48
<211> LENGTH: 26
<212> TYPE: DNA
<213> ORGANISM: Artificial Sequence
<220> FEATURE:
<223> OTHER INFORMATION: Synthetic primer: ANLN-18.19F

<400> SEQUENCE: 48
ggttggatag ttttactttc tgagac                                        26

<210> SEQ ID NO 49
<211> LENGTH: 22
<212> TYPE: DNA
<213> ORGANISM: Artificial Sequence
<220> FEATURE:
<223> OTHER INFORMATION: Synthetic primer: ANLN-18.19R

<400> SEQUENCE: 49
tgcaagtgct taattcctta cc                                            22

<210> SEQ ID NO 50
<211> LENGTH: 20
<212> TYPE: DNA
<213> ORGANISM: Artificial Sequence
<220> FEATURE:
<223> OTHER INFORMATION: Synthetic primer: ANLN-20F

<400> SEQUENCE: 50
ttctactggg atggggtgag                                               20

<210> SEQ ID NO 51
<211> LENGTH: 20
<212> TYPE: DNA
<213> ORGANISM: Artificial Sequence
<220> FEATURE:
<223> OTHER INFORMATION: Synthetic primer: ANLN-20R

<400> SEQUENCE: 51
aaaagcattg tggcatttcc                                               20

<210> SEQ ID NO 52
<211> LENGTH: 26
<212> TYPE: DNA
<213> ORGANISM: Artificial Sequence
<220> FEATURE:
<223> OTHER INFORMATION: Synthetic primer: ANLN-21F

<400> SEQUENCE: 52
tgctctgttt tcaagttgta atagtc                                        26

<210> SEQ ID NO 53
<211> LENGTH: 25

```
<212> TYPE: DNA
<213> ORGANISM: Artificial Sequence
<220> FEATURE:
<223> OTHER INFORMATION: Synthetic primer: ANLN-21R

<400> SEQUENCE: 53
aacaagtctg tatttcacaa aatgg                                          25

<210> SEQ ID NO 54
<211> LENGTH: 24
<212> TYPE: DNA
<213> ORGANISM: Artificial Sequence
<220> FEATURE:
<223> OTHER INFORMATION: Synthetic primer: ANLN-22F

<400> SEQUENCE: 54
cagcatttca ttgttaggac attt                                           24

<210> SEQ ID NO 55
<211> LENGTH: 20
<212> TYPE: DNA
<213> ORGANISM: Artificial Sequence
<220> FEATURE:
<223> OTHER INFORMATION: Synthetic primer: ANLN-22R

<400> SEQUENCE: 55
cagagggaac atttgcatga                                                20

<210> SEQ ID NO 56
<211> LENGTH: 24
<212> TYPE: DNA
<213> ORGANISM: Artificial Sequence
<220> FEATURE:
<223> OTHER INFORMATION: Synthetic primer: ANLN-23F

<400> SEQUENCE: 56
aaatgctgct taatgcttac tgac                                           24

<210> SEQ ID NO 57
<211> LENGTH: 25
<212> TYPE: DNA
<213> ORGANISM: Artificial Sequence
<220> FEATURE:
<223> OTHER INFORMATION: Synthetic primer: ANLN-23R

<400> SEQUENCE: 57
agtggtaagt acatagtggg caatc                                          25

<210> SEQ ID NO 58
<211> LENGTH: 21
<212> TYPE: DNA
<213> ORGANISM: Artificial Sequence
<220> FEATURE:
<223> OTHER INFORMATION: Synthetic primer: ANLN-24F

<400> SEQUENCE: 58
tccctagcaa gagtacatgg g                                              21

<210> SEQ ID NO 59
<211> LENGTH: 23
<212> TYPE: DNA
<213> ORGANISM: Artificial Sequence
<220> FEATURE:
<223> OTHER INFORMATION: Synthetic primer: ANLN-24R

<400> SEQUENCE: 59
```
tgcaatcagt aaatctgatg ctc                                              23

<210> SEQ ID NO 60
<211> LENGTH: 18
<212> TYPE: DNA
<213> ORGANISM: Artificial Sequence
<220> FEATURE:
<223> OTHER INFORMATION: Synthetic primer: VP1.5-F

<400> SEQUENCE: 60
ggactttcca aaatgtcg                                                    18

<210> SEQ ID NO 61
<211> LENGTH: 20
<212> TYPE: DNA
<213> ORGANISM: Artificial Sequence
<220> FEATURE:
<223> OTHER INFORMATION: Synthetic primer: ANLNcdna-1R

<400> SEQUENCE: 61
agacacagga cttggagaac                                                  20

<210> SEQ ID NO 62
<211> LENGTH: 21
<212> TYPE: DNA
<213> ORGANISM: Artificial Sequence
<220> FEATURE:
<223> OTHER INFORMATION: Synthetic primer: ANLNcdna-2F

<400> SEQUENCE: 62
acgctgttct gacaacactg a                                                21

<210> SEQ ID NO 63
<211> LENGTH: 20
<212> TYPE: DNA
<213> ORGANISM: Artificial Sequence
<220> FEATURE:
<223> OTHER INFORMATION: Synthetic primer: ANLNcdna-2R

<400> SEQUENCE: 63
tccctttggg aacagaatgt                                                  20

<210> SEQ ID NO 64
<211> LENGTH: 20
<212> TYPE: DNA
<213> ORGANISM: Artificial Sequence
<220> FEATURE:
<223> OTHER INFORMATION: Synthetic primer: ANLNcdna-3F

<400> SEQUENCE: 64
atttgctcct gggaagatga                                                  20

<210> SEQ ID NO 65
<211> LENGTH: 20
<212> TYPE: DNA
<213> ORGANISM: Artificial Sequence
<220> FEATURE:
<223> OTHER INFORMATION: Synthetic primer: ANLNcdna-3R

<400> SEQUENCE: 65
ggatggcctt tgtatttgga                                                  20

<210> SEQ ID NO 66
<211> LENGTH: 25
<212> TYPE: DNA
<213> ORGANISM: Artificial Sequence
<220> FEATURE:
<223> OTHER INFORMATION: Synthetic primer: ANLNcdna-4F

<400> SEQUENCE: 66
tctgcaatct caatctaaag acaaa                                          25

<210> SEQ ID NO 67
<211> LENGTH: 23
<212> TYPE: DNA
<213> ORGANISM: Artificial Sequence
<220> FEATURE:
<223> OTHER INFORMATION: Synthetic primer: ANLNcdna-4R

<400> SEQUENCE: 67
actgagtttt tgaaacacct tgg                                            23

<210> SEQ ID NO 68
<211> LENGTH: 20
<212> TYPE: DNA
<213> ORGANISM: Artificial Sequence
<220> FEATURE:
<223> OTHER INFORMATION: Synthetic primer: ANLNcdna-5F

<400> SEQUENCE: 68
gaaaaaggcg gaaactcaaa                                                20

<210> SEQ ID NO 69
<211> LENGTH: 20
<212> TYPE: DNA
<213> ORGANISM: Artificial Sequence
<220> FEATURE:
<223> OTHER INFORMATION: Synthetic primer: ANLNcdna-5R

<400> SEQUENCE: 69
gtgccaatgg tgcaagtaaa                                                20

<210> SEQ ID NO 70
<211> LENGTH: 20
<212> TYPE: DNA
<213> ORGANISM: Artificial Sequence
<220> FEATURE:
<223> OTHER INFORMATION: Synthetic primer: ANLNcdna-6F

<400> SEQUENCE: 70
agccaagagg agatggatca                                                20

<210> SEQ ID NO 71
<211> LENGTH: 22
<212> TYPE: DNA
<213> ORGANISM: Artificial Sequence
<220> FEATURE:
<223> OTHER INFORMATION: Synthetic primer: ANLNcdna-6R

<400> SEQUENCE: 71
aaagtgttct cttcccagtt gc                                             22

<210> SEQ ID NO 72
<211> LENGTH: 22
<212> TYPE: DNA
<213> ORGANISM: Artificial Sequence
<220> FEATURE:
<223> OTHER INFORMATION: Synthetic primer: ANLNcdna-7F

<400> SEQUENCE: 72
tctatcaagc tagccaggct ct                                             22

-continued

```
<210> SEQ ID NO 73
<211> LENGTH: 20
<212> TYPE: DNA
<213> ORGANISM: Artificial Sequence
<220> FEATURE:
<223> OTHER INFORMATION: Synthetic primer: ANLNcdna-7R

<400> SEQUENCE: 73
gtgaggagtc gctttggagt                                               20

<210> SEQ ID NO 74
<211> LENGTH: 21
<212> TYPE: DNA
<213> ORGANISM: Artificial Sequence
<220> FEATURE:
<223> OTHER INFORMATION: Synthetic primer: ANLNcdna-8F

<400> SEQUENCE: 74
acagcttggt gcaaagaaa g                                              21

<210> SEQ ID NO 75
<211> LENGTH: 20
<212> TYPE: DNA
<213> ORGANISM: Artificial Sequence
<220> FEATURE:
<223> OTHER INFORMATION: Synthetic primer: ANLNcdna-8R

<400> SEQUENCE: 75
tgcattggct gacaagagtc                                               20

<210> SEQ ID NO 76
<211> LENGTH: 20
<212> TYPE: DNA
<213> ORGANISM: Artificial Sequence
<220> FEATURE:
<223> OTHER INFORMATION: Synthetic primer: ANLNcdna-9F

<400> SEQUENCE: 76
cgcaagaatc ccataggaag                                               20

<210> SEQ ID NO 77
<211> LENGTH: 18
<212> TYPE: DNA
<213> ORGANISM: Artificial Sequence
<220> FEATURE:
<223> OTHER INFORMATION: Synthetic primer: ANLNcdna-9R

<400> SEQUENCE: 77
gttgttgatg gcgtgcag                                                 18

<210> SEQ ID NO 78
<211> LENGTH: 20
<212> TYPE: DNA
<213> ORGANISM: Artificial Sequence
<220> FEATURE:
<223> OTHER INFORMATION: Synthetic primer: ANLNcdna-10F

<400> SEQUENCE: 78
cttctaccac ttcggcacct                                               20

<210> SEQ ID NO 79
<211> LENGTH: 23
<212> TYPE: DNA
<213> ORGANISM: Artificial Sequence
<220> FEATURE:
<223> OTHER INFORMATION: Synthetic primer: ANLNcdna-10R
```

-continued

<400> SEQUENCE: 79
cctagtcaga caaaatgatg caa        23

<210> SEQ ID NO 80
<211> LENGTH: 18
<212> TYPE: DNA
<213> ORGANISM: Artificial Sequence
<220> FEATURE:
<223> OTHER INFORMATION: Synthetic primer: WT1Exon1-1F

<400> SEQUENCE: 80
attcacccac ccacccac        18

<210> SEQ ID NO 81
<211> LENGTH: 17
<212> TYPE: DNA
<213> ORGANISM: Artificial Sequence
<220> FEATURE:
<223> OTHER INFORMATION: Synthetic primer: WT1Exon1-1R

<400> SEQUENCE: 81
tgaaggagtg aggcggc        17

<210> SEQ ID NO 82
<211> LENGTH: 17
<212> TYPE: DNA
<213> ORGANISM: Artificial Sequence
<220> FEATURE:
<223> OTHER INFORMATION: Synthetic primer: WT1Exon1-2F

<400> SEQUENCE: 82
tgtgccctgc ctgtgag        17

<210> SEQ ID NO 83
<211> LENGTH: 20
<212> TYPE: DNA
<213> ORGANISM: Artificial Sequence
<220> FEATURE:
<223> OTHER INFORMATION: Synthetic primer: WT1Exon1-2R

<400> SEQUENCE: 83
taagagctgc ggtcaaaagg        20

<210> SEQ ID NO 84
<211> LENGTH: 18
<212> TYPE: DNA
<213> ORGANISM: Artificial Sequence
<220> FEATURE:
<223> OTHER INFORMATION: Synthetic primer: WT1Exon2F

<400> SEQUENCE: 84
tggttcagac ccactgcc        18

<210> SEQ ID NO 85
<211> LENGTH: 19
<212> TYPE: DNA
<213> ORGANISM: Artificial Sequence
<220> FEATURE:
<223> OTHER INFORMATION: Synthetic primer: WT1Exon2R

<400> SEQUENCE: 85
ggagaggagg atagcacgg        19

<210> SEQ ID NO 86

```
<211> LENGTH: 20
<212> TYPE: DNA
<213> ORGANISM: Artificial Sequence
<220> FEATURE:
<223> OTHER INFORMATION: Synthetic primer: WT1Exon3F

<400> SEQUENCE: 86
ggctcaggat ctcgtgtctc                                               20

<210> SEQ ID NO 87
<211> LENGTH: 18
<212> TYPE: DNA
<213> ORGANISM: Artificial Sequence
<220> FEATURE:
<223> OTHER INFORMATION: Synthetic primer: WT1Exon3R

<400> SEQUENCE: 87
gtgcctccaa gaccctgc                                                 18

<210> SEQ ID NO 88
<211> LENGTH: 22
<212> TYPE: DNA
<213> ORGANISM: Artificial Sequence
<220> FEATURE:
<223> OTHER INFORMATION: Synthetic primer: WT1Exon4F

<400> SEQUENCE: 88
tccattgctt ttgaagaaac ag                                            22

<210> SEQ ID NO 89
<211> LENGTH: 21
<212> TYPE: DNA
<213> ORGANISM: Artificial Sequence
<220> FEATURE:
<223> OTHER INFORMATION: Synthetic primer: WT1Exon4R

<400> SEQUENCE: 89
ctttgaaatg gttcaaacag g                                             21

<210> SEQ ID NO 90
<211> LENGTH: 20
<212> TYPE: DNA
<213> ORGANISM: Artificial Sequence
<220> FEATURE:
<223> OTHER INFORMATION: Synthetic primer: WT1Exon5F

<400> SEQUENCE: 90
cactggattc tgggatctgg                                               20

<210> SEQ ID NO 91
<211> LENGTH: 19
<212> TYPE: DNA
<213> ORGANISM: Artificial Sequence
<220> FEATURE:
<223> OTHER INFORMATION: Synthetic primer: WT1Exon5R

<400> SEQUENCE: 91
gccagtcagc aaggcctac                                                19

<210> SEQ ID NO 92
<211> LENGTH: 20
<212> TYPE: DNA
<213> ORGANISM: Artificial Sequence
<220> FEATURE:
<223> OTHER INFORMATION: Synthetic primer: WT1Exon6F

<400> SEQUENCE: 92
```

```
atttccaaat ggcgactgtg                                               20
```

<210> SEQ ID NO 93
<211> LENGTH: 20
<212> TYPE: DNA
<213> ORGANISM: Artificial Sequence
<220> FEATURE:
<223> OTHER INFORMATION: Synthetic primer: WT1Exon6R

<400> SEQUENCE: 93

```
ggccggtaag taggaagagg                                               20
```

<210> SEQ ID NO 94
<211> LENGTH: 21
<212> TYPE: DNA
<213> ORGANISM: Artificial Sequence
<220> FEATURE:
<223> OTHER INFORMATION: Synthetic primer: WT1Exon7F

<400> SEQUENCE: 94

```
cagtgctcac tctccctcaa g                                             21
```

<210> SEQ ID NO 95
<211> LENGTH: 21
<212> TYPE: DNA
<213> ORGANISM: Artificial Sequence
<220> FEATURE:
<223> OTHER INFORMATION: Synthetic primer: WT1Exon7R

<400> SEQUENCE: 95

```
ctggaaaagg agctcttgaa c                                             21
```

<210> SEQ ID NO 96
<211> LENGTH: 20
<212> TYPE: DNA
<213> ORGANISM: Artificial Sequence
<220> FEATURE:
<223> OTHER INFORMATION: Synthetic primer: WT1Exon8F

<400> SEQUENCE: 96

```
ttgcctttaa tgagatcccc                                               20
```

<210> SEQ ID NO 97
<211> LENGTH: 20
<212> TYPE: DNA
<213> ORGANISM: Artificial Sequence
<220> FEATURE:
<223> OTHER INFORMATION: Synthetic primer: WT1Exon8R

<400> SEQUENCE: 97

```
catgaaatca accctagccc                                               20
```

<210> SEQ ID NO 98
<211> LENGTH: 17
<212> TYPE: DNA
<213> ORGANISM: Artificial Sequence
<220> FEATURE:
<223> OTHER INFORMATION: Synthetic primer: WT1Exon9F

<400> SEQUENCE: 98

```
tgtgggcctc actgtgc                                                  17
```

<210> SEQ ID NO 99
<211> LENGTH: 23
<212> TYPE: DNA

```
<213> ORGANISM: Artificial Sequence
<220> FEATURE:
<223> OTHER INFORMATION: Synthetic primer: WT1Exon9R

<400> SEQUENCE: 99
ctctcatcac aatttcattc cac                                    23

<210> SEQ ID NO 100
<211> LENGTH: 20
<212> TYPE: DNA
<213> ORGANISM: Artificial Sequence
<220> FEATURE:
<223> OTHER INFORMATION: Synthetic primer: WT1Exon10F

<400> SEQUENCE: 100
aattcagagt gggtgccttg                                        20

<210> SEQ ID NO 101
<211> LENGTH: 22
<212> TYPE: DNA
<213> ORGANISM: Artificial Sequence
<220> FEATURE:
<223> OTHER INFORMATION: Synthetic primer: WT1Exon10R

<400> SEQUENCE: 101
gaggagtgga gagtcagact tg                                     22

<210> SEQ ID NO 102
<211> LENGTH: 60
<212> TYPE: PRT
<213> ORGANISM: Human
<220> FEATURE:
<221> NAME/KEY: misc_feature
<222> LOCATION: (1)..(60)
<223> OTHER INFORMATION: Human TNXB Polypeptide segment

<400> SEQUENCE: 102

Gly Pro Phe Asp Ser Phe Met Val Gln Tyr Lys Asp Ala Gln Gly Gln
1               5                   10                  15

Pro Gln Ala Val Pro Val Ala Gly Asp Glu Asn Glu Val Thr Val Pro
            20                  25                  30

Gly Leu Asp Pro Asp Arg Lys Tyr Lys Met Asn Leu Tyr Gly Leu Arg
        35                  40                  45

Gly Arg Gln Arg Val Gly Pro Glu Ser Val Val Ala
    50                  55                  60

<210> SEQ ID NO 103
<211> LENGTH: 60
<212> TYPE: PRT
<213> ORGANISM: Cow
<220> FEATURE:
<221> NAME/KEY: misc_feature
<222> LOCATION: (1)..(60)
<223> OTHER INFORMATION: Cow TNXB POLYPEPTIDE SEGMENT

<400> SEQUENCE: 103

Gly Ser Phe Asp Ser Phe Val Val Gln Tyr Lys Asp Ala Gln Gly Arg
1               5                   10                  15

Pro Gln Ala Val Pro Val Thr Gly Asp Glu Asn Glu Val Ala Ile Pro
            20                  25                  30

Gly Leu Glu Pro Asp Arg Lys Tyr Lys Met Asn Leu Tyr Gly Leu His
        35                  40                  45

Gly Arg Gln Arg Val Gly Pro Val Ser Val Val Ala
    50                  55                  60
```

<210> SEQ ID NO 104
<211> LENGTH: 60
<212> TYPE: PRT
<213> ORGANISM: Pig
<220> FEATURE:
<221> NAME/KEY: misc_feature
<222> LOCATION: (1)..(60)
<223> OTHER INFORMATION: PIG TNXB POLYPEPTIDE SEGMENT

<400> SEQUENCE: 104

Gly Ser Phe Asp Ser Phe Thr Val Gln Tyr Lys Asp Ala Gln Gly Arg
1               5                   10                  15

Pro Gln Val Val Pro Val Lys Gly Asp Glu Asn Glu Val Thr Ile Pro
            20                  25                  30

Gly Leu Glu Ser Asp Arg Lys Tyr Arg Met Asn Leu Tyr Gly Leu His
        35                  40                  45

Gly Arg Gln Arg Val Gly Pro Val Ser Val Val Ala
    50                  55                  60

<210> SEQ ID NO 105
<211> LENGTH: 60
<212> TYPE: PRT
<213> ORGANISM: Dog
<220> FEATURE:
<221> NAME/KEY: misc_feature
<222> LOCATION: (1)..(60)
<223> OTHER INFORMATION: DOG TNXB POLYPEPTIDE SEGMENT

<400> SEQUENCE: 105

Gly Ser Phe Asp Ser Phe Val Val Gln Tyr Lys Asp Ala Gln Gly Gln
1               5                   10                  15

Pro Gln Ala Val Pro Val Arg Gly Asp Glu Asn Glu Val Thr Ile Pro
            20                  25                  30

Gly Leu Glu Ser His Arg Lys Tyr Lys Met Asn Leu Tyr Gly Leu His
        35                  40                  45

Gly Arg Gln Arg Val Gly Pro Val Ser Val Val Ala
    50                  55                  60

<210> SEQ ID NO 106
<211> LENGTH: 60
<212> TYPE: PRT
<213> ORGANISM: Elephant
<220> FEATURE:
<221> NAME/KEY: misc_feature
<222> LOCATION: (1)..(60)
<223> OTHER INFORMATION: ELEPHANT TNXB POLYPEPTIDE SEGMENT

<400> SEQUENCE: 106

Gly His Phe Asp Tyr Phe Met Val Gln Tyr Arg Asn Gly Asp Gly Gln
1               5                   10                  15

Pro Lys Ala Val Arg Val Pro Gly His Glu Asp Glu Val Thr Ile Leu
            20                  25                  30

Gly Leu Glu Pro Asp Gln Lys Tyr Lys Met Asn Leu Tyr Gly Leu His
        35                  40                  45

Gly Gly Gln Arg Val Gly Pro Ile Ser Ala Ile Gly
    50                  55                  60

<210> SEQ ID NO 107
<211> LENGTH: 60
<212> TYPE: PRT
<213> ORGANISM: Mouse
<220> FEATURE:

```
<221> NAME/KEY: misc_feature
<222> LOCATION: (1)..(60)
<223> OTHER INFORMATION: MOUSE TNXB POLYPEPTIDE SEGMENT

<400> SEQUENCE: 107

Gly Pro Phe Asp Ser Phe Val Ile Leu Tyr Lys Asp Ala Gln Gly Gln
1               5                   10                  15

Pro Gln Ser Val Pro Ile Glu Gly Asp Glu Asn Glu Val Thr Val Pro
            20                  25                  30

Gly Leu Glu Ser Asn Arg Lys Tyr Lys Met Asn Leu Tyr Gly Leu Arg
        35                  40                  45

Gly Arg Gln Arg Val Gly Pro Val Ser Val Val Ala
    50                  55                  60

<210> SEQ ID NO 108
<211> LENGTH: 60
<212> TYPE: PRT
<213> ORGANISM: Guinea Pig
<220> FEATURE:
<221> NAME/KEY: misc_feature
<222> LOCATION: (1)..(60)
<223> OTHER INFORMATION: GUINEA PIG TNXB POLYPEPTIDE SEGMENT

<400> SEQUENCE: 108

Gly Pro Phe Asp Ser Phe Val Val Gln Tyr Lys Asp Ala Gln Gly Gln
1               5                   10                  15

Pro Gln Ala Val Pro Val Gly Ala Asp Gln Ser Glu Leu Thr Val Pro
            20                  25                  30

Gly Leu Glu Pro Asn Arg Lys Tyr Lys Met Asn Leu Tyr Gly Leu Arg
        35                  40                  45

Gly Arg Gln Arg Val Gly Pro Ala Ser Val Val Ala
    50                  55                  60

<210> SEQ ID NO 109
<211> LENGTH: 60
<212> TYPE: PRT
<213> ORGANISM: Opossum
<220> FEATURE:
<221> NAME/KEY: misc_feature
<222> LOCATION: (1)..(60)
<223> OTHER INFORMATION: OPOSSUM TNXB POLYPEPTIDE SEGMENT

<400> SEQUENCE: 109

Gly Lys Phe Asp Ser Phe Val Val Gln Tyr Lys Asp Lys Asp Gly Gln
1               5                   10                  15

Ser Gln Val Val Pro Val Glu Val Gly Gln Asn Glu Val Thr Ile Ser
            20                  25                  30

Asp Leu Gln Pro Ser Arg Lys Tyr Lys Met Asn Leu Tyr Gly Leu Gln
        35                  40                  45

Gly Lys Gln Arg Val Gly Pro Ile Ser Val Ile Ala
    50                  55                  60

<210> SEQ ID NO 110
<211> LENGTH: 51
<212> TYPE: PRT
<213> ORGANISM: Human
<220> FEATURE:
<221> NAME/KEY: misc_feature
<222> LOCATION: (1)..(51)
<223> OTHER INFORMATION: Human TNXB Polypeptide Segment

<400> SEQUENCE: 110

Leu Glu Pro Gly Arg Lys Tyr Lys Met His Leu Tyr Gly Leu His Glu
```

```
                1               5                   10                  15
Gly Gln Arg Val Gly Pro Val Ser Thr Val Gly Ile Thr Ala Pro Leu
                20                  25                  30

Pro Thr Pro Leu Pro Val Glu Pro Arg Leu Gly Glu Leu Ala Val Ala
        35                  40                  45

Ala Val Thr
        50

<210> SEQ ID NO 111
<211> LENGTH: 51
<212> TYPE: PRT
<213> ORGANISM: Cow
<220> FEATURE:
<221> NAME/KEY: misc_feature
<222> LOCATION: (1)..(51)
<223> OTHER INFORMATION: COW TNXB POLYPEPTIDE SEGMENT

<400> SEQUENCE: 111

Leu Glu Pro Gly His Lys Tyr Lys Met His Leu Tyr Gly Leu His Gly
1               5                   10                  15

Gly Arg Arg Val Gly Pro Ala Ser Thr Val Gly Val Thr Ala Ser Leu
                20                  25                  30

Thr Thr Glu Arg Pro Leu Ala Pro Arg Leu Gly Glu Leu Ala Val Ala
        35                  40                  45

Val Val Thr
        50

<210> SEQ ID NO 112
<211> LENGTH: 51
<212> TYPE: PRT
<213> ORGANISM: Pig
<220> FEATURE:
<221> NAME/KEY: misc_feature
<222> LOCATION: (1)..(51)
<223> OTHER INFORMATION: PIG TNXB POLYPEPTIDE SEGMENT

<400> SEQUENCE: 112

Leu Glu Pro Asp His Lys Tyr Lys Met His Leu Tyr Gly Phe His Asp
1               5                   10                  15

Gly Gln Arg Val Gly Pro Val Ser Thr Val Gly Met Thr Ala Ser Met
                20                  25                  30

Ile Thr Glu Pro Pro Val Ala Pro Arg Leu Gly Glu Leu Ala Thr Ala
        35                  40                  45

Ala Val Thr
        50

<210> SEQ ID NO 113
<211> LENGTH: 35
<212> TYPE: PRT
<213> ORGANISM: Dog
<220> FEATURE:
<221> NAME/KEY: misc_feature
<222> LOCATION: (1)..(35)
<223> OTHER INFORMATION: DOG TNXB POLYPEPTIDE SEGMENT

<400> SEQUENCE: 113

Leu Glu Pro Gly Arg Lys Tyr Lys Met His Leu Tyr Gly Leu Asp Arg
1               5                   10                  15

Gly Arg Arg Met Gly Pro Val Ser Thr Val Leu Thr Ala Ser Leu Ser
                20                  25                  30

Thr Pro Gly
        35
```

<210> SEQ ID NO 114
<211> LENGTH: 51
<212> TYPE: PRT
<213> ORGANISM: Elephant
<220> FEATURE:
<221> NAME/KEY: misc_feature
<222> LOCATION: (1)..(51)
<223> OTHER INFORMATION: ELEPHANT TNXB POLYPEPTIDE SEGMENT

<400> SEQUENCE: 114

Leu Glu Pro Gly Arg Lys Tyr Lys Leu His Leu Tyr Gly Leu His Glu
1               5                   10                  15

Gly Arg Arg Val Gly Pro Val Ser Ala Val Gly Thr Ile Ala Pro Met
            20                  25                  30

Pro Thr Glu Pro Pro Lys Glu Pro Arg Leu Gly Glu Leu Ser Val Ala
        35                  40                  45

Ala Val Thr
    50

<210> SEQ ID NO 115
<211> LENGTH: 51
<212> TYPE: PRT
<213> ORGANISM: Mouse
<220> FEATURE:
<221> NAME/KEY: misc_feature
<222> LOCATION: (1)..(51)
<223> OTHER INFORMATION: MOUSE TNXB POLYPEPTIDE SEGMENT

<400> SEQUENCE: 115

Leu Asp Pro Gly Arg Lys Tyr Lys Met Asn Leu Tyr Gly Leu His Glu
1               5                   10                  15

Gly Arg Arg Val Gly Pro Val Ser Thr Val Gly Val Thr Ala Ser Leu
            20                  25                  30

Thr Thr Glu Pro Pro Ile Glu Pro Arg Leu Gly Glu Leu Ala Ala Val
        35                  40                  45

Glu Val Thr
    50

<210> SEQ ID NO 116
<211> LENGTH: 51
<212> TYPE: PRT
<213> ORGANISM: Guinea Pig
<220> FEATURE:
<221> NAME/KEY: misc_feature
<222> LOCATION: (1)..(51)
<223> OTHER INFORMATION: GUINEA PIG TNXB POLYPEPTIDE SEGMENT

<400> SEQUENCE: 116

Leu Asp Ala Gly Arg Arg Tyr Lys Met Asn Leu Tyr Gly Leu His Gln
1               5                   10                  15

Ala Gly Arg Val Gly Pro Val Ser Thr Val Ala Val Thr Ala Pro Leu
            20                  25                  30

Pro Thr Trp Pro Ala Val Asp Pro Arg Leu Gly Glu Leu Ala Val Ala
        35                  40                  45

Ala Val Thr
    50

<210> SEQ ID NO 117
<211> LENGTH: 60
<212> TYPE: PRT
<213> ORGANISM: Opossum
<220> FEATURE:

```
<221> NAME/KEY: misc_feature
<222> LOCATION: (1)..(60)
<223> OTHER INFORMATION: OPOSSUM TNXB POLYPEPTIDE SEGMENT

<400> SEQUENCE: 117

Leu Glu Pro Asp His Lys Tyr Lys Met Asn Leu Tyr Gly Phe His Asp
1               5                   10                  15

Gly Gln Arg Val Gly Pro Val Ser Val Ile Gly Lys Thr Glu Thr Pro
                20                  25                  30

Ser Pro Thr Val Leu Thr Thr Glu Ala Pro Thr Glu Val Ser Val Lys
            35                  40                  45

Pro Gln Leu Gly Lys Leu Thr Val Met Lys Thr Thr
    50                  55                  60

<210> SEQ ID NO 118
<211> LENGTH: 20
<212> TYPE: DNA
<213> ORGANISM: Artificial Sequence
<220> FEATURE:
<223> OTHER INFORMATION: Synthetic primer: TNXB-2F

<400> SEQUENCE: 118
cctcatggtg aggaaggagt                                            20

<210> SEQ ID NO 119
<211> LENGTH: 21
<212> TYPE: DNA
<213> ORGANISM: Artificial Sequence
<220> FEATURE:
<223> OTHER INFORMATION: Synthetic primer: TNXB-2R

<400> SEQUENCE: 119
tctccttttt gaagctgctc t                                          21

<210> SEQ ID NO 120
<211> LENGTH: 18
<212> TYPE: DNA
<213> ORGANISM: Artificial Sequence
<220> FEATURE:
<223> OTHER INFORMATION: Synthetic primer: TNXB-3.1F

<400> SEQUENCE: 120
atgccacagt cgtcacca                                              18

<210> SEQ ID NO 121
<211> LENGTH: 20
<212> TYPE: DNA
<213> ORGANISM: Artificial Sequence
<220> FEATURE:
<223> OTHER INFORMATION: Synthetic primer: TNXB-3.1R

<400> SEQUENCE: 121
agagcagagc tgggctacat                                            20

<210> SEQ ID NO 122
<211> LENGTH: 20
<212> TYPE: DNA
<213> ORGANISM: Artificial Sequence
<220> FEATURE:
<223> OTHER INFORMATION: Synthetic primer: TNXB-3.2F

<400> SEQUENCE: 122
gcaatcggtt ccagtgtacc                                            20
```

```
<210> SEQ ID NO 123
<211> LENGTH: 18
<212> TYPE: DNA
<213> ORGANISM: Artificial Sequence
<220> FEATURE:
<223> OTHER INFORMATION: Synthetic primer: TNXB-3.2R

<400> SEQUENCE: 123
ggtcgttgcg tgtgcttt                                          18

<210> SEQ ID NO 124
<211> LENGTH: 20
<212> TYPE: DNA
<213> ORGANISM: Artificial Sequence
<220> FEATURE:
<223> OTHER INFORMATION: Synthetic primer: TNXB-3.3F

<400> SEQUENCE: 124
gcagtcttcc cctgagtagc                                        20

<210> SEQ ID NO 125
<211> LENGTH: 18
<212> TYPE: DNA
<213> ORGANISM: Artificial Sequence
<220> FEATURE:
<223> OTHER INFORMATION: Synthetic primer: TNXB-3.3R

<400> SEQUENCE: 125
gaatgcattt gcgacacg                                          18

<210> SEQ ID NO 126
<211> LENGTH: 19
<212> TYPE: DNA
<213> ORGANISM: Artificial Sequence
<220> FEATURE:
<223> OTHER INFORMATION: Synthetic primer: TNXB-3.4F

<400> SEQUENCE: 126
aggcacactc cttgcacac                                         19

<210> SEQ ID NO 127
<211> LENGTH: 19
<212> TYPE: DNA
<213> ORGANISM: Artificial Sequence
<220> FEATURE:
<223> OTHER INFORMATION: Synthetic primer: TNXB-3.4R

<400> SEQUENCE: 127
gagaacggcg tgtgtgttt                                         19

<210> SEQ ID NO 128
<211> LENGTH: 20
<212> TYPE: DNA
<213> ORGANISM: Artificial Sequence
<220> FEATURE:
<223> OTHER INFORMATION: Synthetic primer: TNXB-3.5F

<400> SEQUENCE: 128
tcttcctcag gctcaggtct                                        20

<210> SEQ ID NO 129
<211> LENGTH: 21
<212> TYPE: DNA
<213> ORGANISM: Artificial Sequence
<220> FEATURE:
<223> OTHER INFORMATION: Synthetic primer: TNXB-3.5R
```

-continued

```
<400> SEQUENCE: 129
aggctacgtg agtgaggact g                                              21

<210> SEQ ID NO 130
<211> LENGTH: 20
<212> TYPE: DNA
<213> ORGANISM: Artificial Sequence
<220> FEATURE:
<223> OTHER INFORMATION: Synthetic primer: TNXB-3.5(2)F

<400> SEQUENCE: 130
catgtctgga tggcacagtc                                                20

<210> SEQ ID NO 131
<211> LENGTH: 19
<212> TYPE: DNA
<213> ORGANISM: Artificial Sequence
<220> FEATURE:
<223> OTHER INFORMATION: Synthetic primer: TNXB-3.5(2)R

<400> SEQUENCE: 131
ctagatgggc ggtgtgtgt                                                 19

<210> SEQ ID NO 132
<211> LENGTH: 21
<212> TYPE: DNA
<213> ORGANISM: Artificial Sequence
<220> FEATURE:
<223> OTHER INFORMATION: Synthetic primer: TNXB-3.5(3)F

<400> SEQUENCE: 132
ccctctacac acacacactg g                                              21

<210> SEQ ID NO 133
<211> LENGTH: 20
<212> TYPE: DNA
<213> ORGANISM: Artificial Sequence
<220> FEATURE:
<223> OTHER INFORMATION: Synthetic primer: TNXB-3.5(3)R

<400> SEQUENCE: 133
ggaaggctac gtgagtgagg                                                20

<210> SEQ ID NO 134
<211> LENGTH: 20
<212> TYPE: DNA
<213> ORGANISM: Artificial Sequence
<220> FEATURE:
<223> OTHER INFORMATION: Synthetic primer: TNXB-3.6F

<400> SEQUENCE: 134
catgctctcc ctccactctt                                                20

<210> SEQ ID NO 135
<211> LENGTH: 19
<212> TYPE: DNA
<213> ORGANISM: Artificial Sequence
<220> FEATURE:
<223> OTHER INFORMATION: Synthetic primer: TNXB-3.6R

<400> SEQUENCE: 135
gtgcaaggag tgtgcctgt                                                 19

<210> SEQ ID NO 136
<211> LENGTH: 20
```

<212> TYPE: DNA
<213> ORGANISM: Artificial Sequence
<220> FEATURE:
<223> OTHER INFORMATION: Synthetic primer: TNXB-4F

<400> SEQUENCE: 136
gccatctgga ctcaaccaat                                           20

<210> SEQ ID NO 137
<211> LENGTH: 20
<212> TYPE: DNA
<213> ORGANISM: Artificial Sequence
<220> FEATURE:
<223> OTHER INFORMATION: Synthetic primer: TNXB-4R

<400> SEQUENCE: 137
ctgagtaaaa ggggctgtgg                                           20

<210> SEQ ID NO 138
<211> LENGTH: 21
<212> TYPE: DNA
<213> ORGANISM: Artificial Sequence
<220> FEATURE:
<223> OTHER INFORMATION: Synthetic primer: TNXB-5F

<400> SEQUENCE: 138
ggcagattcc ctctctagtc c                                         21

<210> SEQ ID NO 139
<211> LENGTH: 20
<212> TYPE: DNA
<213> ORGANISM: Artificial Sequence
<220> FEATURE:
<223> OTHER INFORMATION: Synthetic primer: TNXB-5R

<400> SEQUENCE: 139
gagataaggg ggattgagca                                           20

<210> SEQ ID NO 140
<211> LENGTH: 21
<212> TYPE: DNA
<213> ORGANISM: Artificial Sequence
<220> FEATURE:
<223> OTHER INFORMATION: Synthetic primer: TNXB-6F

<400> SEQUENCE: 140
ccagaagcat tcagaggagt c                                         21

<210> SEQ ID NO 141
<211> LENGTH: 21
<212> TYPE: DNA
<213> ORGANISM: Artificial Sequence
<220> FEATURE:
<223> OTHER INFORMATION: Synthetic primer: TNXB-6R

<400> SEQUENCE: 141
tggactagag agggaatctg c                                         21

<210> SEQ ID NO 142
<211> LENGTH: 19
<212> TYPE: DNA
<213> ORGANISM: Artificial Sequence
<220> FEATURE:
<223> OTHER INFORMATION: Synthetic primer: TNXB-7F

<400> SEQUENCE: 142

```
ccaataaccc cagctcctc                                              19

<210> SEQ ID NO 143
<211> LENGTH: 22
<212> TYPE: DNA
<213> ORGANISM: Artificial Sequence
<220> FEATURE:
<223> OTHER INFORMATION: Synthetic primer: TNXB-7R

<400> SEQUENCE: 143
ggactgggga ttcctttcta gt                                          22

<210> SEQ ID NO 144
<211> LENGTH: 20
<212> TYPE: DNA
<213> ORGANISM: Artificial Sequence
<220> FEATURE:
<223> OTHER INFORMATION: Synthetic primer: TNXB-8F

<400> SEQUENCE: 144
cccaaagcac tgagaaaacc                                             20

<210> SEQ ID NO 145
<211> LENGTH: 20
<212> TYPE: DNA
<213> ORGANISM: Artificial Sequence
<220> FEATURE:
<223> OTHER INFORMATION: Synthetic primer: TNXB-8R

<400> SEQUENCE: 145
atccaggatg gagtgaggtg                                             20

<210> SEQ ID NO 146
<211> LENGTH: 20
<212> TYPE: DNA
<213> ORGANISM: Artificial Sequence
<220> FEATURE:
<223> OTHER INFORMATION: Synthetic primer: TNXB-9F

<400> SEQUENCE: 146
ctgacacagc cagggtatga                                             20

<210> SEQ ID NO 147
<211> LENGTH: 20
<212> TYPE: DNA
<213> ORGANISM: Artificial Sequence
<220> FEATURE:
<223> OTHER INFORMATION: Synthetic primer: TNXB-9R

<400> SEQUENCE: 147
cctatgtggg atttggcttc                                             20

<210> SEQ ID NO 148
<211> LENGTH: 20
<212> TYPE: DNA
<213> ORGANISM: Artificial Sequence
<220> FEATURE:
<223> OTHER INFORMATION: Synthetic primer: TNXB-10F

<400> SEQUENCE: 148
ggcaaaatga gctgagaagg                                             20

<210> SEQ ID NO 149
<211> LENGTH: 20
<212> TYPE: DNA
<213> ORGANISM: Artificial Sequence
```

```
<220> FEATURE:
<223> OTHER INFORMATION: Synthetic primer: TNXB-10R

<400> SEQUENCE: 149
tgtcaggctt cccagaagtt                                               20

<210> SEQ ID NO 150
<211> LENGTH: 20
<212> TYPE: DNA
<213> ORGANISM: Artificial Sequence
<220> FEATURE:
<223> OTHER INFORMATION: Synthetic primer: TNXB-11F

<400> SEQUENCE: 150
ctggagcaag gagagcaact                                               20

<210> SEQ ID NO 151
<211> LENGTH: 20
<212> TYPE: DNA
<213> ORGANISM: Artificial Sequence
<220> FEATURE:
<223> OTHER INFORMATION: Synthetic primer: TNXB-11R

<400> SEQUENCE: 151
tttccatggc tgtcatctgt                                               20

<210> SEQ ID NO 152
<211> LENGTH: 20
<212> TYPE: DNA
<213> ORGANISM: Artificial Sequence
<220> FEATURE:
<223> OTHER INFORMATION: Synthetic primer: TNXB-12F

<400> SEQUENCE: 152
ggaggagtaa aggggtcagg                                               20

<210> SEQ ID NO 153
<211> LENGTH: 20
<212> TYPE: DNA
<213> ORGANISM: Artificial Sequence
<220> FEATURE:
<223> OTHER INFORMATION: Synthetic primer: TNXB-12R

<400> SEQUENCE: 153
ggtgacagcg agactccatc                                               20

<210> SEQ ID NO 154
<211> LENGTH: 20
<212> TYPE: DNA
<213> ORGANISM: Artificial Sequence
<220> FEATURE:
<223> OTHER INFORMATION: Synthetic primer: TNXB-13F

<400> SEQUENCE: 154
caggtggaca aagggaagac                                               20

<210> SEQ ID NO 155
<211> LENGTH: 19
<212> TYPE: DNA
<213> ORGANISM: Artificial Sequence
<220> FEATURE:
<223> OTHER INFORMATION: Synthetic primer: TNXB-13R

<400> SEQUENCE: 155
ccccatctca gttcacagc                                                19
```

```
<210> SEQ ID NO 156
<211> LENGTH: 20
<212> TYPE: DNA
<213> ORGANISM: Artificial Sequence
<220> FEATURE:
<223> OTHER INFORMATION: Synthetic primer: TNXB-14F

<400> SEQUENCE: 156
ctggggccaa ataatggtaa                                                   20

<210> SEQ ID NO 157
<211> LENGTH: 20
<212> TYPE: DNA
<213> ORGANISM: Artificial Sequence
<220> FEATURE:
<223> OTHER INFORMATION: Synthetic primer: TNXB-14R

<400> SEQUENCE: 157
gcagttctgg gttttccag                                                    20

<210> SEQ ID NO 158
<211> LENGTH: 20
<212> TYPE: DNA
<213> ORGANISM: Artificial Sequence
<220> FEATURE:
<223> OTHER INFORMATION: Synthetic primer: TNXB-15F

<400> SEQUENCE: 158
aaaggggcac aaggaaactt                                                   20

<210> SEQ ID NO 159
<211> LENGTH: 20
<212> TYPE: DNA
<213> ORGANISM: Artificial Sequence
<220> FEATURE:
<223> OTHER INFORMATION: Synthetic primer: TNXB-15R

<400> SEQUENCE: 159
cccagtcttc cagaaacagc                                                   20

<210> SEQ ID NO 160
<211> LENGTH: 21
<212> TYPE: DNA
<213> ORGANISM: Artificial Sequence
<220> FEATURE:
<223> OTHER INFORMATION: Synthetic primer: TNXB-16F

<400> SEQUENCE: 160
ttctgaaggc ttctcctcct c                                                 21

<210> SEQ ID NO 161
<211> LENGTH: 20
<212> TYPE: DNA
<213> ORGANISM: Artificial Sequence
<220> FEATURE:
<223> OTHER INFORMATION: Synthetic primer: TNXB-16R

<400> SEQUENCE: 161
tttcgattgc tgactgcttg                                                   20

<210> SEQ ID NO 162
<211> LENGTH: 20
<212> TYPE: DNA
<213> ORGANISM: Artificial Sequence
<220> FEATURE:
<223> OTHER INFORMATION: Synthetic primer: TNXB-17F
```

```
<400> SEQUENCE: 162
accaaagagc aagagggtga                                               20

<210> SEQ ID NO 163
<211> LENGTH: 20
<212> TYPE: DNA
<213> ORGANISM: Artificial Sequence
<220> FEATURE:
<223> OTHER INFORMATION: Synthetic primer: TNXB-17R

<400> SEQUENCE: 163
ctttcagatg gctgggagag                                               20

<210> SEQ ID NO 164
<211> LENGTH: 20
<212> TYPE: DNA
<213> ORGANISM: Artificial Sequence
<220> FEATURE:
<223> OTHER INFORMATION: Synthetic primer: TNXB-18F

<400> SEQUENCE: 164
aggagatgct ggaggctgta                                               20

<210> SEQ ID NO 165
<211> LENGTH: 20
<212> TYPE: DNA
<213> ORGANISM: Artificial Sequence
<220> FEATURE:
<223> OTHER INFORMATION: Synthetic primer: TNXB-18R

<400> SEQUENCE: 165
ccagtcatag ccttggcttc                                               20

<210> SEQ ID NO 166
<211> LENGTH: 19
<212> TYPE: DNA
<213> ORGANISM: Artificial Sequence
<220> FEATURE:
<223> OTHER INFORMATION: Synthetic primer: TNXB-19F

<400> SEQUENCE: 166
agtgaaggca ccagcagaa                                                19

<210> SEQ ID NO 167
<211> LENGTH: 19
<212> TYPE: DNA
<213> ORGANISM: Artificial Sequence
<220> FEATURE:
<223> OTHER INFORMATION: Synthetic primer: TNXB-19R

<400> SEQUENCE: 167
cctcaacacc tccttgcag                                                19

<210> SEQ ID NO 168
<211> LENGTH: 20
<212> TYPE: DNA
<213> ORGANISM: Artificial Sequence
<220> FEATURE:
<223> OTHER INFORMATION: Synthetic primer: TNXB-20F

<400> SEQUENCE: 168
accaaagagc aagagggtga                                               20

<210> SEQ ID NO 169
```

```
<211> LENGTH: 19
<212> TYPE: DNA
<213> ORGANISM: Artificial Sequence
<220> FEATURE:
<223> OTHER INFORMATION: Synthetic primer: TNXB-20R

<400> SEQUENCE: 169
gcaccagcat ccagactgt                                               19

<210> SEQ ID NO 170
<211> LENGTH: 20
<212> TYPE: DNA
<213> ORGANISM: Artificial Sequence
<220> FEATURE:
<223> OTHER INFORMATION: Synthetic primer: TNXB-21F

<400> SEQUENCE: 170
ggtacccatg agggaaaggt                                              20

<210> SEQ ID NO 171
<211> LENGTH: 19
<212> TYPE: DNA
<213> ORGANISM: Artificial Sequence
<220> FEATURE:
<223> OTHER INFORMATION: Synthetic primer: TNXB-21R

<400> SEQUENCE: 171
ccacgacgta agcacatcc                                               19

<210> SEQ ID NO 172
<211> LENGTH: 20
<212> TYPE: DNA
<213> ORGANISM: Artificial Sequence
<220> FEATURE:
<223> OTHER INFORMATION: Synthetic primer: TNXB-22F

<400> SEQUENCE: 172
actgtgagcc ccatcaagac                                              20

<210> SEQ ID NO 173
<211> LENGTH: 20
<212> TYPE: DNA
<213> ORGANISM: Artificial Sequence
<220> FEATURE:
<223> OTHER INFORMATION: Synthetic primer: TNXB-22R

<400> SEQUENCE: 173
agcaaagcaa gttgcccttg                                              20

<210> SEQ ID NO 174
<211> LENGTH: 20
<212> TYPE: DNA
<213> ORGANISM: Artificial Sequence
<220> FEATURE:
<223> OTHER INFORMATION: Synthetic primer: TNXB-23F

<400> SEQUENCE: 174
accaaagagc aagagggtga                                              20

<210> SEQ ID NO 175
<211> LENGTH: 20
<212> TYPE: DNA
<213> ORGANISM: Artificial Sequence
<220> FEATURE:
<223> OTHER INFORMATION: Synthetic primer: TNXB-23R

<400> SEQUENCE: 175
```

-continued gggcactttg tgttttgtga                                       20

<210> SEQ ID NO 176
<211> LENGTH: 20
<212> TYPE: DNA
<213> ORGANISM: Artificial Sequence
<220> FEATURE:
<223> OTHER INFORMATION: Synthetic primer: TNXB-24F

<400> SEQUENCE: 176
catggaaacg tgcaaaagaa                                       20

<210> SEQ ID NO 177
<211> LENGTH: 21
<212> TYPE: DNA
<213> ORGANISM: Artificial Sequence
<220> FEATURE:
<223> OTHER INFORMATION: Synthetic primer: TNXB-24R

<400> SEQUENCE: 177
cttgaagacc tgagcacatc c                                     21

<210> SEQ ID NO 178
<211> LENGTH: 20
<212> TYPE: DNA
<213> ORGANISM: Artificial Sequence
<220> FEATURE:
<223> OTHER INFORMATION: Synthetic primer: TNXB-25F

<400> SEQUENCE: 178
gtcagtcctc agggaagtgg                                       20

<210> SEQ ID NO 179
<211> LENGTH: 20
<212> TYPE: DNA
<213> ORGANISM: Artificial Sequence
<220> FEATURE:
<223> OTHER INFORMATION: Synthetic primer: TNXB-25R

<400> SEQUENCE: 179
aacaaaagat ggcgaggaga                                       20

<210> SEQ ID NO 180
<211> LENGTH: 20
<212> TYPE: DNA
<213> ORGANISM: Artificial Sequence
<220> FEATURE:
<223> OTHER INFORMATION: Synthetic primer: TNXB-26F

<400> SEQUENCE: 180
cgaagactgg agagacagca                                       20

<210> SEQ ID NO 181
<211> LENGTH: 20
<212> TYPE: DNA
<213> ORGANISM: Artificial Sequence
<220> FEATURE:
<223> OTHER INFORMATION: Synthetic primer: TNXB-26R

<400> SEQUENCE: 181
ccttcctcac aagacccaag                                       20

<210> SEQ ID NO 182
<211> LENGTH: 20
<212> TYPE: DNA

<213> ORGANISM: Artificial Sequence
<220> FEATURE:
<223> OTHER INFORMATION: Synthetic primer: TNXB-27F

<400> SEQUENCE: 182
ccaccagtca tcaccaaaga                                               20

<210> SEQ ID NO 183
<211> LENGTH: 20
<212> TYPE: DNA
<213> ORGANISM: Artificial Sequence
<220> FEATURE:
<223> OTHER INFORMATION: Synthetic primer: TNXB-27R

<400> SEQUENCE: 183
gtcctgttct tgggcacttt                                               20

<210> SEQ ID NO 184
<211> LENGTH: 20
<212> TYPE: DNA
<213> ORGANISM: Artificial Sequence
<220> FEATURE:
<223> OTHER INFORMATION: Synthetic primer: TNXB-28F

<400> SEQUENCE: 184
aagaggtgcc aagatccaaa                                               20

<210> SEQ ID NO 185
<211> LENGTH: 20
<212> TYPE: DNA
<213> ORGANISM: Artificial Sequence
<220> FEATURE:
<223> OTHER INFORMATION: Synthetic primer: TNXB-28R

<400> SEQUENCE: 185
ccagtcatag ccttggcttc                                               20

<210> SEQ ID NO 186
<211> LENGTH: 20
<212> TYPE: DNA
<213> ORGANISM: Artificial Sequence
<220> FEATURE:
<223> OTHER INFORMATION: Synthetic primer: TNXB-29F

<400> SEQUENCE: 186
atcagtgggt gctgaggact                                               20

<210> SEQ ID NO 187
<211> LENGTH: 20
<212> TYPE: DNA
<213> ORGANISM: Artificial Sequence
<220> FEATURE:
<223> OTHER INFORMATION: Synthetic primer: TNXB-29R

<400> SEQUENCE: 187
gccgctaaga aatgctcact                                               20

<210> SEQ ID NO 188
<211> LENGTH: 21
<212> TYPE: DNA
<213> ORGANISM: Artificial Sequence
<220> FEATURE:
<223> OTHER INFORMATION: Synthetic primer: TNXB-30F

<400> SEQUENCE: 188
gagggactca ctttcggagt t                                             21

<210> SEQ ID NO 189
<211> LENGTH: 19
<212> TYPE: DNA
<213> ORGANISM: Artificial Sequence
<220> FEATURE:
<223> OTHER INFORMATION: Synthetic primer: TNXB-30R

<400> SEQUENCE: 189
atagcagccc aggaagctc                                                    19

<210> SEQ ID NO 190
<211> LENGTH: 19
<212> TYPE: DNA
<213> ORGANISM: Artificial Sequence
<220> FEATURE:
<223> OTHER INFORMATION: Synthetic primer: TNXB-31F

<400> SEQUENCE: 190
ttgtcttcag cccaaatgc                                                    19

<210> SEQ ID NO 191
<211> LENGTH: 19
<212> TYPE: DNA
<213> ORGANISM: Artificial Sequence
<220> FEATURE:
<223> OTHER INFORMATION: Synthetic primer: TNXB-31R

<400> SEQUENCE: 191
ctcgatcaca gcagggaag                                                    19

<210> SEQ ID NO 192
<211> LENGTH: 19
<212> TYPE: DNA
<213> ORGANISM: Artificial Sequence
<220> FEATURE:
<223> OTHER INFORMATION: Synthetic primer: TNXB-32F

<400> SEQUENCE: 192
ggcagagcta aaggccact                                                    19

<210> SEQ ID NO 193
<211> LENGTH: 20
<212> TYPE: DNA
<213> ORGANISM: Artificial Sequence
<220> FEATURE:
<223> OTHER INFORMATION: Synthetic primer: TNXB-32R

<400> SEQUENCE: 193
gccaagcctg gaagataaaa                                                   20

<210> SEQ ID NO 194
<211> LENGTH: 20
<212> TYPE: DNA
<213> ORGANISM: Artificial Sequence
<220> FEATURE:
<223> OTHER INFORMATION: Synthetic primer: TNXB-33F

<400> SEQUENCE: 194
ccccgtgaag tacaaagacc                                                   20

<210> SEQ ID NO 195
<211> LENGTH: 20
<212> TYPE: DNA
<213> ORGANISM: Artificial Sequence
<220> FEATURE:

<223> OTHER INFORMATION: Synthetic primer: TNXB-33R

<400> SEQUENCE: 195
caagctggtg tgcttctgtc                                        20

<210> SEQ ID NO 196
<211> LENGTH: 20
<212> TYPE: DNA
<213> ORGANISM: Artificial Sequence
<220> FEATURE:
<223> OTHER INFORMATION: Synthetic primer: TNXB-34.35F

<400> SEQUENCE: 196
ccctcctcgt tctctctcaa                                        20

<210> SEQ ID NO 197
<211> LENGTH: 20
<212> TYPE: DNA
<213> ORGANISM: Artificial Sequence
<220> FEATURE:
<223> OTHER INFORMATION: Synthetic primer: TNXB-34.35R

<400> SEQUENCE: 197
atctgcagag cgacttccat                                        20

<210> SEQ ID NO 198
<211> LENGTH: 20
<212> TYPE: DNA
<213> ORGANISM: Artificial Sequence
<220> FEATURE:
<223> OTHER INFORMATION: Synthetic primer: TNXB-36.37F

<400> SEQUENCE: 198
agggaaagca ggaagaggag                                        20

<210> SEQ ID NO 199
<211> LENGTH: 20
<212> TYPE: DNA
<213> ORGANISM: Artificial Sequence
<220> FEATURE:
<223> OTHER INFORMATION: Synthetic primer: TNXB-36.37R

<400> SEQUENCE: 199
gagagaacga ggagggtgaa                                        20

<210> SEQ ID NO 200
<211> LENGTH: 20
<212> TYPE: DNA
<213> ORGANISM: Artificial Sequence
<220> FEATURE:
<223> OTHER INFORMATION: Synthetic primer: TNXB-38.39F

<400> SEQUENCE: 200
atgtcgcaaa acacgttcag                                        20

<210> SEQ ID NO 201
<211> LENGTH: 20
<212> TYPE: DNA
<213> ORGANISM: Artificial Sequence
<220> FEATURE:
<223> OTHER INFORMATION: Synthetic primer: TNXB-38.39R

<400> SEQUENCE: 201
gtagggtctg tggggtgtgt                                        20

```
<210> SEQ ID NO 202
<211> LENGTH: 19
<212> TYPE: DNA
<213> ORGANISM: Artificial Sequence
<220> FEATURE:
<223> OTHER INFORMATION: Synthetic primer: TNXB-40.41F

<400> SEQUENCE: 202
acgcgcatgg agtagtcac                                                 19

<210> SEQ ID NO 203
<211> LENGTH: 19
<212> TYPE: DNA
<213> ORGANISM: Artificial Sequence
<220> FEATURE:
<223> OTHER INFORMATION: Synthetic primer: TNXB-40.41R

<400> SEQUENCE: 203
cgtgtccacc tctttcacc                                                 19

<210> SEQ ID NO 204
<211> LENGTH: 20
<212> TYPE: DNA
<213> ORGANISM: Artificial Sequence
<220> FEATURE:
<223> OTHER INFORMATION: Synthetic primer: TNXB-42.43F

<400> SEQUENCE: 204
ctgttacact gtggggctga                                                20

<210> SEQ ID NO 205
<211> LENGTH: 20
<212> TYPE: DNA
<213> ORGANISM: Artificial Sequence
<220> FEATURE:
<223> OTHER INFORMATION: Synthetic primer: TNXB-42.43R

<400> SEQUENCE: 205
cacagggact ggggaactac                                                20

<210> SEQ ID NO 206
<211> LENGTH: 20
<212> TYPE: DNA
<213> ORGANISM: Artificial Sequence
<220> FEATURE:
<223> OTHER INFORMATION: Synthetic primer: TNXB-44F
<220> FEATURE:
<221> NAME/KEY: misc_feature
<223> OTHER INFORMATION: Wilms Tumor 1 (WT1) wild-type cDNA

<400> SEQUENCE: 206
aaggaccctg gctcttctct                                                20

<210> SEQ ID NO 207
<211> LENGTH: 20
<212> TYPE: DNA
<213> ORGANISM: Artificial Sequence
<220> FEATURE:
<223> OTHER INFORMATION: Synthetic primer: TNXB-44R

<400> SEQUENCE: 207
cagagggagc tggagttgat                                                20

<210> SEQ ID NO 208
<211> LENGTH: 25
<212> TYPE: DNA
<213> ORGANISM: Artificial Sequence
```

```
<220> FEATURE:
<223> OTHER INFORMATION: Synthetic oligonucleotide

<400> SEQUENCE: 208
cctcttacct cagttacaat ttata                                           25

<210> SEQ ID NO 209
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 209
ggcccctgaa aacagttgta tagat                                           25

<210> SEQ ID NO 210
<211> LENGTH: 4675
<212> TYPE: DNA
<213> ORGANISM: Homo sapiens
<220> FEATURE:
<221> NAME/KEY: misc_feature
<223> OTHER INFORMATION: Anillin wild-type cDNA sequence

<400> SEQUENCE: 210
ggcttggcgc tgaaattcaa atttgaacgg ctgcagaggc cgagtccgtc actggaagcc      60
gagaggagag acagctggt tgtgggagag ttcccccgcc tcagactcct ggtttttcc      120 aggagacaca ctgagctgag actcactttt ctcttcctga atttgaacca ccgtttccat    180
cgtctcgtag tccgacgcct ggggcgatgg atccgtttac ggagaaactg ctggagcgaa    240
cccgtgccag gcgagagaat cttcagagaa aaatggctga gaggcccaca gcagctccaa    300
ggtctatgac tcatgctaag cgagctagac agccactttc agaagcaagt aaccagcagc    360
ccctctctgg tggtgaagag aaatcttgta caaaaccatc gccatcaaaa aaacgctgtt    420 ctgacaaacac tgaagtagaa gtttctaact tggaaaataa acaaccagtt gagtcgacat    480
ctgcaaaatc ttgttctcca agtcctgtgt ctcctcaggt gcagccacaa gcagcagata    540
ccatcagtga ttctgttgct gtcccggcat cactgctggg catgaggaga gggctgaact    600
caagattgga agcaactgca gcctcctcag ttaaaacacg tatgcaaaaa cttgcagagc    660
aacggcgccg ttgggataat gatgatatga cagatgacat tcctgaaagc tcactcttct    720
caccaatgcc atcagaggaa aaggctgctt ccccctccag acctctgctt tcaaatgcct    780
cggcaactcc agttggcaga aggggccgtc tggccaatct tgctgcaact atttgctcct    840
gggaagatga tgtaaatcac tcatttgcaa aacaaaacag tgtacaagaa cagcctggta    900
ccgcttgttt atccaaattt tcctctgcaa gtggagcatc tgctaggatc aatagcagca    960
gtgttaagca ggaagctaca ttctgttccc aaagggatgg cgatgcctct ttgaataaag   1020
ccctatcctc aagtgctgat gatgcgtctt tggttaatgc ctcaatttcc agctctgtga   1080
aagctacttc tccagtgaaa tctactacat ctatcactga tgctaaaagt tgtgagggac   1140
aaaatcctga gctacttcca aaaactccta ttagtcctct gaaaacgggg tatcgaaac   1200 caattgtgaa gtcaacttta tcccagacag ttccatccaa gggagaatta agtagagaaa   1260
tttgtctgca atctcaatct aaagacaaat ctacgacacc aggaggaaca ggaattaagc   1320
ctttcctgga acgctttgga gagcgttgtc aagaacatag caagaaagt ccagctcgta   1380 gcacacccca cagaaccccc attattactc caaatacaaa ggccatccaa gaaaaattat   1440
tcaagcaaga cacatcttca tctactaccc atttagcaca acagctcaag caggaacgtc   1500
```

```
aaaaagaact agcatgtctt cgtggccgat ttgacaaggg caatatatgg agtgcagaaa    1560
aaggcggaaa ctcaaaaagc aaacaactag aaaccaaaca ggaaactcac tgtcagagca    1620
ctcccctcaa aaacaccaa ggtgtttcaa aaactcagtc acttccagta acagaaaagg     1680
tgaccgaaaa ccagatacca gccaaaaatt ctagtacaga acctaaagaa gtgatacgtg    1740
aaattgagat gagtgtggat gatgatgata tcaatagttc gaaagtaatt aatgacctct    1800
tcagtgatgt cctagaggaa ggtgaactag atatggagaa gagccaagag gagatggatc    1860
aagcattagc agaaagcagc gaagaacagg aagatgcact gaatatctcc tcaatgtctt    1920
tacttgcacc attggcacaa acagttggtg tggtaagtcc agagagttta gtgtccacac    1980
ctagactgga attgaaagac accagcagaa gtgatgaaag tccaaaacca ggaaaattcc    2040
aaagaactcg tgtccctcga gctgaatctg gtgatagcct tggttctgaa gatcgtgatc    2100
ttctttacag cattgatgca tatagatctc aaagattcaa agaaacagaa cgtccatcaa    2160
taaagcaggt gattgttcgg aaggaagatg ttacttcaaa actggatgaa aaaaataatg    2220
cctttccttg tcaagttaat atcaaacaga aaatgcagga actcaataac gaaataaata    2280
tgcaacagac agtgatctat caagctagcc aggctcttaa ctgctgtgtt gatgaagaac    2340
atggaaaagg gtccctagaa gaagctgaag cagaaagact tcttctaatt gcaactggga    2400
agagaacact tttgattgat gaattgaata aattgaagaa cgaaggacct cagaggaaga    2460
ataaggctag tccccaaagt gaatttatgc catccaaagg atcagttact ttgtcagaaa    2520
tccgcttgcc tctaaaagca gattttgtct gcagtacggt tcagaaacca gatgcagcaa    2580
attactatta cttaattata ctaaaagcag gagctgaaaa tatggtagcc acaccattag    2640
caagtacttc aaactctctt aacggtgatg ctctgacatt cactactaca tttactctgc    2700
aagatgtatc caatgacttt gaaataaata ttgaagttta cagcttggtg caaaagaaag    2760
atccctcagg ccttgataag aagaaaaaaa catccaagtc caaggctatt actccaaagc    2820
gactcctcac atctataacc acaaaaagca acattcattc ttcagtcatg gccagtccag    2880
gaggtcttag tgctgtgcga accagcaact tcgcccttgt tggatcttac acattatcat    2940
tgtcttcagt aggaaatact aagtttgttc tggacaaggt ccccttttta tcttctttgg    3000
aaggtcatat ttatttaaaa ataaaatgtc aagtgaattc cagtgttgaa gaaagaggtt    3060
ttctaaccat atttgaagat gttagtggtt ttggtgcctg gcatcgaaga tggtgtgttc    3120
tttctggaaa ctgtatatct tattggactt atccagatga tgagaaacgc aagaatccca    3180
taggaaggat aaatctggct aattgtacca gtcgtcagat agaaccagcc aacagagaat    3240
tttgtgcaag acgcaacact tttgaattaa ttactgtccg accacaaaga gaagatgacc    3300
gagagactct tgtcagccaa tgcagggaca cactctgtgt taccaagaac tggctgtctg    3360
cagatactaa agaagagcgg gatctctgga tgcaaaaact caatcaagtt cttgttgata    3420
ttcgcctctg gcaacctgat gcttgctaca aacctattgg aaagccttaa accgggaaat    3480
ttccatgcta tctagaggtt tttgatgtca tcttaagaaa cacacttaag agcatcagat    3540
ttactgattg cattttatgc tttaagtacg aaagggtttg tgccaatatt cactacgtat    3600
tatgcagtat ttatatcttt tgtatgtaaa actttaactg atttctgtca ttcatcaatg    3660
agtagaagta aatacattat agttgatttt gctaaatctt aatttaaaag cctcatttttc    3720 ctagaaatct aattattcag ttattcatga caatatttttt ttaaaagtaa gaaattctga    3780
gttgtcttct tggagctgta ggtcttgaag cagcaacgtc tttcagggggt tggagacaga    3840
```

```
aacccattct ccaatctcag tagttttttc gaaaggctgt gatcatttat tgatcgtgat    3900
atgacttgtt actagggtac tgaaaaaaat gtctaaggcc tttacagaaa cattttagt     3960 aatgaggatg agaacttttt caaatagcaa atatatattg gcttaaagca tgaggctgtc    4020
ttcagaaaag tgatgtggac ataggaggca atgtgtgaga cttgggggtt caatatttta    4080
tatagaagag ttaataagca catggtttac atttactcag ctactatata tgcagtgtgg    4140
tgcacatttt cacagaattc tggcttcatt aagatcatta tttttgctgc gtagcttaca    4200
gacttagcat attagttttt tctactccta caagtgtaaa ttgaaaaatc tttatattaa    4260
aaaagtaaac tgttatgaag ctgctatgta ctaataatac tttgcttgcc aaagtgtttg    4320
ggttttgttg ttgtttgttt gtttgtttgt ttttggttca tgaacaacag tgtctagaaa    4380 cccatttga aagtggaaaa ttattaagtc acctatcacc tttaaacgcc ttttttaaa      4440 attataaaat attgtaaagc agggtctcaa cttttaaata cactttgaac ttcttctctg    4500
aattattaaa gttctttatg acctcattta taaacactaa attctgtcac ctcctgtcat    4560 tttattttt attcattcaa atgtattttt tcttgtgcat attataaaaa tatatttat      4620 gagctcttac tcaaataaat acctgtaaat gtctaaagga aaaaaaaaa aaaaa          4675
```

<210> SEQ ID NO 211
<211> LENGTH: 3037
<212> TYPE: DNA
<213> ORGANISM: Homo sapiens
<220> FEATURE:
<221> NAME/KEY: misc_feature
<223> OTHER INFORMATION: Wilms Tumor 1 (WT1) wild-type cDNA

<400> SEQUENCE: 211

```
agctggggta aggagttcaa ggcagcgccc acacccgggg gctctccgca acccgaccgc      60
ctgtccgctc ccccacttcc cgccctccct cccacctact cattcaccca cccacccacc     120
cagagccggg acggcagccc aggcgccggg gccccgccgt ctcctcgccg cgatcctgga     180
cttcctcttg ctgcaggacc cggcttccac gtgtgtcccg gagccggcgt ctcagcacac     240
gctccgctcc gggcctgggt gcctacagca gccagagcag cagggagtcc gggacccggg     300
cggcatctgg gccaagttag gcgccgccga ggccagcgct gaacgtctcc agggccggag     360
gagccgcggg gcgtccgggt ctgagccgca gcaaatgggc tccgacgtgc gggacctgaa     420
cgcgctgctg cccgccgtcc cctccctggg tggcggcggc ggctgtgccc tgcctgtgag     480
cggcgcggcg cagtgggcgc cggtgctgga cttttgcgcc cgggcgcctt cggcttacgg     540
gtcgttgggc ggccccgcgc cgccaccggc tccgccgcca ccccgccgc cgccgcctca     600 ctccttcatc aaacaggagc cgagctgggg cggcgcggag ccgcacgagg agcagtgcct    660
gagcgccttc actgtccact tttccggcca gttcactggc acagccggag cctgtcgcta    720
cgggcccttc ggtcctcctc cgcccagcca ggcgtcatcc ggccaggcca ggatgttcc      780 taacgcgccc tacctgccca gctgcctcga gagccagccc gctattcgca atcagggtta    840
cagcacggtc accttcgacg ggacgcccag ctacggtcac acgccctcgc accatgcggc    900
gcagttcccc aaccactcat tcaagcatga ggatccatg ggccagcagg gctcgctggg    960
tgagcagcag tactcggtgc cgccccggt ctatggctgc cacacccca ccgacagctg     1020 caccggcagc caggctttgc tgctgaggac gccctacagc agtgacaatt tataccaaat    1080
gacatcccag cttgaatgca tgacctgaa tcagatgaac ttaggagcca ccttaaaggg    1140
agttgctgct gggagctcca gctcagtgaa atggacagaa gggcagagca accacagcac   1200
```

| | | | | | |
|---|---|---|---|---|---|
| agggtacgag | agcgataacc | acacaacgcc | catcctctgc | ggagcccaat | acagaataca | 1260 |
| cacgcacggt | gtcttcagag | gcattcagga | tgtgcgacgt | gtgcctggag | tagcccgac | 1320 |
| tcttgtacgg | tcggcatctg | agaccagtga | gaaacgcccc | ttcatgtgtg | cttacccagg | 1380 |
| ctgcaataag | agatatttta | agctgtccca | cttacagatg | cacagcagga | agcacactgg | 1440 |
| tgagaaacca | taccagtgtg | acttcaagga | ctgtgaacga | aggttttctc | gttcagacca | 1500 |
| gctcaaaaga | caccaaagga | gacatacagg | tgtgaaacca | ttccagtgta | aaacttgtca | 1560 |
| gcgaaagttc | tcccggtccg | accacctgaa | gacccacacc | aggactcata | caggtaaaac | 1620 |
| aagtgaaaag | cccttcagct | gtcggtggcc | aagttgtcag | aaaagtttg | cccggtcaga | 1680 |
| tgaattagtc | cgccatcaca | acatgcatca | gagaaacatg | accaaactcc | agctggcgct | 1740 |
| ttgaggggtc | tccctcgggg | accgttcagt | gtcccaggca | gcacagtgtg | tgaactgctt | 1800 |
| tcaagtctga | ctctccactc | ctcctcacta | aaaaggaaac | ttcagttgat | cttcttcatc | 1860 |
| caacttccaa | gacaagatac | cggtgcttct | ggaaactacc | aggtgtgcct | ggaagagttg | 1920 |
| gtctctgccc | tgcctacttt | tagttgactc | acaggccctg | gagaagcagc | taacaatgtc | 1980 |
| tggttagtta | aaagcccatt | gccatttggt | gtggattttc | tactgtaaga | agagccatag | 2040 |
| ctgatcatgt | cccctgacc | cttcccttct | ttttttatgc | tcgttttcgc | tggggatgga | 2100 |
| attattgtac | cattttctat | catggaatat | ttataggcca | gggcatgtgt | atgtgtctgc | 2160 |
| taatgtaaac | tttgtcatgg | tttccattta | ctaacagcaa | cagcaagaaa | taatcagag | 2220 |
| agcaaggcat | cgggggtgaa | tcttgtctaa | cattcccgag | gtcagccagg | ctgctaacct | 2280 |
| ggaaagcagg | atgtagttct | gccaggcaac | ttttaaagct | catgcatttc | aagcagctga | 2340 |
| agaaaaatc | agaactaacc | agtacctctg | tatagaaatc | taaaagaatt | ttaccattca | 2400 |
| gttaattcaa | tgtgaacact | ggcacactgc | tcttaagaaa | ctatgaagat | ctgagatttt | 2460 |
| tttgtgtatg | ttttgactc | ttttgagtgg | taatcatatg | tgtctttata | gatgtacata | 2520 |
| cctccttgca | caaatggagg | ggaattcatt | ttcatcactg | ggagtgtcct | tagtgtataa | 2580 |
| aaaccatgct | ggtatatggc | ttcaagttgt | aaaaatgaaa | gtgactttaa | aagaaaatag | 2640 |
| gggatggtcc | aggatctcca | ctgataagac | tgttttaag | taacttaagg | acctttgggt | 2700 |
| ctacaagtat | atgtgaaaaa | aatgagactt | actgggtgag | gaaatccatt | gtttaaagat | 2760 |
| ggtcgtgtgt | gtgtgtgtgt | gtgtgtgtgt | gtgtgtgttg | tgttgtgttt | tgtttttaa | 2820 |
| gggagggaat | ttattattta | ccgttgcttg | aaattactgt | gtaaatatat | gtctgataat | 2880 |
| gatttgctct | ttgacaacta | aaattaggac | tgtataagta | ctagatgcat | cactgggtgt | 2940 |
| tgatcttaca | agatattgat | gataacactt | aaaattgtaa | cctgcatttt | tcactttgct | 3000 |
| ctcaattaaa | gtctattcaa | aaggaaaaaa | aaaaaaa | | | 3037 |

<210> SEQ ID NO 212
<211> LENGTH: 13143
<212> TYPE: DNA
<213> ORGANISM: Homo sapiens
<220> FEATURE:
<221> NAME/KEY: misc_feature
<223> OTHER INFORMATION: Tenascin X (TNXB) wild-type cDNA

<400> SEQUENCE: 212

| | | | | | |
|---|---|---|---|---|---|
| tcctccctt | ctcctcccct | gctcgctgca | gactccctcc | tcactgtcgc | tgccgagatc | 60 |
| cacagtcggt | tgtggctcag | cccctgttgc | aggggacaag | tgagggagac | ttccctgtcc | 120 |
| tgccctgaga | cgccgccctc | ccggggttgg | ggacagagca | ggtgcagagg | cactgcagct | 180 |

```
gctcggttgc ccagcctcct gaatgatgcc agcccagtat gctctaacct ccagcctggt    240
tctcctggtg ctgctgagca cagccagagc aggcccttc tcttcacggt ccaatgtgac     300
actgccagcc ccccggcccc ctccccagcc aggggggccac acagtggggg ctggagtggg   360
aagcccctct tctcagcttt acgagcacac agtggaagga ggggagaagc aggtggtatt   420
cacccaccgc attaacctgc cccttccac tggctgtggc tgtcccccag caccgagcc     480 cccagtcctt gcttcagagg tacaggccct gagggtccgt ctagagatcc tggaggagtt   540
ggtgaagggg ctcaaggaac agtgcactgg gggatgttgt cctgcctctg cccaagctgg   600
cacaggtcag acagatgtgc ggaccctctg cagtctccat ggtgtgtttg atctgagccg   660
ctgcacctgt tcctgtgagc caggctgggg tgggcccacc tgctcagacc ccacagatgc   720
tgagatccct ccctcttccc caccctcagc ctcgggtcc tgcccagatg actgcaatga    780
tcagggtcgc tgtgtccgtg gtcgttgcgt gtgctttccc ggctacactg gccccagctg   840
tggctggcca tcctgtcccg ggactgccaa aggccgtggg cgctgcgtgc agggcgtgtg   900
tgtgtgccgg gcaggcttct caggcccga ctgcagccag cgctcctgcc ctcgaggttg    960
cagccagagg ggacgctgtg agggtgggcg ctgcgtgtgt gacccaggct acactggtga  1020
cgactgtggc atgaggagct gccctcgcgg ttgcagtcag agggggcgct gtgagaatgg  1080
gcgctgcgtg tgtaaccccg gctacactgg cgaggactgt ggggtgagga gctgccctcg  1140
gggctgcagc cagcggggac gctgcaagga cgggcgctgc gtgtgtgacc ccggctacac  1200
tggcgaggac tgtggtacgc ggagctgccc ctgggactgt ggcgagggcg gcgctgcgt   1260 ggacggccgc tgcgtgtgct ggcccgggta cacaggcgag gactgcagca cgcggacatg  1320
tccgagggac tgccgggggcc gcgggcgctg cgaggacggc gaatgcattt gcgacacggg  1380
ctacagcggg gacgactgcg gcgtgcgcag ctgcccctggc gactgcaacc aaaggggccg  1440
ctgcgaggac ggccgctgcg tgtgctggcc ggggtacact ggaaccgatt gcggctcgcg  1500
cgcctgccca cgcgactgta gaggtcgcgg gcgctgcgag aacggcgtgt gtgtttgcaa  1560
tgcgggctac agcggcgagg actgcggtgt gcgcagctgt cctggggact gtcgtggccg  1620
gggccgctgt gagagtggcc gctgcatgtg ttggccgggg tacacaggcc gggactgcgg  1680
cacgcgcgcc tgtcctggcg actgtcgcgg gcgcgggcgc tgcgtggatg ccgctgcgt   1740 gtgcaacccg ggcttcaccg gtgaggactg tgggagccgt cgctgtcccg gggactgccg  1800
tgggcacggc cttttgcgagg atggcgtgtg cgtgtgtgac gcaggctact caggggaaga  1860
ctgcagcacg cgcagctgcc ccgggggctg ccgaggccgc ggccagtgcc tagatgggcg  1920
gtgtgtgtgc gaggacggct actctggcga ggattgcggt gtgaggcagt gcccgaatga  1980
ctgcagccag cacggcgtgt gccaggacgg tgtgtgcatc tgttgggaag gctacgtgag  2040
tgaggactgc agcatccgca cctgcccctc caactgccac gggaggggcc gctgtgagga  2100
agggcgctgc ctgtgcgacc caggctacac cggccctacc tgtgccaccc gcatgtgccc  2160
ggctgactgc cggggacgtg ggcggtgtgt gcaaggagtg tgcctgtgcc acgtgggcta  2220
tggcggtgag gactgcggc aggaagagcc tccagccagc gcctgccctg gaggctgcgg  2280
gccccgggaa ctgtgccggg caggccagtg tgtgtgtgta gagggcttcc gaggccctga  2340
ctgtgccatc cagacatgcc caggggactg ccgtggccga ggagagtgtc acgatggcag  2400
ctgtgtctgt aaagatgggt atgctggcga agactgcgga gaagaggtgc aaccattga   2460 gggcatgagg atgcatctct tggaggagac aacagttcgg acagagtgga ccccggctcc  2520
tggccccgtg gatgcctatg aaattcagtt catccccacg acagagggggg cgagcccccc  2580
```

-continued

```
attcacagca cggggttccaa gctctgcctc agcctatgac cagagaggac tggcccctgg   2640
acaggagtac caggtcactg tccgagccct tcgaggacc agctgggcc ttcctgcctc       2700
caagaccatc accaccatga tcgatgggcc ccaggacctc cgagtggtgg ctgtgacacc     2760
gacaacactg gagcttggct ggctgcgtcc ccaggctgag gtggaccgat tgtggtgtc      2820
ctacgtcagt gccggcaacc agagggtgag gctggaagtg cccctgaag cagacgggac     2880
gctgctgact gacctgatgc caggcgtaga atatgtggtg actgtcacag cggagcgggg    2940
ccgggcagtc agctacccag cttctgtcag ggccaacaca gggtcctcac ccttgggcct    3000
cttggggact accgatgagc ctcctccctc aggccctcg acgacgcaag ggcccaggc      3060
tcctctcctg cagcagcgcc cccaggagct gggagagttg agggtgctgg cagagatga    3120
gacagggcgc ctccgtgtgg tctgaccgc ccagcctgac acctttgcct acttccaact    3180
gcgcatgcgg gtgcccgagg ggccggggc acatgaggaa gtgctgccag ggacgtccg     3240
ccaggctctg gtgcctccac cccctcctgg aacccgtat gagctgtcac ttcatggggt    3300
ccctcctggg ggcaagccct ctgaccccat catctaccaa ggcattatgg acaaggatga   3360
ggagaagcct gggaagtcct caggcccacc acgcctgggt gagctgacgg tgacagacag   3420
gacctccgac tccttgctcc tgcgctggac ggtccccgag ggcgagtttg actccttcgt   3480
gatccagtac aaagacaggg acgggcagcc ccaggtggtg cccgtggaag accccagcg    3540
ctcggccgtc atcacctccc tggatcctgg ccgcaagtac aaatttgtcc tgtatgggtt   3600
tgttggcaag aagaggcatg gtccgctggt ggctgaagcc aagatcttgc ctcagagtga   3660
cccaagtcca gggactccac cccacctggg aaacctgtgg gtgacagacc ctaccccaga   3720
ttcactgcac ctctcctgga ctgtccctga gggccagttt gacaccttca tggtccagta   3780
cagggacagg gatggacggc cccaggtggt acctgtggaa gggcccgagc gttcattgt    3840
tgtctcctca ctggaccctg accacaagta cagattcact ctgtttggaa ttgcgaacaa   3900
gaagcggtat ggccccctca cggccgatgg caccactgct ccagagagga aagaggagcc   3960
ccccgccct gagttcctgg agcagccct cctgggggaa ctgacagtga ccggcgtgac     4020
cccagactcc ttgcgtctct catggacagt ggccagggc cccttcgact cattcatggt     4080
ccagtacaag gatgcacagg gcagcccca gcagtgcct gttgcggggg atgagaatga      4140
ggttactgtc cccggcctgg atcccgaccg gaagtataag atgaacctct acgggcttcg   4200
tggcaggcag cgtgtggggc ccgagtctgt ggtggccaag actgctcctc aggaggatgt   4260
ggacgagacc cccagcccca cagaactggg cacggaggcc ccggagtccc ccgaggagcc   4320
gctcctgggg gagctgacag tgacaggatc ctcccctgat cgctgagcc tcttctggac    4380
cgtcccccag ggcagcttcg actctttcac cgtgcagtac aaggacaggg atgggcggcc   4440
ccgggcggtg cgtgttgggg caaggagag tgaggtcacc gtgggaggcc tagagcccgg    4500
gcacaagtac aagatgcacc tgtacggcct ccacgagggg cagcgcgtgg gcccggtgtc   4560
cgccgtgggc gtgacagccc cacaacaaga agagaccct ccagccactg agtccccgct    4620
ggagccacgc ctaggagagc tgacagtgac agatgtgacc cccaactctg tgggcctctc   4680
ctggacagtc cccgagggcc agttttgactc cttcatagtc cagtacaagg acaaggacgg   4740
gcagccccag gtggtgccgg tggcggcaga ccagcgagag gtcacagtct acaacctgga   4800
gcctgagaga aaatataaga tgaacatgta tggactacat gatgggcaac gcatgggccc   4860
cctgtctgtg gtcatcgtga cggctcccct cccaccagcc ccagccacag aggcctccaa    4920
```

```
gcctcccctg gagccacgcc taggggagct gacagtgacg gatataaccc ctgactctgt    4980
gggcctctca tggacagtcc ctgagggtga attcgactcc tttgtggttc agtacaagga    5040
cagggacggg cagcccagg tggtgcccgt ggctgcagat cagcgggagg tcactatccc     5100
tgacctggaa ccctcccgca agtacaagtt cctgctcttt gggatccagg atgggaaacg    5160
acgcagccca gtctctgtgg aggcaaagac ggttgcccga ggtgacgcca gcccaggggc    5220
cccaccccgc cttggggagc tgtgggtgac agaccccacc ccagactcac tgcgcctctc    5280
ctggacggtt cctgagggcc agttcgactc ttttgtggtc cagttcaagg acaaagacgg    5340
gccccaggtg gtgcccgtgg agggccatga gcgctctgtc actgtcaccc ctctggatgc    5400
cggccgcaag tacagattcc tcctctatgg cctcctgggc aagaagcgcc atggccctct    5460
cactgccgac ggcaccacgg aagcccgag tgctatggat gatactggaa caaagcgtcc     5520
cccaaaaccc cgtctggggg aggagctgca ggtgaccacc gtgacccaga actccgtggg    5580
cctctcctgg acagtccctg agggccagtt tgactccttt gtggtccagt acaaagacag    5640
ggacgggcag cccaggtgg tgcccgtgga gggcagcctc agggaggtca gcgtgccggg     5700
cctggaccct gcccacaggt acaagctgct gctctacggg ctgcaccacg gcaagcgtgt    5760
gggccccatc tcggccgtcg ccattactgc cggcaggaa gaaacggaaa ctgagaccac     5820
ggccccgacc cctccagcgc ctgagcccca cctcggggag ttgacagtgg aggaggccac    5880
gtcacacacc ctgcatctct cctggatggt gactgaggga gaatttgact ccttcgaaat    5940
ccagtacaca gatagagacg ggcaactcca aatggtccgc ataggaggtg accggaatga    6000
catcaccctc tctggcctgg aatccgacca cagatacctg gtgaccctgt atggtttcag    6060
tgatgggaag catgtaggtc ctgtccatgt cgaggccctg acagtcccgg aggaggagaa    6120
gccttcagaa cctccaccg caaccccga gccccatc aagcctcgcc tgggggagct       6180
gaccgtgaca gatgccaccc ctgactccct cagcctgtcc tggacagttc cgagggaca    6240
gtttgaccac ttcctggtcc agtacaggaa tggagatggg cagcccaagg cagtgagggt    6300
gccagggcac gaggaagggg tcaccatctc gggcctggag ccagaccata aatacaagat    6360
gaacctgtac ggcttccacg gtggccagcg catgggccct gtgtctgtcg tcggggtgac    6420
agctgcagag gaagagaccc ccagccccac agaacccagc atggaggccc ggagcccgc    6480
tgaggagccg ctcctggggg agctaacagt gacaggatcc tcccctgact cgctgagcct    6540
ctcctggacc gtcccccagg gccgcttcga ctccttcacc gtgcagtaca aggacaggga    6600
cgggcggccc caggtggtgc gtgttggggg cgaggagagt gaagtcaccg tggggggcct    6660
ggagcctggg cgcaagtaca agatgcacct gtacggcctc cacgaggggc ggcgcgtggg    6720
cccagtgtct gctgtgggcg tcacggcccc cgaagaggag tcccctgatg ctcctcttgc    6780
aaagctgcgc ctagggcaga tgacagtgag agacatcacc tccgactccc tcagcctctc    6840
ctggacagtc cccgagggcc agtttgacca tttcttggtc cagttaaaga atggggacgg    6900
gcagcccaag gcggtgcggg tgccgggaca cgaggatggg gtcaccatct cgggcctgga    6960
gccagaccac aagtacaaga tgaacctgta cggcttccac ggtggccagc gcgtgggccc    7020
cgtgtctgct gttggtttaa ctgccccagg aaaggatgaa gaaatggccc cagcctcgac    7080
agaacctccc acccctgaac cccccatcaa gcctcgcctg gaggagctga ccgtgacaga    7140
tgcgaccccct gactccctca gcctgtcctg gacggttccc gagggacagt ttgaccactt    7200
cctggtccag tacaagaatg gggatgggca gcccaaggca acacgggtgc aggacatga    7260
ggacagggtc accatctccg gcctggagcc agacaacaag tacaagatga acctgtacgg    7320
```

```
cttccacggt ggccagcgtg tgggcccgt gtctgccatc ggggtgacag ctgcagagga    7380
agagacccc agcccacag aaccagcat ggaggcccg gagcccctg aggagccgct      7440
cctgggggag ctaacagtga caggatcctc ccctgactcg ctgagcctct cctggaccgt   7500
cccccagggc cgcttcgact ccttcaccgt gcagtacaag gacagggacg gcggccca     7560
ggtggtgcgt gttgggggcg aggagagcga ggtcaccgtg ggggcctgg agcctgggcg     7620
caaatacaag atgcacctgt atggcctcca cgaggggcgg cgcgtgggcc cggtgtccac   7680
cgtgggcgtg actgccccac aagaggatgt ggacgagacc cccagcccta cagaaccagg   7740
cacagaggcc ccagggcccc ccgaggagcc tctcctgggg gagctgacag tgacaggatc   7800
ctcccctgac tcgctgagcc tttcctggac cgtcccccag ggccgctttg actccttcac   7860
cgtgcagtac aaggacaggg acgggcgcc ccaggcggtg cgtgttgggg gccaggagag    7920
caaggtcact gtgaggggcc tggagcctgg gcgcaagtac aagatgcacc tgtacggcct   7980
ccacgagggg cggcgcctgg gcccggtgtc tgccgtgggc gtcacagagg atgaagccga   8040
gaccacccaa gcagtgccta ccatgacccc tgagcccccc atcaagcctc gcctggggga   8100
gctgaccatg acagatgcca cccctgactc cctcagcctg tcctggacgg ttcccgaggg   8160
ccagtttgac cacttcctgg tccagtacag gaatggggat gggcagccca aggcggtgcg   8220
ggtgccgggg cacgaggacg gggtcaccat ctcaggcctg gagccagacc ataaatacaa   8280
gatgaacctg tacggcttcc acggtggcca gcgcgtgggc cccatctctg tcattggggt   8340
gacggctgca gaggaagaga ccccagccc cacggaactc agcactgagg ccccggagcc   8400
ccctgaggag ccgctcctgg gggagctgac agtgacagga tcctcccctg actcgctgag   8460
cctctcctgg accatccccc agggccactt cgactccttc accgtgcagt acaaggacag   8520
ggacgggcgg ccccaggtga tgcgtgtcag gggcgaggag agcgaggtca ccgtgggggg   8580
cctggagccc gggcgcaaat acaagatgca cctgtacggc ctccacgagg gcggcgtgt    8640
gggcccggtg tccaccgtgg gtgtgacaga ggatgaagca gagaccaccc aagcagtgcc   8700
caccacaacc cctgagcccc ccaacaagcc tcgcctcggg gagctgaccg tgacagatgc   8760
cacccctgac tccctcagcc tgtcctggat ggtccccgag ggccagtttg accacttcct   8820
ggtccagtac aggaatgggg atgggcagcc caaggtggtg cgggtgccgg ggcacgagga   8880
cggggtcacc atctcaggcc tggagccaga ccacaagtac aagatgaacc tgtacggctt   8940
ccacggtggc cagcgcgtgg gccccatctc tgtcattggg gtgacagctg cagaggaaga   9000
aactcccgcc cccacagaac ccagcacgga ggccccggag cccctgagg agccgctcct    9060
gggggagctg acagtgacag gatcctcccc tgactcgctg agcctctcct ggaccatccc   9120
ccagggccgc ttcgactcct tcactgtgca gtacaaggac agggacgggc ggccccaggt    9180
ggtgcgtgtc aggggcgagg agagcgaggt caccgtgggg ggcctggagc ccgggtgcaa   9240
atacaagatg cacctgtacg gcctccacga ggggcagcgc gtgggcccag tgtccgctgt   9300
gggtgtgaca gctccaaagg atgaagccga gaccacccaa gcagtgccta ccatgacccc   9360
tgagcccccc atcaagcctc gcctggggga gctgaccgtg acagatgcca ccccgactc    9420
cctcagcctg tcctggatgg ttcccgaggg ccagtttgac cacttcctgg tccagtacag   9480
gaatggggat gggcagccca aggcggtgcg ggtgccgggg cacgaggacg gggtcaccat   9540
ctcaggcctg gagccagacc ataaatacaa gatgaacctg tacggcttcc acggtggcca   9600
gcgcgtaggc cctgtgtctg ccattggggt gacggaggaa gagaccccca gccccacaga   9660
```

```
acccagcact gaggccccgg aggcccctga ggagccgctc ctgggggagt tgacagtgac   9720
aggatcctcc cctgactcgc tgagcctctc ctggaccgtc ccccaggccg cttcgactc    9780
cttcaccgtg cagtacaagg acagggacgg gcagcccag gtggtgcgtg tcagggcga    9840
ggagagcgag gtcaccgtgg ggggcctgga gcccgggcgc aaatacaaga tgcatctgta   9900
cggcctccac gaggggcagc gcgtgggccc agtgtccacc gtgggcatca cggcgcccct  9960
gcccacacca ctgccggtgg agcccgcct gggggagctg gcggtggcgg ccgtgacctc   10020
ggactcagtg ggcctctcat ggacggtggc ccagggcccc tttgactcct tcctggtaca   10080
gtacagggac gcgcagggc agccccaggc agtgcctgtg agcggagacc tccgagcggt   10140
cgccgtctcg gggctggacc cggcccgcaa gtacaagttc ctgctctttg gactccagaa   10200
tgggaaacgc cacggcccag tccctgtgga ggccaggacc gccccagaca ccaaaccgtc   10260
tccccgcctg ggggagctga ctgtgacaga tgcgaccct gactccgtgg gcctctcgtg   10320
gacggtccct gagggcgaat tcgactcctt cgtggtccag tacaaggata aggatggtcg   10380
gctccaggtg gtgccggtgg cagccaacca gcgggaggtc acagtccagg gcctggagcc   10440
cagtaggaaa tacaggttcc tgctctatgg tctgtcaggc aggaaacgac tgggccccat   10500
ctctgctgac agcaccacag ctcccctgga aaggagcta cctcccccacc tggggaact   10560
gaccgtggct gaggagacct ccagctctct gcgcctgtcc tggacggtag cccagggccc   10620
ctttgactcc ttcgtggtcc agtacaggga cacgacgggg cagcccaggg cagtgcctgt   10680
ggccgcagac cagcgcacag tcaccgtaga ggacctggag cctggcaaga aatacaagtt   10740
tctgctctac gggctccttg ggggaaagcg cctgggcccg gtctctgccc tgggaatgac   10800
agccccagaa gaggacacac cagccccaga gttagcccca gaggcccctg agcctcctga   10860
agagcccgc ctaggagtgc tgaccgtgac cgacacaacc ccagactcca tgcgcctctc   10920
gtggagcgtg gcccagggcc cctttgattc cttcgtggtc cagtatgagg acacgaacgg   10980
gcagccccag gccttgctcg tggacggcga ccagagcaag atcctcatct caggcctgga   11040
gcccagcacc ccctacaggt tcctcctcta tggcctccat gaagggaagc gcctggggcc   11100
cctctcagct gagggcacca cagggctggc tcctgctggt cagacctcag aggagtcaag   11160
gccccgcctg tcccagctgt ctgtgactga cgtgaccacc agttcactga ggctcaactg   11220
ggaggcccca ccgggggcct tcgactcctt cctgctccgc tttgggttc atcaccaag   11280
cactctggag ccgcatccgc gtccactgct gcagcgcgag ctgatggtgc cggggacgcg   11340
gcactcggcc gtgctccggg acctgcgttc cgggactctg tacagcctga cactgtatgg   11400
gctgcgagga ccccacaagg ccgacagcat ccagggaacc gcccgcaccc tcagcccagt   11460
tctggagagc cccgtgacc tccaattcag tgaaatcagg gagacctcag ccaaggtcaa   11520
ctggatgccc ccaccatccc gggcggacag cttcaaagtc tcctaccagc tggcggacgg   11580
agggagcct cagagtgtgc aggtggatgg ccaggcccgg acccagaaac tccaggggct   11640
gatcccaggc gctcgctatg aggtgaccgt ggtctcggtc cgaggctttg aggagagtga   11700
gcctctcaca ggcttcctca ccacggttcc tgacggtccc acacagttgc gtgcactgaa   11760
cttgaccgag ggattcgccg tgctgcactg gaagcccccc cagaatcctg tggacaccta   11820
tgacgtccag gtcacagccc ctgggggccc gcctctgcag gcggagaccc caggcagcgc   11880
ggtggactac cccctgcatg accttgtcct ccacaccaac tacaccgcca cagtgcgtgg   11940
cctgcggggc cccaacctca cttccccagc cagcatcacc ttcaccacag ggctagaggc   12000
ccctcgggac ttggaggcca aggaagtgac cccccgcacc gccctgctca cttggactga   12060
```

```
gcccccagtc cggcccgcag gctacctgct cagcttccac acccctggtg gacagaacca  12120
ggagatcctg ctcccaggag ggatcacatc tcaccagctc cttggcctct ttccctccac  12180
ctcctacaat gcacggctcc aggccatgtg gggccagagc ctcctgccgc ccgtgtccac  12240
ctctttcacc acgggtgggc tgcggatccc cttccccagg gactgcgggg aggagatgca  12300
gaacggagcc ggtgcctcca ggaccagcac catcttcctc aacggcaacc gcgagcggcc  12360
cctgaacgtg ttttgcgaca tggagactga tgggggcggc tggctggtgt tccagcgccg  12420
catggatgga cagacagact tctggaggga ctgggaggac tatgcccatg gttttgggaa  12480
catctctgga gagttctggc tgggcaatga ggccctgcac agcctgacac aggcaggtga  12540
ctactccatg cgcgtggacc tgcgggctgg ggacgaggct gtgttcgccc agtacgactc  12600
cttccacgta gactcggctg cggagtacta ccgcctccac ttggagggct accacggcac  12660 cgcagggggac tccatgagct accacagcgg cagtgtcttc tctgcccgtg atcgggaccc  12720
caacagcttg ctcatctcct gcgctgtctc ctaccgaggg gcctggtggt acaggaactg  12780
ccactacgcc aacctcaacg ggctctacgg gagcacagtg gaccatcagg gagtgagctg  12840
gtaccactgg aagggcttcg agttctcggt gcccttcacg gaaatgaagc tgagaccaag  12900
aaactttcgc tccccagcgg ggggaggctg agctgctgcc cacctctctc gcaccccagt  12960
atgactgccg agcactgagg ggtcgccccg agagaagagc cagggtcctt caccaccag  13020 ccgctggagg aagccttctc tgccagcgat ctcgcagcac tgtgtttaca gggggagggg  13080
gaggggttcg tacgggagca ataaaggaga aactgaggta cccggaaaaa aaaaaaaaaa  13140
aaa                                                                13143
```